(12) United States Patent
Herchen et al.

(10) Patent No.: US 12,616,716 B2
(45) Date of Patent: May 5, 2026

(54) WOUND HEALING DRESSINGS AND FORMULATIONS AND METHODS OF USE THEREOF

(71) Applicant: Polaroid IP B.V., Enschede (NL)

(72) Inventors: Stephen Robert Herchen, Plymouth, MA (US); Rong-Chang Liang, Cupertino, CA (US); Christian Ewald Janssen, Recklinghausen (DE); Ran Avraham Frenkel, Brookline, MA (US)

(73) Assignee: Polaroid Therapeutics AG, Schlieren (CH)

( * ) Notice: Subject to any disclaimer, the term of this patent is extended or adjusted under 35 U.S.C. 154(b) by 0 days.

(21) Appl. No.: 18/977,672

(22) Filed: Dec. 11, 2024

(65) Prior Publication Data

US 2025/0099646 A1 Mar. 27, 2025

Related U.S. Application Data

(63) Continuation of application No. PCT/IB2024/053809, filed on Apr. 18, 2024.

(60) Provisional application No. 63/460,399, filed on Apr. 19, 2023.

(51) Int. Cl.
*A61K 31/785* (2006.01)
*A61L 26/00* (2006.01)

(52) U.S. Cl.
CPC ........ *A61K 31/785* (2013.01); *A61L 26/0019* (2013.01); *A61L 26/0047* (2013.01); *A61L 26/0066* (2013.01); *A61L 2300/208* (2013.01)

(58) Field of Classification Search
CPC ............... A61K 31/785; A61L 26/0019; A61L 26/0047; A61L 26/0066; A61L 2300/208; A61L 2300/404; A61L 15/46; A01N 33/12; A01P 1/00
See application file for complete search history.

(56) References Cited

U.S. PATENT DOCUMENTS

| | | | |
|---|---|---|---|
| 4,939,289 | A | 7/1990 | Oxenrider et al. |
| 5,783,502 | A | 7/1998 | Swanson |
| 6,261,581 | B1 | 7/2001 | Gebhardt et al. |
| 8,512,722 | B2 | 8/2013 | Lee et al. |
| 9,089,407 | B2 | 7/2015 | Schaer et al. |
| 10,500,317 | B2 | 12/2019 | Schaer et al. |
| 2009/0226394 | A1 | 9/2009 | Champ et al. |
| 2010/0136072 | A1* | 6/2010 | Haldar ................. C09D 179/02 424/78.35 |
| 2010/0292623 | A1 | 11/2010 | Greiner et al. |
| 2011/0124772 | A1 | 5/2011 | Wang et al. |

FOREIGN PATENT DOCUMENTS

| | | |
|---|---|---|
| CN | 106693042 A | 5/2017 |
| CN | 111849328 A | 10/2020 |
| JP | H05-117585 A | 5/1993 |
| JP | 2004-511582 A | 4/2004 |
| WO | WO-96/39821 A1 | 12/1996 |
| WO | WO-2007/024973 A1 | 3/2007 |
| WO | WO-2008/012367 A2 | 1/2008 |
| WO | WO-2012/065610 A1 | 5/2012 |
| WO | WO-2016/148649 A1 | 9/2016 |
| WO | WO 2022/203952 * | 9/2022 |
| WO | WO-2022/203952 A1 | 9/2022 |

OTHER PUBLICATIONS

Mueller et al. Am J Infection Control. 2008; 36: 651-655. (Year: 2008).*
Anjali Jain et al., "Antimicrobial Polymers", Advanced Healthcare Materials, Nov. 19, 2014, vol. 3, No. 12, pp. 1969-1985.
Atar-Froyman et al., "Anti-biofilm properties of wound dressing incorporation nonrelease polycationic antimicrobials," Biomaterials, Elsevier, Amsterdam, NL, vol. 46, Jan. 28, 2015, pp. 141-148.
Cheah, et al., "Antibacterial activity of quaternized chitosan modified nanofiber membrane", Accepted Manuscript to appear in International Journal of Biological Macromolecules https://doi.org/10.1016/j.ijbiomac.2018.12.193.
Chung, S., et al., (2016). "Antimicrobial Nanostructural Polyurethane Scaffolds." Ch. 17 in Advances in Polyurethane Biomaterials, Cooper S.L. and Guan, J. (eds.), Woodhead Publishing, Elsevier Ltd., pp. 503-521.

(Continued)

*Primary Examiner* — David Browe
(74) *Attorney, Agent, or Firm* — Sunit Talapatra; Foley & Lardner LLP

(57) ABSTRACT

Described herein are wound dressings and methods of their use, wherein the wound dressings comprise a polymeric component. The polymeric component is a polyethyleneimine intermediate selected from the group consisting of:

at least one $R^{60}$ is —$(CH_2)_3OH$ but less than 50% of all $R^{60}$ are —$(CH_2)_3OH$; and the polyethyleneimine intermediate has a ratio of total quaternary amines to total hydroxyl groups of at least 1:1.

12 Claims, 18 Drawing Sheets

(56)　　　　References Cited

OTHER PUBLICATIONS

Elena Poverenov et al., "Formation of Contact Active Antimicrobial Surfaces by Covalent Grafting of Quaternary Ammonium Compounds", Elsevier, May 25, 2018, vol. 169, pp. 195-205.

Ellingson, K.D., et al., "Impact of a Novel Antimicrobial Surface Coating on Health Care—Associated Infections and Environmental Bioburden at 2 Urban Hospitals," Clinical Infectious Diseases, vol. 71, No. 8, Oct. 15, 2020, pp. 1807-1813.

Gao, et al. "Studies on the preparation and antibacterial properties of quaternized polyethyleneimine", Journal of Biomaterials Science, Polymer Edition, 18:5, 531-544, Apr. 2012.

Geczi, Z., et al., "Antimicrobial Silver-Polyethyleneimine Polylactic Acid Polymer Composite Film for Coating Methacrylate-Based Denture Surfaces." J. of Nanomaterials, Nov. 4, 2018, vol. 2018, No. 6, 9 pgs.

Guo, et al., "Antibacterial Activity of Cationic Polymers: Side-Chain or Main-Chain Type?", Royal Society of Chemistry, J. Name., 2013, 00, 1-3.

Ikonen, N., et al., "Deposition of respiratory virus pathogens on frequently touched surfaces at airports." BMC Infectious Diseases, Aug. 29, 2018, 18(437), 8 pgs.

International Preliminary Report on Patentability in International Application No. PCT/US2022/020880, dated Sep. 12, 2023, 10 pgs.

International Search Report & Written Opinion on International Patent Application No. PCT/US2022/020880 dated Jul. 19, 2022 (15 pages).

International Search Report and Written Opinion for International Application No. PCT/IB2023/059638, dated Dec. 14, 2023, 17 pgs.

International Search Report and Written Opinion for International Application No. PCT/IB2023/059638, dated Feb. 15, 2024, 17 pgs.

International Search Report and Written Opinion for International Application No. PCT/IB2023/059639, dated Jan. 26, 2024, 18 pgs.

International Search Report and Written Opinion for PCT/IB2024/053809, dated Sep. 2, 2024, 24 pgs.

Jarach, N., et al., "Polymers in the Medical Antiviral Front-Line," Polymers, Jul. 31, 2020, 12(8): 1727, 30 pgs.

Jeong, et al., "Preparation of polyurethane cationomer nanofiber mats for use in antimicrobial nanofilter applications", ScienceDirect, Materials Letter 61 (Jan. 2007) 3991-3994.

Jia, et al., "Electrospun nano-fiber mats containing cationic cellulose derivatives and poly (vinyl alcohol) with antibacterial activity", Carbohydrate Research 346 (2011) 1337-1341.

Larson, "Antiviral Polymeric Drugs and Surface Coatings" Submitted to the Department of Chemistry on Apr. 26, 2013, in Partial Fulfillment of the Requirements for the Degree of Doctor of Philosophy in Biological Chemistry.

Michael Richard Green and Joseph Sambrook, (2012). Molecular Cloning: a Laboratory Manual, 4th ed., Cold Spring Harbor Laboratory Press, Cold Spring Harbor, N.Y., USA (ISBN 1936113414).

Nurdin, N., et al., "Biocidal Polymers Active by Contact. II. Biological Evaluation of Polyurethane Coatings with Pendent Quaternary Ammonium Salts," J. of Applied Polymer Science, Oct. 20, 1993, 50: pp. 663-670.

Park, D., et al., "Antiviral and Antibacterial Polyurethanes of Various Modalities," Appl. Biochem. Biotechnol., Jan. 10, 2013, 169: pp. 1134-1146.

Park, D., et al., "One-Step, Painting-Like Coating Procedures to Make Surfaces Highly and Permanently Bactericidal," Biotechnology Prog., Feb. 18, 2006, 22(2), pp. 584-589.

Park, et al., "Crosslinked poly(phenylene oxide)-based nanofiber composite membranes for alkaline fuel cells", Royal Society of Chemistry, J. Mater. Chem. A, 2016, 4, 132-141.

Robert A. Meyers (ed.), Molecular Biology and Biotechnology: a Comprehensive Desk Reference, published by VCH Publishers, Inc., 1995 (ISBN 9780471185710).

Wang et al., "The antibacterial activity and mechanism of polyurethane coating with quaternary ammonium salt," Journal of Polymer Research, vol. 29, No. 2, Jan. 20, 2022, 13 pgs.

Wu, et al., "Antibacterial efficacy of quaternized chitosan/poly (vinyl alcohol) nanofiber membrane crosslinked with blocked diisocyanate", Carbohydrate Polymers 262 (2021) 117910.

Wu, et al., "Electrospinning of Quaternized Chitosan-Poly(vinyl alcohol) Composite Nanofiber Membrane: Processing Optimization and Antibacterial Efficacy", Membranes 2022, 12(3), 332.

Xue, et al., "Antibacterial/Antiviral Property and Mechanism of Dual-Functional Quaternized Pyridinium-Type Copolymer," Polymers, Nov. 11, 2015, 7(11): pp. 2290-2303.

* cited by examiner

Compound administration

Day-3  Day-2  Day-1  0h  12h  24h  48h  72h

Acclimation

Inoculation          Terminal

⇑ Wound creating and infection with bacterial cells

⇓ Treatments, topically

⇑ Infected wounds are removed and bacterial loads determined

A ⟶ 32-2E [11.4 µM in DMSO-dH$_2$O]    B ⟶ 32-2E [28.5 µM in DMSO-dH$_2$O]

C ⟶ 32-2E [57 µM in DMSO-dH$_2$O]    D ⟶ Vehicle DMSO-H2O

A ━━━ 32-2E [11.4 μM in DMSO-dH₂O]          B ━━━ 32-2E [28.5 μM in DMSO-dH₂O]

C ━━━ 32-2E [57 μM in DMSO-dH₂O]           D ━━━ Vehicle DMSO-H2O

WOUND HEALING DRESSINGS AND FORMULATIONS AND METHODS OF USE THEREOF

CROSS-REFERENCE TO RELATED APPLICATIONS

This application is a continuation of International Application No. PCT/IB2024/053809, filed on Apr. 18, 2024, which claims the benefit of priority to U.S. Provisional Patent Application No. 63/460,399, filed Apr. 19, 2023, both of which are hereby incorporated by reference herein in their entireties.

FIELD

The embodiments of the present disclosure relate to wound healing dressings and formulations comprising compositions of quaternary ammonium polymer structures with broad spectrum antimicrobial properties, and methods of their use.

BACKGROUND

Wound healing is a natural physiological reaction to tissue injury. Wounds generally heal in four to six weeks. Chronic wounds are those that fail to heal within this time frame. One factor that can lead to impaired healing is bacterial colonization. Wound dressings and/or topical formulations with antimicrobial properties can control and reduce or prevent infection, thereby promoting wound healing.

SUMMARY

In one aspect, described herein is a wound dressing comprising a polymeric component selected from a group consisting of:
- (1) a polymer, copolymer, interpenetrating polymer network, polyelectrolyte complex, blend or composite comprising:
  - (i) a first adduct of a first multifunctional crosslinker and a first quaternary ammonium salt, wherein the first quaternary ammonium salt has a reactive linking group to react with the first multifunctional crosslinker;
  - (ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;
  - (iii) optionally a polyol;
  - (iv) optionally a water-soluble polymer; and
  - (v) optionally a third multifunctional crosslinker;
- (2) a polymer, copolymer, interpenetrating polymer network, polyelectrolyte complex, blend or composite comprising the first adduct, the polyol, the water-soluble polymer, and optionally the third multifunctional crosslinker;
- (3) the polyethyleneimine intermediate;
- (4) the second adduct; and
- (5) a combination of two or more thereof.

In some embodiments, (i) the first adduct and (ii) the polyethyleneimine intermediate or the second adduct are prepared separately and mixed thereafter to form the polymer, the copolymer, the interpenetrating polymer network, the polyelectrolyte complex, the blend, or the composite. In some embodiments, the polymeric component is antibacterial against one of or both gram negative strain bacteria and gram positive strain bacteria. In some embodiments, the polyethyleneimine intermediate has a ratio of total quaternary amines to total hydroxyl groups of at least 1:1. In some embodiments, an outer layer of the wound dressing contains the polymeric component. In some embodiments, the polymeric component is impregnated into the wound dressing. In some embodiments, the wound dressing is selected from the group consisting of a wrap, a covering, a barrier, a layer, a packing, a gauze, a plaster, a bandage, a lint, a suture, a film, a foamed product, a hydrogel, a hydrocolloid, an alginate product, a bioactive product, a tissue-engineered skin substitute, a medicated product, a liquid bandage, a smart dressing, and a composite, or any combination of the foregoing. In some embodiments, the wound dressing is configured to provide an indication of one or more parameters relating to a status of the wound site.

In another aspect, described herein is a topical formulation comprising a polymeric component selected from a group consisting of:
- (1) a polymer, copolymer, interpenetrating polymer network, polyelectrolyte complex, blend or composite comprising:
  - (i) a first adduct of a first multifunctional crosslinker and a first quaternary ammonium salt, wherein the first quaternary ammonium salt has a reactive linking group to react with the first multifunctional crosslinker;
  - (ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;
  - (iii) optionally a polyol;
  - (iv) optionally a water-soluble polymer; and
  - (v) optionally a third multifunctional crosslinker; or
- (2) a polymer, copolymer, interpenetrating polymer network, polyelectrolyte complex, blend or composite comprising the first adduct, the polyol, the water-soluble polymer, and optionally the third multifunctional crosslinker;
- (3) the polyethyleneimine intermediate;
- (4) the second adduct; and
- (5) a combination of two or more thereof;
- and at least one pharmaceutically acceptable excipient;
- wherein the polyethyleneimine intermediate has a ratio of total quaternary amines to total hydroxyl groups of at least 1:1.

In some embodiments, the topical formulation is in the form of a cream, a gel, a paste, a foam, a spray, a powder, an emulsion, a liquid, or an ointment. In some embodiments, the polymeric component is antibacterial against one of or both gram negative strain bacteria and gram positive strain bacteria.

In another aspect, described herein is a method of preventing or reducing bacterial growth or reducing infection in a wound, a surgical site, or an implant of a subject, the method comprising applying or coating the wound, the surgical site, or the implant with a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, described herein is a method of treating a wound or a surgical site in a subject in need thereof, the method comprising applying, to the wound or the surgical site, a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, described herein is a method of promoting healing of a wound or a surgical site in a subject in need thereof, the method comprising applying, to the wound or the surgical site, a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the wound is an external wound. In some embodiments, the wound is an internal wound. In some embodiments, the method is part of a regimen for acute wound care. In some embodiments, the method is part of a regimen for chronic wound care. In some embodiments, the wound is infected. In some embodiments, the wound is not infected.

In another aspect, described herein is a method of protecting a wound site in a subject in need thereof, the method comprising surrounding at least a portion of the wound site with a dressing, and contacting the wound site with a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, described herein is a method of preventing or reducing infection in a subject in need thereof, the method comprising administering to the subject a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, described herein is a method to treat infection in a subject in need thereof, the method comprising administering to the subject a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the infection is a local infection. In some embodiments, the infection is a systemic infection.

In another aspect, described herein is a method to treat sepsis in a subject in need thereof, the method comprising administering to the subject a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, described herein is a method of preventing or reducing necrosis in a subject in need thereof, the method comprising administering to the subject a composition comprising a polymeric component selected from a group consisting of:

(1) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (2) a polymer, copolymer, interpenetrating polymer network, polyelectrolyte complex, blend or composite comprising the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the subject is a human or animal subject. In some embodiments, the composition is antibacterial against one of or both gram negative strain bacteria and gram positive strain bacteria. In some embodiments, the polyethyleneimine intermediate has a ratio of total quaternary amines to total hydroxyl groups of at least 1:1.

In some embodiments, the polyethyleneimine intermediate comprises a reaction product of reagents comprising a polyethyleneimine and an alkylating agent. In some embodiments, the reagents further comprise a mono-epoxide or a lactone. In some embodiments, the mono-epoxide or the lactone is optionally substituted with $C_1$-$C_6$ alkyl optionally substituted with a substituent selected from —($C_6$-$C_{10}$ aryl), and —($C_1$-$C_6$ alkoxy) optionally substituted with hydroxy, $C_1$-$C_6$ alkoxy, $C_6$-$C_{10}$ aryl optionally substituted with $C_1$-$C_6$ alkyl, and carboxy. In some embodiments, the mono-epoxide is a $C_1$-$C_6$ alkyl oxirane. In some embodiments, the $C_1$-$C_6$ alkyl epoxide is selected from the group consisting of methyl oxirane, ethyl oxirane, propyl oxirane, and butyl oxirane. In some embodiments, the polyethyleneimine intermediate comprises a reaction product of reagents comprising a polyethyleneimine, a mono-epoxide, and optionally an alkylating agent; the mono-epoxide is substituted with —($C_1$-$C_6$ alkylene)-$N^+(R^{20})_3X^-$; each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl); and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives. In some embodiments, the alkylating agent comprises one or more $R^{21}$-LG, wherein each $R^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH; and each LG is a leaving group. In some embodiments, the alkylating agent is phenacyl halide, benzyl halide, or hexyl halide.

In some embodiments, the reagents for the reaction product comprised in the polyethyleneimine intermediate further comprise a monoisocyanate. In some embodiments, the monoisocyanate comprises one or more $R^{30}$—NCO, wherein each $R^{30}$ is independently selected from (1) $C_6$-$C_{20}$ alkyl optionally substituted with 1-3 substituents independently selected from halogen, —SiR$^a$(OR$^b$)(OR$^c$), and —($C_6$-$C_{10}$ aryl); and (2) $C_6$-$C_{10}$ aryl optionally substituted with 1-3 substituents independently selected from halogen, —($C_1$-$C_6$ alkyl), and —SiR$^a$(OR$^b$)(OR$^c$); wherein each R$^a$ is independently $C_1$-$C_6$ alkyl; and each R$^b$ and each R$^c$ are independently selected from —($C_1$-$C_6$ alkyl) and —Si($C_1$-$C_6$ alkyl)$_3$. In some embodiments, the monoisocyanate comprises octylisocyanate, octadecylisocyanate, or a combination thereof.

In some embodiments, the polyethyleneimine has a molecular weight of about 300 to about 270,000 daltons. In some embodiments, the polyethyleneimine has a molecular weight of about 10,000 to about 200,000 daltons. In some embodiments, the polyethyleneimine has a molecular weight of about 25,000 to about 120,000 daltons. In some embodiments, the polyethyleneimine is branched. In some embodiments, the polyethyleneimine is hyperbranched. In some embodiments, the polyethyleneimine has a ratio of primary to secondary to tertiary amines of about 1:2:1 to about 1:1:1. In some embodiments, the polyethyleneimine has a ratio of primary to secondary to tertiary amines of about 1:1:0.7. In some embodiments, the polyethyleneimine intermediate is one or more selected from -continued and a copolymer or blend of any two or more thereof, wherein:

each $Y^3$ is independently H or —O—$Y^2$ each $Y^2$ is independently H or —C(O)—NHR$^{30}$;

each n is an integer independently selected from 1 to 3000, preferably an integer independently selected from 10 to 1000;

Z is —($C_2$-$C_6$ alkylene)-;

each $R^{10}$ is independently selected from hydrogen; $C_1$-$C_6$ alkyl optionally substituted with a substituent selected from —$N^+(R^{20})_3X^-$, —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy; and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl);

each $R^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH;

each $R^{30}$ is independently selected from (1) $C_6$-$C_{20}$ alkyl optionally substituted with 1-3 substituents independently selected from halogen, —SiR$^a$(OR$^b$)(OR$^c$), and —($C_6$-$C_{10}$ aryl); and (2) $C_6$-$C_{10}$ aryl optionally substituted with 1-3 substituents independently selected from halogen, —($C_1$-$C_6$ alkyl), and —SiR$^a$(OR$^b$)(OR$^c$); wherein each $R^a$ is independently —($C_1$-$C_6$ alkyl); and each $R^b$ and each $R^c$ are independently selected from —($C_1$-$C_6$ alkyl) and —Si($C_1$-$C_6$ alkyl)$_3$; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives;

provided:

when $R^{10}$ is $C_1$-$C_6$ alkyl optionally substituted with a substituent selected from —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy, then the polyethylene-imine intermediate is independently selected from In some embodiments, the polyethyleneimine intermediate is wherein each $R^{60}$ is independently selected from —$Y^4$— ($C_1$-$C_{18}$ alkyl) optionally substituted with 1-3 substituents selected from —OH, —$N^+(R^{20})_3X^-$, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH; and at least one $R^{60}$ is substituted with —OH but less than 50% of all $R^{60}$ are substituted with —OH;

$Y^4$ is absent or —C(O)—;

and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —$(C_1$-$C_6$ alkyl), —$(C_1$-$C_6$ alkoxy), —C(O)O—$(C_1$-$C_6$ alkyl), —C(O)NH($C_1$-$C_6$ alkyl), —C(O)N($C_1$-$C_6$ alkyl)$_2$, or —OC(O)—$(C_1$-$C_6$ alkyl);

each n is an integer independently selected from 1 to 3000, preferably an integer independently selected from 10 to 1000; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the polyethyleneimine intermediate is wherein each $R^{60}$ is independently selected from —$Y^4$—$(C_1$-$C_{18}$ alkyl) optionally substituted with 1-3 substituents selected from —OH, —$N^+(R^{20})_3X^-$, —$(C_6$-$C_{10}$ aryl), —C(O)O($C_1$-$C_6$ alkyl), and —C(O)—$(C_6$-$C_{10}$ aryl); and at least one $R^{60}$ is substituted with —OH but less than 50% of all $R^{60}$ are substituted with —OH;

$Y^4$ is absent or —C(O)—;

and each $R^{20}$ is independently selected from a group consisting of $C_1$-$C_6$ alkyl;

each n is an integer independently selected from 1 to 3000, preferably an integer independently selected from 10 to 1000; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, each $R^{60}$ is independently selected from —$(C_1$-$C_{18}$ alkyl) optionally substituted with —OH; and at least one $R^{60}$ is substituted with —OH but less than 50% of all $R^{60}$ are substituted with —OH.

In some embodiments, the polyethyleneimine intermediate is selected from a group consisting of:

12

| Compound | General Structure | PEI MW* | $R^{60}$ (mole %)** |
|---|---|---|---|
| 20-1 (batch 105159) | B | 270 kDa (branched) | —CH$_2$CH(CH$_3$)OH (<50%) —C$_6$H$_{13}$ (>50%) |
| 20-1 (batch 99367) | B | 270 kDa (branched) | —CH$_2$CH(CH$_3$)OH (50%) —C$_6$H$_{13}$ (50%) |
| 21-1 | A | 25 kDa (hyperbranched) | —CH$_2$CH(CH$_3$)OH (50%) —C$_6$H$_{13}$ (50%) |
| 22-1 | B | 70 kDa (branched) | —CH$_2$CH(CH$_3$)OH (50%) —C$_6$H$_{13}$ (50%) |
| 23-1 | B | 70 kDa (branched) | —CH$_2$CH(CH$_3$)OH (50%) —CH$_2$C(O)Ph (50%) |
| 24-1 | B | 70 kDa (branched) | —CH$_2$CH(CH$_3$)OH (50%) —CH$_2$Ph (50%) |
| 26-1 | B | 70 kDa (branched) | —CH$_2$CH(OH)CH$_2$N$^+$(CH$_3$)$_3$ Cl$^-$ (100%) |
| 29-1 | B | 70 kDa (branched) | —(CH$_2$)$_3$OH (1%) —C$_6$H$_{13}$ (99%) |
| 30-1 | A | 25 kDa (hyperbranched) | —(CH$_2$)$_3$OH (10%) 75:25 —C$_{18}$H$_{37}$:—C$_8$H$_{17}$ (90%) |
| 31-1 | B | 70 kDa (branched) | —C(O)(CH$_2$)$_5$OH (7%) —C$_6$H$_{13}$ (93%) |
| 32-1 | B | 70 kDa (branched) | —(CH$_2$)$_3$OH (10%) —C$_6$H$_{13}$ (90%) |
| 32-2 | B | 70 kDa (branched) | —(CH$_2$)$_3$OH (5%) —C$_6$H$_{13}$ (95%) |
| 32-3 | B | 70 kDa (branched) | —CH$_2$CH(CH$_3$)OH (5%) —C$_6$H$_{13}$ (95%) |
| 32-4 | B | 70 kDa (branched) | —C(O)(CH$_2$)$_5$OH (7.5%) —C$_6$H$_{13}$ (92.5%) |
| 32-5 | A | 25 kDa (hyperbranched) | —CH$_2$CH(CH$_3$)OH (50%) 50:50 —C$_{18}$H$_{37}$:—C$_8$H$_{17}$ (50%) |
| 32-6 | B | 72 kDa (branched) | —(CH$_2$)$_3$OH (13%) 75:25 —C$_{18}$H$_{37}$:—C$_8$H$_{17}$ (87%) |
| 32-7 | B | 72 kDa (branched) | —C(O)(CH$_2$)$_5$OH (6.5%) 75:25 —C$_{18}$H$_{37}$:—C$_8$H$_{17}$ (93.5%) |
| 32-8 | A | 25 kDa (hyperbranched) | —C(O)(CH$_2$)$_5$OH (7%) 75:25 —C$_{18}$H$_{37}$:—C$_8$H$_{17}$ (93%) |
| 32-9 | A | 25 kDa (hyperbranched) | —CH$_2$CH(CH$_3$)OH (50%) 25:75 —C$_{18}$H$_{37}$:—C$_8$H$_{17}$ (50%) |

*indicates molecular weight of polyethyleneimine precursor
**theoretical stoichiometric ratio (based on amount of reactants used in the synthetic protocol) wherein A is B is and each n is an integer independently selected from 1 to 3000, preferably an integer independently selected from 10 to 100. In some embodiments, one or more bromide anions is replaced with $X^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the polyethyleneimine intermediate is selected from a group consisting of:

| Compound | General Structure | PEI MW* | $R^{60}$ (mole %)** |
|---|---|---|---|
| 32-10 | A | 25 kDa (hyperbranched) | —C(O)(CH$_2$)$_5$OH (11%) —C$_6$H$_{13}$ (89%) |

-continued

| Compound | General Structure | PEI MW* | $R^{60}$ (mole %)** |
|---|---|---|---|
| 32-11 | B | 70 kDa (branched) | —C(O)(CH$_2$)$_5$OH (9%)<br>—C$_6$H$_{13}$ (91%) |
| 32-13 | B | 70 kDa (branched) | —(CH$_2$)$_3$OH (7%)<br>75:25 —C$_{18}$H$_{37}$:—C$_8$H$_{17}$ (93%) |
| 32-14 | A | 25 kDa (hyperbranched) | —(CH$_2$)$_3$OH (7%)<br>75:25 —C$_{18}$H$_{37}$:—C$_8$H$_{17}$ (93%) |
| 32-15 | B | 70 kDa (branched) | —C(O)(CH$_2$)$_5$OH (9%)<br>75:25 —C$_{18}$H$_{37}$:—C$_8$H$_{17}$ (91%) |
| 32-16 | A | 25 kDa (hyperbranched) | —C(O)(CH$_2$)$_5$OH (11%)<br>75:25 —C$_{18}$H$_{37}$:—C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |
| 32-1A | B | 70 kDa (branched) | —(CH$_2$)$_3$OH (10%)<br>—C$_6$H$_{13}$ (90%) |
| 32-1B | B | 70 kDa (branched) | —(CH$_2$)$_3$OH (10%)<br>—C$_6$H$_{13}$ (90%) |
| 32-2A | B | 70 kDa (branched) | —(CH$_2$)$_3$OH (5%)<br>—C$_6$H$_{13}$ (95%) |
| 32-2B | B | 70 kDa (branched) | —(CH$_2$)$_3$OH (5%)<br>—C$_6$H$_{13}$ (95%) |
| 32-2C | B | 70 kDa (branched) | —(CH$_2$)$_3$OH (15%)***<br>—C$_6$H$_{13}$ (85%) |
| 32-2D | B | 70 kDa (branched) | —(CH$_2$)$_3$OH (5%)<br>—C$_6$H$_{13}$ (95%) |
| 32-2E | B | 70 kDa (branched) | —(CH$_2$)$_3$OH (12%)*<br>—C$_6$H$_{13}$ (88%) |
| 32-2F | B | 70 kDa (branched) | —(CH$_2$)$_3$OH (5%)<br>—C$_6$H$_{13}$ (95%) |
| 32-2G | B | 70 kDa (branched) | —(CH$_2$)$_3$OH (5%)<br>—C$_6$H$_{13}$ (95%) |
| 32-2H | B | 70 kDa (branched) | —(CH$_2$)$_3$OH (5%)<br>—C$_6$H$_{13}$ (95%) |
| 32-2I | B | 70 kDa (branched) | —(CH$_2$)$_3$OH (5%)<br>—C$_6$H$_{13}$ (95%) |

*indicates molecular weight of polyethyleneimine precursor

**theoretical stoichiometric ratio (based on amount of reactants used in the synthetic protocol) unless otherwise indicated wherein A is

3 X⁻

B is

4 X⁻ each n is an integer independently selected from 1 to 3000, preferably an integer independently selected from 10 to 100; and each X⁻ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, at least 20% of the nitrogen atoms of the polyethyleneimine intermediate are quaternized.

In some embodiments, the polymeric component is the polyethyleneimine intermediate.

In some embodiments, the first quaternary ammonium salt has a chemical structure of wherein $R^1$ is selected from a group consisting of —(C$_8$-C$_{30}$ alkyl), —(C$_8$-C$_{30}$ heteroalkyl), —(C$_8$-C$_{30}$ heteroalkyl)-(C$_6$-C$_{10}$ aryl), —(C$_6$-C$_{10}$ aryl), —(C$_6$-C$_{10}$ aryl)-(C$_5$-C$_{30}$ alkyl), —(C$_6$-C$_{10}$ aryl)-(C$_5$-C$_{30}$ heteroalkyl), —(CR$^m$R$^n$)$_{x10}$—W$^{10}$—(CR$^p$R$^q$)$_{y10}$—H, and —(CR$^m$R$^n$)$_{x11}$—W$^{11}$—(CR$^p$R$^q$)$_{y11}$H—; wherein —(C$_8$-C$_{30}$ heteroalkyl), —(C$_8$-C$_{30}$ heteroalkyl)-(C$_6$-C$_{10}$ aryl), and —(C$_6$-C$_{10}$ aryl)-(C$_1$-C$_{30}$ heteroalkyl) have 1 to 4 heteroatoms independently selected from O, S, and Si;

$R^2$ is selected from a group consisting of —(C$_1$-C$_4$ alkyl), —(C$_1$-C$_4$ heteroalkyl), —(C$_1$-C$_4$ heteroalkyl)-(C$_6$-C$_{10}$ aryl), —(C$_6$-C$_{10}$ aryl), —(C$_6$-C$_{10}$ aryl)-(C$_1$-C$_4$ alkyl), —(C$_6$-C$_{10}$ aryl)-(C$_1$-C$_4$ heteroalkyl); —(CR$^m$R$^n$)$_{x20}$—W$^{20}$—(CR$^p$R$^q$)$_{y20}$—H, and —(CR$^m$R$^n$)$_{x21}$—W$^{21}$—(CR$^p$R$^q$)$_{y21}$—H; wherein —(C$_1$-C$_4$ heteroalkyl), —(C$_1$-C$_4$ heteroalkyl)-(C$_6$-C$_{10}$ aryl), and —(C$_6$-C$_{10}$ aryl)-(C$_1$-C$_4$ heteroalkyl) have 1 to 4 heteroatoms independently selected from O, S, and Si;

$R^3$ is selected from a group consisting of —(C$_1$-C$_{30}$ alkyl), —(C$_1$-C$_{30}$ heteroalkyl), —(C$_1$-C$_{30}$ heteroalkyl)-(C$_6$-C$_{10}$ aryl), —(C$_6$-C$_{10}$ aryl), —(C$_6$-C$_{10}$ aryl)-(C$_1$-C$_{30}$ alkyl), —(C$_6$-C$_{10}$ aryl)-(C$_1$-C$_{30}$ heteroalkyl), —(CR$^m$R$^n$)$_{x30}$—W$^{30}$—(CR$^p$R$^q$)$_{y30}$—H, and —(CR$^m$R$^n$)$_{x31}$—W$^{31}$—(CR$^p$R$^q$)$_{y31}$—H; wherein —(C$_1$-C$_{30}$ heteroalkyl), —(C$_1$-C$_{30}$ heteroalkyl)-(C$_6$-C$_{10}$ aryl), and —(C$_6$-C$_{10}$ aryl)-(C$_1$-C$_{30}$ heteroalkyl) have 1 to 4 heteroatoms independently selected from O, S, and Si;

A is a linking group selected from a group consisting of —(C$_3$-C$_{20}$ alkylene)-, —(C$_3$-C$_{20}$ heteroalkylene)-, —(C$_6$-C$_{10}$ arylene)-(C$_3$-C$_{20}$ alkylene)-, —(CR$^m$R$^n$)$_{x40}$—W$^{40}$—(CR$^p$R$^q$)$_{y40}$—, and —(CR$^m$R$^n$)$_{x41}$—W$^{41}$—(CR$^p$R$^q$)$_{y41}$—, wherein —(C$_3$-C$_{20}$ heteroalkylene)- has 1 to 4 heteroatoms independently selected from O, S, and Si; and —(C$_3$-C$_{20}$ alkylene)- and —(C$_3$-C$_{20}$ heteroalkylene)- are optionally substituted with 1 to 6 substituents independently selected from —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl);

each R$^m$, R$^n$, R$^p$, and R$^q$ is independently selected from H and C$_1$-C$_4$ alkyl;

W$^{10}$, W$^{20}$, W$^{30}$, and W$^{40}$ are independently selected from —C(O)—; —C(O)O—; —OC(O)—; —C(O)NH—; and —NHC(O)—;

W$^{11}$, W$^{21}$, W$^{31}$, and W$^{41}$ are independently selected from 5- to 6-membered cycloalkyl, C$_6$-C$_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x10 is an integer from 1 to 30 and y10 is an integer from 0 to 29, wherein 8≤(x10+y10)≤30;

x11 is an integer from 1 to 30 and y11 is an integer from 0 to 29, wherein 8≤(x11+y11)≤30;

x20 is an integer from 1 to 4 and y20 is an integer from 0 to 3, wherein x20+y20≤4;

x21 is an integer from 1 to 4 and y21 is an integer from 0 to 3, wherein x21+y21≤4;

x30 is an integer from 1 to 30 and y30 is an integer from 0 to 29, wherein x30+y30≤30;

x31 is an integer from 1 to 30 and y31 is an integer from 0 to 29, wherein x31+y31≤30;

x40 is an integer from 1 to 19 and y40 is an integer from 1 to 19, wherein 3≤(x40+y40)≤20;

x41 is an integer from 1 to 20, and y41 is an integer from 0 to 19, wherein 3≤(x41+y41)≤20;

Y is selected from a group consisting of —OH, —NHR⁴, —SH, —CO₂H, —C(O)NHR⁴, —C(S)NHR⁴, $$\text{R}^4 \quad \text{and} \quad \text{R}^4;$$

each R⁴ is independently selected from a group consisting of H, —(C₆-C₁₀ aryl)-(C₁-C₃ alkyl), —(C₆-C₁₀ aryl)-(C₁-C₃ heteroalkyl), —(C₁-C₃ alkyl)-(C₆-C₁₀ aryl), —(C₁-C₃ heteroalkyl)-(C₆-C₁₀ aryl), and —(C₆-C₁₀ aryl), wherein —(C₆-C₁₀ aryl)-(C₁-C₃ heteroalkyl) and —(C₁-C₃ heteroalkyl)-(C₆-C₁₀ aryl) have 1 to 4 heteroatoms independently selected from O, S, and Si; and X⁻ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

In some embodiments, R¹ is selected from a group consisting of —(C₁₂-C₃₀ alkyl), —(C₁₂-C₃₀ heteroalkyl), —(C₁₂-C₃₀ alkyl)-(C₆-C₁₀ aryl), —(C₁₂-C₃₀ heteroalkyl)-(C₆-C₁₀ aryl), —(C₆-C₁₀ aryl)-(C₁₂-C₃₀ alkyl), and —(C₆-C₁₀ aryl)-(C₁₂-C₃₀ heteroalkyl); wherein —(C₁₂-C₃₀ heteroalkyl), —(C₁₂-C₃₀ heteroalkyl)-(C₆-C₁₀ aryl), and —(C₆-C₁₀ aryl)-(C₁₂-C₃₀ heteroalkyl) have 1 to 4 heteroatoms independently selected from O, S, and Si. In some embodiments, R³ is selected from a group consisting of —(C₁-C₄ alkyl), —(C₁-C₄ heteroalkyl), —(C₁-C₄ alkyl)-(C₆-C₁₀ aryl), —(C₁-C₄ heteroalkyl)-(C₆-C₁₀ aryl), —(C₆-C₁₀ aryl)-(C₁-C₄ alkyl), and —(C₆-C₁₀ aryl)-(C₁-C₄ heteroalkyl); wherein —(C₁-C₄ heteroalkyl), —(C₁-C₄ heteroalkyl)-(C₆-C₁₀ aryl), and —(C₆-C₁₀ aryl)-(C₁-C₄ heteroalkyl) have 1 to 4 heteroatoms independently selected from O, S, and Si. In some embodiments, at least one of R² and R³ is —(C₁-C₄ alkyl). In some embodiments, R² and R³ are methyl. In some embodiments, A is —(CH₂)ₘ— or —(CH₂CHR⁵—O—)ₙ—CH₂CHR⁵—, wherein m is an integer from 2 to 20; n is 0, 1, 2, 3, 4, or 5; and each R⁵ is independently selected from a group consisting of H, —(C₆-C₁₀ aryl)-(C₁-C₃ alkyl), —(C₆-C₁₀ aryl)-(C₁-C₃ heteroalkyl), —(C₁-C₃ alkyl)-(C₆-C₁₀ aryl), —(C₁-C₃ heteroalkyl)-(C₆-C₁₀ aryl), and —(C₆-C₁₀ aryl), wherein —(C₆-C₁₀ aryl)-(C₁-C₃ heteroalkyl) and —(C₁-C₃ heteroalkyl)-(C₆-C₁₀ aryl) have 1 to 4 heteroatoms independently selected from O, S, and Si. In some embodiments, R⁵ is H or methyl. In some embodiments, the first quaternary ammonium salt is $$\text{C}_{18}\text{H}_{37}\text{—N}^+\text{—}\quad\text{Br}^-\quad\text{—OH,}$$

-continued $$\text{C}_{18}\text{H}_{37}\text{—N}^+\quad\text{Br}^-\quad\text{—O—OH,}$$

$$\text{C}_{16}\text{H}_{33}\text{—N}^+\quad\text{Br}^-\quad\text{—OH,}$$

$$\text{C}_{16}\text{H}_{33}\text{—N}^+\quad\text{Br}^-\quad\text{—O—OH,}$$

$$\text{C}_{14}\text{H}_{29}\text{—N}^+\quad\text{Br}^-\quad\text{—OH,}$$

$$\text{C}_{14}\text{H}_{29}\text{—N}^+\quad\text{Br}^-\quad\text{—O—OH,}$$

$$\text{C}_{12}\text{H}_{25}\text{—N}^+\quad\text{Br}^-\quad\text{—OH,}$$

$$\text{C}_{12}\text{H}_{25}\text{—N}^+\quad\text{Br}^-\quad\text{—O—OH,}$$

or a combination of two or more thereof. In some embodiments, the first quaternary ammonium salt is present in the polymer, the copolymer, or the interpenetrating polymer network of polymeric component (1) or (2) in an amount of about 1 wt. % to about 50 wt. %.

In some embodiments, the first multifunctional crosslinker is a bisfunctional crosslinker. In some embodiments, the bisfunctional crosslinker is a diisocyanate. In some embodiments, the a diisocyanate is selected from a group consisting of hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI). In some embodiments, the second multifunctional crosslinker, when present, is a second polyisocyanate; the third multifunctional crosslinker, when present, is a third polyisocyanate; and the second polyisocyanate and the third polyisocyanate are different. In some embodiments, the second multifunctional crosslinker, when present, is a second polyisocyanate; the third multifunctional crosslinker, when present, is a third polyisocyanate; and the second polyisocyanate and the third polyisocyanate are the same. In some embodiments, the first multifunctional crosslinker is a first polyisocyanate; the second multifunctional crosslinker, when present, is a second polyisocyanate; the third multifunctional crosslinker, when present, is a third polyisocyanate; and the first polyisocyanate, the second polyisocyanate, and the third polyisocyanate are different. In some embodiments, the first multifunctional crosslinker is a first polyisocyanate; the second multifunctional crosslinker, when present, is a second polyisocyanate; the third multifunctional crosslinker, when present, is a third polyisocyanate; and the first polyisocyanate, the second polyisocyanate, and the third polyisocyanate are the same. In some embodiments, each of the first, second, and third polyisocyanates has an average isocyanate functionality of 2 to 5. In some embodiments, each of the first, second, and third polyisocyanates has an average isocyanate functionality of 3 to 4. In some embodiments, each of the first, second, and third polyisocyanates is prepared from a diisocyanate independently selected from a group consisting of hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI). In some embodiments, each of the first, second, and third polyisocyanates is independently selected from a group consisting of DESMODUR® N-3300, DESMODUR® N-100, DESMODUR® Z4470SN, WANNATE® T series polyisocyanates, and LUPRANATE® M series polyisocyanates. In some embodiments, the first adduct has an average isocyanate functionality of 2 to 3. In some embodiments, the first adduct has an average isocyanate functionality of about 2.05 to about 2.3. In some embodiments, the first multifunctional crosslinker is present in the polymer, the copolymer, or the interpenetrating polymer network of polymeric component (1) or (2) in an amount of about 2 wt. % to about 25 wt. %. In some embodiments, the second multifunctional crosslinker is present in the polymer, the copolymer, or the interpenetrating polymer network of polymeric component (1) or in polymeric component (4) in an amount of about 0.1 wt. % to about 10 wt. %. In some embodiments, the third multifunctional crosslinker is present in the polymer, the copolymer, or the interpenetrating polymer network of polymeric component (1) or (2) in an amount of about 0.1 wt. % to about 20 wt. %.

In some embodiments, the polyol is selected from a group consisting of polyether polyols, polyester polyols, polyacrylic polyols, polymethacrylic polyols, polycaprolactone polyols, polybutadiene polyols, poly(acrylonitrile-co-butadiene) polyols, polysiloxane polyols, a copolymer of any two or more thereof, and a combination of any two or more thereof. In some embodiments, the polyol is selected from a group consisting of poly(tetramethylene glycol), polyethylene glycol, polypropylene glycol, poly(ethylene glycol-b-propylene glycol-b-ethylene glycol), and poly(propylene glycol-b-polyethylene glycol-b-propylene glycol). In some embodiments, the polyol has a weight average molecular weight from about 300 to about 3000. In some embodiments, the polyol has a weight average molecular weight from about 400 to about 2000. In some embodiments, the polyol has a weight average molecular weight from about 600 to about 1500. In some embodiments, the polyol is present in the polymer, the copolymer, or the interpenetrating polymer network of polymeric component (1) or (2) in an amount of about 1 wt. % to about 40 wt. %.

In some embodiments, polymeric component (1) further comprises (vi) a third adduct of the first multifunctional crosslinker and a second quaternary ammonium salt $$R^{2a}\!-\!\underset{R^{3a}}{\overset{\displaystyle R^{1a}}{\underset{\displaystyle |}{\overset{\displaystyle |}{N^+}}}}\!\underset{A^1}{\overset{X^-}{\diagdown}}\!Y^1,$$

wherein $R^{1a}$, $R^{2a}$, and $R^{3a}$ are each independently —($C_1$-$C_{20}$ alkyl), —($C_1$-$C_{20}$ alkyl)-($C_6$-$C_{10}$ aryl), or —($C_6$-$C_{10}$ aryl)-($C_1$-$C_{20}$ alkyl);

$A^1$ is a linking group selected from a group consisting of —($C_3$-$C_{20}$ alkylene)-, —($C_3$-$C_{20}$ heteroalkylene)-, —($C_6$-$C_{10}$ arylene)-($C_3$-$C_{20}$ alkylene)-, —($CR^{m1}$ $R^{n1}$)$_{x42}$—$W^{42}$—($CR^{p1}R^{q1}$)$_{y42}$—, and —($CR^{m1}$ $R^{n1}$)$_{x43}$—$W^{43}$—($CR^{p1}R^{q1}$)$_{y43}$—, wherein —($C_3$-$C_{20}$ heteroalkylene)- has 1 to 4 heteroatoms independently selected from O, S, and Si; and —($C_3$-$C_{20}$ alkylene)- and —($C_3$-$C_{20}$ heteroalkylene)- are optionally substituted with 1 to 6 substituents independently selected from —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl);

each $R^{m1}$, $R^{n1}$, $R^{p1}$, and $R^{q1}$ is independently selected from H and $C_1$-$C_4$ alkyl;

$W^{42}$ is selected from —C(O)—; —C(O)O—; —OC (O)—; —C(O)NH—; and —NHC(O)—;

$W^{43}$ is selected from 5- to 6-membered cycloalkyl, $C_6$-$C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein 3≤(x42+y42)≤20;

x43 is an integer from 1 to 20, and y43 is an integer from 0 to 19, wherein 3≤(x43+y43)≤20;

$Y^1$ is selected from a group consisting of —OH, —NHR$^{4a}$, —SH, —CO$_2$H, —C(O)NHR$^{4a}$, —C(S) NHR$^{4a}$, $$\text{and}$$

each $R^{4a}$ is independently selected from a group consisting of H, —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si; and $X^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

In some embodiments, at least one of $R^{1a}$, $R^{2a}$, and $R^{3a}$ is —($C_1$-$C_4$ alkyl). In some embodiments, two of $R^{1a}$, $R^{2a}$, and $R^{3a}$ is —($C_1$-$C_4$ alkyl).

In some embodiments, polymeric component (1) further comprises (vi) a third adduct of a fourth multifunctional crosslinker and a second quaternary ammonium salt $$R^{2a}\!-\!\underset{R^{3a}}{\overset{\displaystyle R^{1a}}{\underset{\displaystyle |}{\overset{\displaystyle |}{N^+}}}}\!\underset{A^1}{\overset{X^-}{\diagdown}}\!Y^1,$$

wherein $R^{1a}$, $R^{2a}$, and $R^{3a}$ are each independently —($C_1$-$C_{20}$ alkyl), —($C_1$-$C_{20}$ alkyl)-($C_6$-$C_{10}$ aryl), or —($C_6$-$C_{10}$ aryl)-($C_1$-$C_{20}$ alkyl);

$A^1$ is a linking group selected from a group consisting of —($C_3$-$C_{20}$ alkylene)-, —($C_3$-$C_{20}$ heteroalkylene)-, —($C_6$-$C_{10}$ arylene)-($C_3$-$C_{20}$ alkylene)-, —($CR^{m1}$ $R^{n1}$)$_{x42}$—$W^{42}$—($CR^{p1}R^{q1}$)$_{y42}$—, and —($CR^{m1}$ $R^{n1}$)$_{x43}$—$W^{43}$—($CR^{p1}R^{q1}$)$_{y43}$—, wherein —($C_3$-$C_{20}$ heteroalkylene)- has 1 to 4 heteroatoms independently selected from O, S, and Si; and —($C_3$-$C_{20}$ alkylene)- and —($C_3$-$C_{20}$ heteroalkylene)- are optionally substituted with 1 to 6 substituents independently selected from —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl);

each $R^{m1}$, $R^{n1}$, $R^{p1}$, and $R^{q1}$ is independently selected from H and $C_1$-$C_4$ alkyl;

$W^{42}$ is selected from —C(O)—; —C(O)O—; —OC (O)—; —C(O)NH—; and —NHC(O)—;

$W^{43}$ is selected from 5- to 6-membered cycloalkyl, $C_6$-$C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein $3 \leq (x42+y42) \leq 20$;

x43 is an integer from 1 to 20, and y43 is an integer from 0 to 19, wherein $3 \leq (x43+y43) \leq 20$;

$Y^1$ is selected from a group consisting of —OH, —NHR$^{4a}$, —SH, —CO$_2$H, —C(O)NHR$^{4a}$, —C(S)NHR$^{4a}$, each R$^{4a}$ is independently selected from a group consisting of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si; and X$^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

In some embodiments, at least one of R$^{1a}$, R$^{2a}$, and R$^{3a}$ is —(C$_1$-C$_4$ alkyl). In some embodiments, two of R$^{1a}$, R$^{2a}$, and R$^{3a}$ is —(C$_1$-C$_4$ alkyl).

In some embodiments, the fourth multifunctional crosslinker is present in the polymer, the copolymer, or the interpenetrating polymer network of polymeric component (1) in an amount of about 0.1 wt. % to about 15 wt. %. In some embodiments, the fourth multifunctional crosslinker is different from the first multifunctional crosslinker and, when present, from the second multifunctional crosslinker and, when present, from the third multifunctional crosslinker. In some embodiments, the fourth multifunctional crosslinker is a fourth polyisocyanate. In some embodiments, the fourth polyisocyanate is prepared from a diisocyanate selected from the group consisting of: hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI). In some embodiments, the fourth polyisocyanate is selected from the group consisting of DESMODUR® N-3300, DESMODUR® N-100, DESMODUR® Z4470SN, WANNATE® T series polyisocyanates, and LUPRANATE® M series polyisocyanates.

In some embodiments, the second quaternary ammonium salt is (C18DMDEG-Br)

(C2DMDEG-Br)

In some embodiments, the second quaternary ammonium salt is present in the polymer, the copolymer, or the interpenetrating polymer network of polymeric component (1) in an amount of about 1 wt. % to about 15 wt. %. In some embodiments, the third adduct has an average isocyanate functionality of 2 to 3. In some embodiments, the third adduct has an average isocyanate functionality of about 2.05 to about 2.3. In some embodiments, the third adduct is present in the polymer, the copolymer, or the interpenetrating polymer network of polymeric component (1) in an amount of about 2 wt. % to about 30 wt. %.

In some embodiments, the polyethyleneimine intermediate is present in the polymer, the copolymer, or the interpenetrating polymer network of polymeric component (1), (3) or (4) in an amount of about 0.1 wt. % to about 50 wt. %. In some embodiments, the second adduct is present in the polymer, the copolymer, or the interpenetrating polymer network of polymeric component (1) or (4) in an amount of about 1 wt. % to about 30 wt. %.

In some embodiments, the water-soluble polymer is crosslinked with (a) the first multifunctional crosslinker as incorporated in the first adduct; (b) when present, the second multifunctional crosslinker as incorporated in the second adduct; (c) when present, the third multifunctional crosslinker; or (d) any combination of two or more thereof. In some embodiments, the water-soluble polymer is selected from a group consisting of hydroxyethyl cellulose (HEC), hydroxypropyl cellulose, polyvinyl alcohol, poly(hydroxyethyl methacrylate-co-alkyl methacrylate), poly(hydroxyethyl methacrylate-co-alkyl acrylate), poly(hydroxyethyl acrylate-co-alkyl methacrylate), poly(hydroxyethyl acrylate-co-alkyl acrylate), polyacrylamide, polyethyleneimine intermediate, a copolymer of two or more thereof, a copolymer of one or more thereof with polyvinylpyrrolidone poly(glycidyl acrylate) or with poly(glycidyl methacrylate), and a combination or blend of two or more thereof. In some embodiments, the water-soluble polymer is hydroxyethyl cellulose or a hydrophobically modified derivative thereof. In some embodiments, the water-soluble polymer is another polyethyleneimine intermediate. In some embodiments, the water-soluble polymer is present in the polymer, the copolymer, or the interpenetrating polymer network of polymeric component (1) or (2) in an amount of about 0.5 wt. % to about 15 wt. %. In some embodiments, polymeric components (1) and (2) further comprise a chain extender selected from a group consisting of HO—(C$_n$H$_{2n}$)—OH and HO—(C$_n$H$_{2n-2}$)—OH, or a combination thereof, wherein n is an integral between 2 and 8. In some embodiments, the chain extender is propanediol, 1,4-butanediol, neopentyl glycol, hexanediol, cyclohexane dimethanol, or a combination of two or more thereof. In some embodiments, the chain extender is present in the polymeric component in an amount of about 0.5 wt. % to about 10 wt. %.

In some embodiments, the polymeric component further comprises a third quaternary ammonium salt wherein R$^{1a}$, R$^{2a}$, and R$^{3a}$ are each independently methyl or ethyl;

A$^2$ is selected from a group consisting of —(C$_3$-C$_{20}$ alkylene)-, —(C$_3$-C$_{20}$ heteroalkylene)-, —(C$_6$-C$_{10}$ arylene)-(C$_3$-C$_{20}$ alkylene)-, —(CR$^{m1}$R$^{n1}$)$_{x42}$—W$^{42}$—(CR$^{p1}$R$^{q1}$)$_{y42}$—, and —(CR$^{m1}$R$^{n1}$)$_{x43}$—W$^{43}$—(CR$^{p1}$R$^{q1}$)$_{y43}$—, wherein —(C$_3$-C$_{20}$ heteroalkylene)- has 1 to 4 heteroatoms independently selected from O, S, and Si; and —(C$_3$-C$_{20}$ alkylene)- and —(C$_3$-C$_{20}$ heteroalkylene)- are optionally substituted with 1 to 6 substituents independently selected from —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl);

each R$^{m1}$, R$^{n1}$, R$^{p1}$, and R$^{q1}$ is independently selected from H and C$_1$-C$_4$ alkyl;

W$^{42}$ is selected from —C(O)—; —C(O)O—; —OC(O)—; —C(O)NH—; and —NHC(O)—;

W$^{43}$ is selected from 5- to 6-membered cycloalkyl, C$_6$-C$_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein 3≤(x42+y42)≤20;

x43 is an integer from 1 to 20, and y43 is an integer from 0 to 19, wherein 3≤(x43+y43)≤20;

Y$^{1a}$ is H;

each R$^{4a}$ is independently selected from a group consisting of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si; and X$^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

In another aspect, described herein is a method of making the wound dressing described herein, comprising integrating a composition including the polymeric component into a fibrous material by one of:

(i) spraying the fibrous material with the composition, (ii) submerging the fibrous material in a fluid containing the composition, (iii) impregnating fibers of the fibrous material with a fluid containing the composition, (iv) applying a coating layer containing the composition to a surface of the fibrous material, (v) adhering a backing containing the composition to the fibrous material, (vi) applying microneedles containing the composition to the fibrous material, (vii) embedding a layer containing the composition within the fibrous material;

(viii) constructing fibers of the fibrous material with the composition by electrospinning; or (ix) interleaving fibers containing the composition with fibers of the fibrous material.

In another aspect, provided herein is a method of making a polyurethane foam wound dressing described herein, comprising integrating a composition including the polymeric component into the polyurethane foam wound dressing by mixing the composition with polyurethane prior to curing to provide the polyurethane foam wound dressing.

In another aspect, described herein is a polymer having wound healing properties comprising a polyethyleneimine intermediate, wherein the polyethyleneimine intermediate has a ratio of total quaternary amines to total hydroxyl groups of at least 1:1. In some embodiments, the polymer is selected from a group consisting of:

| Compound | General Structure | PEI MW* | R$^{60}$ (mole %)** |
|---|---|---|---|
| 20-1 (batch 105159) | B | 270 kDa (branched) | —CH$_2$CH(CH$_3$)OH (<50%) —C$_6$H$_{13}$ (>50%) |
| 20-1 (batch 99367) | B | 270 kDa (branched) | —CH$_2$CH(CH$_3$)OH (50%) —C$_6$H$_{13}$ (50%) |
| 21-1 | A | 25 kDa (hyperbranched) | —CH$_2$CH(CH$_3$)OH (50%) —C$_6$H$_{13}$ (50%) |
| 22-1 | B | 70 kDa (branched) | —CH$_2$CH(CH$_3$)OH (50%) —C$_6$H$_{13}$ (50%) |
| 23-1 | B | 70 kDa (branched) | —CH$_2$CH(CH$_3$)OH (50%) —CH$_2$C(O)Ph (50%) |
| 24-1 | B | 70 kDa (branched) | —CH$_2$CH(CH$_3$)OH (50%) —CH$_2$Ph (50%) |
| 26-1 | B | 70 kDa (branched) | —CH$_2$CH(OH)CH$_2$N$^+$(CH$_3$)$_3$ Cl$^-$ (100%) |
| 29-1 | B | 70 kDa (branched) | —(CH$_2$)$_3$OH (1%) —C$_6$H$_{13}$ (99%) |
| 30-1 | A | 25 kDa (hyperbranched) | —(CH$_2$)$_3$OH (10%) 75:25 —C$_{18}$H$_{37}$:—C$_8$H$_{17}$ (90%) |
| 31-1 | B | 70 kDa (branched) | —C(O)(CH$_2$)$_5$OH (7%) —C$_6$H$_{13}$ (93%) |
| 32-1 | B | 70 kDa (branched) | —(CH$_2$)$_3$OH (10%) —C$_6$H$_{13}$ (90%) |
| 32-2 | B | 70 kDa (branched) | —(CH$_2$)$_3$OH (5%) —C$_6$H$_{13}$ (95%) |
| 32-3 | B | 70 kDa (branched) | —CH$_2$CH(CH$_3$)OH (5%) —C$_6$H$_{13}$ (95%) |
| 32-4 | B | 70 kDa (branched) | —C(O)(CH$_2$)$_5$OH (7.5%) —C$_6$H$_{13}$ (92.5%) |
| 32-5 | A | 25 kDa (hyperbranched) | —CH$_2$CH(CH$_3$)OH (50%) 50:50 —C$_{18}$H$_{37}$:—C$_8$H$_{17}$ (50%) |
| 32-6 | B | 72 kDa (branched) | —(CH$_2$)$_3$OH (13%) 75:25 —C$_{18}$H$_{37}$:—C$_8$H$_{17}$ (87%) |
| 32-7 | B | 72 kDa (branched) | —C(O)(CH$_2$)$_5$OH (6.5%) 75:25 —C$_{18}$H$_{37}$:—C$_8$H$_{17}$ (93.5%) |
| 32-8 | A | 25 kDa (hyperbranched) | —C(O)(CH$_2$)$_5$OH (7%) 75:25 —C$_{18}$H$_{37}$:—C$_8$H$_{17}$ (93%) |
| 32-9 | A | 25 kDa (hyperbranched) | —CH$_2$CH(CH$_3$)OH (50%) 25:75 —C$_{18}$H$_{37}$:—C$_8$H$_{17}$ (50%) |

*indicates molecular weight of polyethyleneimine precursor

**theoretical stoichiometric ratio (based on amount of reactants used in the synthetic protocol) wherein A is 3 Br$^-$ B is 4 Br$^-$ and each n is an integer independently selected from 2 to 3000, preferably an integer independently selected from 10 to 100. In some embodiments, one or more bromide anions is replaced with X$^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives. In some embodiments, the polymer is selected from a group consisting of:

| Compound | General Structure | PEI MW* | R^{60} (mole %)** |
|---|---|---|---|
| 32-10 | A | 25 kDa (hyperbranched) | —C(O)(CH$_2$)$_5$OH (11%) —C$_6$H$_{13}$ (89%) |
| 32-11 | B | 70 kDa (branched) | —C(O)(CH$_2$)$_5$OH (9%) —C$_6$H$_{13}$ (91%) |
| 32-13 | B | 70 kDa (branched) | —(CH$_2$)$_3$OH (7%) 75:25 —C$_{18}$H$_{37}$:—C$_8$H$_{17}$ (93%) |
| 32-14 | A | 25 kDa (hyperbranched) | —(CH$_2$)$_3$OH (7%) 75:25 —C$_{18}$H$_{37}$:—C$_8$H$_{17}$ (93%) |
| 32-15 | B | 70 kDa (branched) | —C(O)(CH$_2$)$_5$OH (9%) 75:25 —C$_{18}$H$_{37}$:—C$_8$H$_{17}$ (91%) |
| 32-16 | A | 25 kDa (hyperbranched) | —C(O)(CH$_2$)$_5$OH (11%) 75:25 —C$_{18}$H$_{37}$:—C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |
| 32-1A | B | 70 kDa (branched) | —(CH$_2$)$_3$OH (10%) —C$_6$H$_{13}$ (90%) |
| 32-1B | B | 70 kDa (branched) | —(CH$_2$)$_3$OH (10%) —C$_6$H$_{13}$ (90%) |
| 32-2A | B | 70 kDa (branched) | —(CH$_2$)$_3$OH (5%) —C$_6$H$_{13}$ (95%) |
| 32-2B | B | 70 kDa (branched) | —(CH$_2$)$_3$OH (5%) —C$_6$H$_{13}$ (95%) |
| 32-2C | B | 70 kDa (branched) | —(CH$_2$)$_3$OH (15%)* —C$_6$H$_{13}$ (85%) |
| 32-2D | B | 70 kDa (branched) | —(CH$_2$)$_3$OH (5%) —C$_6$H$_{13}$ (95%) |
| 32-2E | B | 70 kDa (branched) | —(CH$_2$)$_3$OH (12%)**** —C$_6$H$_{13}$ (88%) |
| 32-2F | B | 70 kDa (branched) | —(CH$_2$)$_3$OH (5%) —C$_6$H$_{13}$ (95%) |
| 32-2G | B | 70 kDa (branched) | —(CH$_2$)$_3$OH (5%) —C$_6$H$_{13}$ (95%) |
| 32-2H | B | 70 kDa (branched) | —(CH$_2$)$_3$OH (5%) —C$_6$H$_{13}$ (95%) |
| 32-21 | B | 70 kDa (branched) | —(CH$_2$)$_3$OH (5%) —C$_6$H$_{13}$ (95%) |

*indicates molecular weight of polyethyleneimine precursor
**theoretical stoichiometric ratio (based on amount of reactants used in the synthetic protocol) unless otherwise indicated
***actual stoichiometric ratio as determined by NMR analysis wherein A is

3 X$^-$

B is

4 X$^-$ each n is an integer independently selected from 2 to 3000, preferably an integer independently selected from 10 to 100; and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo—substituted derivatives.

*aureus* biofilms. All time points compared to control (0 hr) using a one-way ANOVA followed by Bonferroni's multiple comparison test. \*p=0.01, \*\*p=0.001, \*\*\*p=0.0001, \*\*\*\*p=<0.0001. Data shown mean (±SEM), n=3.

Figure 3A:
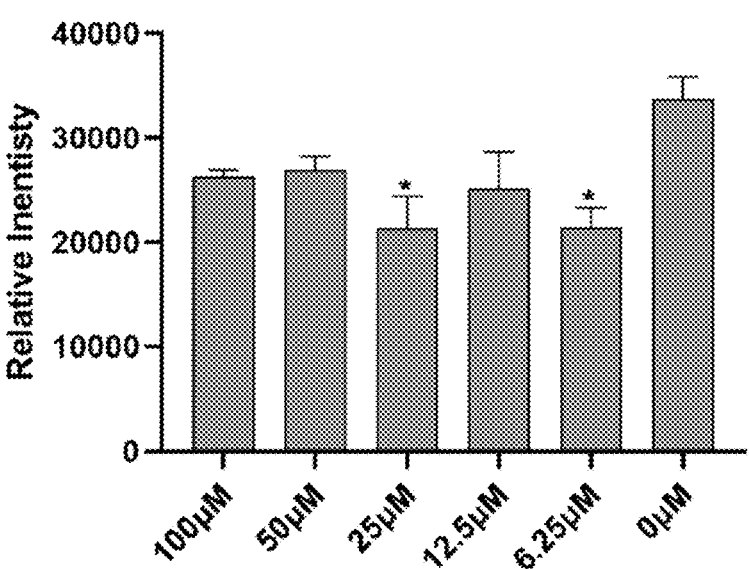
Figure 3B:
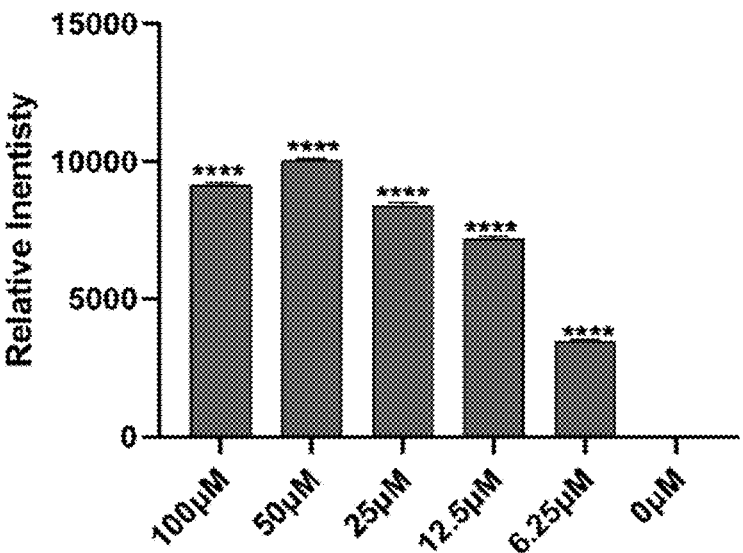

FIG. 3A and FIG. 3B depict quantification using SYTO 9 staining or propidium iodide staining, respectively, of activity of a compound disclosed herein in various concentrations (6.25, 12.5, 25, 50, 100 μM) on *S. aureus* biofilms. All concentrations compared to control (0 μM) using a one-way ANOVA followed by Bonferroni's multiple comparison test. \*p=0.01, \*\*p=0.001, \*\*\*p=0.0001, \*\*\*\*p=<0.0001. Data shown mean (±SEM), n=3.

Figure 4C:

FIGS. 4A and 4B depict non-limiting examples of a bandage, and FIG. 4C depicts a non-limiting example of a foamed product in the form of a pad.

Figure 5:
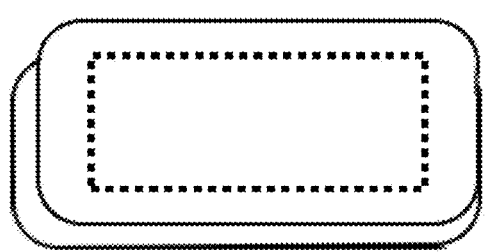

FIG. 5 depicts the study design for an efficacy study in a mouse *Staphylococcus aureus*-induced wound infection model.

Figure 6A:
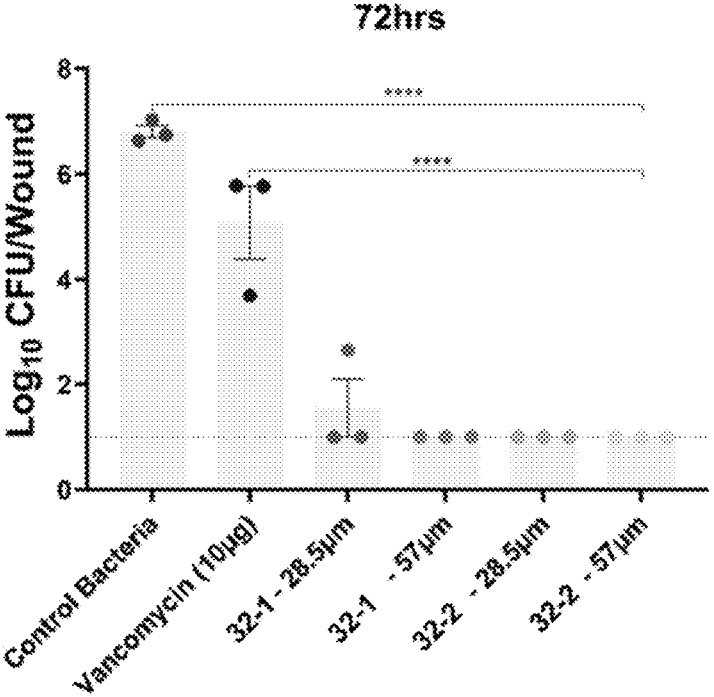
Figure 6B:
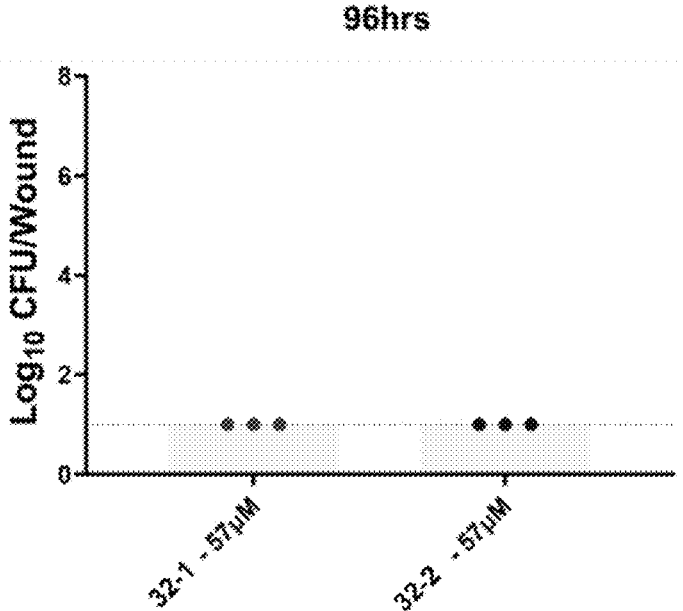

FIG. 6A and FIG. 6B depict in vivo antimicrobial efficacy of two compounds disclosed herein in a murine wound infection model at 72 hours and 96 hours, respectively, post-seeding. *S. aureus* NRS 384 was seeded at 1×10$^5$ CFU/wound. Treatments were applied in a total volume of 10 μL. Concentrations used are indicated on the x-axis. Total bacteria from wounds were enumerated on TSA plates. Individual symbols represent biological replicates (mice, n=3). Bar plots represent mean±sem for each group. Limit of Detection (LOD) for CFU set at 1 Log CFU for spread plate (1, Log). For statistical comparison, all treatment groups were compared to the Control Bacteria or the antibiotic control (Vancomycin) groups using an ordinary one-way ANOVA followed by Dunnett's multiple comparisons test. \*\*\*\*p<0.0001.

Figure 7A:
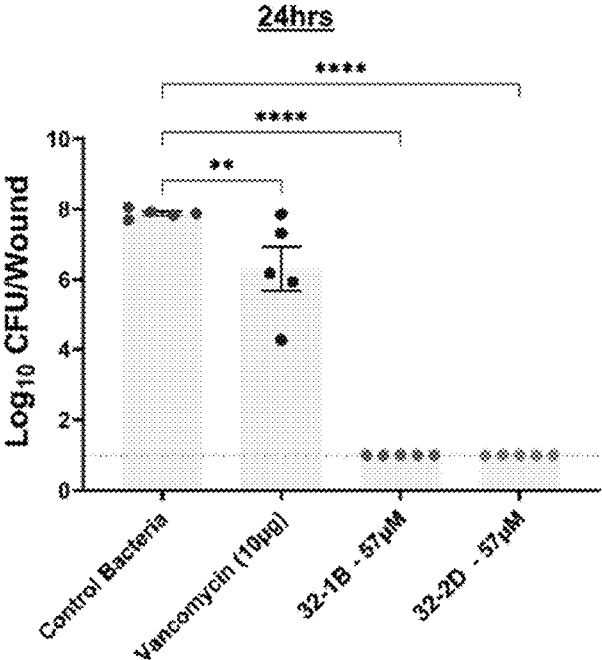
Figure 7B:
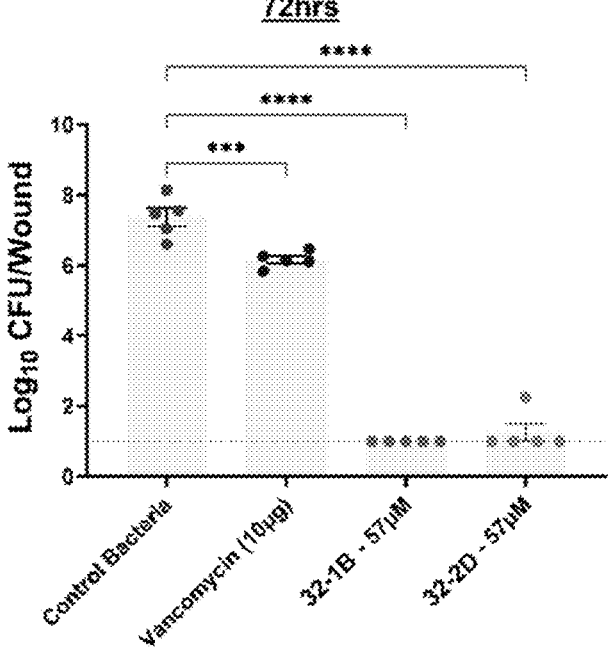

FIG. 7A and FIG. 7B depict in vivo antimicrobial efficacy of two compounds disclosed herein in a murine wound infection model at 24 hours and 72 hours, respectively, post-seeding. *S. aureus* NRS 384 was seeded at 1×10$^5$ CFU/wound. Treatments were applied in a total volume of 10 μL, concentrations used are indicated on the x-axis. Total bacteria were enumerated from wounds on TSA plates at (A) 24 hrs and (B) 72 hrs post treatments. Individual symbols represent biological replicates (mice, n=5). Bar plots and lines represent mean±sem for each group. Limit of Detection (LOD) for CFU set at 1 Log CFU for spread plate (1, Log). For statistical comparison, all treatment groups were compared to the Control Bacteria group using an ordinary one-way ANOVA followed by Dunnett's multiple comparisons test. \*\*p<0.005, \*\*\*p<0.001, \*\*\*\*p<0.0001.

Figure 8A:
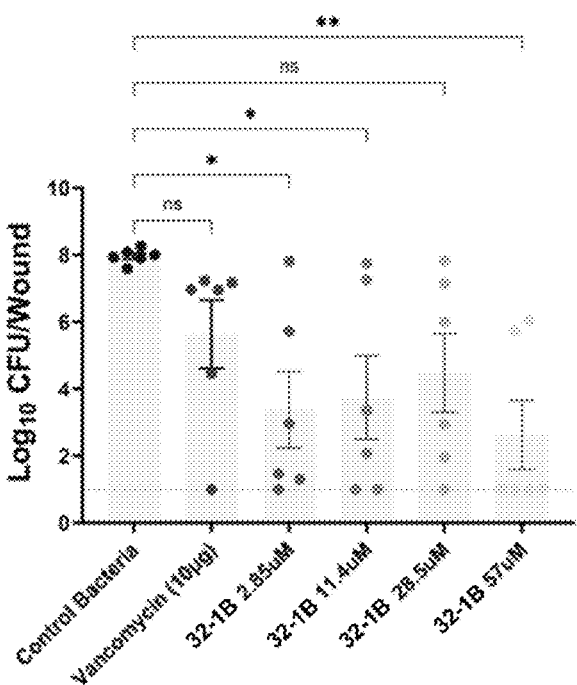
Figure 8B:
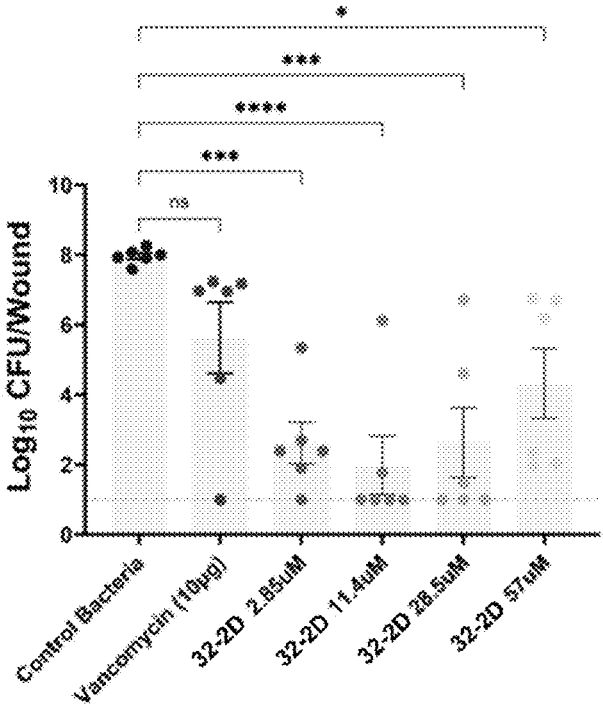

FIG. 8A and FIG. 8B depict in vivo antimicrobial efficacy of two compounds disclosed herein in a murine wound infection model at 72 hours post-seeding. *S. aureus* NRS 384 was seeded at 1×10$^5$ CFU/wound. Treatments were applied in a total volume of 10 μL, concentrations used are indicated on the x-axis. Total bacteria were enumerated from wounds on TSA plates at 72 hrs post treatments. Individual symbols represent biological replicates (mice, n=5). Bar plots and lines represent mean±sem for each group. Limit of Detection (LOD) for CFU set at 1 Log CFU for spread plate (1, Log). For statistical comparison, all treatment groups were compared to the Control Bacteria group using an ordinary one-way ANOVA followed by Dunnett's multiple comparisons test. ns=not significant. \*p<0.01, \*\*p<0.005, \*\*\*p<0.001, \*\*\*\*p<0.0001.

Figure 9:
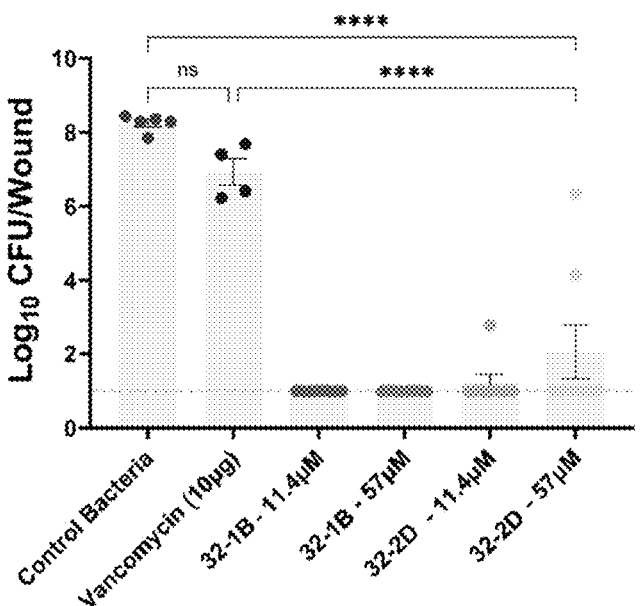

FIG. 9 depicts in vivo antimicrobial efficacy of two compounds disclosed herein in a murine wound infection model at 7-days post-seeding and treatment. *S. aureus* NRS 384 was seeded at 1×10$^5$ CFU/wound. Treatments were applied in a total volume of 10 μL, concentrations used are indicated on the x-axis. Total bacteria were enumerated from wounds on TSA plates at 7-days post treatments. Individual symbols represent biological replicates (mice, n=5). Bar plots and lines represent mean±sem for each group. Limit of Detection (LOD) for CFU set at 1 Log CFU for spread plate (1, Log). For statistical comparison, all treatment groups were compared to the Control Bacteria group using an ordinary one-way ANOVA followed by Dunnett's multiple comparisons test. ****p<0.0001. ns=not significant.

Figure 10:
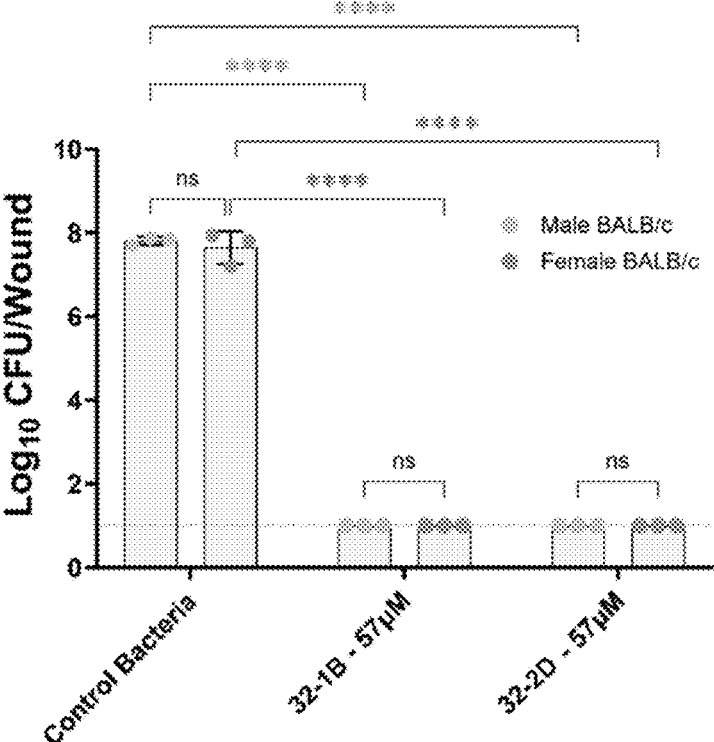

FIG. 10 depicts in vivo antimicrobial efficacy of two compounds disclosed herein in a murine wound infection model at 24 hrs post-seeding and treatment. S. aureus NRS 384 was seeded at $1\times10^5$ CFU/wound. Treatments were applied in a total volume of 10 μL, concentrations used are indicated on the x-axis. Total bacteria were enumerated from wounds on TSA plates at 24 hrs post treatments. Individual symbols represent biological replicates (mice, n=3). Bar plots and lines represent mean±sem for each group. The dotted line denotes Limit of Detection (LOD) for CFU set at 1 Log CFU for spread plate (1, Log). Female BALB/c mice from the same groups from pilot study depicted in FIG. 7A were used to compare efficacy of the same test compounds with male BALB/c mice. For statistical comparison, both groups were compared across all groups using a two-way ANOVA followed by Tukey's multiple comparisons test. ns=not significant. ****p<0.0001. There were no statistical differences in antimicrobial efficacy for both compounds between male and female BALB/c mice.

Figure 11A:
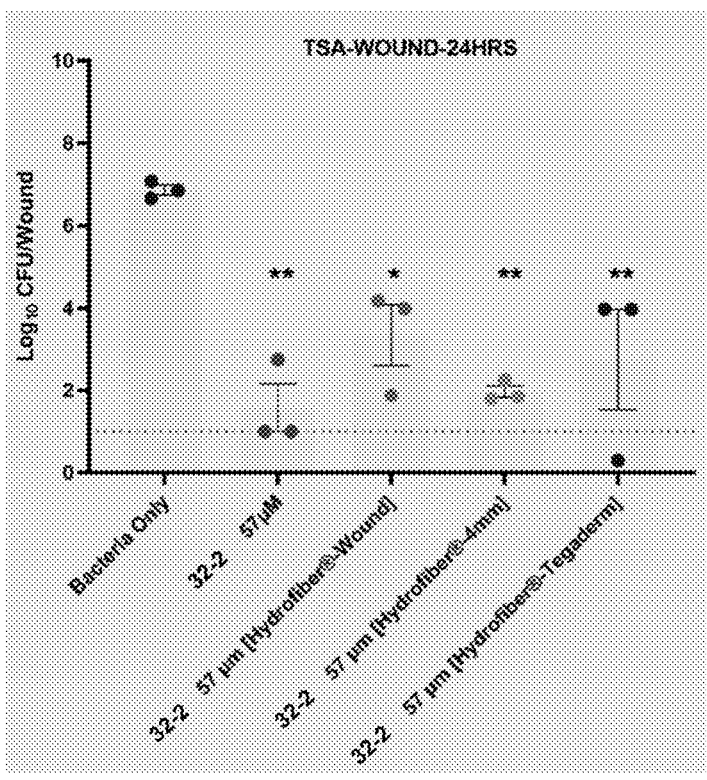
Figure 11B:
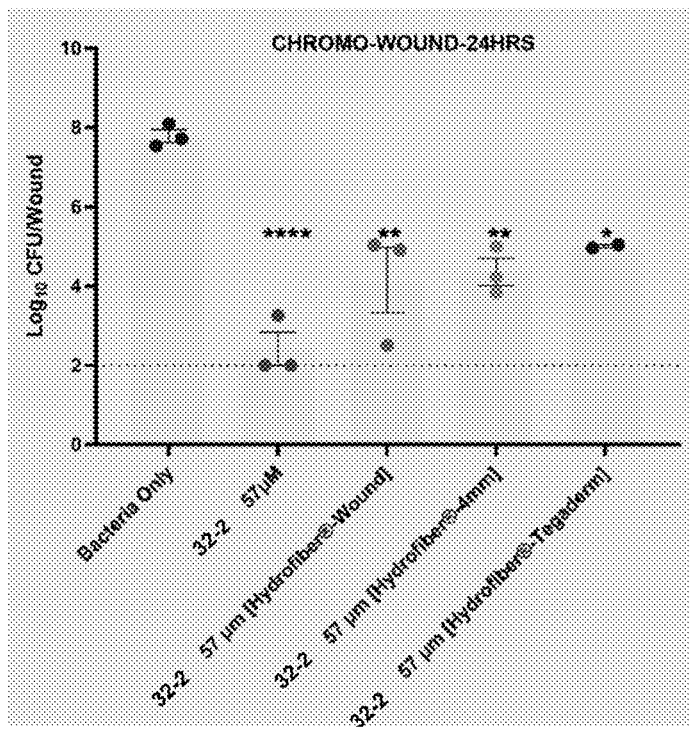

FIG. 11A and FIG. 11B depict antimicrobial efficacy of a compound disclosed herein in HYDROFIBER®-loaded dressings. S. aureus NRS 384 was seeded at $1\times10^5$ CFU/wound. Treatments were applied in a total volume of 10 μL, concentrations used are indicated on the x-axis. Total bacteria enumerated on (A) TSA and (B) CHROMagar™ Staph aureus (CHROMO). Individual symbols represent biological replicates (n=3 mice). Mean±SEM for each group. Limit of Detection (LOD) for CFU set at 10 CFU (1, Log) for TSA and 100 CFU (2, Log) for CHROMO as shown with red, dotted lines. Control group=no bacteria. For statistical comparison, an ordinary one-way ANOVA followed by Dunnett's multiple comparisons test was used to compare all treatment groups to the "Bacteria Only" group. *p<0.01, p<0.005, **p<0.0001.

Figure 12:
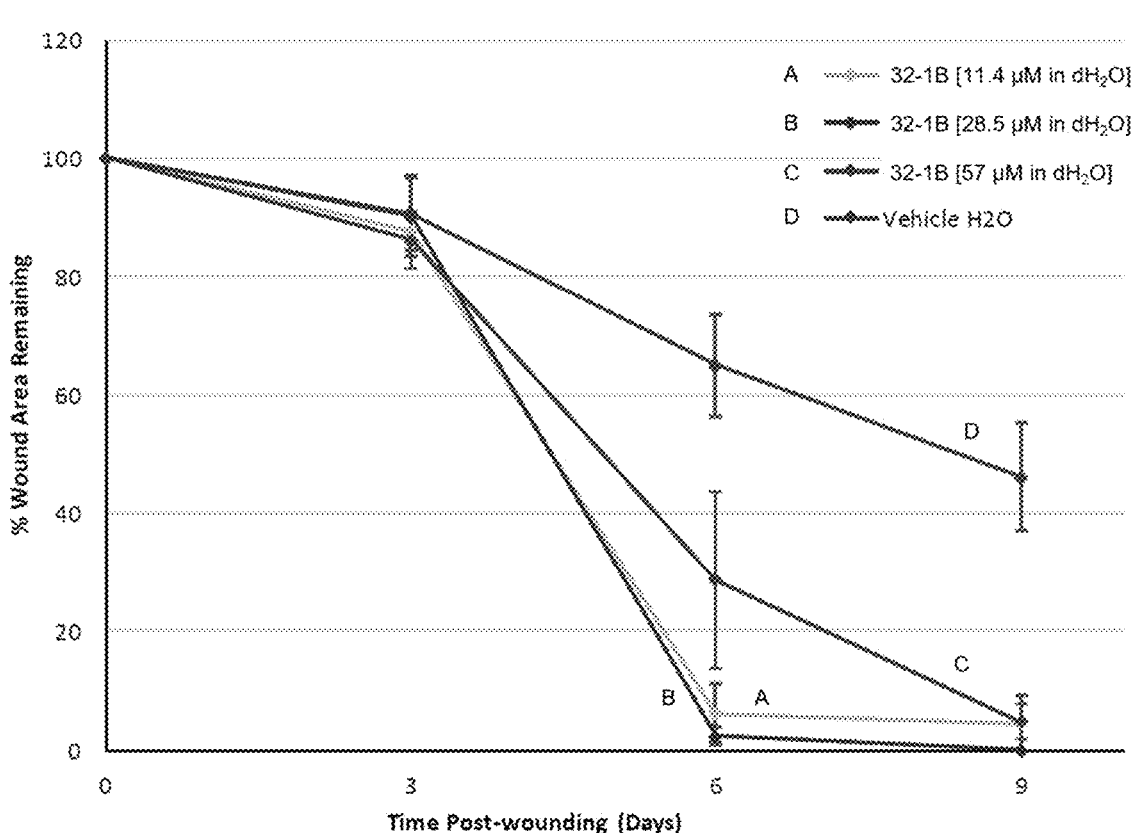

FIG. 12 depicts percentage of wound area remaining after up to 9 days post-wounding after treatment with a compound disclosed herein at various concentrations or with vehicle.

Figure 13:
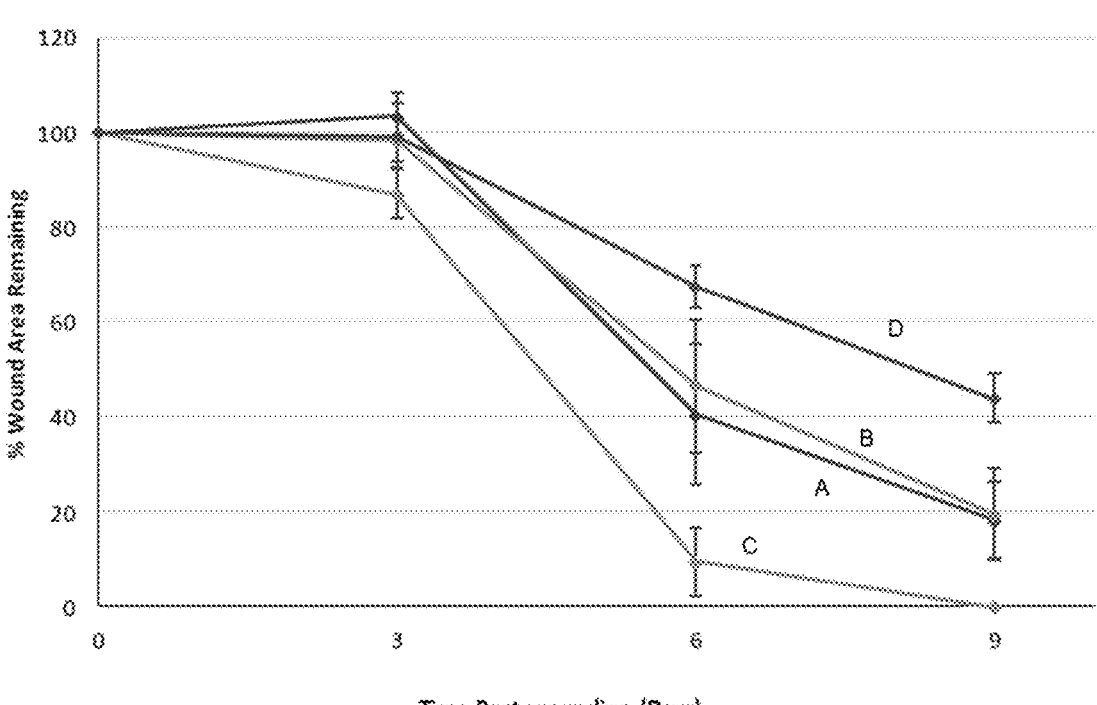

FIG. 13 depicts percentage of wound area remaining after up to 9 days post-wounding after treatment with a compound disclosed herein at various concentrations or with vehicle.

Figure 14:
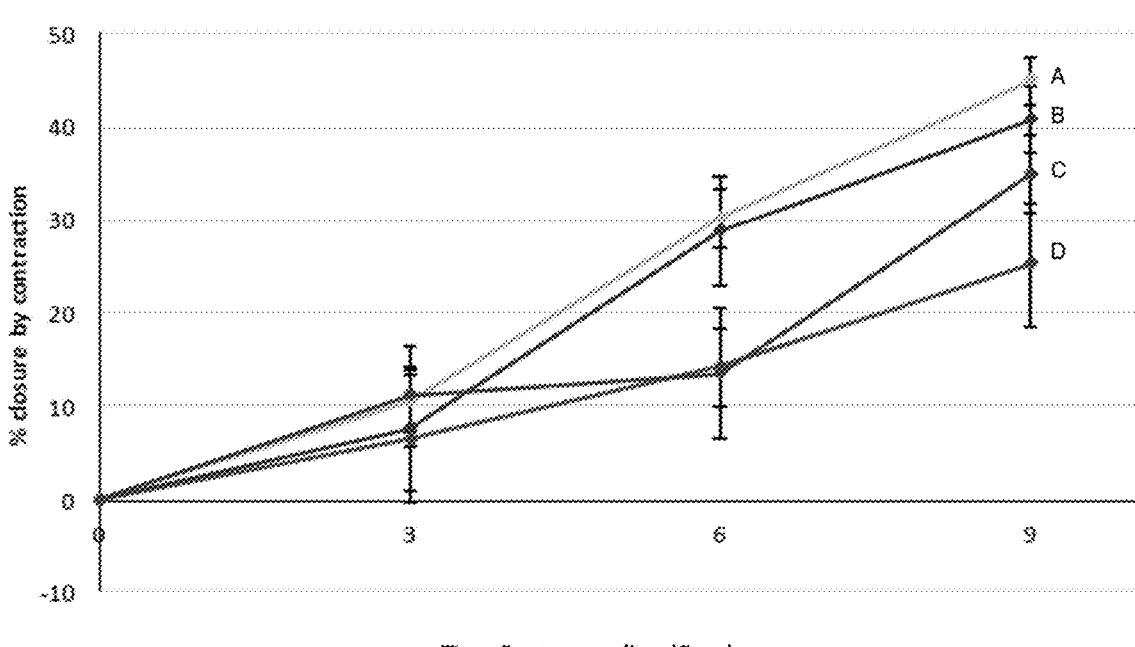
Figure 14:
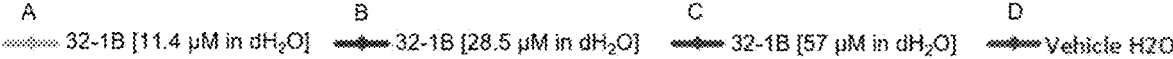

FIG. 14 depicts percentage of wound closure by contraction after up to 9 days post-wounding after treatment with a compound disclosed herein at various concentrations or with vehicle.

Figure 15:
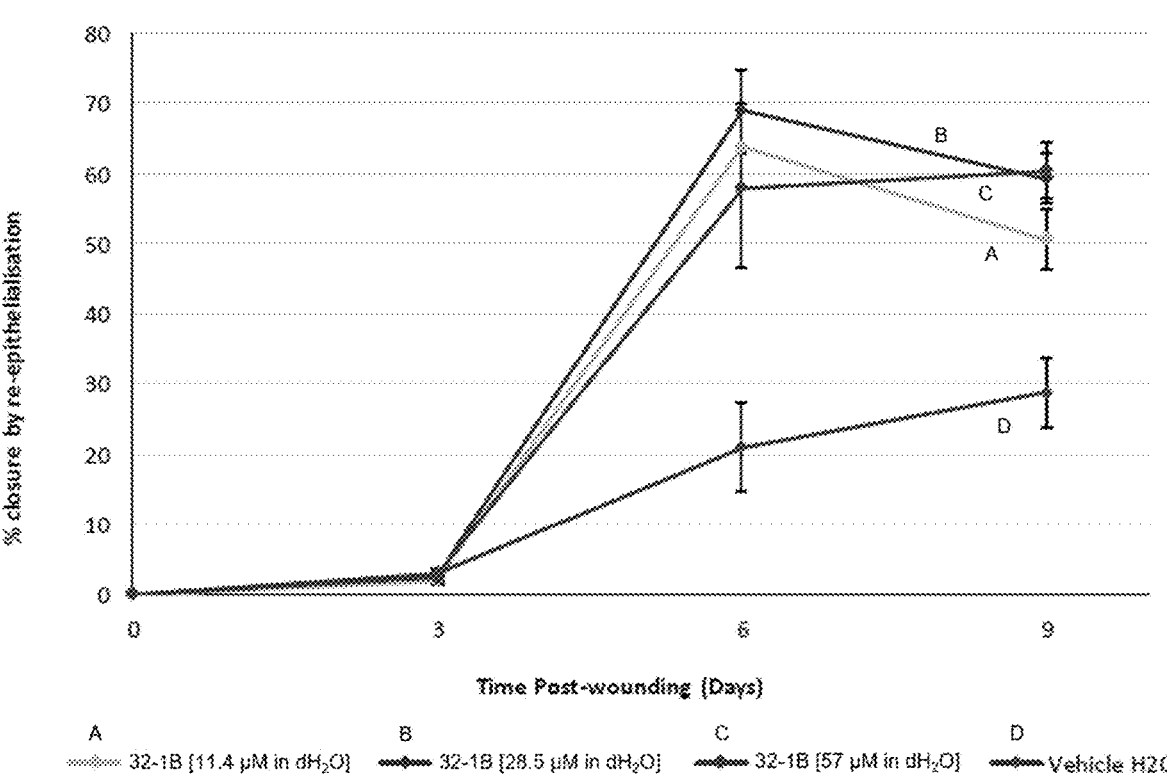

FIG. 15 depicts percentage of wound closure by re-epithelialization after up to 9 days post-wounding after treatment with a compound disclosed herein at various concentrations or with vehicle.

Figure 16:
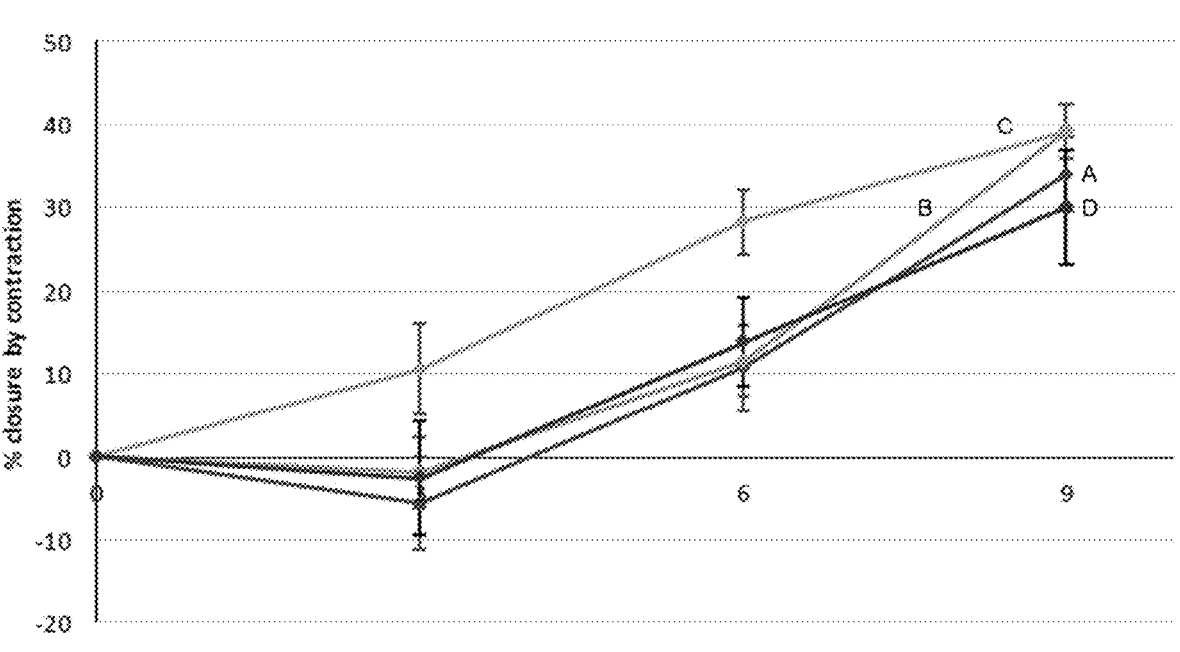

FIG. 16 depicts percentage of wound closure by contraction after up to 9 days post-wounding after treatment with a compound disclosed herein at various concentrations or with vehicle.

Figure 17:
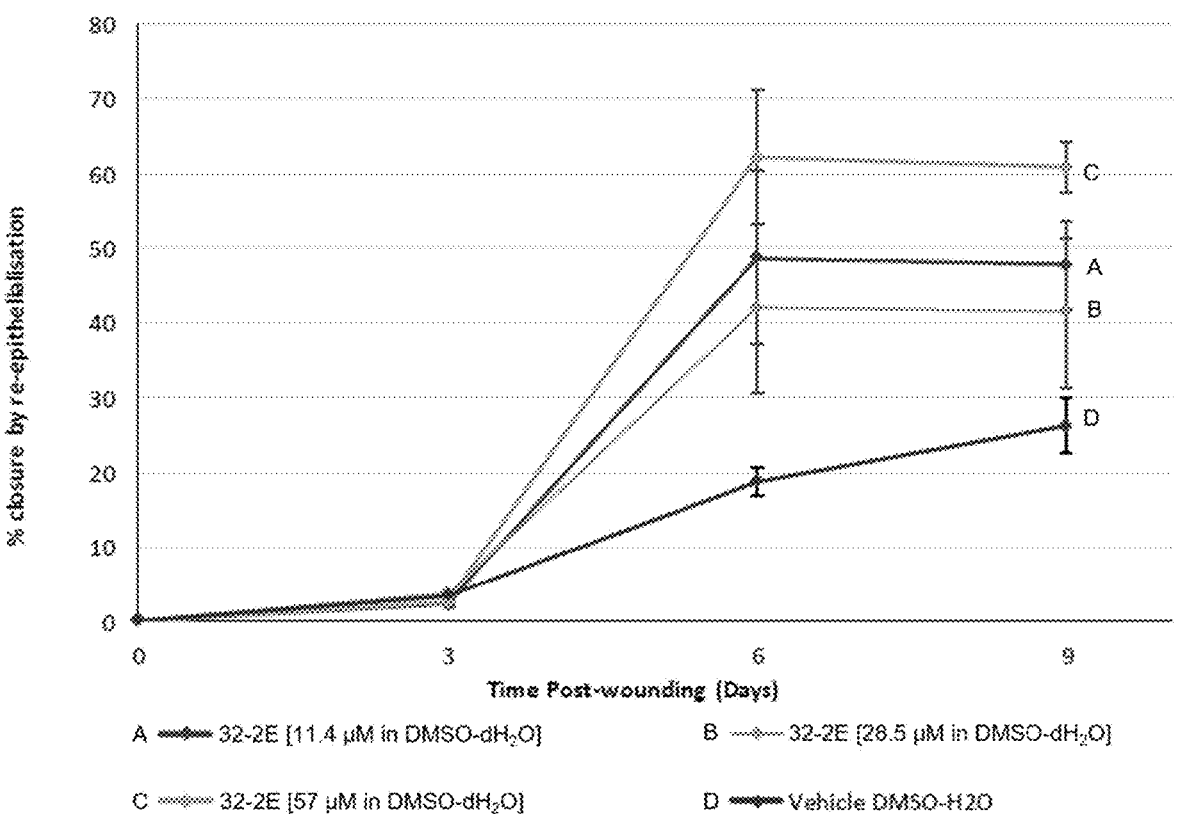

FIG. 17 depicts percentage of wound closure by re-epithelialization after up to 9 days post-wounding after treatment with a compound disclosed herein at various concentrations or with vehicle.

Figure 18:
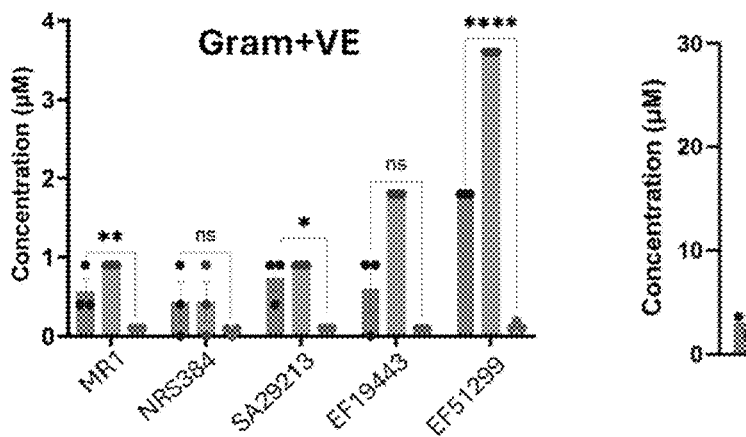
Figure 18:
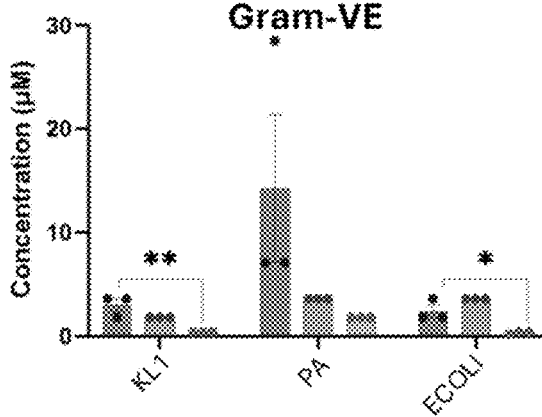

FIG. 18 depicts MIC of select compounds disclosed herein against a range of wound bacteria (Gram-positive or Gram-negative). For each trio of bars, compound 32-1 is represented by the left bar, compound 32-1A is represented by the center bar, and compound 32-1B is represented by the right bar. *p<0.01, p<0.005, *p<0.001, ****p<0.0001.

Figure 19A:
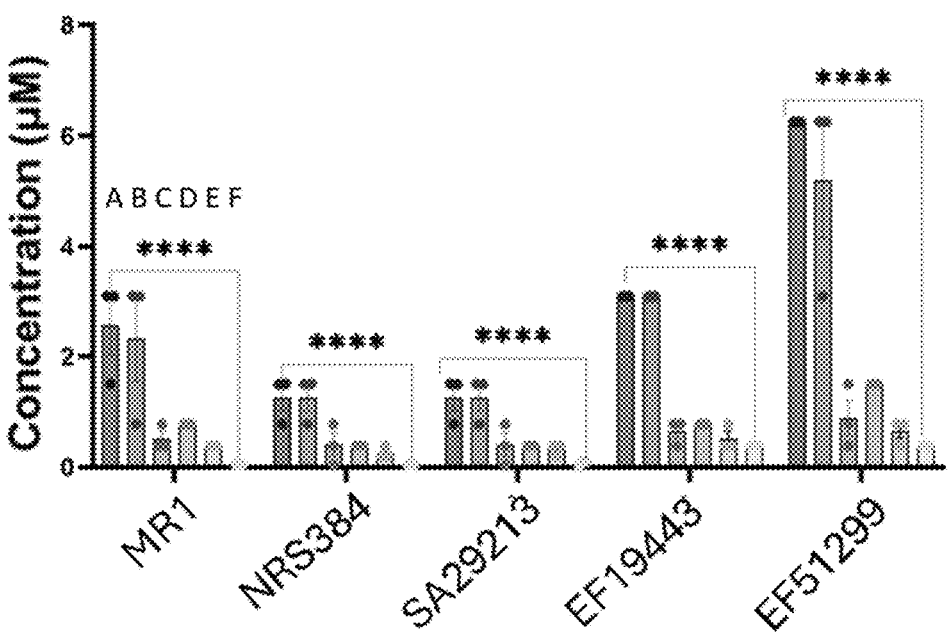
Figure 19B:
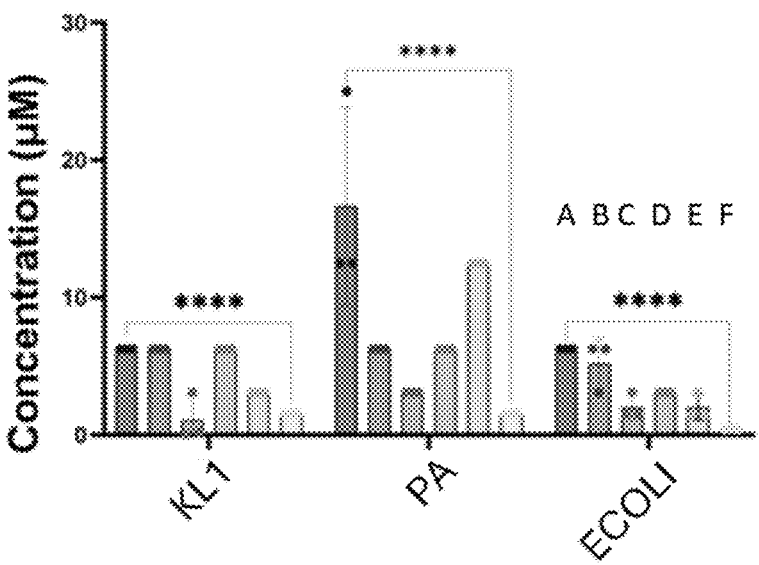

FIG. 19A and FIG. 19B depict MIC of select compounds disclosed herein against a range of wound bacteria (Gram-positive or Gram-negative). For each set of bars, A=compound 32-2, B=compound 32-2A, C=compound 32-2B, D=compound 32-2C, E=compound 32-2D, F=compound 32-2E. *p<0.01, p<0.005, *p<0.001, ****p<0.0001.

Figure 20:
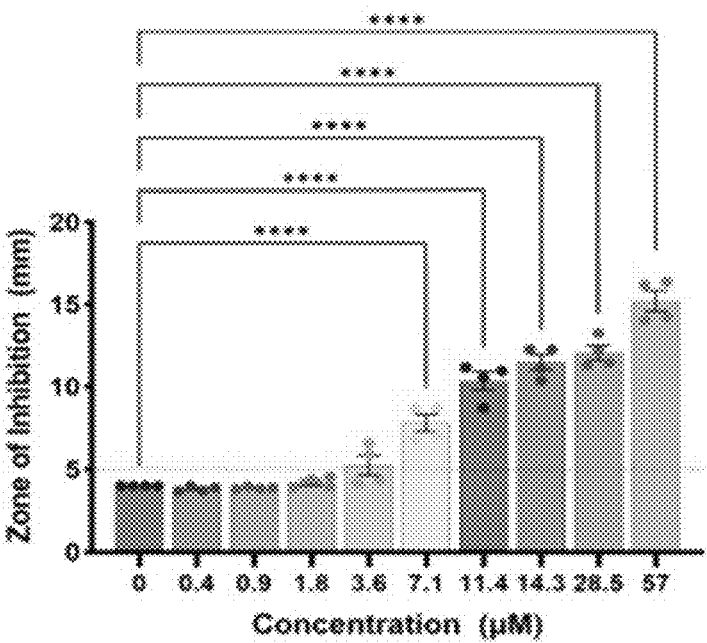
Figure 21:
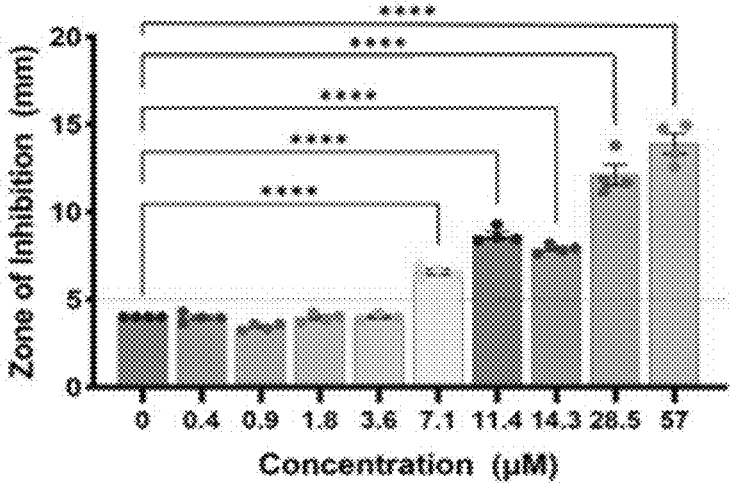

FIG. 20 and FIG. 21 depict dose-dependent zone of inhibition against methicillin resistant Gram+VE (NRS 384/MRSA) bacteria by compound-impregnated wound dressings. ****p<0.0001.

DETAILED DESCRIPTION

In the following description, for purposes of explanation, numerous specific details are set forth in order to provide a thorough understanding of the present technology. It may be evident, however, that the present technology may be practiced without these specific details. It is to be appreciated that certain aspects, modes, embodiments, variations and features of the technology are described below in various levels of detail in order to provide a substantial understanding of the present technology.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed subject-matter. Unless otherwise defined, all technical and scientific terms used herein have the same meaning as commonly understood by one of ordinary skill in the art to which this present technology belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the present technology.

As used herein, "aryl" refers to a carbocyclic (all carbon) ring that is fully aromatized. An "aryl" group can be made up of two or more fused rings (rings that share two adjacent carbon atoms). When an aryl group is a fused ring system, then the ring that is connected to the rest of the molecule is fully aromatized. The other ring(s) in the fused ring system may or may not be fully aromatized. Examples of aryl groups include, without limitation, the radicals of benzene, naphthalene and azulene.

As used herein, "alkyl" refers to a straight or branched chain fully saturated (no double or triple bonds) hydrocarbon group. An alkyl group of the presently disclosed compounds may comprise from 1 to 15 carbon atoms. An alkyl group herein may have 1 to 4 carbon atoms, 1 to 5 carbon atoms, 1 to 6 carbon atoms, 1 to 7 carbon atoms, 1 to 8 carbon atoms, 1 to 9 carbon atoms, 1 to 10 carbon atoms, 1 to 11 carbon atoms, 1 to 12 carbon atoms, 1 to 13 carbon atoms, 1 to 14 carbon atoms, or 1 to 15 carbon atoms. As used herein, a $C_1$-$C_6$ alkyl represents an alkyl group having 1 to 6 carbon atoms, a $C_1$-$C_4$ alkyl represents an alkyl group having 1 to 4 carbon atoms and a $C_1$-$C_3$ alkyl represents an alkyl group having 1 to 3 carbon atoms, etc. Examples of alkyl groups include, without limitation, methyl, ethyl, n-propyl, isopropyl, n-butyl, i-butyl, sec-butyl, t-butyl, amyl, t-amyl, hexyl, heptyl, octyl, nonyl, decyl, undecyl and dodecyl.

As used herein, "alkoxy" refers to an alkyl group, as defined above, appended to the parent molecular moiety through an oxy group, —O—. As used herein, a $C_1$-$C_6$ alkoxy represents an alkoxy group containing 1 to 6 carbon atoms and a $C_1$-$C_3$ alkoxy represents an alkoxy group containing 1 to 3 carbon atoms. Representative examples of alkoxy include, but are not limited to, methoxy, ethoxy, propoxy, 2-propoxy, butoxy, tert-butoxy, pentyloxy, hexyloxy etc.

As used herein, "cycloalkyl" refers to a monocyclic, bicyclic or polycyclic hydrocarbon ring system having, in some embodiments, 3 to 14 carbon atoms (e.g., $C_3$-$C_{14}$ cycloalkyl), or 3 to 10 carbon atoms (e.g., $C_3$-$C_{10}$ cycloalkyl), or 3 to 8 carbon atoms (e.g., $C_3$-$C_8$ cycloalkyl), or 3 to 6 carbon atoms (e.g., $C_3$-$C_6$ cycloalkyl) or 5 to 6 carbon atoms (e.g., $C_5$-$C_6$ cycloalkyl). Cycloalkyl groups can be saturated or characterized by one or more points of unsaturation (i.e., carbon-carbon double and/or triple bonds), provided that the points of unsaturation do not result in an aromatic system. Examples of monocyclic cycloalkyl groups include, but are not limited to, cyclopropyl, cyclobutyl, cyclopentyl, cyclohexyl, cyclohexeneyl, cyclohexynyl, cycloheptyl, cyclohepteneyl, cycloheptadieneyl, cyclooctyl, cycloocteneyl, cyclooctadieneyl and the like. The rings of bicyclic and polycyclic cycloalkyl groups can be fused, bridged, or spirocyclic.

As used herein, unless otherwise stated, "heteroalkyl" refers to an alkyl group, as defined herein, in which one or more of the constituent carbon atoms have been replaced by nitrogen, oxygen, sulfur, or silicon. A representative example of a heteroalkyl group is an alkoxy. A heteroalkylene is a divalent heteroalkyl group.

As used herein, unless otherwise stated, term "heteroaryl" refers to monocyclic or fused bicyclic aromatic groups (or rings) having, in some embodiments, from 5 to 14 (i.e., 5- to 14-membered heteroaryl), or from 5 to 10 (i.e., 5- to 10-membered heteroaryl), or from 5 to 6 (i.e., 5- to 6-membered heteroaryl) members (i.e., ring vertices), and containing from one to five, one to four, one to three, one to two or one heteroatom selected from nitrogen (N), oxygen (O), and sulfur (S). A heteroaryl group can be attached to the remainder of the molecule through a carbon atom or a heteroatom of the heteroaryl group, when chemically permissible. Non-limiting examples of heteroaryl groups include pyridyl, pyridazinyl, pyrazinyl, pyrimindinyl, triazinyl, purinyl, thienopyridinyl, thienopyrimidinyl, pyrazolopyrimidinyl, pyrazolopyridinyl, imidazopyridines, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

The term "heterocycloalkyl" refers to a non-aromatic monocyclic, bicyclic or polycyclic cycloalkyl ring having, in some embodiments, 3 to 14 members (e.g., 3- to 14-membered heterocycle), or 3 to 10 members (e.g., 3- to 10-membered heterocycle), or 3 to 8 members (e.g., 3- to 8-membered heterocycle), or 3 to 6 members (e.g., 3- to 6-membered heterocycle), or 5 to 6 members (e.g., 5- to 6-membered heterocycle), and having from one to five, one to four, one to three, one to two or one heteroatom selected from nitrogen (N), oxygen (O), sulfur (S) and silicon (Si). Heterocycloalkyl groups are saturated or characterized by one or more points of unsaturation (e.g., one or more carbon-carbon double bonds, carbon-carbon triple bonds, carbon-nitrogen double bonds, and/or nitrogen-nitrogen double bonds), provided that the points of unsaturation do not result in an aromatic system. The rings of bicyclic and polycyclic heterocycloalkyl groups can be fused, bridged, or spirocyclic. Non-limiting examples of heterocycloalkyl groups include aziridine, oxirane, thiirane, pyrrolidine, imidazolidine, pyrazolidine, dioxolane, phthalimide, piperidine, 1,4-dioxane, morpholine, thiomorpholine, thiomorpholine-S-oxide, thiomorpholine-S, S-oxide, piperazine, 3,4,5,6-tetrahydropyridazine, tetrahydropyran, pyran, decahydroisoquinoline, 3-pyrroline, thiopyran, tetrahydrofuran, tetrahydrothiophene, quinuclidine, and the like. A heterocycloalkyl group can be attached to the remainder of the molecule through a ring carbon atom, or a ring heteroatom, when chemically permissible.

As used herein, unless otherwise stated, "independently selected" indicates that each one of a designated group is selected independently from a subsequent list of species.

The term "statistically significant" or "significantly" refers to statistical significance and generally means a two standard deviation (2SD) or greater difference.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, the term "polyisocyanates" generally represents the family of polyisocyanates containing more than one isocyanate reactive group such as, but not limited to, DESMODUR® N3300 and N100 (made by Covestro Deutschland AG of Leverkusen, Germany) which are aliphatic polyisocyanates based on HDI (hexamethylene diisocyanate) trimer, DESMODUR® Z4470SN (made by Covestro Deutschland AG of Leverkusen, Germany) which is a multifunctional polyisocyanate based on IPDI (isophorone diisocyanate), WANNATE® T series polyisocyanates which are toluene diisocyanate (TDI)-based aromatic polyisocyanates, and LUPRANATE® M series polyisocyanates which are 4,4-diphenylmethane diisocyanate (MDI)-based aromatic polyisocyanates.

As used herein, the term "antimicrobial" is used generally to indicate at least some level of microbe kill by a composition or a coating on a portion of a surface (e.g., on a wound). For example, antimicrobial may be used to indicate a biostatic efficacy, sanitizing level (3-log, or 99.9%) reduction in at least one organism, or a disinfection level (5-log, or 99.999%) reduction in at least one organism, or sterilization (no detectable organisms). Microbes, or microorganisms, may include any species of bacteria, virus, fungus including mold and yeast, or spore. Thus, antimicrobial herein encompasses antiviral, antibacterial and antifungal.

The term polymer herein includes random polymer, alternating polymer, block polymer, and graft polymer. The term copolymer herein includes random copolymer, block copolymer, graft copolymer, interpolymer complex, interpenetration network, etc., and their blends.

As used herein, and unless otherwise indicated, the term "wt. %" takes on the ordinary meaning of percent (%) by weight of an ingredient in a chemical composition, based on the total weight of the composition "as made." For example, an aqueous composition comprising 1 wt. % amine "based on the total weight of the composition" equates to a composition containing 99.0 grams water and 1.0 gram amine. Wt. % in a composition indicates the wt. % of active material, unless indicated otherwise. "As made" means that a written composition shows what was added to a mixing vessel, and not what might end up in the mixture after certain ingredients react, such as if an ingredient hydrolyzes or polymerizes.

As used herein, "subject" refers to an animal, such as a mammal (including a human), that has been or will be the object of treatment, observation or experiment. "Subject" and "patient" may be used interchangeably, unless otherwise indicated. Mammals include, but are not limited to, mice, rodents, rats, simians, humans, farm animals, dogs, cats, sport animals, and pets. The methods described herein may be useful in human therapy and/or veterinary applications. In some embodiments, the subject is a mammal. In some embodiments, the subject is a human.

The terms "therapeutically effective amount" refers to an amount of a compound that is sufficient to effect treatment as defined below, when administered to a patient (e.g., a human) in need of such treatment in one or more doses. The therapeutically effective amount will vary depending upon the patient, the disease being treated, the weight and/or age of the patient, the severity of the disease or disorder, or the manner of administration as determined by a qualified prescriber or caregiver.

The term "treatment" or "treating" means administering a formulation disclosed herein for the purpose of: (i) delaying the onset of a disease/disorder, that is, causing the clinical symptoms of the disease/disorder not to develop or delaying the development thereof (ii) inhibiting the disease/disorder, that is, arresting the development of clinical symptoms; and/or (iii) relieving the disease/disorder, that is, causing the regression of clinical symptoms or the severity thereof.

As used herein, the terms "dressing" or "wound dressing" include any type of wrap, covering, barrier, layer, packing, gauze, plaster, bandage, lint, suture, film, foamed product, hydrogel, hydrocolloid, alginate product, bioactive product, tissue-engineered skin substitute, medicated product, liquid bandage, or composite product (which can include two or more of any of the foregoing or alternative products) designed to be placed over or applied to a portion of tissue. For example, such a dressing may be used on or near the stratum corneum or other portion of the skin, or for internal wound healing. In some embodiments, the dressing may be provided as an over-the-skin bandage (FIG. 1A) or foam pad (FIG. 1B).

Unless otherwise defined herein, scientific and technical terms used in connection with the present application shall have the meanings that are commonly understood by those of ordinary skill in the art to which this disclosure belongs. It should be understood that this present technology is not limited to the particular methodology, protocols, and reagents, etc., described herein and as such can vary. The terminology used herein is for the purpose of describing particular embodiments only and is not intended to limit the scope of the present technology, which is defined solely by the claims. Definitions of common terms in immunology and molecular biology can be found in The Merck Manual of Diagnosis and Therapy (2011), 19$^{th}$ Edition, published by Merck Sharp & Dohme Corp. (ISBN 978-0-911910-19-3); The Encyclopedia of Molecular Cell Biology and Molecular Medicine, Robert S. Porter et al. (eds.), published by Blackwell Science Ltd., 1999-2012 (ISBN 9783527600908); Molecular Biology and Biotechnology: a Comprehensive Desk Reference (1995). Robert A. Meyers (ed.), published by VCH Publishers, Inc. (ISBN 1-56081-569-8); Immunology (2006). Werner Luttmann, published by Elsevier; Janeway's Immunobiology (2014). Kenneth Murphy, Allan Mowat, Casey Weaver (eds.), Taylor & Francis Limited, (ISBN 0815345305, 9780815345305); Lewin's Genes XI, (2014). Published by Jones & Bartlett Publishers (ISBN-1449659055); Molecular Cloning: A Laboratory Manual., 4$^{th}$ ed., 2012, Cold Spring Harbor Laboratory Press, Cold Spring Harbor, N.Y., USA (ISBN 1936113414); Basic Methods in Molecular Biology, 2012, Elsevier Science Publishing, Inc., New York, USA (ISBN 044460149X); Laboratory Methods in Enzymology: DNA, (2013). Jon Lorsch (ed.) Elsevier (ISBN 0124199542); Current Protocols in Molecular Biology (CPMB) (2014). Frederick M. Ausubel (ed.), John Wiley and Sons (ISBN 047150338X, 9780471503385); Current Protocols in Protein Science (CPPS) (2005). John E. Coligan (ed.), John Wiley and Sons, Inc.; and Current Protocols in Immunology (CPI) (2003). Coligan, J. E., et al., (eds.) John Wiley and Sons, Inc. (ISBN 0471142735, 9780471142737).

Other terms are defined herein within the description of the various aspects of the present technology.

Polymeric Components of the Wound Dressings, Compositions, and Formulations of the Present Technology The polymeric components described herein are anti-infective. In some embodiments, the polymeric component is antibacterial against one of or both gram negative strain bacteria and gram positive strain bacteria.

In one aspect, provided herein is a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof.

As used in this instance, the "combination of two or more thereof" encompasses a blend of two or more polymeric components. For example, the polymeric component may be a blend of a polymer of polymeric component (1) and a polymer of polymeric component (2). In another example, the polymeric component may be a blend of an interpenetrating polymer network of polymeric component (1) and an interpenetrating polymer network of polymeric component (2). The term "blend" refers to a physical mixture without further chemical reaction between components within the blend.

In some embodiments, the polymeric component is a polymer, copolymer, interpenetrating polymer network, polyelectrolyte complex, blend, or composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker.

In some embodiments, the polymeric component is a polymer, copolymer, interpenetrating polymer network, polyelectrolyte complex, blend, or composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker.

In some embodiments, the polymeric component is the polyethyleneimine intermediate.

In some embodiments, the polymeric component is the second adduct.

In some embodiments, the polymeric component is a polymer, interpenetrating polymer network, polyelectrolyte complex, blend, or composite, each of which comprises or consists essentially of a random polymerization/crosslinking product of reagents comprising, consisting essentially of, or consisting of (i) a first adduct of a first multifunctional crosslinker and a first quaternary ammonium salt; (ii) a polyethyleneimine intermediate or a second adduct of the polyethyleneimine intermediate and a second multifunctional crosslinker; and (iii) a water-soluble polymer. In some embodiments, the polymer consists of the random polymerization/crosslinking product of reagents comprising, consisting essentially of, or consisting of (i) a first adduct of a first multifunctional crosslinker and a first quaternary ammonium salt; (ii) a polyethyleneimine intermediate or a second adduct of the polyethyleneimine intermediate and a second multifunctional crosslinker; and (iii) a water-soluble polymer.

In some embodiments, the polymeric component is a polymer, interpenetrating polymer network, polyelectrolyte complex, blend, or composite, each of which comprises or consists essentially of a random polymerization/crosslinking product of reagents comprising, consisting essentially of, or consisting of (i) a first adduct of a first multifunctional crosslinker and a first quaternary ammonium salt; and (ii) a polyethyleneimine intermediate or a second adduct of the polyethyleneimine intermediate and a second multifunctional crosslinker. In some embodiments, the polymer consists of the random polymerization/crosslinking product of reagents comprising, consisting essentially of, or consisting of (i) a first adduct of a first multifunctional crosslinker and a first quaternary ammonium salt; and (ii) a polyethyleneimine intermediate or a second adduct of the polyethyleneimine intermediate and a second multifunctional crosslinker.

In some embodiments, the polymeric component is a polymer, interpenetrating polymer network, polyelectrolyte complex, blend, or composite, each of which comprises or consists essentially of a random polymerization/crosslinking product of reagents comprising, consisting essentially of, or consisting of (i) a first adduct of a first multifunctional crosslinker and a first quaternary ammonium salt; (ii) optionally a polyol; (iii) a polyethyleneimine intermediate or a second adduct of the polyethyleneimine intermediate and a second multifunctional crosslinker; (iv) optionally a third multifunctional crosslinker; and (v) a water-soluble polymer. In some embodiments, the polymer consists of the random polymerization/crosslinking product of reagents comprising, consisting essentially of, or consisting of (i) a first adduct of a first multifunctional crosslinker and a first quaternary ammonium salt; (ii) optionally a polyol; (iii) a polyethyleneimine intermediate or a second adduct of the polyethyleneimine intermediate and a second multifunctional crosslinker; (iv) optionally a third multifunctional crosslinker; and (v) a water-soluble polymer.

In some embodiments, (i) the first adduct and (ii) the polyethyleneimine intermediate or the second adduct are prepared separately and mixed thereafter to form the polymer, the copolymer, the interpenetrating polymer network, the polyelectrolyte complex, the blend, or the composite.

The water-soluble polymer comprises, consists essentially of, or consists of hydroxyethyl cellulose, hydroxypropyl cellulose, methylcellulose, hydrophobically modified cellulose, polyvinyl alcohol poly(hydroxyethyl methacrylate-co-alkyl methacrylate), poly(hydroxyethyl methacrylate-co-alkyl acrylate), poly(hydroxyethyl acrylate-co-alkyl methacrylate), poly(hydroxyethyl acrylate-co-alkyl acrylate), polyethyleneimine, polyacrylamide, or their modified polymers or copolymers on the side-chain or main-chain (e.g., modification(s) that provide reactive functional groups, hydrophobicity, and/or surface activity), or a combination or blend of two or more thereof, or a copolymer of two or more thereof, or a copolymer of one or more thereof with polyvinylpyrrolidone, poly(glycidyl acrylate) or with poly(glycidyl methacrylate).

The water-soluble polymer may be present in the polymer, the copolymer, or the interpenetrating polymer network of polymeric component (1) or (2) in an amount of from about 0.5 wt. % to about 15 wt. %. This includes about 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 wt. %, or any value therebetween. In some embodiments, the water-soluble polymer is present in the polymer, the copolymer, or the interpenetrating polymer network of polymeric component (1) or (2) in an amount of from about 0.5 wt. % to about 15 wt. %, about 3 wt. % to about 12 wt. %, or about 5 wt. % to about 10 wt. %.

In some embodiments, the polymeric component is a polymer, interpenetrating polymer network, polyelectrolyte complex, blend, or composite, each of which comprises or consists essentially of a random polymerization/crosslinking product of reagents comprising, consisting essentially of, or consisting of (i) a first adduct of a first multifunctional crosslinker and a first quaternary ammonium salt; (ii) optionally a polyol; (iii) a polyethyleneimine intermediate or a second adduct of the polyethyleneimine intermediate and a second multifunctional crosslinker; and (iv) optionally a third multifunctional crosslinker.

The first quaternary ammonium salt may have a chemical structure of:

wherein:

$R^1$ is selected from a group consisting of —($C_8$-$C_{30}$ alkyl), —($C_8$-$C_{30}$ heteroalkyl), —($C_8$-$C_{30}$ heteroalkyl)-($C_6$-$C_{10}$ aryl), —($C_6$-$C_{10}$ aryl), —($C_6$-$C_{10}$ aryl)-($C_1$-$C_{30}$ alkyl), —($C_6$-$C_{10}$ aryl)-($C_1$-$C_{30}$ heteroalkyl), —($CR'''R''$)$_{x10}$—$W^{10}$—($CR^pR^q$)$_{y10}$—H, and —($CR'''R''$)$_{x11}$—W—($CR^pR^q$)$_{y11}$H—; wherein —($C_8$-$C_{30}$ heteroalkyl), —($C_8$-$C_{30}$ heteroalkyl)-($C_6$-$C_{10}$ aryl), and —($C_6$-$C_{10}$ aryl)-($C_1$-$C_{30}$ heteroalkyl) have 1 to 4 heteroatoms independently selected from O, S, and Si;

$R^2$ is selected from a group consisting of —($C_1$-$C_4$ alkyl), —($C_1$-$C_4$ heteroalkyl), —($C_1$-$C_4$ heteroalkyl)-($C_6$-$C_{10}$ aryl), —($C_6$-$C_{10}$ aryl), —($C_6$-$C_{10}$ aryl)-($C_1$-$C_4$alkyl), —($C_6$-$C_{10}$ aryl)-($C_1$-$C_4$ heteroalkyl); —($CR'''R''$)$_{x20}$—$W^{20}$—($CR^pR^q$)$_{y20}$—H, and —($CR'''R''$)$_{x21}$—$W^{21}$—($CR^pR^q$)$_{y21}$—H; wherein —($C_1$-$C_4$ heteroalkyl), —($C_1$-$C_4$ heteroalkyl)-($C_6$-$C_{10}$ aryl), and —($C_6$-$C_{10}$ aryl)-($C_1$-$C_4$ heteroalkyl) have 1 to 2 heteroatoms independently selected from O, S, and Si;

$R^3$ is selected from a group consisting of —($C_1$-$C_{30}$ alkyl), —($C_1$-$C_{30}$ heteroalkyl), —($C_1$-$C_{30}$ heteroalkyl)-($C_6$-$C_{10}$ aryl), —($C_6$-$C_{10}$ aryl), —($C_6$-$C_{10}$ aryl)-($C_1$-$C_{30}$ alkyl), —($C_6$-$C_{10}$ aryl)-($C_1$-$C_{30}$ heteroalkyl), —($CR'''R''$)$_{x30}$—$W^{30}$—($CR^pR^q$)$_{y30}$—H, and —($CR'''R''$)$_{x31}$—$W^{31}$—($CR^pR^q$)$_{y31}$—H; wherein —($C_1$-$C_{30}$ heteroalkyl), —($C_1$-$C_{30}$ heteroalkyl)-($C_6$-$C_{10}$ aryl), and —($C_6$-$C_{10}$ aryl)-($C_1$-$C_{30}$ heteroalkyl) have 1 to 4 heteroatoms independently selected from O, S, and Si;

A is a linking group selected from a group consisting of —($C_3$-$C_{20}$ alkylene)-, —($C_3$-$C_{20}$ heteroalkylene)-, —($C_6$-$C_{10}$ arylene)-($C_3$-$C_{20}$ alkylene), —($CR'''R''$)$_{x40}$—$W^{40}$—($CR^pR^q$)$_{y40}$—, and —($CR'''R''$)$_{x41}$—$W^{41}$—($CR^pR^q$)$_{y41}$—, wherein —($C_3$-$C_{20}$ heteroalkylene)- has 1 to 4 heteroatoms independently selected from O, S, and Si; and —($C_3$-$C_{20}$ alkylene)- and —($C_3$-$C_{20}$ heteroalkylene)- are optionally substituted with 1 to 6 substituents independently selected from —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl);

each $R'''$, $R''$, $R^p$, and $R^q$ is independently selected from H and $C_1$-$C_4$ alkyl;

$W^{10}$, $W^{20}$, $W^{30}$, and $W^{40}$ are independently selected from —C(O)—; —C(O)O—; —OC(O)—; —C(O)NH—; and —NHC(O)—;

$W^{11}$, $W^{21}$, $W^{31}$, and $W^{41}$ are independently selected from 5- to 6-membered cycloalkyl, $C_6$-$C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x10 is an integer from 1 to 30 and y10 is an integer from 0 to 29, wherein $8 \leq (x10+y10) \leq 30$;

x11 is an integer from 1 to 30 and y11 is an integer from 0 to 29, wherein $8 \leq (x11+y11) \leq 30$;

x20 is an integer from 1 to 4 and y20 is an integer from 0 to 3, wherein $x20+y20 \leq 4$;

x21 is an integer from 1 to 4 and y21 is an integer from 0 to 3, wherein $x21+y21 \leq 4$;

x30 is an integer from 1 to 30 and y30 is an integer from 0 to 29, wherein $x30+y30 \leq 30$;

x31 is an integer from 1 to 30 and y31 is an integer from 0 to 29, wherein $x31+y31 \leq 30$;

x40 is an integer from 1 to 19 and y40 is an integer from 1 to 19, wherein $3 \leq (x40+y40) \leq 20$;

x41 is an integer from 1 to 20, and y41 is an integer from 0 to 19, wherein $3 \leq (x41+y41) \leq 20$;

Y is selected from a group consisting of —OH, —NHR$^4$, —SH, —CO$_2$H, —C(O)NHR$^4$, —C(S)NHR$^4$, each R$^4$ is independently selected from a group consisting of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si; and X$^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

In some embodiments, R$^1$ is selected from a group consisting of —(C$_{12}$-C$_{30}$ alkyl), —(C$_{12}$-C$_{30}$ heteroalkyl), —(C$_{12}$-C$_{30}$ alkyl)-(C$_6$-C$_{10}$ aryl), —(C$_{12}$-C$_{30}$ heteroalkyl)-(C$_6$-C$_{10}$ aryl), —(C$_6$-C$_{10}$ aryl)-(C$_{12}$-C$_{30}$ alkyl), and —(C$_6$-C$_{10}$ aryl)-(C$_{12}$-C$_{30}$ heteroalkyl); wherein —(C$_{12}$-C$_{30}$ heteroalkyl), —(C$_{12}$—C$_{30}$ heteroalkyl)-(C$_6$-C$_{10}$ aryl), and —(C$_6$-C$_{10}$ aryl)-(C$_{12}$-C$_{30}$ heteroalkyl) have 1 to 4 heteroatoms independently selected from O, S, and Si. In some embodiments, R$^1$ is —(C$_{12}$-C$_{30}$ alkyl). In some embodiments, R$^1$ is —(C$_5$-C$_{30}$ heteroalkyl) with 1 to 4 heteroatoms independently selected from O, S, and Si. In some embodiments, R$^1$ is —(C$_6$-C$_{10}$ aryl)-(C$_{12}$-C$_{30}$ alkyl). In some embodiments, R$^1$ is —(C$_{12}$-C$_{30}$ alkyl)-(C$_6$-C$_{10}$ aryl). In some embodiments, R$^1$ is —(C$_6$-C$_{10}$ aryl)-(C$_{12}$-C$_{30}$ heteroalkyl) with 1 to 4 heteroatoms independently selected from O, S, and Si. In some embodiments, R$^1$ is —(C$_{12}$-C$_{30}$ heteroalkyl)-(C$_6$-C$_{10}$ aryl) with 1 to 4 heteroatoms independently selected from O, S, and Si. In some embodiments, R$^1$ is —(CR$^m$R$^n$)$_{x10}$—W$^{10}$—(CR$^p$R$^q$)$_{y10}$—H. In some embodiments, R$^1$ is —(CR$^m$R$^n$)$_{x11}$—W$^{11}$—(CR$^p$R$^q$)$_{y11}$—H.

In some embodiments, R$^2$ is —(C$_1$-C$_4$ alkyl). In some embodiments, R$^2$ is —(C$_1$-C$_4$ heteroalkyl) with 1 to 4 heteroatoms independently selected from O, S, and Si. In some embodiments, R$^2$ is —(C$_6$-C$_{10}$ aryl)-(C$_1$-C$_4$ alkyl). In some embodiments, R$^2$ is —(C$_1$-C$_4$ alkyl)-(C$_6$-C$_{10}$ aryl). In some embodiments, R$^2$ is —(C$_6$-C$_{10}$ aryl). In some embodiments, R$^2$ is —(C$_6$-C$_{10}$ aryl)-(C$_1$-C$_4$ heteroalkyl) with 1 to 4 heteroatoms independently selected from O, S, and Si. In some embodiments, R$^2$ is —(C$_1$-C$_4$ heteroalkyl)-(C$_6$-C$_{10}$ aryl) with 1 to 4 heteroatoms independently selected from O, S, and Si. In some embodiments, R$^2$ is —(CR$^m$R$^n$)$_{x20}$—W$^{20}$—(CR$^p$R$^q$)$_{y20}$—H. In some embodiments, R$^2$ is —(CR$^m$R$^n$)$_{x21}$—W$^{21}$—(CR$^p$R$^q$)$_{y21}$—H.

In some embodiments, R$^3$ is selected from a group consisting of —(C$_1$-C$_4$ alkyl), —(C$_1$-C$_4$ heteroalkyl), —(C$_1$-C$_4$ alkyl)-(C$_6$-C$_{10}$ aryl), —(C$_1$-C$_4$ heteroalkyl)-(C$_6$-C$_{10}$ aryl), —(C$_6$-C$_{10}$ aryl)-(C$_1$-C$_4$ alkyl), and —(C$_6$-C$_{10}$ aryl)-(C$_1$-C$_4$ heteroalkyl); wherein —(C$_1$-C$_4$ heteroalkyl), —(C$_1$-C$_4$ heteroalkyl)-(C$_6$-C$_{10}$ aryl), and —(C$_6$-C$_{10}$ aryl)-(C$_1$-C$_4$ heteroalkyl) have 1 to 4 heteroatoms independently selected from O, S, and Si. In some embodiments, R$^3$ is —(C$_1$-C$_4$ alkyl). In some embodiments, R$^3$ is —(C$_1$-C$_4$ heteroalkyl)

with 1 to 4 heteroatoms independently selected from O, S, and Si. In some embodiments, R$^3$ is —(C$_6$-C$_{10}$ aryl)-(C$_1$-C$_4$ alkyl). In some embodiments, R$^3$ is —(C$_1$-C$_4$ alkyl)-(C$_6$-C$_{10}$ aryl). In some embodiments, R$^3$ is —(C$_6$-C$_{10}$ aryl)-(C$_1$-C$_4$ heteroalkyl) with 1 to 4 heteroatoms independently selected from O, S, and Si. In some embodiments, R$^3$ is —(C$_1$-C$_4$ heteroalkyl)-(C$_6$-C$_{10}$ aryl) with 1 to 4 heteroatoms independently selected from O, S, and Si. In some embodiments, R$^3$ is —(CR$^m$R$^n$)$_{x30}$—W$^{30}$—(CR$^p$R$^q$)$_{y30}$—H. In some embodiments, R$^3$ is —(CR$^m$R$^n$)$_{x31}$—W$^{31}$—(CR$^p$R$^q$)$_{y31}$—H.

In some embodiments, at least one of R$^2$ and R$^3$ is —(C$_1$-C$_4$ alkyl). In some embodiments, R$^2$ and R$^3$ are methyl. In some embodiments, R$^1$ is C$_{12}$-C$_{30}$ alkyl, and R$^2$ and R$^3$ are methyl.

In some embodiments, A is —(C$_3$-C$_{20}$ alkylene)- optionally substituted with 1 to 6 substituents independently selected from —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl). In some embodiments, A is —(C$_3$-C$_{20}$ heteroalkylene)- with 1 to 4 heteroatoms independently selected from O, S, and Si, and optionally substituted with 1 to 6 substituents independently selected from —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ ary). In some embodiments, A is —(C$_6$-C$_{10}$ arylene)-(C$_3$-C$_{20}$ alkylene)-. In some embodiments, A is —(C$_3$-C$_{20}$ alkylene)-(C$_6$-C$_{10}$ arylene)-.

In some embodiments, A is —(CR$^m$R$^n$)$_{x40}$—W$^{40}$—(CR$^p$R$^q$)$_{y40}$—. In some embodiments, A is —(CR$^m$R$^n$)$_{x41}$—W$^{41}$—(CR$^p$R$^q$)$_{y41}$—.

In some embodiments, A is —(CH$_2$)$_m$— or —(CH$_2$CHR$^5$—O—)$_n$CH$_2$CHR$^5$—, wherein m is an integer from 2 to 20; n is 0, 1, 2, 3, 4, or 5; and each R$^5$ is independently selected from a group consisting of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si. In some embodiments, R$^5$ is H or methyl.

In some embodiments, Y is —OH. In some embodiments, Y is —NHR$^4$. In some embodiments, Y is —SH. In some embodiments, Y is —CO$_2$H. In some embodiments, Y is —C(O)NHR$^4$, wherein R$^4$ is selected from a group consisting of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si. In some embodiments, Y is —C(S)NHR$^4$, wherein R$^4$ is selected from a group consisting of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si. In some embodiments, Y is wherein each $R^4$ is independently selected from a group consisting of H, —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si. In some embodiments, Y is wherein each $R^4$ is independently selected from a group consisting of H, —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si.

$X^-$ may be independently selected from the group consisting of acetate, halide (e.g., chloride, bromide, or iodide), sulfate, sulfonate, phosphate, phosphonate, carbonate, silicate, hexafluorophosphate, hexafluoroantimonate, triflate, and borate, and their organo-substituted derivatives. As used herein, and unless stated otherwise, "organo-substituted derivatives" refers to anions wherein a sulfur atom, a phosphorous atom, a boron atom, a silicon atom or carbonyl group is substituted with either an alkyl or an aryl group. Non-limiting examples include methylsulfate, methanesulfonate, p-toluene sulfonate, trifluoromethylsulfonate, and trifluoroacetate.

In some embodiments, the first quaternary ammonium salt is or a combination of two or more thereof.

The first quaternary ammonium salt may be present in the polymer, the copolymer, or the interpenetrating polymer network of polymeric component (1) or (2) in an amount of about 1 wt. % to about 50 wt. %. This includes about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt. %, or any value therebetween. In some embodiments, the first quaternary ammonium salt is present in the polymer, the copolymer, or the interpenetrating polymer network of polymeric component (1) or (2) in an amount of about 5 wt. % to about 25 wt. %. More precisely, the amount of quaternary ammonium salt may be represented by millinormal/g (mN/g) instead of wt. % based on the total weight of the polymer, the copolymer, or the interpenetrating polymer network of polymeric component (1) or (2). The first quaternary ammonium salt may be present in the polymer, the copolymer, or the interpenetrating polymer network of polymeric component (1) or (2) in an amount of from about 0.1 mN/g to about 1.0 mN/g. This includes 0.1, 0.2, 0.3, 0.4, 0.5, 0.6, 0.7, 0.8, 0.9, or 1.0 mN/g, or any value therebetween. In some embodiments, the first quaternary ammonium salt is present in the polymer, the copolymer, or the interpenetrating polymer network of polymeric component (1) or (2) in an amount of from about 0.4 mN/g to about 0.9 mN/g. In some embodiments, the first quaternary ammonium salt is present in the polymer, the copolymer, or the interpenetrating polymer network of polymeric component (1) or (2) in an amount of from about 0.5 mN/g to about 0.8 mN/g.

The first multifunctional crosslinker may be a bisfunctional crosslinker. In some embodiments, the bisfunctional crosslinker is a diisocyanate. In some embodiments, the diisocyanate is selected from the group consisting of: hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethyl-xylene diisocyanate (TMXDI), and trimethylhexamethylene diisocyanate (TMDI).

The first multifunctional crosslinker may be a first polyisocyanate. In some embodiments, the first polyisocyanate has an average isocyanate functionality of 2 to 5. This includes an average isocyanate functionality of 2, 3, 4, or 5. In some embodiments, the first polyisocyanate has an average isocyanate functionality of 3 to 4.

The second multifunctional crosslinker may be a second polyisocyanate. In some embodiments, the second polyisocyanate has an average isocyanate functionality of 2 to 5. This includes an average isocyanate functionality of 2, 3, 4, or 5. In some embodiments, the second polyisocyanate has an average isocyanate functionality of 3 to 4.

The third multifunctional crosslinker may be a third polyisocyanate. In some embodiments, the third polyisocyanate has an average isocyanate functionality of 2 to 5. This includes an average isocyanate functionality of 2, 3, 4, or 5. In some embodiments, the third polyisocyanate has an average isocyanate functionality of 3 to 4.

In some embodiments, the first multifunctional crosslinker is a first polyisocyanate; the second multifunctional crosslinker, when present, is a second polyisocyanate; the third multifunctional crosslinker, when present, is a third polyisocyanate; wherein the first polyisocyanate, the second polyisocyanate, and the third polyisocyanate are different. In some embodiments, the first multifunctional crosslinker is a first polyisocyanate; the second multifunctional crosslinker, when present, is a second polyisocyanate; the third multifunctional crosslinker, when present, is a third polyisocyanate; wherein the first polyisocyanate, the second polyisocyanate, and the third polyisocyanate are the same.

Each of the first, second, and third polyisocyanates may be prepared from a diisocyanate independently selected from the group consisting of: hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI).

In some embodiments, each of the first, second, and third polyisocyanates is independently selected from the group consisting of DESMODUR® N-3300, DESMODUR® N-100, DESMODUR® Z4470SN, WANNATE® T series polyisocyanates, and LUPRANATE® M series polyisocyanates. DESMODUR® N-3300 and DESMODUR® N-100 are aliphatic polyisocyanates based on HDI (hexamethylene diisocyanate) trimer. DESMODUR® Z4470SN is a multifunctional polyisocyanate based on IPDI (isophorone diisocyanate). WANNATE® T series polyisocyanates are toluene diisocyanate (TDI)-based aromatic polyisocyanates. LUPRANATE® M series polyisocyanates are 4,4-diphenylmethane diisocyanate (MDI)-based aromatic polyisocyanates.

The first multifunctional crosslinker may be present in the polymer, the copolymer, or the interpenetrating polymer network of polymeric component (1) or (2) in an amount of about 2 wt. % to about 25 wt. %. This includes 2, 3, 4, 5, 6, 7, 8, 9, 10, 11, 12, 13, 14, 15, 16, 17, 18, 19, 20, 21, 22, 23, 24, or 25 wt. %, or any value therebetween. In some embodiments, the first multifunctional crosslinker is present in the polymer, the copolymer, or the interpenetrating polymer network of polymeric component (1) or (2) in an amount of about 7 wt. % to about 15 wt. %, or about 5 wt. % to about 20 wt. %.

The second multifunctional crosslinker may be present in the polymer, the copolymer, or the interpenetrating polymer network of polymeric component (1) or in polymeric component (4) in an amount of about 0.1 wt. % to about 10 wt. %, This includes 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, or 10 wt. %, or any value therebetween. In some embodiments, the second multifunctional crosslinker is present in the polymer, the copolymer, or the interpenetrating polymer network of polymeric component (1) or in polymeric component (4) in an amount of about 1 wt. % to about 10 wt. %, about 2 wt. % to about 8 wt. %, or about 3 wt. % to about 6 wt. %.

The third multifunctional crosslinker may be present in the polymer, the copolymer, or the interpenetrating polymer network of polymeric component (1) or (2) in an amount of about 0.1 wt. % to about 20 wt. %. This includes 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 wt. %, or any value therebetween. In some embodiments, the third multifunctional crosslinker is present in the polymer, the copolymer, or the Interpenetrating polymer network of polymeric component (1) or (2) in an amount of about 1 wt. % to about 20 wt. %, or about 2 wt. % to about 15 wt. %.

In some embodiments, the first adduct has an average isocyanate functionality of 2 to 3. In some embodiments, the first adduct has an average isocyanate functionality of about 2.05 to about 2.3.

The first adduct may be present in the polymer, the copolymer, or the interpenetrating polymer network of polymeric component (1) or (2) in an amount of about 5 wt. % to about 70 wt. %. This includes about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 wt. %, or any value therebetween. In some embodiments, the first adduct is present in the polymer, the copolymer, or the interpenetrating polymer network of polymeric component (1) or (2) in an amount of about 10 wt. % to about 50 wt. %, about 15 wt. % to about 65 wt. %, about 15 wt. % to about 60 wt. %, about 15 wt. % to about 50 wt. %, about 20 wt. % to about 70 wt. %, about 20 wt. % to about 60 wt. %, or about 20 wt. % to about 50 wt. %.

The polyol may be present in the polymer, the copolymer, or the interpenetrating polymer network of polymeric component (1) or (2) in an amount of about 1 wt. % to about 40 wt. %. This includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 wt. %, or any value therebetween. In some embodiments, the polyol is present in the polymer, the copolymer, or the interpenetrating polymer network of polymeric component (1) or (2) in an amount of about 5 wt. % to about 25 wt. %.

The polyol may be selected from a group consisting of polyether polyols, polyester polyols, polyacrylic polyols, polymethacrylic polyols, polycaprolactone polyols, polybutadiene polyols, poly(acrylonitrile-co-butadiene) polyols, polysiloxane polyols, a copolymer of any two or more thereof, and a combination of any two or more thereof.

In some embodiments, the polyol comprises, consists essentially of, or consists of polytetramethylene glycol (PTMG), polyethylene glycol (PEG), polypropylene glycol (PPG), or a combination of two or more thereof, or a copolymer of one or more thereof with polyester, polycaprolactone, polybutadiene, poly(acrylonitrile-butadiene), polysiloxane, or polyacrylate. In some embodiments, the polyol is selected from a group consisting of poly(tetramethylene glycol), polyethylene glycol, polypropylene glycol, poly (ethylene glycol-b-propylene glycol-b-ethylene glycol), and poly(propylene glycol-b-polyethylene glycol-b-propylene glycol).

In some embodiments, the polyol comprises, consists essentially of, or consists of a polyether polyol, a polyester polyol, or a combination thereof.

The polyol may have an average molecular weight of about 300 to about 3000 daltons. This includes about 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 daltons, or any value therebetween. In some embodiments, the polyol has an average molecular weight of about 400 to about 2000, or about 600 to about 1500 daltons.

In some embodiments, the polyol is pre-reacted with the first polyisocyanate to form an isocyanate end-capped prepolymer. In some embodiments, the polyol is pre-reacted with the third polyisocyanate to form an isocyanate end-capped prepolymer.

In some embodiments, the polyethyleneimine intermediate has a ratio of total quaternary amines to total hydroxyl groups of at least 1:1. This includes a ratio of 1:1, 1.1:1, 1.2:1, 1.3:1, 1.4:1, 1.5:1, 1.6:1, 1.7:1, 1.8:1, 1.9:1, 2:1, 2.2:1, 2.4:1, 2.6:1, 2.8:1, 3:1, 3.2:1, 3.4:1, 3.6:1, 3.8:1, 4:1, 4.2:1, 4.4:1, 4.6:1, 4.8:1, 5:1, 5.2:1, 5.4:1, 5.6:1, 5.8:1, 6:1, 6.2:1, 6.4:1, 6.6:1, 6.8:1, 7:1, 7.2:1, 7.4:1, 7.6:1, 7.8:1, 8:1, 8.2:1, 8.4:1, 8.6:1, 8.8:1, 9:1, 9.2:1, 9.4:1, 9.6:1, 9.8:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 99:1, or higher, or any value therebetween.

In some embodiments, the polyethyleneimine intermediate comprises optionally substituted hydroxyalkylene functionality that reacts with the first adduct and, if present, the second multifunctional crosslinker. In some embodiments, the polyethyleneimine intermediate comprises optionally substituted hydroxyalkylene functionality that reacts with the first adduct and, if present, the second multifunctional crosslinker, and if present, the third multifunctional crosslinker.

In some embodiments, the hydroxyalkylene functionality is optionally substituted with $C_1$-$C_6$ alkyl optionally substituted with a substituent selected from —$N^+(R^{20})_3X^-$, —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy; each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl); and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives. In some embodiments, the hydroxyalkylene functionality is substituted with $C_1$-$C_6$ alkyl substituted with —$N^+(R^{20})_3X^-$, each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl); and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives. In some embodiments, the hydroxyalkylene functionality is substituted with —(CH$_2$)—N$^+$(Me)$_3$Cl$^-$. In some embodiments, the hydroxyalkylene functionality is hydroxyethylene, hydroxypropylene, hydroxybutylene, or an oligomer thereof.

In some embodiments, the polyethyleneimine intermediate comprises a reaction product of reagents comprising a polyethyleneimine and an alkylating agent. In some embodiments, the reagents further comprise a mono-epoxide or a lactone. In some embodiments, the mono-epoxide or the lactone is optionally substituted with $C_1$-$C_6$ alkyl optionally substituted with a substituent selected from —($C_6$-$C_{10}$ aryl), and —($C_1$-$C_6$ alkoxy) optionally substituted with hydroxy, $C_1$-$C_6$ alkoxy, $C_6$-$C_{10}$ aryl optionally substituted with $C_1$-$C_6$ alkyl, and carboxy.

In some embodiments, the polyethyleneimine intermediate comprises a reaction product of reagents comprising a polyethyleneimine, a mono-epoxide, and an alkylating agent, wherein the mono-epoxide is optionally substituted with $C_1$-$C_6$ alkyl optionally substituted with a substituent selected from —($C_6$-$C_{10}$ aryl), and —($C_1$-$C_6$ alkoxy) optionally substituted with hydroxy, $C_1$-$C_6$ alkoxy, $C_6$-$C_{10}$ aryl optionally substituted with $C_1$-$C_6$ alkyl, and carboxy.

In some embodiments, the mono-epoxide is a $C_1$-$C_6$ alkyl oxirane. In some embodiments, the $C_1$-$C_6$ alkyl oxirane is selected from the group consisting of methyl oxirane (propylene oxide), ethyl oxirane (1-butylene oxide or 1,2-epoxy butane), propyl oxirane (1-pentene oxide), butyl oxirane (1-hexene oxide), and hexyl oxirane (1-octene oxide). In some embodiments, the $C_1$-$C_6$ alkyl oxirane is methyl oxirane or propylene oxide. In some embodiments, the $C_1$-$C_6$ alkyl oxirane is butyl oxirane or 1-hexene oxide. In some embodiments, the $C_1$-$C_6$ alkyl oxirane is hexyl oxirane or octene oxide.

In some embodiments, the polyethyleneimine intermediate comprises a reaction product of reagents comprising a polyethyleneimine, a mono-epoxide, and optionally an alkylating agent; the mono-epoxide is substituted with —($C_1$-$C_6$ alkylene)-N$^+$(R$^{20}$)$_3$X$^-$; each R$^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl); and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the polyethyleneimine intermediate comprises a reaction product of reagents comprising a polyethyleneimine and a mono-epoxide; the mono-epoxide is substituted with —($C_1$-$C_6$ alkylene)-N$^+$(R$^{20}$)$_3$X$^-$; each R$^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl); and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the alkylating agent comprises one or more R$^{21}$-LG, wherein each R$^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH; and each LG is a leaving group. As used herein, and unless otherwise indicated, the leaving group may be a halide, a sulfonate, or the like. In some embodiments, the alkylating agent is phenacyl halide, benzyl halide, or hexyl halide.

In some embodiments, the reagents for the reaction product comprised in the polyethyleneimine intermediate further comprise a monoisocyanate. In some embodiments, the monoisocyanate comprises one or more R$^{30}$—NCO, wherein each R$^{30}$ is independently selected from (1) $C_6$-$C_{20}$ alkyl optionally substituted with 1-3 substituents independently selected from halogen, —SiR$^a$(OR$^b$)(OR$^c$), and —($C_6$-$C_{10}$ aryl); and (2) $C_6$-$C_{10}$ aryl optionally substituted with 1-3 substituents independently selected from halogen, —($C_1$-$C_6$ alkyl), and —SiR$^a$(OR$^b$)(OR$^c$); wherein each R$^a$ is independently $C_1$-$C_6$ alkyl; and each R$^b$ and each R$^c$ are independently selected from —($C_1$-$C_6$ alkyl) and —Si($C_1$-$C_6$ alkyl)$_3$. In some embodiments, the monoisocyanate comprises octylisocyanate, octadecylisocyanate, or a combination thereof.

The polyethyleneimine intermediate may be present in the polymer, the copolymer, or the interpenetrating polymer network of polymeric component (1), (3) or (4) in an amount of about 0.1 wt. % to about 50 wt. %. This includes 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 wt. %, or any value therebetween. In some embodiments, the polyethyleneimine intermediate is present in the polymer, the copolymer, or the interpenetrating polymer network of polymeric component (1), (3) or (4) in an amount of about 3 wt. % to about 30 wt. %.

In some embodiments, at least 20% of the nitrogen atoms of the polyethyleneimine intermediate are quaternized. In some embodiments, at least 30% of the nitrogen atoms of the polyethyleneimine intermediate are quaternized.

The polyethyleneimine may have a molecular weight of about 300 to about 270,000 daltons. This includes about 300; 400; 500; 600; 700; 800; 900; 1000; 2500; 5000; 10,000; 25,000; 50,000; 75,000; 100,000; 125,000; 150,000; 175,000; 200,000; 225,000; 250,000; or 270,000 daltons, or any value therebetween. In some embodiments, the polyethyleneimine has a molecular weight of about 10,000 to about 200,000 daltons, or about 25,000 to about 120,000 daltons.

In some embodiments, the polyethyleneimine is branched. In some embodiments, the polyethyleneimine is hyperbranched.

In some embodiments, the polyethyleneimine has a ratio of primary to secondary to tertiary amines of about 1:2:1 to about 1:1:1. In some embodiments, the polyethyleneimine has a ratio of primary to secondary to tertiary amines of about 1:1:0.7.

In some embodiments, the polyethyleneimine intermediate is selected from

-continued and a copolymer or blend of any two or more thereof, wherein:

each $Y^3$ is independently H or —O—$Y^2$ each $Y^2$ is independently H or —C(O)—NHR$^{30}$;

each n is an integer independently selected from 1 to 3000, preferably an integer independently selected from 10 to 1000;

Z is —(C$_2$-C$_6$ alkylene)-;

each $R^{10}$ is independently selected from hydrogen; C$_1$-C$_6$ alkyl optionally substituted with a substituent selected from —N(R$^{20}$)$_3$, —(C$_6$-C$_{10}$ aryl), and —(C$_1$-C$_6$ alkoxy) optionally substituted with —OH, —(C$_1$-C$_6$ alkoxy), —(C$_6$-C$_{10}$ aryl) optionally substituted with —(C$_1$-C$_6$ alkyl), and carboxy; and each $R^{20}$ is independently selected from a group consisting of C$_1$-C$_{18}$ alkyl; C$_1$-C$_{18}$ heteroalkyl having 1 to 4 heteroatoms independently selected from O, S, Si and tertiary-substituted N; and C$_6$-C$_{10}$ aryl optionally substituted with —(C$_1$-C$_6$ alkyl), —(C$_1$-C$_6$ alkoxy), —C(O)O—(C$_1$-C$_6$ alkyl), —C(O)NH(C$_1$-C$_6$ alkyl), —C(O)N(C$_1$-C$_6$ alkyl)$_2$, or —OC(O)—(C$_1$-C$_6$ alkyl);

each $R^{21}$ is independently selected from C$_1$-C$_6$ alkyl optionally substituted with a substituent selected from —OH, —(C$_1$-C$_6$ alkoxy), carboxy, —(C$_6$-C$_{10}$ aryl), —C(O)O(C$_1$-C$_6$ alkyl), —C(O)—(C$_6$-C$_{10}$ aryl), and —(C$_1$-C$_6$ alkoxy) optionally substituted with —OH;

each $R^{30}$ is independently selected from (1) C$_6$-C$_{20}$ alkyl optionally substituted with 1-3 substituents independently selected from halogen, —SiR$^a$(OR$^b$)(OR$^c$), and —(C$_6$-C$_{10}$ aryl); and (2) C$_6$-C$_{10}$ aryl optionally substituted with 1-3 substituents independently selected from halogen, —(C$_1$-C$_6$ alkyl), and —SiR$^a$(OR$^b$)(OR$^c$); wherein each R$^a$ is independently —(C$_1$-C$_6$ alkyl); and each $R^b$ and each $R^c$ are independently selected from —($C_1$-$C_6$ alkyl) and —Si($C_1$-$C_6$ alkyl)$_3$; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives;

provided:

when $R^{10}$ is $C_1$-$C_6$ alkyl optionally substituted with a substituent selected from —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy, then the polyethyleneimine intermediate is independently selected from In some embodiments, the polyethyleneimine intermediate is:

3 X⁻

46

-continued

4 X⁻ wherein each $R^{60}$ is independently selected from —$Y^4$—($C_1$-$C_{18}$ alkyl) optionally substituted with 1-3 substituents selected from —OH, —$N^+(R^{20})_3X^-$, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH; and at least one $R^{60}$ is substituted with —OH but less than 50% of all $R^{60}$ are substituted with —OH;

$Y^4$ is absent or —C(O)—;

and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl);

each n is an integer independently selected from 1 to 3000, preferably an integer independently selected from 10 to 1000; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the polyethyleneimine intermediate is:

3 X⁻

4 X⁻ wherein each $R^{60}$ is independently selected from —$Y^4$—($C_1$-$C_{18}$ alkyl) optionally substituted with 1-3 substituents selected from —OH, —$N^+(R^{20})_3X^-$, —($C_6$-$C_{10}$ aryl), —C(O)O($C_1$-$C_6$ alkyl), and —C(O)—($C_6$-$C_{10}$ aryl); and at least one $R^{60}$ is substituted with —OH but less than 50% of all $R^{60}$ are substituted with —OH;

$Y^4$ is absent or —C(O)—;

47 and each $R^{20}$ is independently selected from a group consisting of $C_1$-$C_6$ alkyl;

each n is an integer independently selected from 1 to 3000, preferably an integer independently selected from 10 to 1000; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, each $R^{60}$ is independently selected from —($C_1$-$C_{18}$ alkyl) optionally substituted with —OH; and at least one $R^{60}$ is substituted with —OH but less than 50% of all $R^{60}$ are substituted with —OH.

In some embodiments, each $R^{60}$ is independently selected from the group consisting of —$CH_3$, —$C_4H_9$, —$C_6H_{13}$, —$C_8H_{17}$, —$C_{18}H_{37}$, —$CH_2Ph$, —$CH_2C(O)OCH_2CH_3$, —$CH_2C(O)Ph$, —$(CH_2)_3OH$, —$CH_2CH(CH_3)OH$, —$CH_2CH(OH)CH_2N^+(CH_3)_3$, and —$C(O)(CH_2)_5OH$. In some embodiments, each $R^{60}$ is independently selected from the group consisting of —$CH_3$, —$C_4H_9$, —$C_6H_{13}$, —$C_6H_{17}$, —$C_{18}H_{37}$, —$CH_2Ph$, —$CH_2C(O)OCH_2CH_3$, —$CH_2C(O)Ph$, —$(CH_2)_3OH$, —$CH_2CH(CH_3)OH$, —$CH_2CH(OH)CH_2N^+(CH_3)_3$, and —$C(O)(CH_2)_5OH$; and at least one $R^{60}$ is substituted with —OH but less than 50% of all $R^{60}$ are substituted with —OH.

In some embodiments, at least one $R^{60}$ is substituted with —OH but less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of all $R^{60}$ are substituted with —OH. In some embodiments, about 1% to about 49% of all $R^{60}$ are substituted with —OH. This includes about 1% to about 40%, about 1% to about 30%, about 1% to about 20%, about 1% to about 18%, about 1% to about 15%, about 1% to about 10%, about 5% to about 40%, about 5% to about 30%, about 5% to about 20%, about 5% to about 18%, about 5% to about 15%, about 5% to about 10%, and any range therebetween.

In some embodiments, the polyethyleneimine intermediate is selected from a group consisting of:

| Compound | General Structure | PEI MW* | $R^{60}$ (mole %)** |
|---|---|---|---|
| 20-1 (batch 105159) | B | 270 kDa (branched) | —$CH_2CH(CH_3)OH$ (<50%) —$C_6H_{13}$ (>50%) |
| 20-1 (batch 99367) | B | 270 kDa (branched) | —$CH_2CH(CH_3)OH$ (50%) —$C_6H_{13}$ (50%) |
| 21-1 | A | 25 kDa (hyper-branched) | —$CH_2CH(CH_3)OH$ (50%) —$C_6H_{13}$ (50%) |
| 22-1 | B | 70 kDa (branched) | —$CH_2CH(CH_3)OH$ (50%) —$C_6H_{13}$ (50%) |
| 23-1 | B | 70 kDa (branched) | —$CH_2CH(CH_3)OH$ (50%) —$CH_2C(O)Ph$ (50%) |
| 24-1 | B | 70 kDa (branched) | —$CH_2CH(CH_3)OH$ (50%) —$CH_2Ph$ (50%) |
| 26-1 | B | 70 kDa (branched) | —$CH_2CH(OH)CH_2N^+(CH_3)_3$ $Cl^-$(100%) |

48

-continued

| Compound | General Structure | PEI MW* | $R^{60}$ (mole %)** |
|---|---|---|---|
| 29-1 | B | 70 kDa (branched) | —$(CH_2)_3OH$ (1%) —$C_6H_{13}$ (99%) |
| 30-1 | A | 25 kDa (hyper-branched) | —$(CH_2)_3OH$ (10%) 75:25 —$C_{18}H_{37}$:—$C_8H_{17}$ (90%) |
| 31-1 | B | 70 kDa (branched) | —$C(O)(CH_2)_5OH$ (7%) —$C_6H_{13}$ (93%) |
| 32-1 | B | 70 kDa (branched) | —$(CH_2)_3OH$ (10%) —$C_6H_{13}$ (90%) |
| 32-2 | B | 70 kDa (branched) | —$(CH_2)_3OH$ (5%) —$C_6H_{13}$ (95%) |
| 32-3 | B | 70 kDa (branched) | —$CH_2CH(CH_3)OH$ (5%) —$C_6H_{13}$ (95%) |
| 32-4 | B | 70 kDa (branched) | —$C(O)(CH_2)_5OH$ (7.5%) —$C_6H_{13}$ (92.5%) |
| 32-5 | A | 25 kDa (hyper-branched) | —$CH_2CH(CH_3)OH$ (50%) 50:50 —$C_{18}H_{37}$:—$C_8H_{17}$ (50%) |
| 32-6 | B | 72 kDa (branched) | —$(CH_2)_3OH$ (13%) 75:25 —$C_{18}H_{37}$:—$C_8H_{17}$ (87%) |
| 32-7 | B | 72 kDa (branched) | —$C(O)(CH_2)_5OH$ (6.5%) 75:25 —$C_{18}H_{37}$:—$C_8H_{17}$ (93.5%) |
| 32-8 | A | 25 kDa (hyper-branched) | —$C(O)(CH_2)_5OH$ (7%) 75:25 —$C_{18}H_{37}$:—$C_8H_{17}$ (93%) |
| 32-9 | A | 25 kDa (hyper-branched) | —$CH_2CH(CH_3)OH$ (50%) 25:75 —$C_{18}H_{37}$:—$C_8H_{17}$ (50%) |

*indicates molecular weight of polyethyleneimine precursor

**theoretical stoichiometric ratio (based on amount of reactants used in the synthetic protocol) wherein A is B is and each n is an integer independently selected from 1 to 3000, preferably an integer independently selected from 10 to 100. In some embodiments, one or more bromide anions is replaced with $X^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the polyethyleneimine intermediate is selected from a group consisting of

| Compound | General Structure | PEI MW* | $R^{60}$ (mole %)** |
|---|---|---|---|
| 32-10 | A | 25 kDa (hyperbranched) | —C(O)(CH$_2$)$_5$OH (11%)<br>—C$_6$H$_{13}$ (89%) |
| 32-11 | B | 70 kDa (branched) | —C(O)(CH$_2$)$_5$OH (9%)<br>—C$_6$H$_{13}$ (91%) |
| 32-13 | B | 70 kDa (branched) | —(CH$_2$)$_3$OH (7%)<br>75:25 —C$_{18}$H$_{37}$:—C$_8$H$_{17}$ (93%) |
| 32-14 | A | 25 kDa (hyperbranched) | —(CH$_2$)$_3$OH (7%)<br>75:25 —C$_{18}$H$_{37}$:—C$_8$H$_{17}$ (93%) |
| 32-15 | B | 70 kDa (branched) | —C(O)(CH$_2$)$_5$OH (9%)<br>75:25 —C$_{18}$H$_{37}$:—C$_8$H$_{17}$ (91%) |
| 32-16 | A | 25 kDa (hyperbranched) | —C(O)(CH$_2$)$_5$OH (11%)<br>75:25 —C$_{18}$H$_{37}$:—C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |
| 32-1A | B | 70 kDa (branched) | —(CH$_2$)$_3$OH (10%)<br>—C$_6$H$_{13}$ (90%) |
| 32-1B | B | 70 kDa (branched) | —(CH$_2$)$_3$OH (10%)<br>—C$_6$H$_{13}$ (90%) |
| 32-2A | B | 70 kDa (branched) | —(CH$_2$)$_3$OH (5%)<br>—C$_6$H$_{13}$ (95%) |
| 32-2B | B | 70 kDa (branched) | —(CH$_2$)$_3$OH (5%)<br>—C$_6$H$_{13}$ (95%) |
| 32-2C | B | 70 kDa (branched) | —(CH$_2$)$_3$OH (15%)***<br>—C$_6$H$_{13}$ (85%) |
| 32-2D | B | 70 kDa (branched) | —(CH$_2$)$_3$OH (5%)<br>—C$_6$H$_{13}$ (95%) |
| 32-2E | B | 70 kDa (branched) | —(CH$_2$)$_3$OH (12%)***<br>—C$_6$H$_{13}$ (88%) |
| 32-2F | B | 70 kDa (branched) | —(CH$_2$)$_3$OH (5%)<br>—C$_6$H$_{13}$ (95%) |
| 32-2G | B | 70 kDa (branched) | —(CH$_2$)$_3$OH (5%)<br>—C$_6$H$_{13}$ (95%) |
| 32-2H | B | 70 kDa (branched) | —(CH$_2$)$_3$OH (5%)<br>—C$_6$H$_{13}$ (95%) |
| 32-2I | B | 70 kDa (branched) | —(CH$_2$)$_3$OH (5%)<br>—C$_6$H$_{13}$ (95%) |

*indicates molecular weight of polyethyleneimine precursor

**theoretical stoichiometric ratio (based on amount of reactants used in the synthetic protocol) unless otherwise indicated

***actual stoichiometric ratio as determined by NMR analysis wherein A is

B is each n is an integer independently selected from 1 to 3000, preferably an integer independently selected from 10 to 100; and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivative.

In some embodiments, the second adduct is of formula (I):

formula (I)

wherein:

each A is independently selected from

-continued or a copolymer or blend of any two or more thereof; and attachment of each A forms a carbamate linkage;

each $Y^3$ is independently H or $-O-Y^2$, wherein every $Y^3$ cannot be H;

each $Y^2$ is independently H or $-C(O)-NHR^{30}$, wherein every $Y^2$ cannot be $-C(O)-NHR^{30}$;

each n is an integer independently selected from 1 to 3000, preferably an integer independently selected from 10 to 1000;

Z is $-(C_2-C_6$ alkylene)-;

each $R^{10}$ is independently selected from hydrogen; $C_1-C_6$ alkyl optionally substituted with a substituent selected from $-N(R^{20})_3$, $-(C_6-C_{10}$ aryl), and $-(C_1-C_6$ alkoxy) optionally substituted with $-OH$, $-(C_1-C_6$ alkoxy), $-(C_6-C_{10}$ aryl) optionally substituted with $-(C_1-C_6$ alkyl), and carboxy; and each $R^{20}$ is independently selected from a group consisting of $C_1-C_{18}$ alkyl; $C_1-C_{18}$ heteroalkyl having 1 to 4 heteroatoms independently selected from O, S, Si and tertiary-substituted N; and $C_6-C_{10}$ aryl optionally substituted with $-(C_1-C_6$ alkyl), $-(C_1-C_6$ alkoxy), $-C(O)O-(C_1-C_6$ alkyl), $-C(O)NH(C_1-C_6$ alkyl), $-C(O)N(C_1-C_6$ alkyl$)_2$, or $-OC(O)-(C_1-C_6$ alkyl);

each $R^{21}$ is independently selected from $C_1-C_6$ alkyl optionally substituted with a substituent selected from $-OH$, $-(C_1-C_6$ alkoxy), carboxy, $-(C_6-C_{10}$ aryl), $-C(O)O(C_1-C_6$ alkyl), $-C(O)-(C_6-C_{10}$ aryl), and $-(C_1-C_6$ alkoxy) optionally substituted with $-OH$;

each $R^{30}$ is independently selected from (1) $C_6-C_{20}$ alkyl optionally substituted with 1-3 substituents independently selected from halogen, $-SiR^a(OR^b)(OR^c)$, and $-(C_6-C_{10}$ aryl); (2) $C_6-C_{10}$ aryl optionally substituted with 1-3 substituents independently selected from halogen, $-(C_1-C_6$ alkyl), and $-SiR^a(OR^b)(OR^c)$; and (3)

wherein each $R^a$ is independently —($C_1$-$C_6$ alkyl); and each $R^b$ and each $R^c$ are independently selected from —($C_1$-$C_6$ alkyl) and —Si($C_1$-$C_6$ alkyl)$_3$;

each $R^{40}$ is independently —($C_1$-$C_{10}$ alkylene)- optionally substituted with phenyl or a 3- to 8-member cycloalkyl ring; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives;

provided:

when $R^{10}$ is $C_1$-$C_6$ alkyl optionally substituted with a substituent selected from —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy, then each A is independently selected from In some embodiments, the second adduct is of formula (II):

formula (II)

wherein:

each A is independently selected from

55

-continued or a copolymer or blend of any two or more thereof;
and attachment of each A forms a carbamate linkage;

each $Y^3$ is independently H or —O—$Y^2$, wherein every $Y^3$ cannot be H;

each $Y^2$ is independently H or —C(O)—NHR$^{30}$, wherein every $Y^2$ cannot be —C(O)—NHR$^{30}$;

each n is an integer independently selected from 1 to 3000, preferably an integer independently selected from 10 to 1000;

Z is —(C$_2$-C$_6$ alkylene)-;

each $R^{10}$ is independently selected from hydrogen; C$_1$-C$_6$ alkyl optionally substituted with a substituent selected from —N(R$^{20}$)$_3$, —(C$_6$-C$_{10}$ aryl), and —(C$_1$-C$_6$ alkoxy) optionally substituted with —OH, —(C$_1$-C$_6$ alkoxy), —(C$_6$-C$_{10}$ aryl) optionally substituted with —(C$_1$-C$_6$ alkyl), and carboxy; and each R$^{20}$ is independently selected from a group consisting of C$_1$-C$_{18}$ alkyl; C$_1$-C$_{18}$ heteroalkyl having 1 to 4 heteroatoms independently selected from O, S, Si and tertiary-substituted N; and C$_6$-C$_{10}$ aryl optionally substituted with —(C$_1$-C$_6$ alkyl), —(C$_1$-C$_6$ alkoxy), —C(O)O—(C$_1$-C$_6$ alkyl), —C(O)NH(C$_1$-C$_6$ alkyl), —C(O)N(C$_1$-C$_6$ alkyl)$_2$, or —OC(O)—(C$_1$-C$_6$ alkyl);

each R$^{21}$ is independently selected from C$_1$-C$_6$ alkyl optionally substituted with a substituent selected from —OH, —(C$_1$-C$_6$ alkoxy), carboxy, —(C$_6$-C$_{10}$ aryl), —C(O)O(C$_1$-C$_6$ alkyl), —C(O)—(C$_6$-C$_{10}$ aryl), and —(C$_1$-C$_6$ alkoxy) optionally substituted with —OH;

each R$^{30}$ is independently selected from (1) C$_6$-C$_{20}$ alkyl optionally substituted with 1-3 substituents independently selected from halogen, —SiR$^a$(OR$^b$)(OR$^c$), and —(C$_6$-C$_{10}$ aryl); (2) C$_6$-C$_{10}$ aryl optionally substituted with 1-3 substituents independently selected from halogen, —(C$_1$-C$_6$ alkyl), and —SiR$^a$(OR$^b$)(OR$^c$); and (3)

wherein each R$^a$ is independently —(C$_1$-C$_6$ alkyl); and each R$^b$ and each R$^c$ are independently selected from —(C$_1$-C$_6$ alkyl) and —Si(C$_1$-C$_6$ alkyl)$_3$;

each R$^{40}$ is independently —(C$_1$-C$_{10}$ alkylene)- optionally substituted with phenyl or a 3- to 8-member cycloalkyl ring; and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives;

provided:

when R$^{10}$ is C$_1$-C$_6$ alkyl optionally substituted with a substituent selected from —(C$_6$-C$_{10}$ aryl), and —(C$_1$-C$_6$ alkoxy) optionally substituted with —OH, —(C$_1$-C$_6$ alkoxy), —(C$_6$-C$_{10}$ aryl) optionally substituted with —(C$_1$-C$_6$ alkyl), and carboxy, then each A is independently selected from -continued In some embodiments, the second adduct is present in the polymer, the copolymer, or the interpenetrating polymer network of polymeric component (1) or (4) in an amount of about 1 wt. % to about 30 wt. %. This includes about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt. %, or any value therebetween. In some embodiments, the second adduct is present in the polymer, the copolymer, or the interpenetrating polymer network of polymeric component (1) or (4) in an amount of from about 3 wt. % to about 15 wt. %.

The reagents for the random polymerization/crosslinking product may further comprise a third adduct of (i) the first multifunctional crosslinker or a fourth multifunctional crosslinker; and (ii) a second quaternary ammonium salt wherein $R^{1a}$, $R^{2a}$, and $R^{3a}$ are each independently —($C_1$-$C_{20}$ alkyl), —($C_1$-$C_{20}$ alkyl)-($C_6$-$C_{10}$ aryl), or —($C_6$-$C_{10}$ aryl)-($C_1$-$C_{20}$ alkyl);

$A^1$ is a linking group selected from a group consisting of —($C_3$-$C_{20}$ alkylene)-, —($C_3$-$C_{20}$ heteroalkylene)-, —($C_6$-$C_{10}$ arylene)-($C_3$-$C_{20}$ alkylene), —($CR^{m1}R^{n1}$)$_{x42}$ —$W^{42}$—($CR^{p1}R^{q1}$)$_{y42}$—, and —($CR^{m1}R^{n1}$)$_{x43}$— $W^{43}$—($CR^{p1}R^{q1}$)$_{y43}$—, wherein —($C_3$-$C_{20}$ heteroalkylene)- has 1 to 4 heteroatoms independently selected from O, S, and Si; and —($C_3$-$C_{20}$ alkylene)- and —($C_3$-$C_{20}$ heteroalkylene)- are optionally substituted with 1 to 6 substituents independently selected from —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl);

each $R^{m1}$, $R^{n1}$, $R^{p1}$, and $R^{q1}$ is independently selected from H and $C_1$-$C_4$ alkyl;

$W^{42}$ is selected from —C(O)—; —C(O)O—; —OC (O)—; —C(O)NH—; and —NHC(O)—;

$W^{43}$ is selected from 5- to 6-membered cycloalkyl, $C_6$-$C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein 3≤(x42+y42)≤20;

x43 is an integer from 1 to 20, and y43 is an integer from 0 to 19, wherein 3≤(x43+y43)≤20;

$Y^1$ is selected from a group consisting of —OH, —$NHR^{4a}$, —SH, —$CO_2H$, —C(O)$NHR^{4a}$, —C(S) $NHR^{4a}$, each $R^{4a}$ is independently selected from a group consisting of H, (C—($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$- $C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si; and $X^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

The fourth multifunctional crosslinker may be present in the polymer, the copolymer, or the interpenetrating polymer network of polymeric component (1) in an amount of about 0.1 wt. % to about 15 wt. %. This includes 0.1, 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 11, 12, 13, 14, or 15 wt. %, or any value therebetween. In some embodiments, the fourth multifunctional crosslinker is present in the polymer, the copolymer, or the interpenetrating polymer network of polymeric component (1) in an amount of about 2 wt. % to about 8 wt. %.

The fourth multifunctional crosslinker may be different from the first multifunctional crosslinker and, if present, from the second multifunctional crosslinker, and if present, from the third multifunctional crosslinker.

In some embodiments, the fourth multifunctional crosslinker is a fourth polyisocyanate. In some embodiments, the fourth polyisocyanate is prepared from diisocyanates selected from the group consisting of: hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI). In some embodiments, the fourth polyisocyanate is selected from the group consisting of DESMODUR® N-3300, DESMODUR® N-100, DESMODUR® Z4470SN, WANNATE® T series polyisocyanates, and LUPRANATE® M series polyisocyanates.

In some embodiments of the second quaternary ammonium salt, at least one of $R^{1a}$, $R^{2a}$, and $R^{3a}$ is —($C_1$-$C_4$ alkyl). In some embodiments of the second quaternary ammonium salt, two of $R^{1a}$, $R^{2a}$, and $R^{3a}$ is —($C_1$-$C_4$ alkyl). In some embodiments, the second quaternary ammonium salt is (C18DMDEG-Br)

(C2DMDEG-Br)

The second quaternary ammonium salt may be present in the polymer, the copolymer, or the interpenetrating polymer network of polymeric component (1) in an amount of about 1 wt. % to about 15 wt. %. This includes about 1, 2, 3, 4, 5, 6, 7, 8, 9, 10, 11, 12, 13, 14, or 15 wt. %, or any value therebetween. In some embodiments, the second quaternary ammonium salt is present in the polymer, the copolymer, or the interpenetrating polymer network of polymeric component (1) in an amount of about 3 wt. % to about 10 wt. %.

In some embodiments, the third adduct has an average isocyanate functionality of 2 to 3. In some embodiments, the third adduct has an average isocyanate functionality of 2.05 to about 2.3.

The third adduct may be present in the polymer, the copolymer, or the interpenetrating polymer network of polymeric component (1) in an amount of about 2 wt. % to about 30 wt. %. This includes about 2, 3, 4, 5, 6, 7, 8, 9, 10, 11, 12, 13, 14, 15, 16, 17, 18, 19, 20, 21, 22, 23, 24, 25, 26, 27, 28, 29, or 30 wt. %, or any value therebetween. In some embodiments, the second quaternary ammonium salt is present in the polymer, the copolymer, or the interpenetrating polymer network of polymeric component (1) in an amount of about 3 wt. % to about 20 wt. %.

The reagents for the random polymerization/crosslinking product may further comprise a chain extender selected from a group consisting of HO—($C_nH_{2n}$)—OH and HO—($C_nH_{2n-2}$)—OH, or a combination thereof, wherein n is an integral between 2 and 8. In some embodiments, the chain extender is propanediol, 1,4-butanediol, neopentyl glycol, hexanediol, cyclohexane dimethanol, or a combination of two or more thereof. The chain extender may be present in the polymer, copolymer, or interpenetrating polymer network of polymeric components (1) and (2) in an amount of about 0.5 wt. % to about 10 wt. %. This includes about 0.5, 1, 2, 3, 4, 5, 6, 7, 8, 9, or 10 wt. %, or any value therebetween. In some embodiments, the chain extender may be present in the polymer, copolymer, or interpenetrating polymer network of polymeric components (1) and (2) in an amount of about 1 wt. % to about 5 wt. %.

In some embodiments, the polymeric component is a polymer, interpenetrating polymer network, polyelectrolyte complex, blend, or composite, each of which comprises or consists essentially of a random polymerization/crosslinking product of reagents comprising, consisting essentially of, or consisting of (i) a first adduct of a first multifunctional crosslinker and a first quaternary ammonium salt; (ii) optionally a polyol; (iii) a polyethyleneimine intermediate or a second adduct of the polyethyleneimine intermediate and a second multifunctional crosslinker; (iv) optionally a third multifunctional crosslinker; (v) optionally a third adduct of (a) the first multifunctional crosslinker or a fourth multifunctional crosslinker, and (b) a second quaternary ammonium salt; (vi) optionally a chain extender; and (vii) a water-soluble polymer.

In some embodiments, the polymeric component is a polymer, interpenetrating polymer network, polyelectrolyte complex, blend, or composite, each of which comprises or consists essentially of a random polymerization/crosslinking product of reagents comprising, consisting essentially of, or consisting of (i) a first adduct of a first multifunctional crosslinker and a first quaternary ammonium salt; (ii) optionally a polyol; (iii) a polyethyleneimine intermediate or a second adduct of the polyethyleneimine intermediate and a second multifunctional crosslinker; (iv) optionally a third multifunctional crosslinker; (v) optionally a third adduct of (a) the first multifunctional crosslinker or a fourth multifunctional crosslinker, and (b) a second quaternary ammonium salt; and (vi) optionally a chain extender.

In some embodiments, the polymeric component further comprises a third quaternary ammonium salt wherein $R^{1a}$, $R^{2a}$, and $R^{3a}$ are each independently methyl or ethyl;

$A^2$ is selected from a group consisting of —($C_3$-$C_{20}$ alkylene)-, —($C_3$-$C_{20}$ heteroalkylene)-, —($C_6$-$C_{10}$ arylene)-($C_3$-$C_{20}$ alkylene)-, —($CR^{m1}R^{n1})_{x42}$—$W^{42}$—($CR^{p1}R^{q1})_{y42}$—, and —($CR^{m1}R^{n1})_{x43}$—$W^{43}$—($CR^{p1}R^{q1})_{y43}$—, wherein —($C_3$-$C_{20}$ heteroalkylene)- has 1 to 4 heteroatoms independently selected from O, S, and Si; and —($C_3$-$C_{20}$ alkylene)- and —($C_3$-$C_{20}$ heteroalkylene)- are optionally substituted with 1 to 6 substituents independently selected from —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl);

each $R^{m1}$, $R^{n1}$, $R^{p1}$, and $R^{q1}$ is independently selected from H and $C_1$-$C_4$ alkyl;

$W^{42}$ is selected from —C(O)—; —C(O)O—; —OC(O)—; —C(O)NH—; and —NHC(O)—;

$W^{43}$ is selected from 5- to 6-membered cycloalkyl, $C_6$-$C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein 3≤(x42+y42)≤20;

x43 is an integer from 1 to 20, and y43 is an integer from 0 to 19, wherein 3≤(x43+y43)≤20;

$Y^{1a}$ is H;

each $R^{4a}$ is independently selected from a group consisting of H, —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si; and X⁻ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

In some embodiments, a first quaternary ammonium salt reacts with a first polyisocyanate to form a first adduct, wherein the first adduct retains unreacted isocyanate functionality from the first polyisocyanate. In some embodiments, about 10% to about 40%, preferably about 25% to about 33% of isocyanate functionality on the first polyisocyanate is converted to, for example, urethane or urea by reaction with the first quaternary ammonium salt. The unreacted isocyanate functionality subsequently reacts with one or more of the polyol (if present), the chain extender (if present), the polyethyleneimine intermediate or the second adduct, water, and the water-soluble polymer (if reactive). Similarly, in some embodiments, the second quaternary ammonium salt reacts with the first polyisocyanate or a fourth polyisocyanate to form a third adduct, wherein the third adduct retains unreacted isocyanate functionality from the first or fourth polyisocyanate. In some embodiments, about 10% to about 40%, preferably about 25% to 33% of isocyanate functionality on the first or fourth polyisocyanate is converted to, for example, urethane or urea by reaction with the second quaternary ammonium salt. If present, the third multifunctional crosslinker and/or third adduct may also react with one or more of the polyol (if present), the chain extender (if present), the polyethyleneimine intermediate or the second adduct, water, and the water-soluble polymer (if reactive). The first adduct and the third adduct are pre-formed prior to interaction with the polyol (if present), the chain extender (if present), the polyethyleneimine intermediate or the second adduct, and the water-soluble polymer (if reactive).

In another aspect, a polymer or interpenetrating polymer network is prepared by (a) reacting a first multifunctional crosslinker with a first quaternary ammonium salt to form a first adduct;

(b) optionally reacting a polyethyleneimine intermediate with a second multifunctional crosslinker to form a second adduct;

(c) optionally reacting the first multifunctional crosslinker or a fourth multifunctional crosslinker with a second quaternary ammonium salt to form a third adduct;

(d) combining (i) the first adduct, (ii) the polyethyleneimine intermediate or the second adduct, and (iii) when present, the third adduct, with optionally a polyol and optionally a third multifunctional crosslinker to form an oil phase;

(e) dissolving a water-soluble polymer in water to form an aqueous phase;

(f) combining the oil phase and the aqueous phase to form an oil-in-water emulsion; and (g) applying the emulsion onto a surface and allowing the emulsion to dry and cure on the surface to form the polymer or interpenetrating polymer network on the surface.

In some embodiments, a blocking agent is added to the oil phase after step (d) but before step (f).

In some embodiments, step (d) further comprises combining (i) the first adduct, (ii) the polyethyleneimine intermediate or the second adduct, and (iii) when present, the third adduct with optionally the polyol and optionally the second multifunctional crosslinker in an organic solvent or diluent to form the oil phase.

In some embodiments, step (d) further comprises adding a chain extender to the oil phase. In some embodiments, step I further comprises adding a chain extender to the aqueous phase.

In some embodiments, step I further comprises adding a surfactant to the aqueous phase. In some embodiments, step I further comprises adding a defoamer or antifoamer to the aqueous phase. In some embodiments, step I further comprises adding a surfactant and either a defoamer or antifoamer to the aqueous phase.

In some embodiments, step (f) further comprises performing a direct emulsification process whereby the emulsion is formed by vigorous shear and mixing. In some embodiments, step (f) further comprises performing a direct emulsification process whereby the emulsion is formed by sonication.

In some embodiments, step (f) further comprises performing a phase inversion emulsification process whereby a water-in-oil emulsion is first prepared, followed by phase inversion to form the oil-in-water emulsion. The phase inversion may be conducted by, for example, changing the phase ratio, temperature, surfactant, solvent, or any combination of two or more thereof.

In some embodiments, a multiphase water-in-oil-in-water emulsion is formed prior to conversion to the oil-in-water emulsion in step (f).

In some embodiments, combining the oil phase and the aqueous phase in step (f) forms a combination of the oil-in-water emulsion and a multiphase water-in-oil-in-water emulsion.

In another aspect, reagents for the preparation of a polymer or interpenetrating polymer network described herein are comprised in a composition.

Accordingly, in another aspect, provided herein is a composition comprising an oil-in-water emulsion, wherein the oil-in-water emulsion comprises (i) an oil phase comprising a first adduct of a first multifunctional crosslinker and a first quaternary ammonium salt, wherein the first quaternary ammonium salt has a reactive linking group to react with the first multifunctional crosslinker;

optionally a polyol;

a polyethyleneimine intermediate, or a second adduct of the polyethyleneimine intermediate and a second multifunctional crosslinker; and optionally a third multifunctional crosslinker; and (ii) an aqueous phase comprising a water-soluble polymer.

This composition may be applied to a surface and allowed to dry and cure, thereby forming a polymer or interpenetrating polymer network of the present technology.

The reactive linking group of the first quaternary ammonium salt may be selected from a group consisting of —OH, —NHR⁴, —SH, —CO₂H, —C(O)NHR⁴, —C(S)NHR⁴, wherein each R⁴ is independently selected from a group consisting of H, —(C₆-C₁₀ aryl)-(C₁-C₃ alkyl), —(C₆-C₁₀ aryl)-(C₁-C₃ heteroalkyl), —(C₁-C₃ alkyl)-(C₆-C₁₀ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si.

The first quaternary ammonium salt, as described herein and incorporated into the first adduct, may be present in the oil phase in an amount of about 1% to about 50% by weight based on the dry weight of the oil phase. As used herein, and unless otherwise indicated, "dry weight of the oil phase" refers to weight of the oil phase in the absence of any organic solvent and any water. This includes about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%, or any value therebetween. In some embodiments, the first quaternary ammonium salt, incorporated into the first adduct, is present in the oil phase in an amount of about 1% to about 25%, or about 5% to about 25% by weight based on the dry weight of the oil phase.

The first multifunctional crosslinker (e.g., the first polyisocyanate), as described herein and incorporated into the first adduct, may be present in the oil phase in an amount of about 2% to about 25% by weight based on the dry weight of the oil phase. This includes about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, or any value therebetween. In some embodiments, the first multifunctional crosslinker (e.g., the first polyisocyanate), incorporated into the first adduct, is present in the oil phase in an amount of about 5% to about 20% by weight based on the dry weight of the oil phase.

The first adduct as described herein may be present in the oil phase in an amount of about 5% to about 70% by weight based on the dry weight of the oil phase. This includes about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%, or any value therebetween. In some embodiments, the first adduct is present in an amount of about 10% to about 50%, about 15% to about 65%, about 15% to about 60%, about 15% to about 50%, about 20% to about 70%, about 20% to about 60%, or about 20% to about 50%, by weight based on the dry weight of the oil phase.

The polyethyleneimine intermediate as described herein may be present in the oil phase in an amount of about 0.1% to about 50% by weight based on the dry weight of the oil phase. This includes 0.1%, 0.25%, 0.5%, 0.75%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%, or any value therebetween. In some embodiments, the polyethyleneimine intermediate is present in the oil phase in an amount of about 3% to about 30% by weight based on the dry weight of the oil phase.

The second multifunctional crosslinker (e.g., the second polyisocyanate), as described herein and incorporated into the second adduct, may be present in the oil phase in an amount of about 0.1% to about 10% by weight based on the dry weight of the oil phase. This includes about 0.1%, 0.25%, 0.5%, 0.75%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%, or any value therebetween. In some embodiments, the second multifunctional crosslinker (e.g., the second polyisocyanate) is present in the oil phase in an amount of about 2% to about 8%, or about 3% to about 6%, by weight based on the dry weight of the oil phase.

The second adduct as described herein may be present in the oil phase in an amount of about 1% to about 30% by weight based on the dry weight of the oil phase. This includes about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any value therebetween. In some embodiments, the second adduct is present in the oil phase in an amount of about 3% to about 15% by weight based on the dry weight of the oil phase.

In some embodiments, the oil phase further comprises a third multifunctional crosslinker as described herein. The third multifunctional crosslinker (e.g., the third polyisocyanate) may be present in the oil phase in an amount of about 5% to about 25% by weight based on the dry weight of the oil phase. This includes about 5%, 6%, 7%, 8%, 9%, 10%, 11%, 12%, 13%, 14%, 15%, 16%, 17%, 18%, 19%, 20%, 21%, 22%, 23%, 24%, or 25%, or any value therebetween. In some embodiments, the third multifunctional crosslinker (e.g., the third polyisocyanate) is present in the oil phase in an amount of about 5% to about 20% by weight based on the dry weight of the oil phase.

In some embodiments, the oil phase further comprises a third adduct as described herein. The third adduct may be present in the oil phase in an amount of about 2% to about 30% by weight based on the dry weight of the oil phase. This includes about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, or any value therebetween. In some embodiments, the third adduct is present in the oil phase in an amount of about 3% to about 20% by weight based on the dry weight of the oil phase.

In some embodiments, the second quaternary ammonium salt, as described herein and incorporated into the third adduct, is present in the oil phase in an amount of about 1% to about 15% by weight based on the dry weight of the oil phase. This includes about 1%, 2%, 3%, 4%, 5%, 6%, 7%, 8%, 9%, 10%, 11%, 12%, 13%, 14%, or 15%, or any value therebetween. In some embodiments, the second quaternary ammonium salt, as described herein and incorporated into the third adduct, is present in the oil phase in an amount of about 3% to about 10% by weight based on the dry weight of the oil phase.

The fourth multifunctional crosslinker (e.g., the fourth polyisocyanate), as described herein and incorporated into the third adduct, may be present in the oil phase in an amount of about 0.1% to about 15% by weight based on the dry weight of the oil phase. This includes about 0.1%, 0.25%, 0.5%, 0.75%, 1%, 1.5%, 2%, 2.5%, 3%, 3.5%, 4%, 4.5%, 5%, 4.5%, 6%, 6.5%, 7%, 7.5%, 8%, 8.5%, 9%, 9.5%, 10%, 11%, 12%, 13%, 14%, or 15%, or any value therebetween. In some embodiments, the fourth multifunctional crosslinker (e.g., the fourth polyisocyanate), as described herein and incorporated into the third adduct, is present in the oil phase in an amount of about 2% to about 8% by weight based on the dry weight of the oil phase.

In some embodiments, reactive isocyanate functionality on the first adduct and/or the third adduct is protected with a blocking agent. Reaction with the blocking agent converts the reactive isocyanate functionality to blocked isocyanates (i.e., the isocyanate group is reversibly protected from immediate reaction with a nucleophile). This decreases the rate of polyisocyanate reaction with water in a subsequent emulsification step and/or the cross-linking reaction with, for example, any polyol(s) in the oil phase and/or the water-soluble polymer (such as hydroxyethyl cellulose) in the aqueous phase. In some embodiments, there is significant improvement in the reproducibility of the rheology properties, particle size and distribution of the resultant emulsion. In some embodiments, the coatability and process window of the coating process are also significantly improved. In some embodiments, the defect rate of resultant surface coatings is reduced and the yield rate of coated products is also improved. In some embodiments, no blocking agent is used in order to provide a more rapidly curing coating.

In some embodiments, the blocking agent is selected from a group consisting of oximes, phenols, malonates, alcohols, lactams, dicarbonyl compounds, hydroxamates, bisulfite addition compounds, hydroxylamines, esters of p-hydroxybenzoic acid and salicylic acid. In some embodiments, the blocking agent is selected from a group consisting of acetone oxime, methyl ethyl ketone oxime, sodium bisulfite, diethyl malonate, and 3,5-dimethylpyrazole.

In some embodiments, the composition further comprises a de-blocking agent. The de-blocking agent includes, but is not limited to, organotin, organobismuth, and tert-amines. Non-limiting examples include triethanolamine; N,N,N'N'-tetrakis(2-hydroxyethyl) ethylene diamine; and K-KAT XK-651 (bismuth carboxylate catalyst).

In some embodiments, the oil phase further comprises a chain extender selected from a group consisting of HO—$(C_nH_{2n})$—OH and HO—$(C_nH_{2n-2})$—OH, or a combination thereof, wherein n is an integral between 2 and 8. In some embodiments, the chain extender is propanediol, 1,4-butanediol, neopentyl glycol, hexanediol, cyclohexane dimethanol, or a combination of two or more thereof. The chain extender may be present in the oil phase in an amount of up to about 10% by weight based on the dry weight of the oil phase. This includes about 0.5%, 1%, 2%, 3%, 4%, 5%, 6%, 7%, 8%, 9%, 10%, or any value therebetween. In some embodiments, the chain extender is present in the oil phase in an amount of about 0.5% to about 10%, or about 1% to about 5% by weight based on the dry weight of the oil phase.

In some embodiments, the oil phase further comprises an organic solvent or diluent. In some embodiments, the organic solvent or diluent in the oil phase is water miscible. In some embodiments, the organic solvent or diluent is acetone. In some embodiments, the organic solvent or diluent is present in the oil phase in an amount of about 5% to about 35% by weight based on the weight of the oil phase. This includes about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%, or any value therebetween. In some embodiments, the organic solvent or diluent is present in the oil phase in an amount of about 10% to about 30% by weight based on the weight of the oil phase.

The polyol may be present in the oil phase in an amount of about 1% to about 40% by weight based on the dry weight of the oil phase. This includes about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%, or any value therebetween. In some embodiments, the polyol is present in the oil phase in an amount of about 5% to about 25% by weight based on the dry weight of the oil phase.

Weight percentage of the water-soluble polymer in the aqueous phase is calculated by the amount present in the oil phase for interaction with the oil phase itself and/or oil phase constituents (e.g., the first adduct, the optional second multifunctional crosslinker). The water-soluble polymer as described herein may be present in the aqueous phase in amount of about 0.5% to about 15% by weight of the dry weight of the oil phase. This includes about 0.5%, 1%, 2%, 3%, 4%, 5%, 6%, 7%, 8%, 9%, 10%, 11%, 12%, 13%, 14%, or 15%, or any value therebetween. In some embodiments, the water-soluble polymer as described herein is present in the aqueous phase in amount of about 3% to about 12%, or about 5% to about 10% by weight of the dry weight of the oil phase.

The water-soluble polymer may be a reactive water-soluble polymer and crosslinks with one or more of the first adduct and the third multifunctional crosslinker (if present). In some embodiments, the water-soluble polymer is a reactive water-soluble polymer and crosslinks with the first adduct, the third multifunctional crosslinker (if present), the third adduct (if present), or any combination of two or more thereof.

In some embodiments, the water-soluble polymer is a non-reactive water-soluble polymer and does not covalently bond to any component (e.g., the first adduct, the third multifunctional crosslinker (if present), the third adduct (if present), or any combination of two or more thereof) in the oil or water phase.

In some embodiments, the aqueous phase further comprises a water-soluble low molecular weight chain extender or crosslinker. The inclusion of the water-soluble low molecular weight chain extender or crosslinker may increase the degree of crosslinking of the random polymerization product. Examples of a water-soluble low molecular weight chain extender or crosslinker include, but are not limited to, multifunctional amines such as ethylene diamine, diethylene triamine, and triethylene tetraamine.

In some embodiments, the aqueous phase further comprises a surfactant. In some embodiments, the surfactant is a non-ionic surfactant. In some embodiments, the non-ionic surfactant preferably has an average HLB (hydrophilic-lipophilic balance) value of about 12 to about 15. Non-ionic surfactants include, but are not limited to, TRITON™ X-114 ((1,1,3,3-tetramethylbutyl)phenyl-polyethylene glycol), SILWET™ L-7604 (siloxane polyalkyleneoxide copolymer), and a combination thereof.

Weight percentage of the surfactant in the aqueous phase is calculated by the amount present in the oil phase for interaction with or adsorption on the oil phase. The surfactant may be present in the aqueous phase in an amount of about 0.01% to about 2% by weight based on the dry weight of the oil phase. This includes about 0.05%, 0.075%, 0.1%, 0.25%, 0.5%, 0.75%, 1%, 1.25%, 1.5%, 1.75%, or 2%, or any value therebetween. In some embodiments, the surfactant is present in the aqueous phase in an amount of about 0.05% to about 2%, or about 0.1% to about 1% by weight based on the dry weight of the oil phase.

In some embodiments, the aqueous phase further comprises a defoamer or antifoamer. In some embodiments, the defoamer is FOAMSTAR® ST 2410 (star polymer-based defoamer).

The polyethyleneimine intermediates may be used as antimicrobial compounds. In some embodiments, quaternization is not on the polyethyleneimine backbone, but on pendant substitution. Accordingly, in another aspect, provided herein is an antimicrobial compound selected from:

-continued or a copolymer or a blend of any two or more thereof, wherein:

each $Y^3$ is independently H or —O—$Y^2$;

each $Y^2$ is independently H or —C(O)—NHR$^{30}$;

each n is an integer independently selected from 1 to 3000, preferably an integer independently selected from 10 to 1000;

Z is —(C$_2$-C$_6$ alkylene)-;

each $R^{10}$ is C$_1$-C$_6$ alkyl substituted with —N$^+$(R$^{20}$)$_3$X$^-$, and each $R^{20}$ is independently selected from a group consisting of C$_1$-C$_{18}$ alkyl; C$_1$-C$_{18}$ heteroalkyl having 1 to 4 heteroatoms independently selected from O, S, Si and tertiary-substituted N; and C$_6$-C$_{10}$ aryl optionally substituted with —(C$_1$-C$_6$ alkyl), —(C$_1$-C$_6$ alkoxy), —C(O)O—(C$_1$-C$_6$ alkyl), —C(O)NH(C$_1$-C$_6$ alkyl), —C(O)N(C$_1$-C$_6$ alkyl)$_2$, or —OC(O)—(C$_1$-C$_6$ alkyl);

each $R^{21}$ is independently selected from C$_1$-C$_6$ alkyl optionally substituted with a substituent selected from —OH, —(C$_1$-C$_6$ alkoxy), carboxy, —(C$_6$-C$_{10}$ aryl), —C(O)O(C$_1$-C$_6$ alkyl), —C(O)—(C$_6$-C$_{10}$ aryl), and —(C$_1$-C$_6$ alkoxy) optionally substituted with —OH;

each $R^{30}$ is independently selected from (1) C$_6$-C$_{20}$ alkyl optionally substituted with 1-3 substituents independently selected from halogen, —SiR$^a$(OR$^b$)(OR$^c$), and —(C$_6$-C$_{10}$ aryl); and (2) C$_6$-C$_{10}$ aryl optionally substituted with 1-3 substituents independently selected from halogen, —(C$_1$-C$_6$ alkyl), and —SiR$^a$(OR$^b$)(OR$^c$); wherein each $R^a$ is independently —(C$_1$—C$_6$ alkyl); and each $R^b$ and each $R^c$ are independently selected from —(C$_1$-C$_6$ alkyl) and —Si(C$_1$-C$_6$ alkyl)$_3$; and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, each $Y^2$ is H.

In some embodiments, the compound is selected from:

| Compound | General Structure | PEI MW* | $R^{60}$ (mole %)** |
|---|---|---|---|
| 20-1 (batch 105159) | B | 270 kDa (branched) | —CH$_2$CH(CH$_3$)OH (<50%) <br> —C$_6$H$_{13}$ (>50%) |
| 20-1 (batch 99367) | B | 270 kDa (branched) | —CH$_2$CH(CH$_3$)OH (50%) <br> —C$_6$H$_{13}$ (50%) |
| 21-1 | A | 25 kDa (hyperbranched) | —CH$_2$CH(CH$_3$)OH (50%) <br> —C$_6$H$_{13}$ (50%) |
| 22-1 | B | 70 kDa (branched) | —CH$_2$CH(CH$_3$)OH (50%) <br> —C$_6$H$_{13}$ (50%) |
| 23-1 | B | 70 kDa (branched) | —CH$_2$CH(CH$_3$)OH (50%) <br> —CH$_2$C(O)Ph (50%) |
| 24-1 | B | 70 kDa (branched) | —CH$_2$CH(CH$_3$)OH (50%) <br> —CH$_2$Ph (50%) |
| 26-1 | B | 70 kDa (branched) | —CH$_2$CH(OH)CH$_2$N$^+$(CH$_3$)$_3$ Cl$^-$ (100%) |
| 29-1 | B | 70 kDa (branched) | —(CH$_2$)$_3$OH (1%) <br> —C$_6$H$_{13}$ (99%) |
| 30-1 | A | 25 kDa (hyperbranched) | —(CH$_2$)$_3$OH (10%) <br> 75:25 —C$_{18}$H$_{37}$:—C$_8$H$_{17}$ (90%) |
| 31-1 | B | 70 kDa (branched) | —C(O)(CH$_2$)$_5$OH (7%) <br> —C$_6$H$_{13}$ (93%) |
| 32-1 | B | 70 kDa (branched) | —(CH$_2$)$_3$OH (10%) <br> —C$_6$H$_{13}$ (90%) |
| 32-2 | B | 70 kDa (branched) | —(CH$_2$)$_3$OH (5%) <br> —C$_6$H$_{13}$ (95%) |
| 32-3 | B | 70 kDa (branched) | —CH$_2$CH(CH$_3$)OH (5%) <br> —C$_6$H$_{13}$ (95%) |
| 32-4 | B | 70 kDa (branched) | —C(O)(CH$_2$)$_5$OH (7.5%) <br> —C$_6$H$_{13}$ (92.5%) |
| 32-5 | A | 25 kDa (hyperbranched) | —CH$_2$CH(CH$_3$)OH (50%) <br> 50:50 —C$_{18}$H$_{37}$:—C$_8$H$_{17}$ (50%) |
| 32-6 | B | 72 kDa (branched) | —(CH$_2$)$_3$OH (13%) <br> 75:25 —C$_{18}$H$_{37}$:—C$_8$H$_{17}$ (87%) |
| 32-7 | B | 72 kDa (branched) | —C(O)(CH$_2$)$_5$OH (6.5%) <br> 75:25 —C$_{18}$H$_{37}$:—C$_8$H$_{17}$ (93.5%) |
| 32-8 | A | 25 kDa (hyperbranched) | —C(O)(CH$_2$)$_5$OH (7%) <br> 75:25 —C$_{18}$H$_{37}$:—C$_8$H$_{17}$ (93%) |
| 32-9 | A | 25 kDa (hyperbranched) | —CH$_2$CH(CH$_3$)OH (50%) <br> 25:75 —C$_{18}$H$_{37}$:—C$_8$H$_{17}$ (50%) |

*indicates molecular weight of polyethyleneimine precursor

**theoretical stoichiometric ratio (based on amount of reactants used in the synthetic protocol) wherein A is B is and each n is an integer independently selected from 1 to 3000, or 2 to 3000, preferably an integer independently selected from 10 to 100. In some embodiments, one or more bromide anions is replaced with X$^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the compound is selected from:

| Compound | General Structure | PEI MW* | $R^{60}$ (mole %)** |
|---|---|---|---|
| 32-10 | A | 25 kDa (hyperbranched) | —C(O)(CH$_2$)$_5$OH (11%) <br> —C$_6$H$_{13}$ (89%) |

-continued

| Compound | General Structure | PEI MW* | $R^{60}$ (mole %)** |
|---|---|---|---|
| 32-11 | B | 70 kDa (branched) | —C(O)(CH$_2$)$_5$OH (9%)<br>—C$_6$H$_{13}$ (91%) |
| 32-13 | B | 70 kDa (branched) | —(CH$_2$)$_3$OH (7%)<br>75:25 —C$_{18}$H$_{37}$:—C$_8$H$_{17}$ (93%) |
| 32-14 | A | 25 kDa (hyperbranched) | —(CH$_2$)$_3$OH (7%)<br>75:25 —C$_{18}$H$_{37}$:—C$_8$H$_{17}$ (93%) |
| 32-15 | B | 70 kDa (branched) | —C(O)(CH$_2$)$_5$OH (9%)<br>75:25 —C$_{18}$H$_{37}$:—C$_8$H$_{17}$ (91%) |
| 32-16 | A | 25 kDa (hyperbranched) | —C(O)(CH$_2$)$_5$OH (11%)<br>75:25 —C$_{18}$H$_{37}$:— C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |
| 32-1A | B | 70 kDa (branched) | —(CH$_2$)$_3$OH (10%)<br>—C$_6$H$_{13}$ (90%) |
| 32-1B | B | 70 kDa (branched) | —(CH$_2$)$_3$OH (10%)<br>—C$_6$H$_{13}$ (90%) |
| 32-2A | B | 70 kDa (branched) | —(CH$_2$)$_3$OH (5%)<br>—C$_6$H$_{13}$ (95%) |
| 32-2B | B | 70 kDa (branched) | —(CH$_2$)$_3$OH (5%)<br>—C$_6$H$_{13}$ (95%) |
| 32-2C | B | 70 kDa (branched) | —(CH$_2$)$_3$OH (15%)***<br>—C$_6$H$_{13}$ (85%) |
| 32-2D | B | 70 kDa (branched) | —(CH$_2$)$_3$OH (5%)<br>—C$_6$H$_{13}$ (95%) |
| 32-2E | B | 70 kDa (branched) | —(CH$_2$)$_3$OH (12%)***<br>—C$_6$H$_{13}$ (88%) |
| 32-2F | B | 70 kDa (branched) | —(CH$_2$)$_3$OH (5%)<br>—C$_6$H$_{13}$ (95%) |
| 32-2G | B | 70 kDa (branched) | —(CH$_2$)$_3$OH (5%)<br>—C$_6$H$_{13}$ (95%) |
| 32-2H | B | 70 kDa (branched) | —(CH$_2$)$_3$OH (5%)<br>—C$_6$H$_{13}$ (95%) |
| 32-21 | B | 70 kDa (branched) | —(CH$_2$)$_3$OH (5%)<br>—C$_6$H$_{13}$ (95%) |

*indicates molecular weight of polyethyleneimine precursor

**theoretical stoichiometric ratio (based on amount of reactants used in the synthetic protocol) unless otherwise indicated

***actual stoichiometric ratio as determined by NMR analysis wherein A is

3 X⁻

B is

4 X⁻ each n is an integer independently selected from 1 to 3000, or 2 to 3000, preferably an integer independently selected from 10 to 100; and each X⁻ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivative.

The second adduct, which is a random polymerization product of the polyethyleneimine intermediates disclosed herein with a (multifunctional) crosslinker, may be used as an antimicrobial compound. Accordingly, provided herein, in another aspect, is a random polymerization product of a polyethyleneimine intermediate and a crosslinker, wherein the polyethyleneimine intermediate is selected from:

73

74

-continued or a copolymer or blend of any two or more thereof, wherein:

each $Y^3$ is independently H or —O—$Y^2$, wherein every $Y^3$ cannot be H;

each $Y^2$ is independently H or —C(O)—$NHR^{30}$, wherein every $Y^2$ cannot be —C(O)—$NHR^{3a}$;

each n is an integer independently selected from 1 to 3000, preferably an integer independently selected from 10 to 1000;

Z is —($C_2$-$C_6$ alkylene)-;

each $R^{10}$ is $C_1$-$C_6$ alkyl substituted with —$N^+(R^{20})_3X^-$, and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl);

each $R^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH;

each $R^{30}$ is independently selected from (1) $C_6$-$C_{20}$ alkyl optionally substituted with 1-3 substituents independently selected from halogen, —$SiR^a(OR^b)(OR^c)$, and —($C_6$-$C_{10}$ aryl); and (2) $C_6$-$C_{10}$ aryl optionally substituted with 1-3 substituents independently selected from halogen, —($C_1$-$C_6$ alkyl), and —$SiR^a(OR^b)(OR^c)$; wherein each $R^a$ is independently —($C_1$—$C_6$ alkyl); and each $R^b$ and each $R^c$ are independently selected from —($C_1$-$C_6$ alkyl) and —$Si(C_1$-$C_6$ alkyl)$_3$; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the crosslinker is a polyisocyanate. In some embodiments, the polyisocyanate is prepared from a diisocyanate independently selected from a group consisting of hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethyl-hexamethylene diisocyanate (TMDI). In some embodiments, the polyisocyanate is independently selected from a group consisting of DESMODUR® N-3300, DESMODUR® N-100, DESMODUR® Z4470SN, WANNATE® T series polyisocyanates, and LUPRANATE® M series polyisocyanates.

In some embodiments, the random polymerization product is of formula (I):

formula (I)

wherein:

each A is independently selected from

-continued or a copolymer or a blend of any two or more thereof; and attachment of each A forms a carbamate linkage;

each $Y^3$ is independently H or —O—$Y^2$, wherein every $Y^3$ cannot be H;

each $Y^2$ is independently H or —C(O)—$NHR^{30}$, wherein every $Y^2$ cannot be —C(O)—$NHR^{30}$;

each n is an integer independently selected from 1 to 3000, preferably an integer independently selected from 10 to 1000;

Z is —($C_2$-$C_6$ alkylene)-;

each $R^{10}$ is $C_1$-$C_6$ alkyl substituted with —$N^+(R^{20})_3X^-$, and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl);

each $R^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH;

each $R^{30}$ is independently selected from (1) $C_6$-$C_{20}$ alkyl optionally substituted with 1-3 substituents independently selected from halogen, —$SiR^a(OR^b)(OR^c)$, and —($C_6$-$C_{10}$ aryl); (2) $C_6$-$C_{10}$ aryl optionally substituted with 1-3 substituents independently selected from halogen, —($C_1$-$C_6$ alkyl), and —$SiR^a(OR^b)(OR^c)$; and (3)

wherein each $R^a$ is independently —$(C_1$-$C_6$ alkyl); and each $R^b$ and each $R^c$ are independently selected from —$(C_1$-$C_6$ alkyl) and —$Si(C_1$-$C_6$ alkyl)$_3$;

each $R^{40}$ is independently —$(C_1$-$C_{10}$ alkylene)- optionally substituted with phenyl or a 3- to 8-member cycloalkyl ring; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the random polymerization product is of formula (II):

formula (II)

wherein:

each A is independently selected from or a copolymer or a blend of any two or more thereof; and attachment of each A forms a carbamate linkage;

each $Y^3$ is independently H or —O—$Y^2$, wherein every $Y^3$ cannot be H;

each $Y^2$ is independently H or —C(O)—$NHR^{30}$, wherein every $Y^2$ cannot be —C(O)—$NHR^{30}$;

each n is an integer independently selected from 1 to 3000, preferably an integer independently selected from 10 to 1000;

Z is —$(C_2$-$C_6$ alkylene)-;

each $R^{10}$ is $C_1$-$C_6$ alkyl substituted with —$N^+(R^{20})_3X^-$, and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —$(C_1$-$C_6$ alkyl), —$(C_1$-$C_6$ alkoxy), —C(O)O—$(C_1$-$C_6$ alkyl), —C(O)NH$(C_1$-$C_6$ alkyl), —C(O)N$(C_1$-$C_6$ alkyl)$_2$, or —OC(O)—$(C_1$-$C_6$ alkyl);

each $R^{21}$ is independently selected from $C_1$-$C_6$ alkyl optionally substituted with a substituent selected from —OH, —$(C_1$-$C_6$ alkoxy), carboxy, —$(C_6$-$C_{10}$ aryl), —C(O)O$(C_1$-$C_6$ alkyl), —C(O)—$(C_6$-$C_{10}$ aryl), and —$(C_1$-$C_6$ alkoxy) optionally substituted with —OH;

each $R^{3b}$ is independently selected from (1) $C_6$-$C_{20}$ alkyl optionally substituted with 1-3 substituents independently selected from halogen, —SiR$^a$(OR$^b$)(OR$^c$), and —$(C_6$-$C_{10}$ aryl); (2) $C_6$-$C_{10}$ aryl optionally substituted with 1-3 substituents independently selected from halogen, —$(C_1$-$C_6$ alkyl), and —SiR$^a$(OR$^b$)(OR$^c$); and (3)

wherein each $R^a$ is independently —$(C_1$-$C_6$ alkyl); and each $R^b$ and each $R^c$ are independently selected from —$(C_1$-$C_6$ alkyl) and —Si$(C_1$-$C_6$ alkyl)$_3$;

each $R^{40}$ is independently —$(C_1$-$C_{10}$ alkylene)- optionally substituted with phenyl or a 3- to 8-member cycloalkyl ring; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

Provided herein, in another aspect, is a polymer having wound healing properties comprising, consisting essentially of, or consisting of a polyethyleneimine intermediate, wherein the polyethyleneimine intermediate has a ratio of total quaternary amines to total hydroxyl groups of at least 1:1.

In some embodiments, the polymer is selected from a group consisting of:

| Compound | General Structure | PEI MW* | $R^{60}$ (mole %)** |
|---|---|---|---|
| 20-1 (batch 105159) | B | 270 kDa (branched) | —CH$_2$CH(CH$_3$)OH (<50%) —C$_6$H$_{13}$ (>50%) |
| 20-1 (batch 99367) | B | 270 kDa (branched) | —CH$_2$CH(CH$_3$)OH (50%) —C$_6$H$_{13}$ (50%) |
| 21-1 | A | 25 kDa (hyperbranched) | —CH$_2$CH(CH$_3$)OH (50%) —C$_6$H$_{13}$ (50%) |
| 22-1 | B | 70 kDa (branched) | —CH$_2$CH(CH$_3$)OH (50%) —C$_6$H$_{13}$ (50%) |
| 23-1 | B | 70 kDa (branched) | —CH$_2$CH(CH$_3$)OH (50%) —CH$_2$C(O)Ph (50%) |
| 24-1 | B | 70 kDa (branched) | —CH$_2$CH(CH$_3$)OH (50%) —CH$_2$Ph (50%) |
| 26-1 | B | 70 kDa (branched) | —CH$_2$CH(OH)CH$_2$N$^+$(CH$_3$)$_3$ Cl$^-$ (100%) |
| 29-1 | B | 70 kDa (branched) | —(CH$_2$)$_3$OH (1%) —C$_6$H$_{13}$ (99%) |
| 30-1 | A | 25 kDa (hyperbranched) | —(CH$_2$)$_3$OH (10%) 75:25 —C$_{18}$H$_{37}$:—C$_8$H$_{17}$ (90%) |
| 31-1 | B | 70 kDa (branched) | —C(O)(CH$_2$)$_5$OH (7%) —C$_6$H$_{13}$ (93%) |
| 32-1 | B | 70 kDa (branched) | —(CH$_2$)$_3$OH (10%) —C$_6$H$_{13}$ (90%) |
| 32-2 | B | 70 kDa (branched) | —(CH$_2$)$_3$OH (5%) —C$_6$H$_{13}$ (95%) |
| 32-3 | B | 70 kDa (branched) | —CH$_2$CH(CH$_3$)OH (5%) —C$_6$H$_{13}$ (95%) |
| 32-4 | B | 70 kDa (branched) | —C(O)(CH$_2$)$_5$OH (7.5%) —C$_6$H$_{13}$ (92.5%) |
| 32-5 | A | 25 kDa (hyperbranched) | —CH$_2$CH(CH$_3$)OH (50%) 50:50 —C$_{18}$H$_{37}$:—C$_8$H$_{17}$ (50%) |
| 32-6 | B | 72 kDa (branched) | —(CH$_2$)$_3$OH (13%) 75:25 —C$_{18}$H$_{37}$:—C$_8$H$_{17}$ (87%) |

-continued

| Compound | General Structure | PEI MW* | $R^{60}$ (mole %)** |
|---|---|---|---|
| 32-7 | B | 72 kDa (branched) | —C(O)(CH$_2$)$_5$OH (6.5%)<br>75:25 —C$_{18}$H$_{37}$:—C$_8$H$_{17}$ (93.5%) |
| 32-8 | A | 25 kDa (hyperbranched) | —C(O)(CH$_2$)$_5$OH (7%)<br>75:25 —C$_{18}$H$_{37}$:—C$_8$H$_{17}$ (93%) |
| 32-9 | A | 25 kDa (hyperbranched) | —CH$_2$CH(CH$_3$)OH (50%)<br>25:75 —C$_{18}$H$_{37}$:—C$_8$H$_{17}$ (50%) |

*indicates molecular weight of polyethyleneimine precursor
**theoretical stoichiometric ratio (based on amount of reactants used in the synthetic protocol) wherein A is $$3\ Br^-$$

B is $$4\ Br^-$$

and each n is an integer independently selected from 2 to 3000, preferably an integer independently selected from 10 to 100.

In some embodiments, the polymer is selected from a group consisting of:

| Compound | General Structure | PEI MW* | $R^{60}$ (mole %)** |
|---|---|---|---|
| 20-1 (batch 105159) | B | 270 kDa (branched) | —CH$_2$CH(CH$_3$)OH (<50%)<br>—C$_6$H$_{13}$ (>50%) |
| 29-1 | B | 70 kDa (branched) | —(CH$_2$)$_3$OH (1%)<br>—C$_6$H$_{13}$ (99%) |
| 30-1 | A | 25 kDa (hyperbranched) | —(CH$_2$)$_3$OH (10%)<br>75:25 —C$_{18}$H$_{37}$:—C$_8$H$_{17}$ (90%) |
| 31-1 | B | 70 kDa (branched) | —C(O)(CH$_2$)$_5$OH (7%)<br>—C$_6$H$_{13}$ (93%) |
| 32-1 | B | 70 kDa (branched) | —(CH$_2$)$_3$OH (10%)<br>—C$_6$H$_{13}$ (90%) |
| 32-2 | B | 70 kDa (branched) | —(CH$_2$)$_3$OH (5%)<br>—C$_6$H$_{13}$ (95%) |
| 32-3 | B | 70 kDa (branched) | —CH$_2$CH(CH$_3$)OH (5%)<br>—C$_6$H$_{13}$ (95%) |
| 32-4 | B | 70 kDa (branched) | —C(O)(CH$_2$)$_5$OH (7.5%)<br>—C$_6$H$_{13}$ (92.5%) |
| 32-5 | A | 25 kDa (hyperbranched) | —CH$_2$CH(CH$_3$)OH (50%)<br>50:50 —C$_{18}$H$_{37}$:—C$_8$H$_{17}$ (50%) |
| 32-6 | B | 72 kDa (branched) | —(CH$_2$)$_3$OH (13%)<br>75:25 —C$_{18}$H$_{37}$:—C$_8$H$_{17}$ (87%) |
| 32-7 | B | 72 kDa (branched) | —C(O)(CH$_2$)$_5$OH (6.5%)<br>75:25 —C$_{18}$H$_{37}$:—C$_8$H$_{17}$ (93.5%) |

-continued

| Compound | General Structure | PEI MW* | R$^{60}$ (mole %)** |
|---|---|---|---|
| 32-8 | A | 25 kDa (hyperbranched) | —C(O)(CH$_2$)$_5$OH (7%) 75:25 —C$_{18}$H$_{37}$:—C$_8$H$_{17}$ (93%) |
| 32-9 | A | 25 kDa (hyperbranched) | —CH$_2$CH(CH$_3$)OH (50%) 25:75 —C$_{18}$H$_{37}$:—C$_8$H$_{17}$ (50%) |

*indicates molecular weight of polyethyleneimine precursor
**theoretical stoichiometric ratio (based on amount of reactants used in the synthetic protocol) wherein A is 3 Br$^-$ B is 4 Br$^-$ and each n is an integer independently selected from 2 to 3000, preferably an integer independently selected from 10 to 100. In some embodiments, one or more bromide anions is replaced with X$^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

In some embodiments, the polymer is selected from a group consisting of:

| Compound | General Structure | PEI MW* | R$^{60}$ (mole %)** |
|---|---|---|---|
| 32-10 | A | 25 kDa (hyperbranched) | —C(O)(CH$_2$)$_5$OH (11%) —C$_6$H$_{13}$ (89%) |
| 32-11 | B | 70 kDa (branched) | —C(O)(CH$_2$)$_5$OH (9%) —C$_6$H$_{13}$ (91%) |
| 32-13 | B | 70 kDa (branched) | —(CH$_2$)$_3$OH (7%) 75:25 —C$_{18}$H$_{37}$:—C$_8$H$_{17}$ (93%) |
| 32-14 | A | 25 kDa (hyperbranched) | —(CH$_2$)$_3$OH (7%) 75:25 —C$_{18}$H$_{37}$:—C$_8$H$_{17}$ (93%) |
| 32-15 | B | 70 kDa (branched) | —C(O)(CH$_2$)$_5$OH (9%) 75:25 —C$_{18}$H$_{37}$:—C$_8$H$_{17}$ (91%) |
| 32-16 | A | 25 kDa (hyperbranched) | —C(O)(CH$_2$)$_5$OH (11%) 75:25 —C$_{18}$H$_{37}$:—C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |
| 32-1A | B | 70 kDa (branched) | —(CH$_2$)$_3$OH (10%) —C$_6$H$_{13}$ (90%) |
| 32-1B | B | 70 kDa (branched) | —(CH$_2$)$_3$OH (10%) —C$_6$H$_{13}$ (90%) |
| 32-2A | B | 70 kDa (branched) | —(CH$_2$)$_3$OH (5%) —C$_6$H$_{13}$ (95%) |
| 32-2B | B | 70 kDa (branched) | —(CH$_2$)$_3$OH (5%) —C$_6$H$_{13}$ (95%) |
| 32-2C | B | 70 kDa (branched) | —(CH$_2$)$_3$OH (15%)*** —C$_6$H$_{13}$ (85%) |
| 32-2D | B | 70 kDa (branched) | —(CH$_2$)$_3$OH (5%) —C$_6$H$_{13}$ (95%) |
| 32-2E | B | 70 kDa (branched) | —(CH$_2$)$_3$OH (12%)*** —C$_6$H$_{13}$ (88%) |
| 32-2F | B | 70 kDa (branched) | —(CH$_2$)$_3$OH (5%) —C$_6$H$_{13}$ (95%) |
| 32-2G | B | 70 kDa (branched) | —(CH$_2$)$_3$OH (5%) —C$_6$H$_{13}$ (95%) |

-continued

| Compound | General Structure | PEI MW* | R$^{60}$ (mole %)** |
|---|---|---|---|
| 32-2H | B | 70 kDa (branched) | —(CH$_2$)$_3$OH (5%) —C$_6$H$_{13}$ (95%) |
| 32-21 | B | 70 kDa (branched) | —(CH$_2$)$_3$OH (5%) —C$_6$H$_{13}$ (95%) |

*indicates molecular weight of polyethyleneimine precursor
**theoretical stoichiometric ratio (based on amount of reactants used in the synthetic protocol) unless otherwise indicated
***actual stoichiometric ratio as determined by NMR analysis wherein A is

3 X⁻

B is

4 X⁻ each n is an integer independently selected from 1 to 3000, preferably an integer independently selected from 10 to 100; and
each X⁻ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

It will be appreciated that the polymers described herein and the general method to prepare them offers a great deal of versatility to adjust and fine-tune physical and chemical properties and their antimicrobial properties for a wide range of different surfaces, substrates and applications. Examples of variables available for this fine-tuning include, but are not limited to, the structure and amount of the first quaternary ammonium salt, the optional polyol, the optional chain extender, the water-soluble polymer, the first multifunctional crosslinker (e.g., the first polyisocyanate), the polyethyleneimine intermediate or the second adduct (with its second multifunctional crosslinker, e.g., the second polyisocyanate), the optional third multifunctional crosslinker (e.g., the third polyisocyanate), the optional second quaternary ammonium salt, the optional fourth multifunctional crosslinker (e.g., the fourth polyisocyanate), and the degree of cross-linking. It will also be appreciated that multifunctional crosslinker(s) other than polyisocyanates may be used such as, but not limited to, multifunctional epoxides, imines, carbodiimides and aldehydes.

COMPOSITIONS AND FORMULATIONS

In another aspect, provided herein a composition comprising, consisting essentially of, or consisting of a polymeric component described herein.

In another aspect, provided herein a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:
  (i) a first adduct of a first multifunctional crosslinker and a first quaternary ammonium salt, wherein the first quaternary ammonium salt has a reactive linking group to react with the first multifunctional crosslinker;
  (ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;
  (iii) optionally a polyol;
  (iv) optionally a water-soluble polymer; and
  (v) optionally a third multifunctional crosslinker;
(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;
(3) the polyethyleneimine intermediate;
(4) the second adduct; and
(5) a combination of two or more thereof;
and at least one pharmaceutically acceptable excipient.

In some embodiments, the composition comprises, consists essentially of, or consists of a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:
  (i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker.

In some embodiments, the composition comprises, consists essentially of, or consists of a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of a first adduct, a polyol, a water-soluble polymer, and optionally a third multifunctional crosslinker.

In some embodiments, the composition comprises, consists essentially of, or consists of a polyethyleneimine intermediate described herein.

In some embodiments, the composition comprises, consists essentially of, or consists of a second adduct described herein.

In some embodiments, the polymeric component comprises, consists essentially of, or consists of a polymer or interpenetrating polymer network as described in U.S. Provisional Application No. 63/410,714 or U.S. Provisional Application No. 63/410,722, the contents of both of which are hereby incorporated by reference herein.

In some embodiments, the polymeric component is present in the composition at the time of administration to a subject or to the wound site of a subject. In some embodiments, precursors to the polymeric component are present in the composition at the time of administration to a subject or to the wound site of a subject, and the precursors react with one another to provide the polymeric component. In a non-limiting example, the composition comprises, consists essentially of, or consists of an oil-in-water emulsion described herein. In some embodiments, the oil-in-water emulsion is as described in U.S. Provisional Application No. 63/410,714 or U.S. Provisional Application No. 63/410,722.

The compositions described herein may include at least one pharmaceutically acceptable excipient.

The compositions described herein may be formulated for topical administration. Topical formulations include, but are not limited to, a cream, a gel, a paste, a foam, a spray, a powder, an emulsion, a liquid, or an ointment. In some embodiments, the liquid is a solution. In some embodiments, the liquid is a suspension. In some embodiments, the liquid is an oil.

Pharmaceutically acceptable excipients include solvents, thickeners, preservatives, emulsifiers and/or surfactants, pH adjusters and buffering agents, penetration enhancers, antioxidants, chelating agents, solubilizers, viscosity enhancers, emollients, and the like. By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

Examples of solvents include, but are not limited to, sterile water, glycerin, medium chain triglycerides, isopropyl myristate, diisopropyl adipate, isopropyl palmitate, propylene glycol, olive oil, castor oil, coconut oil, light mineral oil, diethylene glycol monoethylether (TRANSCUTOL® P), diethyl sebacate, benzyl alcohol, cyclomethicone, PEG 400, dehydrated alcohol, and dimethyl isosorbide.

Thickeners may be selected from a cross-linked polyacrylic acid polymer (e.g, a carbomer); a cellulose derivative (e.g., hydroxyethylcellulose, ethyl cellulose, hydroxypropyl cellulose, carboxymethyl cellulose, sodium carboxymethyl cellulose); xanthan gum, locust beam gum, guar gum or derivative thereof alginic acid; inorganic polymer (such as Weegum, a silicate of aluminum and magnesium); PEMULEN™ (a copolymer of acrylic acid and C10-C30 alkyl acrylate cross-linked with allyl pentaerythritol); or any combination thereof. Examples of thickeners include, but are not limited to, xanthan gum, cetearyl alcohol, PROMULGEN® D, CARBOPOL®974P NF Polymer, PEMULEN® TR-2, PEMULEN® TR-1, KLUCEL® HG Pharm, CARBOPOL® 980 NF, Polymer, and SEPINEO® P 600. Commercial carbomers include, but are not limited to, CARBOPOL® polymers such as CARBOPOL® Ultrez 10 NF, CARBOPOL® Ultrez 20, CARBOPOL® ETD 2020 NF, CARBOPOL® 71 G NF, CARBOPOL® 971P NF, CARBOPOL® 974P NF, CARBOPOL® 980 NF, CARBOPOL® 981 NF, and CARBOPOL® 5984 EP. CARBOPOL® Ultrez 10 NF and CARBOPOL® ETD 2020 NF are carbomer homopolymers or copolymers that contain a block copolymer of polyethylene glycol and a long chain alkyl acid ester.

Examples of preservatives include, but are not limited to, phenoxyethanol, urea derivatives (such as, but not limited to, diazolidinyl urea and imidazolidinyl urea), ethylhexylglycerine, hydantoin, benzoic acid, sorbic acid, anisic acid, methylparaben and propylparaben.

Examples of emulsifiers include, but are not limited to, BRIJ® L4, ARLACEL® 165, TWEEN® 20, BRIJ® S721, BRIJ® S2, PROMULGEN® D, Stearalkonium Chloride, PEMULEN® TR-2, PEMULEN® TR-1, Sodium Monostearate, SEPINEO® P 600, Laureth-4, Polysorbate 20, Sorbitan Monostearate, and PEG-35 Castor Oil. Non-ionic emulsifiers include, but are not limited to, BRIJ® L4, ARLACEL® 165, Sodium Monostearate, Laureth-4, Polysorbate 20, and PEG-35 Castor Oil. Cationic surfactants include, but are not limited to, stearalkonium chloride.

Examples of pH adjusters and buffering agents include, but are not limited to, triethanolamine, hydrogen chloride, sodium hydroxide, potassium hydroxide, and cocoamidodiethylamine.

Examples of penetration enhancers include, but are not limited to, sulfoxides such as dimethylsulfoxide (DMSO) and decylmethylsulfoxide ($C_{10}$ MSO); ethers such as diethylene glycol monoethyl ether (available commercially as TRANSCUTOL® P) and diethylene glycol monomethyl ether; 1-substituted azacycloheptan-2-ones, such as 1-n-dodecyl-cyclazacycloheptan-2-one; alcohols such as propanol, octanol, benzyl alcohol, and the like; fatty acids such as lauric acid, oleic acid, and valeric acid; fatty acid esters such as isopropyl myristate, isopropyl palmitate, methylpropionate, and ethyl oleate; polyol esters such as butanediol and polyethylene glycol monolaurate, amides and other nitrogenous compounds such as urea, N,N-dimethylacetamide (DMA), N,N-dimethylformamide (DMF), 2-pyrrolidone, 1-methyl-2-pyrrolidone, ethanolamine, diethanolamine, and triethanolamine; terpenes and terpinoids; alkanones; organic acids, such as salicylic acid and salicylates, citric acid and succinic-acid and the like; and any mixtures thereof. Suitable penetration enhancers also include, but are not limited to, medium chain triglycerides, isopropyl myristate, diisopropyl adipate, isopropyl palmitate, propylene glycol, diethylene glycol monoethylether (TRANSCUTOL® P), oleyl alcohol, dehydrated alcohol, benzyl alcohol, laureth-4, diethyl sebacate, and dimethyl isosorbide.

Examples of antioxidants include, but are not limited to, citric acid, butylated hydroxytoluene, ascorbic acid, glutathione, retinol, α-tocopherol, β-carotene, α-carotene, ubiquinone, butylated hydroxyanisole, ethylenediaminetetraacetic acid, selenium, zinc, lignan, uric acid, lipoic acid, and N-acetylcysteine.

Examples of chelating agents include, but are not limited to, EDTA, or a salt and/or solvate thereof citric acid; and tartaric acid.

Examples of solubilizers include, but are not limited to, Laureth-4.

Examples of viscosity enhancers include, but are not limited to, PEG 3350.

Examples of emollients include, but are not limited to, olive oil, medium chain triglycerides, isopropyl myristate, diisopropyl adipate, isopropyl palmitate, castor oil, light mineral oil, cyclomethicone, diethyl sebacate, benzyl alcohol, PEG-35 castor oil, and coconut oil.

Wound Dressings

In another aspect, provided herein is a wound dressing comprising a polymeric component described herein.

In another aspect, provided herein is a wound dressing comprising a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof.

In some embodiments, an outer layer of the wound dressing contains the polymeric component. In some embodiments, the polymeric component is impregnated into the wound dressing.

The dressings described herein include or are provided with a coating, coating fluid, or spraying fluid comprising, consisting essentially of, or consisting of a composition as described herein. The dressing beneficially is configured to absorb exudate, maintain moisture, allow gas exchange, provide for thermal isolation, serve as an anti-infective (e.g., between a wound site and the environment), readily removable, and biocompatible. In some embodiments, the dressing is configured to be disposable and/or sterilizable. In some embodiments, the dressing is configured for use in topical negative pressure therapy.

For example, such a dressing can include a wrap, a covering, a barrier, a layer, a packing, a gauze, a plaster, a bandage, a lint, a suture, a film, a foamed product, a hydrogel, a hydrocolloid, an alginate product, a bioactive product, a tissue-engineered skin substitute, a medicated product, a liquid bandage, a smart dressing, or a composite product (which can include two or more of any of the foregoing or alternatives), or any combination of any of the foregoing.

In particular, a dressing may be constructed from one or more natural polymers, one or more synthetic polymers, or a blend thereof. The natural polymers include (a) polysaccharides, including (i) cellulose and its compounds, which can be used, e.g., for dressing of ulcers, including for improvements in pain reduction and recovery time, (ii) alginates, which are made up of polysaccharide chains and which contribute to coagulation in wound healing and drug release, (ii) dextran, a complex branched glucan including an extra polysaccharide made up of glucose molecules, (iii) chitosan, a linear polysaccharide, and chitin, an amide derivative of glucose, and (iv) hyaluronic acid, a glycosaminoglycan that is injectable, e.g., in gel form; (b) polysaccharide sulfates, including (i) heparin, which has blood coagulative effects, and (ii) chondroitin; and (c) protein, including (i) collagen and (ii) fibrin, a blood coagulant. The synthetic polymers include, for example, (a) polycaprolactone, (b) polyglycolic acid, a biodegradable polystyrene, (c) polylactic acid, which is also a biodegradable polystyrene, (c) polylactic co-glyolic acid, a polymer of polylactic acid and glycolic acid, (d) polyvinyl alcohol, I polyurethanes, (f) polyorthoesters, and (g) polytetrafluroethylene.

In another aspect, by providing a dressing as described above with a composition as described herein (e.g., in the form of a coating, a coating fluid or a spraying fluid), an antibacterial barrier can thus be applied to a wound site, which allows for control of bacteriostatic activity while promoting cell and tissue proliferation and regeneration. Further, by preventing or reducing the likelihood of infection, a composition according to the techniques of the present disclosure impede damage and/or loss of function that may otherwise result from infection. The compositions disclosed herein are antibacterial against both gram negative and gram positive bacterial strains, including, e.g., methicillin resistant *Staphylococcus aureus* (MRSA) without creating bacterial resistance. In some embodiments, the compositions described herein may be used alone or in combination with one or more drugs and/or one or more medical devices for a plurality of indications including, e.g., acute wound care, chronic wound care, burn care, local infections, systemic infections, sepsis, and necrosis, among other indications, for both human and veterinary use.

In some embodiments, a dressing as provided with a composition as described herein is further provided with at least one indicator. The at least one indicator can be, for example, an internal or external indicator. The at least one indicator is configured to provide an indication of one or more parameters, e.g., temperature, pH, humidity, or oxygenation. For example, in some embodiments, the dressing may undergo a change of color in response to contact with the microenvironment of a bacterial infection. The selection of a particular type of dressing, composition, and, optionally, an indicator, allows for treatment to be personalized. Further, by providing an indicator, a level of efficacy is communicated, e.g., to a care provider by such "smart dressings" such as wound status and/or recovery status.

In some embodiments, a dressing as provided with a composition as described herein is a medicated product. As used herein, the "medicated product" dressing contains at least one additional pharmaceutical agent. Suitable additional pharmaceutical agents include, but are not limited to, an anti-inflammatory agent, an anesthetic, an additional anti-infective agent, or a combination thereof.

In an aspect, the dressing consists of, comprises, or substantially consists of the composition according to the embodiments of the present disclosure. In an aspect, the dressing is made by modifying an existing dressing to include—e.g., by combination or addition—the composition according to the embodiments of the present disclosure.

In another aspect, a method of making an antimicrobial dressing comprises providing a dressing containing one or more of the natural polymers or the synthetic polymers discussed above, and applying a coating, coating fluid or spraying fluid to the dressing, the coating or coating fluid consisting essentially of, or consisting of a composition as described herein. For example, the method can include contacting the natural and/or synthetic polymers with the coating, coating fluid or spraying fluid, e.g., (i) by spraying a dressing with the spraying fluid, (ii) by submerging the dressing in the fluid to thereby soak the dressing in the fluid, (iii) by impregnating fibers of the dressing with the fluid, (iv) by applying a layer of the coating to a surface of the dressing, (v) by adhering a backing containing the coating to the dressing, (vi) by applying microneedles containing the composition to the natural or synthetic polymers of the dressing, or (vii) by constructing fibers of the dressing with the polymeric component therein, e.g., by using electrospinning to produce nanofibers containing the polymer(s), copolymer(s) or interpenetrating polymer network(s) described herein, or by alternative techniques.

Accordingly, in another aspect, provided herein is a method of making the wound dressing described herein, comprising integrating a composition including the polymeric component into a fibrous material by one of:

(i) spraying the fibrous material with the composition, (ii) submerging the fibrous material in a fluid containing the composition, (iii) impregnating fibers of the fibrous material with a fluid containing the composition, (iv) applying a coating layer containing the composition to a surface of the fibrous material, (v) adhering a backing containing the composition to the fibrous material, (vi) applying microneedles containing the composition to the fibrous material, (vii) embedding a layer containing the composition within the fibrous material;

(viii) constructing fibers of the fibrous material with the composition by electrospinning; or (ix) interleaving fibers containing the composition with fibers of the fibrous material.

In another aspect, provided herein is a method of making a polyurethane foam wound dressing described herein, comprising integrating a composition including the polymeric component into the polyurethane foam wound dressing by mixing the composition with polyurethane prior to curing to provide the polyurethane foam wound dressing.

Methods of Use

In another aspect, provided herein is a method of preventing or reducing bacterial growth or reducing infection in a wound, a surgical site, or an implant of a subject, the method comprising, consisting essentially of, or consisting of applying or coating the wound, the surgical site, or the implant with a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, provided herein is a method of treating a wound or a surgical site in a subject in need thereof, the method comprising, consisting essentially of, or consisting of applying, to the wound or the surgical site, a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, provided herein is a method of promoting healing of a wound or a surgical site in a subject in need thereof, the method comprising, consisting essentially of, or consisting of applying, to the wound or the surgical site, a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the wound is infected. In some embodiments, the wound is not infected.

In another aspect, provided herein is a method of protecting a wound site in a subject in need thereof, the method comprising, consisting essentially of, or consisting of surrounding at least a portion of the wound site with a dressing, and contacting the wound site with a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the composition is located on the dressing prior to contact with the wound site. In some embodiments, the composition is applied to the wound site prior to contacting the wound site with the dressing.

In another aspect, provided herein is a method of preventing or reducing infection in a subject in need thereof, the method comprising, consisting essentially of, or consisting of administering to the subject a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In another aspect, provided herein is a method to treat infection in a subject in need thereof, the method comprising, consisting essentially of, or consisting of administering to the subject a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the infection is a local infection. In some embodiments, the infection is a systemic infection.

In another aspect, provided herein is a method to treat sepsis in a subject in need thereof, the method comprising, consisting essentially of, or consisting of administering to the subject a composition comprising, consisting essentially of, or consisting of a polymeric component selected from a group consisting of (1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof; and at least one pharmaceutically acceptable excipient.

In another aspect, provided herein is a method of preventing or reducing necrosis in a subject in need thereof, the method comprising, consisting essentially of, or consisting of administering to the subject a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof; and at least one pharmaceutically acceptable excipient.

In another aspect, provided herein is a method of preventing or reducing bacterial growth or reducing infection in a wound, a surgical site, or an implant of a subject in need thereof, the method comprising, consisting essentially of, or consisting of applying or coating the wound, the surgical site, or the implant with a composition comprising, consisting essentially of, or consisting of a polymeric component selected from a group consisting of:

(1) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of:

(i) a first adduct of a first multifunctional crosslinker and a first quaternary ammonium salt, wherein the first quaternary ammonium salt has a reactive linking group to react with the first multifunctional crosslinker;

(ii) a polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(2) a polymer, copolymer, interpenetrating polymer network, polyelectrolyte complex, blend, and composite, wherein the polymer, copolymer, interpenetrating polymer network, polyelectrolyte complex, blend, and composite comprise, consist essentially of, or consist of the first adduct, the polyol, the water-soluble polymer, and optionally the third multifunctional crosslinker;

(3) the polyethyleneimine intermediate;

(4) the second adduct; and (5) a combination of two or more thereof;

and at least one pharmaceutically acceptable excipient.

In some embodiments, the subject is a human or animal subject.

In some embodiments, the wound is an external wound. External wounds include, but are not limited to, abrasions, lacerations, punctures, avulsions, skin tears, and burns. In some embodiments, the wound is an internal wound. In some embodiments, the wound originates from complications of disease or disorder. Non-limiting examples include diabetic ulcers, venous ulcers, and arterial ulcers.

The composition disclosed herein is administered to the subject in an effective amount or therapeutically effective amount. The "effective amount" refers to an amount of compound that is sufficient to provide the desired effect, e.g., prevent bacterial growth, prevent necrosis, and/or prevent infection.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The present technology now being generally described, it will be more readily understood by reference to the following examples. These are included merely for purposes of illustration of certain aspects and embodiments of the present technology and are not intended to limit the present technology.

SYNTHESIS EXAMPLES

Examples 1-4. Water-Based Compositions with or without a Water-Soluble Polyethyleneimine Intermediate

| | | Examples (dry wt % in the dry film) | | | |
|---|---|---|---|---|---|
| | | 1 | 2 | 3 | 4 |
| Oil Phase | First Adduct (N100-C18DMDEG(Br—)) | 75 | 70 | 70 | 70 |
| | PTMG (MW1000) | 6 | 6 | 6 | 6 |
| | N100 | 14 | 14 | 14 | 14 |
| Polyethyleneimine Intermediate (QPEI) Used in the Aqueous Phase (wt. %) | | None | 37169 | HB37169 | HB37478 |
| Aqueous Phase | QPEI | 0 | 5 | 5 | 5 |
| | HEC (MW 380K) | 5 | 5 | 5 | 5 |

Preparation of the Aqueous Phase 3.1 parts of HEC 380K ((2-hydroxyethyl cellulose, average Mw=380,000 from Aldrich) were dissolved thoroughly in 96.9 parts of DI water. The pH of the solution was adjusted to 4.5 by a 5% solution of $H_3PO_4$.

Example 1: Preparation of Polymer without Polyethyleneimine Intermediate

Preparation of the Oil-Phase 5.0 g (10.7 mmol) of thoroughly dried C18DMDEG was added to a solution of 7.67 g (16.03 mmol, 48 mmol reactive NCO) of DESMODUR® N100 in 5 g dry toluene at 90° C.

under nitrogen and allowed to react for 15 hours. A clear viscous liquid (first adduct) was obtained after the toluene was removed under reduced pressure.

4.144 parts of the first adduct (N100-C18DMDEG (Br—)), 0.356 parts of PTMG 1000 (Poly(tetramethylene glycol), Average Mn=1000 from Aldrich) and 1.5 parts of MEK (methyl ethyl ketone) were pre-reacted at 70° C. for 1 hour. The mixture was cooled to room temperature and dried under vacuum until the solid content reached about 90% by weight. To the solution, 0.828 parts of polyisocyanate N100 (DESMODUR N100 from Convestro) and 1.276 parts of dried acetone were added and mixed homogeneously.

Preparation of Oil-In-Water Emulsion

The aqueous phase solution as prepared above was added into the oil phase at room temperature and emulsified by ultrasonication (100 Watt) for 10 sec, 5 times with a 10 sec pulse between each ultrasonication. The total emulsification time was about 90-120 sec. Heating for 15 hours at 60° C. provided the polymer product.

Examples 2-4

Preparation of QPEI 37169

PEI 70 kDa

QPEI 37169 was prepared as shown in the reaction scheme above.

For the purposes of the chemistry described herein, the ratio of primary, secondary and tertiary amines in branched PEI is assumed to be 1:2:1 as has been reported in the literature. See, e.g., Klibanov, A., et al., (2006). "One-Step Painting-Like Coating Procedures to make Surfaces Highly and Permanently Bactericidal." Biotechnol. Prog., 22(2): 584-589; and Gao, B., et al., (2007). "Studies on the Preparation and Antibacterial Properties of Quaternized Polyethyleneimine." J. Biomaterials Science, Polymer Edition, 18(5): 531-544.

The procedure used is essentially as described in Gao et al. (2007). The structure for QPEI 37169 is intended to be an approximation indicating that most of the primary and secondary amines have been reacted with the epoxide with most of the tertiary amines quaternized by alkylation with the benzyl chloride.

To a 25 mL two-neck flask under nitrogen was added 3.33 g of 70 kDa PEI solution (30% in water/1 g PEI, assume mw=43.1 g/mol, 23.2 mmol) and was cooled to 0° C. To this mixture, 5.4 g (92.8 mmol) propylene oxide was added dropwise at 0-3° C. After the addition was completed, the reaction mixture was stirred at 0-3° C. for seven hours. Then the temperature of the reaction mixture was increased to 35° C. and the unreacted propylene oxide was distilled out (~3.60 mL). Added to the resulting solution was 11.75 g (10.6 mL, 92.8 mmol) of benzylchloride and the reaction was heated to 50° C. for 30 hours. The reaction was extracted with diethyl ether (3×20 mL) to remove unreacted benzylchloride, residual propylene oxide, and oleophilic side products or impurities, if there are any. The water phase was separated and vaporized under vacuum and dried by lyophilization leaving QPEI 37169 as a transparent solid (2.85 g). The product was characterized by proton NMR and Infrared (IR) spectroscopy. QPEI 37169 contains a ratio of about 1:1 of nitrogen functionalization by benzylchloride to nitrogen functionalization by propylene oxide (i.e., the number of benzyl groups is about equal to the number of 2-hydroxypropyl groups on the nitrogen atoms).

Preparation of QPEI HB37169

The same reaction as in the preparation of QPEI 37169 was used for the preparation QPEI HB37169 except that a hyperbranched polyethyleneimine of the same molecular weight was used.

Preparation of QPEI HB37478

The same reaction as in the preparation of QPEI 37169 was used for the preparation QPEI HB37478 except that the quaternization agent benzyl bromide was replaced by hexyl bromide, and a hyperbranched polyethyleneimine of the same molecular weight was used.

Examples 5-9. QPEI 37169 as the Polyethyleneimine Intermediate in the Aqueous Phase

TABLE 3

| Composition (wt % in the dry film) | Examples | | | | | |
|---|---|---|---|---|---|---|
| | 2 | 5 | 6 | 7 | 8 | 9 |
| First Adduct (N100-C18DMDEG(Br—)) | 70 | 65 | 68 | 63 | 65 | 60 |
| PTMG (MW1000) | 6 | 6 | 8 | 8 | 11 | 11 |
| N100 | 14 | 14 | 14 | 14 | 14 | 14 |
| QPEI 37169 | 5 | 10 | 5 | 5 | 5 | 5 |
| HEC (MW 380K) | 5 | 5 | 5 | 10 | 5 | 10 |

The same procedures as those in Examples 1-4 were used to prepare the compositions of Examples 5-9, except that the composition was changed as shown in Table 3.

Examples 10-20 describe additional examples of polyethyleneimine intermediates or second adducts that can be used in the present technology.

Example 10. Synthesis of Polyethyleneimine
Intermediate 40840

Example 11. Synthesis of Polyethyleneimine
Intermediate 40660

70 kDa Branched PEI (30% by weight in
water) 18 mmole amine/gram solid
Ratio of primary, secondary, tertiary
amines = 1:2:1 t-Amyl Alcohol 70 kDa Branched PEI (30% by weight in
water) 18 mmole amine/gram solid
Ratio of primary, secondary, tertiary
amines = 1:2:1

Triethylamine $H_2O$

4 Br–

4 Cl–

A 500 mL 3 neck round bottom flask was fitted with a thermometer, condenser and magnetic stirrer. The reaction flask was flushed with nitrogen gas and the reaction carried out under a nitrogen gas flow.

10 g of PEI (70 kDa branched, 30% by weight aqueous solution, amine content 18 mmole/gram solid polymer, ratio of primary, secondary, tertiary amines=1:2:1) and potassium carbonate (37.07 g, 0.232 mol) and 150 mL t-Amyl Alcohol were added to the round bottom flask. This mixture was stirred under nitrogen for 30 minutes and then 3-bromo-1-propanol (64.5 g, 0.464 mol, 1.3 equivalents for complete quaternization) was added dropwise at room temperature. The resulting mixture was heated and stirred at 95° C. for 96 hours.

After 96 hours, the mixture was allowed to cool to room temperature and filtered to remove insoluble solid. The filtered solid was washed with 150 mL methanol. The combined filtrates were treated with 250 mL diethyl ether and a white precipitate was formed. The organic phase was decanted and the white solid was dissolved in 200 mL methanol and precipitated with 200 mL diethyl ether. This dissolution/precipitation process was carried out two more times and the resulting white pasty solid was dried in a rotary evaporator and then further dried under high vacuum for 5 hours. Then yield of dry produce was 17.4 g. The product was characterized by $^1H$ NMR and the degree of quaternization analyzed using the Mohr argentometric titration method to measure the amount of bromide.

A 2-L 3 neck round bottom flask was fitted with a dropping funnel, condenser and magnetic stirrer. The reaction flask was flushed with nitrogen gas and the reaction carried out under a nitrogen gas flow.

10 g of PEI (70 kDa branched, 30% by weight aqueous solution, amine content 18 mmole/gram solid polymer, ratio of primary, secondary, tertiary amines=1:2:1) was added to the reaction flask and 835 mL water added to it. 114.3 g glycidyltrimethylammonium chloride (0.754 mol, ~4 equivalents for theoretical full conversion) was dissolved in 130 mL water and added dropwise to the reaction mixture. 153 g (210 mL, 1.5 mol) Triethylamine was added dropwise to the reaction mixture at room temperature. The resulting two-phased reaction mixture was vigorously stirred at room temperature for 4 days after which time the reaction mixture was one clear phase. All solvents were removed in a rotary evaporator at 55° C. The pasty liquid residue was dissolved in 200 mL methanol and the polymer product precipitated with 400 mL diethyl ether. This methanol/diethyl ether dissolution and precipitation was repeated six times. The final precipitate was dried in a rotary evaporator and then under high vacuum yielding 46.5 g of the final product. The product was characterized by $^1H$ NMR and the degree of quaternization analyzed using the Mohr argentometric titration method to measure the amount of chloride.

Example 12. Synthesis of Polyethyleneimine Intermediate 40818

A 100-mL 1 neck round bottom flask was fitted with a condenser, a heating cup and magnetic stirrer. The reaction flask was flushed with nitrogen gas and the reaction carried out under a nitrogen gas flow.

2 g of the glycidyl functionalized PEI (3.3 mmol 13.3 mmol reactive N), bromohexane (7 g, 40 mmol, 3 equivalents) and 4.4 mL t-amyl alcohol were added to the flask and the reaction mixture was heated at 96° C. for 96 hours. The reaction mixture turned from colorless to light orange in color. The reaction was cooled to room temperature and the resulting solution was poured into Tertiary Butyl Methyl Ether (TBME) with vigorous stirring causing a precipitate to form. The liquid was decanted away from the precipitated solid and the solid dissolved in methanol and reprecipitated with TBME. This process was repeated 3 times yielding 4.06 g of the product after drying with a rotary evaporator and then high vacuum. The product was characterized by $^1$H NMR and the degree of quaternization analyzed using the Mohr argentometric titration method to measure the amount of halide.

Example 13. Synthesis of a Polyethyleneimine Intermediate Capped with Monoisocyanate (Approximately 85% of Free OH Groups)

The structure for the polymer product, as shown below, is intended to be an approximation indicating that most of the hydroxyl groups (~85% molar equivalent) have been reacted with the blend of monoisocyanates to form urethanes with some hydroxyl groups remaining unreacted.

QPEI 37169-capped

The concentration of reactive hydroxyl groups (mmol/ gram of dry polymer) was determined by titrating a known amount (grams) of the dried Hydroxyl Alkyl Quaternary Polyethyleneimine (HA-Q-PEI) with a known excess amount (grams, mmoles) of Octadecylisocyanate. The percentage of monoisocyanate which was consumed in the reaction was determined by monitoring the reaction progress using infrared (IR) spectroscopy to monitor the drop in the isocyanate peak at 2263 cm$^{-1}$. From the percentage drop in this peak, the number of mmoles of isocyanate consumed was estimated. This value was equivalent to the number of mmoles of polymer hydroxyl groups which reacted with the isocyanate. In this way, a hydroxyl group concentration of the polymer (mmoles reactive hydroxyl groups/g dry polymer) was calculated and then used in subsequent reactions to determine the amount of monoisocyanate(s) required to functionalize specific percentages of the reactive hydroxyl groups in the polymer and by doing so, would fine-tune the hydrophilic/hydrophobic properties of the polymer.

Using the procedure described in Example 2, 2.0 g (2.27 mmol assuming a molecular weight of 881 g/mole for the polymer unit cell) of the Hydroxypropyl Quaternary Ammonium PEI, QPEI 37169, was prepared and then dried under vacuum at 60° C. for two hours followed by storing overnight in a desiccator at room temperature. To the dried polymer was added 13.8 g t-butyl alcohol and 9.2 g of dimethyl acetamide. The resulting mixture was stirred under nitrogen until the polymer completely dissolved. Both of these solvents were dried thoroughly with molecular sieve 4

Å before use. A mixture of 1.6 g (5.41 mmol) of octadecylisocyanate and 0.36 g (2.32 mmol) of octylisocyanate was added dropwise to the polymer solution. This mixture totaled 7.73 mmol of monoisocyanate which corresponds to approximately 85% of the available hydroxyl groups. The reaction mixture turned slightly cloudy. The resulting reaction mixture was stirred at room temperature under nitrogen for twelve hours. The resulting reaction mixture was filtered with a PTFE filter (1 μm pore size) affording the 20.83 grams of QPEI 37169-capped as a 12.19% solid solution. IR spectroscopy showed the expected new peak corresponding to the urethane carbonyls and no residual isocyanate peak.

In some embodiments, after the reaction with monoisocyanate(s) is complete, the reaction mixture was added to water to precipitate the capped product. This product was isolated and washed with water to remove any water soluble impurities and then dried for use in subsequent steps. This water precipitation step was useful for removing any water soluble impurities that may contribute to toxicity.

Example 14. Process for Crosslinking Reaction of Octadecyl/Octyl Urethane Quaternary Ammonium PEI (Example of Second Adduct Formation)

The structure for the polymer Compound (A), as shown below, is intended to be an approximation indicating that some of the unreacted hydroxyl groups in QPEI 37169-capped have been reacted with the polyisocyanate to form urethane cross-links.

QPEI 37169-capped

-continued

Compound (A)

Using the procedure described in Example 13, 20 g of the Octadecyl/Octyl Urethane Quaternary Ammonium PEI was prepared, to which was added 1.25 g of Desmodur N3300 (50% solution in anhydrous acetone) and 0.18 g of a Dibutyltin Dilaurate 1% solution in dry toluene. The resulting mixture was mixed thoroughly and a reaction to form Compound (A) occurred in 30 min at 60° C. to provide the second adduct.

It should be noted that the above crosslinking procedure has also been carried out without the Dibutyltin Dilaurate catalyst.

Example 15. Aqueous Solutions of HA-Q-PEI Polymers with Varied PEI Molecular Weights, Nitrogen Quaternization Groups, and Anionic Counter Ions Various HA-Q-PEI (Hydroxy Alkyl Quaternary PEI) of the following formula:

HA-Q-PEI
Hydroxyalky Quaternary PEI were prepared using analogous procedures as that which is described in Example 2 (preparation of QPEI 37169). See Table 5 ($R_1$=methyl for each polymer).

TABLE 5

| sample | MW | $R_2$ | X— |
|---|---|---|---|
| 2-1 | 600 | n-Hexyl | Bromide |
| 2-2 | 10,000 | n-Hexyl | Bromide |
| 2-3 | 100,000 | n-Hexyl | Bromide |
| 2-4 | 70,000 | n-Hexyl | Bromide |
| 2-5 | 70,000 | Benzyl | Chloride |
| 2-6 | 70,000 | Methyl | Iodide |
| 2-7 | 70,000 | n-Butyl | Bromide |
| 2-8 | 70,000 | —$CH_2C(O)OCH_2CH_3$ | Bromide |
| 2-9 | 70,000 | —$CH_2C(O)Ph$ | Bromide |

Example 16. Aqueous Solutions of HA-Q-PEI Polymers with Varied PEI Molecular Weights Additional HA-Q-PEI polymers ($R_1$=methyl, $R_2$=hexyl, X=bromide) of the following formula:

HA-Q-PEI
Hydroxyalky Quaternary PEI having various molecular weights were prepared using analogous procedures as that which is described in Example 2 (preparation of QPEI 37169). See Table 6.

TABLE 6

| sample | MW (kDa) |
|---|---|
| 3-1 | 0.6 |
| 3-2 | 0.6 |
| 3-3 | 10 |
| 3-4 | 10 |
| 3-5 | 25 |
| 3-6 | 70 |
| 3-7 | 100 |
| 3-8 | 270 |
| 3-9 | 270 |

Example 17. Preparation of Second Adducts

Second adducts of the following formula:

were prepared (see Table 7) using analogous procedures as that which is described in Example 14, replacing the Octadecyl/Octyl Urethane Quaternary Ammonium PEI with a HA-Q-PEI (prepared from PEI: molecular weight=70,000 (branched), $R_1$=methyl, $R_2$=hexyl, X=bromide), and varying the amounts of crosslinker Z (DESMODUR® N100):

(DESMODUR® N100)

TABLE 7

| sample | wt. % crosslinker* |
|---|---|
| 4-1 | 6.5 |
| 4-2 | 17.7 |
| 4-3 | 26.5 |
| 4-4 | 33.3 |
| 4-5 | 39.2 |
| 4-6 | 44.1 |

*wt. % with respect to second adduct

Example 18. Polyethyeleneimine Intermediates with or without Monoisocyanate Substitution Polyethyeleneimine intermediates with monoisocyanate substitution (MUA-Q-PEI-A polymers, wherein $R_3$=$C_{18}$ alkyl or $C_8$ alkyl) of the following formula:

were prepared from HA-Q-PEI (prepared from PEI: molecular weight=70,000 (branched), $R_1$=methyl, $R_2$=benzyl) and a monoisocyanate mixture (7:3 ratio of octadecylisocyanate to octylisocyanate), wherein approximately 90% of HA-Q-PEI hydroxyl groups reacted with the monoisocyanate mixture (see similar protocol in Example 13). MUA-Q-PEI-A100 polymers were also similarly prepared, in which approximately 100% of the HA-Q-PEI hydroxyl groups reacted with the monoisocyanate mixture. See Table 8.

TABLE 8

| sample | polymer system |
| --- | --- |
| 5-1 | 1% water solution HA-Q-PEI |
| 5-2 | dry film MUA-Q-PEI-A |
| 5-3 | dry film MUA-Q-PEI-A |
| 5-4 | dry film MUA-Q-PEI-A |
| 5-5 | dry film MUA-Q-PEI-A100 |
| 5-6 | dry film MUA-Q-PEI-A100 |
| 5-7 | dry film MUA-Q-PEI-A100 |

Example 19. Second Adducts Using N3300 Polyisocyanate Crosslinker

Second Adducts (PUA-Q-PEI-B polymers, wherein $R_3$=$C_{18}$ alkyl or $C_8$ alkyl) of the following formula:

were prepared using analogous procedures as that which is described in Example 14. In particular, the HA-Q-PEI (prepared from PEI: molecular weight=25,000 (Hyper Branched), $R_1$=methyl, $R_2$=hexyl, X=bromide) was reacted with a monoisocyanate mixture (7:3 ratio of octadecylisocyanate to octylisocyanate), wherein approximately 90% of HA-Q-PEI hydroxyl groups reacted with the monoisocyanate mixture, before the remaining hydroxyl groups were reacted with varying amounts of crosslinker Z (DESMODUR® N3300):

(DESMODUR® N3300)

TABLE 9

| Sample | wt. % crosslinker* |
| --- | --- |
| 6-1 | 0 |
| 6-2 | 1.62 |
| 6-3 | 4.75 |
| 6-4 | 7.61 |
| 6-5 | 10.37 |

*wt. % crosslinker with respect to PUA-Q-PEI-B polymer product

Example 20. Compound 20-1

Compound 20-1 is analogous to QPEI samples 3-8 and 3-9 of Example 16, and was prepared from a PEI with MW=270 kDa. Compound 20-1 (batch 105159) contains a ratio of more than 1:1 of nitrogen functionalization by hexyl halide to nitrogen functionalization by propylene oxide (i.e., there are more hexyl groups than 2-hydroxypropyl groups on the nitrogen atoms). Compound 20-1 (batch 99367) contains a ratio of about 1:1 of nitrogen functionalization by hexyl halide to nitrogen functionalization by propylene oxide (i.e., the number of hexyl groups is about equal to the number of 2-hydroxypropyl groups on the nitrogen atoms).

Example 21. Compound 21-1

Compound 21-1 is analogous to compound HB37478, but is prepared from a PEI with MW=25 kDa. Compound 21-1 contains a ratio of about 1:1 of nitrogen functionalization by hexyl halide to nitrogen functionalization by propylene oxide (i.e., the number of hexyl groups is about equal to the number of 2-hydroxypropyl groups on the nitrogen atoms).

Example 22. Compound 22-1

Compound 22-1 (batch 109590) is analogous to HB37478 of Example 4, but a branched 70 kDa PEI was used rather than a hyperbranched 70 kDa PEI. Compound 22-1 (batch 109590) contains a ratio of about 1:1 of nitrogen functionalization by hexyl halide to nitrogen functionalization by propylene oxide (i.e., the number of hexyl groups is about equal to the number of 2-hydroxypropyl groups on the nitrogen atoms).

Example 23. Compound 23-1

Compound 23-1 (batch 105402 and batch 109634) is analogous to QPEI sample 2-9 of Example 15 (prepared from a PEI with MW=70 kDa). Compound 23-1 (batch 105402 and batch 109634) contains a ratio of about 1:1 of nitrogen functionalization by phenacyl halide to nitrogen functionalization by propylene oxide (i.e., the number of phenacyl groups is about equal to the number of 2-hydroxy-propyl groups on the nitrogen atoms).

Example 24. Compound 24-1

Compound 24-1 (batch 109781) is analogous to QPEI 37169 of Example 2 (prepared from a PEI with MW=70 kDa). Compound 24-1 (batch 109781) contains a ratio of about 1:1 of nitrogen functionalization by benzyl halide to nitrogen functionalization by propylene oxide (i.e., the number of benzyl groups is about equal to the number of 2-hydroxypropyl groups on the nitrogen atoms).

Example 25. Compound 25-1

Compound 25-1 (batch 110417) is analogous to compound 23-1, but is prepared from a PEI with MW=750 kDA.

Example 26. Compound 26-1

Compound 26-1 (batch 109831) is analogous to polyethyleneimine intermediate 40660 of Example 11 (prepared from a PEI with MW=70 kDa).

Example 27. Compound 27-1

Compound 27-1 (batch 110420) is analogous to polyethyleneimine intermediate 40818 of Example 12 (prepared from a PEI with MW=70 kDa).

Example 28. Compound 28-1

Compound 28-1 corresponds to the intermediate compound in the synthesis of QPEI 37169 of Example 2, resulting from reaction of PEI (MW=70 kDa) with propylene oxide. Accordingly, there are no quaternary amines in compound 28-1.

Example 29. Compound 29-1

R: ~1 mol % ——C$_3$H$_6$OH, 99 mol % ——C$_6$H$_{13}$

A 1-L 3-neck round bottom flask was fitted with a dropping funnel, condenser, water bath and mechanical stirrer. The flask was flushed with nitrogen gas, and the reaction carried out under a nitrogen gas flow.

20 g of a 50% aqueous solution of 70 kDa branched PEI (10 g PEI polymer, 0.180 mole amine content with a ratio of primary to secondary to tertiary amines of approximately 1:2:1) was added to the flask and stirred at ~200 RPM. Note that 0.180 mole nitrogen content with this ratio of primary, secondary, and tertiary amines in theory can react with 0.36 mole of alkyl halide. This is defined as "1 equivalent of alkyl halide" for this example.

tert-Amyl alcohol (150 ml) was added to the flask at ambient temperature followed by K$_2$CO$_3$ (32.1 g, 0.232 mole). A mixture of bromopropanol (1.29 g, 0.0093 mole) and 1-bromohexane (151.86 g, 0.92 mole), (total alkyl halide=0.93 mole, 2.6 equivalents with mole % content of each alkyl halide=1% bromopropanol/99% 1-bromo-hexane), was added dropwise over 1-2 hours at ambient temperature.

The reaction temperature was increased to 96° C., and the reaction stirred at 96° C. for 98 hours. The reaction was allowed to cool to 25-30° C., filtered, and the filtered material washed with methanol (50 ml). The filtrate was evaporated to dryness under vacuum keeping the temperature below 50° C. To the residue was added diethyl ether (200 ml), and the mixture was stirred for 30-60 minutes at room temperature after which time a light brown slurry had formed. This mixture was allowed to settle, and the supernatant decanted off. This diethyl ether trituration and decanting was repeated 3-4 times until the residual alkyl halide content in the decant layer was less than 0.5% as determined by GC analysis.

After completing the trituration/decantation process, the mixture was evaporated to dryness under reduced pressure while keeping the temperature below 40° C., resulting in an off-white sticky solid. This solid was dissolved in methyl ethyl ketone (100 ml) at 25-30° C., filtered through Celite, and the filtrate evaporated to dryness under reduced pressure at 45° C. The resulting solid was oven-dried for 4-6 hours at below 45° C. providing the product (37.8 g) as an off-white solid. Water content was measured by Karl-Fischer analysis to be 0.24%. Bromine content was measured by AgNO$_3$ titration to be 23.6%. The theoretical mole % of PEI reaction with 1-bromopropanol and 1-bromohexane is 1% and 99%, respectively, assuming similar alkylation rates between the two alkyl halides.

Example 30. Compound 30-1

-continued

3 Br⁻

R: ~6.4 mol % ——(CH₂)₃OH, ~93.6 mol % C₁₈/C₈ (75/25)

A 1-L 4-neck round bottom flask was fitted with a dropping funnel, condenser, water bath and mechanical stirrer. The flask was flushed with nitrogen gas, and the reaction carried out under a nitrogen gas flow.

10 g of 25 kDa hyperbranched PEI (0.180 mole amine content with a ratio of primary to secondary to tertiary amines of approximately 1:1:1) was added to the flask along with water (10 ml). Note that 0.180 mole nitrogen content with this ratio of primary, secondary, and tertiary amines in theory can react with 0.36 mole of alkyl halide. This is defined as "1 equivalent of alkyl halide" for this example.

tert-Amyl alcohol (50 ml) was added to the flask at ambient temperature, and this suspension was stirred at 160-180 RPM. After 15-30 minutes stirring, the mixture was cooled to 0-5° C., and bromopropanol (3.2 g, 0.023 mole, 0.064 equivalents) was added dropwise over 15-30 minutes at 0-5° C. The reaction mixture was stirred at 0-5° C. for 4-5 hours and then the temperature was allowed to increase to ambient temperature. The reaction was stirred at ambient temperature for 14-15 hours after which time the reaction mixture was a hazy solution.

The water content of the reaction was reduced by azeotropic distillation of solvent (~10 mL). This volume of tert-Amyl alcohol was added to the reaction, and the distillation process repeated 3 times. Tert-Amyl alcohol was added to make up the original reaction volume, and the resulting mixture was stirred for 60-90 minutes at 50-60° C. after which time a clear solution was obtained.

A mixture (0.928 mole, 2.6 equivalents of alkyl halide) of 1-bromooctadecane (232.1 g, 0.696 mole) and 1-bromooctane (44.8 g, 0.232 mole) was added at 50-60° C. The temperature was raised to 94-98° C., and the reaction stirred at at this temperature for 48 hours, resulting in a clear brown solution. The solvent was removed under reduced pressure at below 60° C., the resulting residue cooled to 25-30° C., and 500 mL acetone was added. The resulting suspension was stirred at 25-30° C. for 30-60 minutes. Stirring was stopped, and the suspension allowed to settle for 1 hour. The supernatant liquid was decanted away from solid, and acetone (500 ml) was added to the solid residue. This suspension was stirred at 25-30° C. for 30-60 minutes after which time the stirring was stopped, and the suspension was allowed to settle over 30-60 minutes, and the supernatant liquid decanted away from the settled solid. This suspension stirring, settling and decanting process was repeated several more times until the 1-bromooctadecane and 1-bromooctane in the supernatant was less than 0.5% as measured by GC analysis.

The remaining solvent was removed under reduced pressure at below 35° C. The solid product was further dried for 8-10 hours at below 35° C., affording 40.6 g of the QPEI product as a light brown solid. Bromine content was determined to be ~23% as measured by AgNO₃ titration. The theoretical mole % of reaction with 1-bromopropanol and the 75/25 mixture of 1-bromooctadecane and 1-bromooctane is 6.4% and 93.6%, respectively.

Example 31. Compound 31-1

0.2 equiv. caprolactone
Excess bromohexane

NH₂

3 Br⁻

R: ~7 mol % ——C(O)—(CH₂)₅-OH, ~93 mol % — C₆H₁₃

A 0.5-L 4-neck round bottom flask was fitted with a dropping funnel, condenser, water bath and mechanical stirrer. The flask was flushed with nitrogen gas and the reaction carried out under a nitrogen gas flow.

10 g of 25 kDa hyperbranched PEI (0.180 mole amine content with a ratio of primary to secondary to tertiary amines of approximately 1:1:1) was added to the flask and stirred at 160-180 RPM. Note that 0.180 mole nitrogen content with this ratio of primary, secondary, and tertiary amines in theory can react with 0.120 mole of caprolactone ("1 equivalent of caprolactone" for this example) and 0.360 mole of 1-bromohexane ("1 equivalent of 1-bromohexane" for this example).

Water (10 g) was added to the flask along with tert-amyl alcohol (50 ml), and the resulting solid suspension was cooled to 0-5° C.

Caprolactone (2.65 g, 0.0238 mole, 0.2 equivalent) was added dropwise over 15-30 minutes at 0-5° C. The resulting mixture was stirred at 0-5° C. for 4-5 hours. The temperature was increased to 25-30° C., and the reaction was stirred at this temperature for 14-15 hours resulting in a hazy solution.

tert-Amyl alcohol was distilled off to azeotropically remove water from the reaction mixture, and fresh tert-amyl alcohol was added to replace the solvent that was distilled off. The reaction temperature was increased to 50-60° C., and the reaction stirred for 60-90 minutes resulting in a clear solution. 1-Bromohexane (153.2 g, 0.928 mole, 2.6 equivalents) was added. The resulting reaction mixture was stirred for 15-30 minutes at 50-60° C. and then the temperature was increased to 94-98° C. The reaction was stirred at this temperature for 48 hours resulting in a solid suspension.

The reaction was cooled to 25-30° C. Diethyl ether (100 ml) was added dropwise, and the resulting suspension was stirred at 25-30° C. for 30-60 minutes. Stirring was stopped and the suspension was allowed to settle for 1 hour. The supernatant liquid was decanted away from the settled solid, and fresh diethyl ether (100 ml) was added. This suspension stirring, settling and decanting process was repeated several times until the 1-bromohexane content in the decanted liquid was less than 0.5% as measured by GC analysis.

The remaining solvent was removed under reduced pressure at less than 35° C. The crude solid product was further dried for 10-12 hours at below 35° C., affording the QPEI product (32 g) as a beige solid. The water content was measured to be 1200 PPM as measured by Karl Fischer analysis. The bromine content was determined to be (35% as measured by AgNO$_3$ titration.

The theoretical mole % of PEI reaction with caprolactone and 1-bromohexane is ~7% and ~93%, respectively, assuming that the caprolactone primarily reacts with the primary amines.

Example 32. Additional Compounds

The following compounds were prepared using procedures analogous to those in the above-described examples.

Compounds 32-1 and 32-2 were prepared in a similar manner as described in Example 29. The general steps for the synthesis of compounds 32-1 and 32-2 were as follows.

(1) A mixture of a water solution of 70 kDa PEI, bromopropanol, bromohexane and K$_2$CO$_3$ and t-amyl alcohol was heated at 96-98° C. for 4 days and then allowed to cool to room temperature.

(2) The resulting mixture was filtered to remove inorganic salts and the filtered solid was washed with t-amyl alcohol.

(3) The filtrate was evaporated under reduced pressure.

(4) The residue was triturated 5-6 times with diethyl ether.

| Compound | General Structure | PEI MW* | R$^{60}$ (mole %)** |
|---|---|---|---|
| 32-1 | B | 70 kDa (branched) | —(CH$_2$)$_3$OH (10%) —C$_6$H$_{13}$ (90%) |
| 32-2 | B | 70 kDa (branched) | —(CH$_2$)$_3$OH (5%) —C$_6$H$_{13}$ (95%) |
| 32-3 | B | 70 kDa (branched) | —CH$_2$CH(CH$_3$)OH (5%) —C$_6$H$_{13}$ (95%) |
| 32-4 | B | 70 kDa (branched) | —C(O)(CH$_2$)$_5$OH (7.5%) —C$_6$H$_{13}$ (92.5%) |
| 32-5 | A | 25 kDa (hyperbranched) | —CH$_2$CH(CH$_3$)OH (50%) 50:50 —C$_{18}$H$_{37}$:—C$_8$H$_{17}$ (50%) |
| 32-6 | B | 72 kDa (branched) | —(CH$_2$)$_3$OH (13%) 75:25 —C$_{18}$H$_{37}$:—C$_8$H$_{17}$ (87%) |
| 32-7 | B | 72 kDa (branched) | —C(O)(CH$_2$)$_5$OH (6.5%) 75:25 —C$_{18}$H$_{37}$:—C$_8$H$_{17}$ (93.5%) |
| 32-8 | A | 25 kDa (hyper-branched) | —C(O)(CH$_2$)$_5$OH (7%) 75:25 —C$_{18}$H$_{37}$:—C$_8$H$_{17}$ (93%) |
| 32-9 | A | 25 kDa (hyperbranched) | —CH$_2$CH(CH$_3$)OH (50%) 25:75 —C$_{18}$H$_{37}$:—C$_8$H$_{17}$ (50%) |
| 32-10 | A | 25 kDa (hyperbranched) | —C(O)(CH$_2$)$_5$OH (11%) —C$_6$H$_{13}$ (89%) |
| 32-11 | B | 70 kDa (branched) | —C(O)(CH$_2$)$_5$OH (9%) —C$_6$H$_{13}$ (91%) |
| 32-13 | B | 70 kDa (branched) | —(CH$_2$)$_3$OH (7%) 75:25 —C$_{18}$H$_{37}$:—C$_8$H$_{17}$ (93%) |
| 32-14 | A | 25 kDa (hyperbranched) | —(CH$_2$)$_3$OH (7%) 75:25 —C$_{18}$H$_{37}$:—C$_8$H$_{17}$ (93%) |
| 32-15 | B | 70 kDa (branched) | —C(O)(CH$_2$)$_5$OH (9%) 75:25 —C$_{18}$H$_{37}$:—C$_8$H$_{17}$ (91%) |
| 32-16 | A | 25 kDa (hyperbranched) | —C(O)(CH$_2$)$_5$OH (11%) 75:25 —C$_{18}$H$_{37}$:—C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |

*indicates molecular weight of polyethyleneimine precursor

**theoretical stoichiometric ratio (based on amount of reactants used in the synthetic protocol)

A =

B =

(5) The resulting crude product was dissolved in methyl ethyl ketone, filtered and evaporated to dryness under reduced pressure.

The stoichiometric ratio of $R^{61}$ groups for each of the following compounds (32-1A, 32-1B, and 32-2A to 32-2I) is a theoretical value calculated based on amount of reactants used in the synthetic protocol, unless otherwise indicated.

Compound 32-1A [general structure B; 70 kDa PEI (branched); $R^{61}$: —$(CH_2)_3OH$ (10%), —$C_6H_{13}$ (90%)] was synthesized in a similar manner to compound 32-1, but the crude product dissolved in methyl ethyl ketone was treated with aqueous sodium bicarbonate to increase the pH of the QPEI product closer to neutral prior to filtration and evaporation to dryness.

Compound 32-1B [general structure B; 70 kDa PEI (branched); $R^{61}$: —$(CH_2)_3OH$ (10%), —$C_6H_{13}$ (90%)] was synthesized in a similar manner to compound 32-1, but the residue from step (3) was dissolved in dichloromethane and washed with aqueous sodium bicarbonate before the dichloromethane layer was separated from the aqueous layer and evaporated to dryness under reduced pressure. The crude product was then used in steps (4) and (5).

Compound 32-2A [general structure B; 70 kDa PEI (branched); $R^{60}$: —$(CH_2)_3OH$ (5%), —$C_6H_{13}$ (95%)] was synthesized in a similar manner to compound 32-2, but the crude product dissolved in methyl ethyl ketone was treated with aqueous sodium bicarbonate to increase the pH of the QPEI product closer to neutral prior to filtration and evaporation to dryness.

Compound 32-2B [general structure B; 70 kDa PEI (branched); $R^{60}$: —$(CH_2)_3OH$ (5%), —$C_6H_{13}$ (95%)] was synthesized in a similar manner to compound 32-2, but the residue from step (3) was dissolved in dichloromethane and washed with aqueous sodium bicarbonate before the dichloromethane layer was separated from the aqueous layer and evaporated to dryness under reduced pressure. The crude product was then used in steps (4) and (5).

Compound 32-2C [general structure B; 70 kDa PEI (branched); $R^{60}$: —$(CH_2)_3OH$ (15%), —$C_6H_{13}$ (85%)— actual determination via NMR analysis] was synthesized in a similar manner to compound 32-2, but the residue from step (3) was dissolved in an aqueous KOH/ethanol solution, filtered, and concentrated under reduced pressure. The crude product was then used in steps (4) and (5). The crude product from step (5) was dissolved in ethanol for biological testing.

Compound 32-2D [general structure B; 70 kDa PEI (branched); $R^{60}$: —$(CH_2)_3OH$ (5%), —$C_6H_{13}$ (95%)] was synthesized in a similar manner to compound 32-2, but additional water was added to the initial reaction mixture of step (1). The crude product from step (5) was dissolved in ethanol for biological testing.

Compound 32-2E [general structure B; 70 kDa PEI (branched); $R^{60}$: —$(CH_2)_3OH$ (12%), —$C_6H_{13}$ (88%)— actual determination via NMR analysis] was synthesized in a similar manner to compound 32-2C, wherein the residue from step (3) was dissolved in an aqueous KOH/ethanol solution, filtered, and concentrated under reduced pressure. The crude product was then used in steps (4) and (5). The crude product from step (5) was dissolved in ethanol for biological testing.

Compound 32-2F [general structure B; 70 kDa PEI (branched); $R^{60}$: —$(CH_2)_3OH$ (5%), —$C_6H_{13}$ (95%)] was synthesized in a similar manner to compound 32-2, but the mixture in step (1) was heated to 80° C. rather than 96-98° C. The crude product from step (5) was dissolved in ethanol for biological testing.

Compound 32-2G [general structure B; 70 kDa PEI (branched); $R^{60}$: —$(CH_2)_3OH$ (5%), —$C_6H_{13}$ (95%)] was synthesized in a similar manner to compound 32-2, but the mixture in step (1) was heated to 80° C. rather than 96-98° C., and trituration in step (4) was performed using methyl t-butyl ether (MTBE) rather than diethyl ether. The crude product from step (5) was dissolved in ethanol for biological testing.

Compound 32-2H [general structure B; 70 kDa PEI (branched); $R^{60}$: —$(CH_2)_3OH$ (5%), —$C_6H_{13}$ (95%)] was synthesized in a similar manner to compound 32-2, but the mixture in step (1) had i-propyl alcohol rather than t-amyl alcohol, the mixture in step (1) was heated to 80° C. rather than 96-98° C., and trituration in step (4) was performed using methyl t-butyl ether (MTBE) rather than diethyl ether. The crude product from step (5) was dissolved in i-propyl alcohol for biological testing.

Compound 32-2I [general structure B; 70 kDa PEI (branched); $R^{60}$: —$(CH_2)_3OH$ (5%), —$C_6H_{13}$ (95%)] was synthesized in a similar manner to compound 32-2, but the mixture in step (1) had i-propyl alcohol rather than t-amyl alcohol, and the mixture in step (1) was heated to 80° C. rather than 96-98° C. The crude product from step (5) was dissolved in i-propyl alcohol for biological testing.

BIOLOGICAL EXAMPLES

Example 1. Efficacy Studies of Polymers in a Mouse *Staphylococcus aureus*-Induced Wound Infection Model Grouping This project involved five separate efficacy studies, which usually included wound control group, Infection control group, vancomycin group, and several test article (e.g., polymers of the present technology) groups.

Preparation of Inoculum i. Defined the infection date as Day 0 or 0 h.
ii. Streaked the bacterial from −80° C. glycerol stock on a TSA on Day-1. The plate was incubated overnight (20-24 h) at a 35±2° C. incubator.
iii. On Day 0, picked single colonies from TSA plate and suspended in sterile saline, and monitored OD600 (Biochrom-ultrospec-10). Adjusted the bacterial concentration to required level by adding more colonies or more saline. (The CFU/OD600 ratio is roughly 2.50E+08 CFU/ml at OD600=0.30 for Biochrom-ultrospec-10). This was the Inoculum.
iv. Counted the actual CFU level of the inoculum: took 200 µL of the inoculum into a 96-well plate then performed a series of 10-fold dilution to obtain 6 dilutions from $10^0$ to $10^{-5}$. For each dilutions, took 10 µL on TSA plates then cultured in incubator at 35±2° C. for overnight. On the second day, counted the CFU numbers of each dilutions then further calculated the actual CFU level of Inoculum. The calculation formula was:

$$\frac{\text{Number of } \textit{CFU} \text{ grown under the dilution gradient} * \text{Dilution factor}}{10 \text{ µl}} * 1000.$$

The inoculum was administered topically. Total 20 µl of inoculum was used for each mouse.

Establishment of Wound Infection Model i. On day 0, the day of wounding and inoculation, mice were anesthetized with injections of zoletil at 50 mg/kg and xylazine at 10 mg/kg.

ii. Hair was clipped from the cervical to mid-lumbar dorsum, and the skin was scrubbed with iodine solution followed by an ethanol rinse. A 10.0-mm disposable skin biopsy punch was used to create a full-thickness skin wound on the dorsal side of each mouse.

iii. 20 μL of Inoculum containing around 5.0E+06 NRS384 cells in a saline suspension were pipetted into the wound and allowed to absorb for 3~5 min. A TEGADERM™ bandage was placed over the wound to avoid cross-infection.

Treatment

Preparation of Vancomycin Solution

Vancomycin solution: Vancomycin was weighed and added to the corresponding volume of saline to prepare the solution at Conc. Of 1 mg/mL or 0.2 mg/mL. The dose volume is 10 μL or 50 μL/wound site.

Preparation of Test Article Solution

Compound 20-1 solution: Compound 20-1 (batch 105159) was weighed and added to the corresponding volume of dd water to prepare the solution at Conc. Of 300 μM or 30 μM. The dose volume was 10 μL or 50 μL/wound site.

A solution of compound 21-1 was also prepared similarly.

A solution of control compound 39637 was also prepared similarly.

(Compound 39637)

$C_{18}H_{37}$

N+

Br−

O

OH

Treatment of Vancomycin 5 minutes after the infection, treatments started according to the study design. See FIG. 5. Preparation of the formulations was based on the target concentrations. 10 μL/50 μL of vancomycin was pipetted into the wound site and allowed to absorb for 5 min. Then A TEGADERM™ bandage was placed over the wound to avoid cross-infection. At 12 h post infection, the TEGADERM™ bandage was taken off, the wound was dry at this time. 10 μL/50 μL of vancomycin was pipetted into the wound site and allowed to absorb for 5 min. Then the original TEGADERM™ bandage was placed over the wound to avoid cross-infection. At 24 h post infection, the TEGADERM™ bandage was taken off, the wound was dry at this time. 10 μL/50 μL of vancomycin was pipetted into the wound site and allowed to absorb for 5 min. Then a new TEGADERM™ bandage was placed over the wound to avoid cross-infection. At 36 h post infection, the TEGADERM™ bandage was taken off. There was a little exudation from the wound. Dry swabs were used to absorb the exudation around the edges of the wound without touching the surface of the wound. 10 μL/50 μL of vancomycin was pipetted into the wound site and allowed to absorb for 5 min. Then the TEGADERM™ bandage (not a new one) was placed over the wound to avoid cross-infection. Follow the above process for the next few days. TEGADERM™ bandage was changed every day. At 72 h post infection, the TEGADERM™ bandage was taken off. There was also a little exudation from the wound. Dry swabs were used to absorb the exudation around the edges of the wound without touching surface of wound. Then collected the wound site to detect the bacterial load.

Treatment of Test Article 5 minutes after the infection, treatments start according to the study design. Preparation of the formulations was based on the target concentrations. 50 μL of test article was pipetted into the wound site and allowed to absorb for 5 min. Then a TEGADERM™ bandage was placed over the wound to avoid cross-infection. At 24 h post infection, the TEGADERM™ bandage was taken off, the wound was dry at this time. 50 μL of test article is pipetted into the wound site and allowed to absorb for 5 min. Then a new TEGADERM™ bandage was placed over the wound to avoid cross-infection. At 48 h post infection, the TEGADERM™ bandage was taken off. There was a little exudation from the wound. Dry swabs were used to absorb the exudation around the edges of the wound without touching the surface of the wound. 50 μL of the test article was pipetted into the wound site and allowed to absorb for 5 min. Then a new TEGADERM™ bandage was placed over the wound to avoid cross-infection. At 72 h post infection, the TEGADERM™ bandage was taken off. There was also a little exudation from the wound. Dry swabs were used to absorb the exudation around the edges of the wound without touching the surface of the wound. Then collected the wound site to detect the bacterial load.

Determination of Bacteria Load in Wound Site

At a certain time point after infection, the animals were euthanized by $CO_2$. Each wound sample was excised and collected in 5 ml sterile saline for homogenization. IKA T10 homogenizer with S10N-10G dispersing tool was used at maximum speed. Homogenized tissues were 10× serially diluted in 96 well plates and 10 μL of each dilution was spotted on TSA agar plate. Incubated the plates in a 35±2° C. incubator overnight or until colonies reached countable size. CFUs were counted by visual inspection.

Statistical Analysis

The data was analyzed using GraphPad Prism 7 and represented with Mean±SEM.

Summary of Results

Study I

At 12 h and 24 h after infection with *Staphylococcus aureus*, the bacterial load of wound site was similar, increasing to 8.59 Ig CFU/wound site and 8.78 Ig CFU/wound site, respectively. After the intervention of the compound 20-1 (batch 105159), bacterial loads at 12-hour post infection and 24-hour post infection were significantly reduced to 4.07 Ig CFU/wound site and 4.06 Ig CFU/wound site compared with the corresponding infection control groups ($P<0.05$, $P<0.05$). At the same time, in vancomycin group, the effect of a single dose at 10 μg was not manifest at 12-hour post infection, but after twice administrations, the bacterial load decreased by 1.12 Ig CFU/wound site compared with 24 h infection control group ($P<0.05$). See Table 10.

TABLE 10

Design and Results of Study I

| Groups | #Animals | Inoculum size | Dosage regimen Starting at 5 min p.i. | Terminal | Ig(CFU/wound site) 12 h p.i. | ΔIg(CFU/wound site) vs 12 h infection control | Ig(CFU/wound site)24 h p.i. | ΔIg(CFU/wound site) vs 24 h infection control |
|---|---|---|---|---|---|---|---|---|
| Wound control | 3 | *S. aureus* NRS 384 | — | 24 h p.i. | — | — | — | — |
| Infection control | 3/3 | 4.20E+06 CFU/wound | — | 12 h/24 h p.i. | 8.59 ± 0.23 | — | 8.78 ± 0.22 | — |
| 38637 | 3/3 | site | 100 μM 50 μL wound site; once a day | | 8.35 ± 0.06 | −0.23 ± 0.06 | 8.49 ± 0.30 | −0.29 ± 0.30 |
| 20-1 | 3/3 | | 100 μM; 50 μL/wound site; once a day | | 4.07 ± 0.26 | −4.51 ± 0.26* | 4.06 ± 1.08 | 4.72 ± 1.08* |
| Vancomycia | 3/3 | | 10 μL/wound site; twice a day | | 8.47 ± 0.22 | −0.11 ± 0.22 | 7.67 ± 0.60 | −1.12 ± 0.60* |

Note:
*P < 0.05 vs infection group by T-test analysis.

Study II

At 12 h and 24 h after infection with *Staphylococcus aureus*, the bacterial loads of wound site were similar, increasing to 8.59 Ig CFU/wound site and 8.86 Ig CFU/wound site, respectively. After intervention of compound 20-1 (batch 105159) in a concentration of 300 μM, bacterial loads at 12-hour and 24-hour were significantly reduced to 3.05 Ig CFU/wound site and 4.97 Ig CFU/wound site compared with the corresponding infection control groups (P<0.05, P<0.05).

At 12 h and 24 h after infection with *Staphylococcus aureus*, the bacterial loads of wound site were similar, increasing to 8.59 Ig CFU/wound site and 8.86 Ig CFU/wound site, respectively. After intervention of compound 20-1 (batch 105159) in a concentration of 100 μM, bacterial loads at 12-hour and 24-hour were significantly reduced to 3.36 Ig CFU/wound site and 4.21 Ig CFU/wound site compared with the corresponding infection control groups (P<0.05, P<0.05).

At 12 h and 24 h after infection with *Staphylococcus aureus*, the bacterial loads of wound site were similar, increasing to 8.59 Ig CFU/wound site and 8.86 Ig CFU/wound site, respectively. After intervention of compound 20-1 (batch 105159) in a concentration of 30 μM, bacterial loads at 12-hour and 24-hour were significantly reduced to 5.69 Ig CFU/wound site and 5.70 Ig CFU/wound site compared with the corresponding infection control groups (P<0.05, P<0.05).

At 12 h and 24 h after infection with *Staphylococcus aureus*, the bacterial loads of wound site were similar, increasing to 8.59 Ig CFU/wound site and 8.86 Ig CFU/wound site, respectively. After intervention of compound 20-1 (batch 105159) in a concentration of 10 μM, bacterial loads at 12-hour and 24-hour were significantly reduced to 5.83 Ig CFU/wound site and 6.54 Ig CFU/wound site compared with the corresponding infection control groups (P<0.05, P<0.05).

Compared with the corresponding infection control groups, compound 20-1 (batch 105159) showed manifest anti-bacterial activity under the four different test concentrations, 300 μM and 100 μM, 30 μM and 10 μM and this activity showed a dose-effect relationship. Among them, the concentration at 300 μM and 100 μM showed the best efficacy. See Table 11.

TABLE 11

Design and results of Study II

| Groups | #Animals | Inoculum size | Dosage regimen Starting at 5 min p.i. | Terminal | Ig(CFU/wound site) 12 h p.i. | ΔIg(CFU/wound site) vs 12 h infection control | Ig(CFU/wound site)24 h p.i. | ΔIg(CFU/wound site) vs 24 h infection control |
|---|---|---|---|---|---|---|---|---|
| Wound control | 5 | *S. aureus* NRS 384 | — | 24 h p.i. | — | — | — | — |
| Infection Control | 5/5 | 2.50E+06 CFU/wound | — | 12 h/24 h p.i. | 8.59 ± 0.14 | — | 8.86 ± 0.16 | — |
| 20-1 | 5/5 | site | 300 μM; 50 μL/wound site; once a day | | 3.05 ± 0.32 | −5.54 ± 0.32** | 4.97 ± 0.48 | −3.90 ± 0.48** |
| | 5/5 | | 100 μM; 50 μL/wound site; once a day | | 3.36 ± 0.75 | −5.23 ± 0.75** | 4.21 ± 0.53 | −4.66 ± 0.53** |
| | 5/5 | | 30 μM; 50 μL/wound site; once a day | | 5.69 ± 1.72 | −2.90 ± 1.72** | 5.70 ± 1.37 | −3.17 ± 1.37** |
| | 5/5 | | 10 μM; 50 μL/wound site; once a day | | 5.83 ± 0.86 | −2.75 ± 0.86** | 6.54 ± 0.91 | −2.32 ± 0.91** |

TABLE 11-continued

Design and results of Study II

| Groups | #Animals | Inoculum size | Dosage regimen Starting at 5 min p.i. | Terminal | Ig(CFU/wound site) 12 h p.i. | ΔIg(CFU/wound site) vs 12 h infection control | Ig(CFU/wound site)24 h p.i. | ΔIg(CFU/wound site) vs 24 h infection control |
|--------|----------|---------------|---------------------------------------|----------|------------------------------|-----------------------------------------------|------------------------------|-----------------------------------------------|
| 39637 | 5/5 | | 1000 μM; 50 μL/wound site; once a day | | 5.44 ± 0.94 | −3.15 ± 0.94** | 5.81 ± 1.79 | −3.06+1.79** |
| | 5/5 | | 300 μM; 50 μL/wound site; once a day | | 8.14 ± 0.40 | −0.45 ± 0.40* | 8.90 ± 0.10 | 0.04 ± 0.10 |
| Vancomycin | 5/5 | | 1 mg/ml; 10 μL/wound site; twice a day | | 7.83 ± 0.44 | −0.76 ± 0.44* | 7.50 ± 0.54 | −1.36 ± 0.54** |

Note:
**P < 0.001 vs infection group by T-test analysis;
*P < 0.05 vs infection group by T-test analysis.

Study II

At 24 h, 48 h and 72 h after infection with *Staphylococcus aureus*, the bacterial loads of wound site reached to 8.77 Ig CFU/wound site, 8.57 Ig CFU/wound site and 7.96 Ig CFU/wound site, respectively. After the intervention of compound 20-1 (batch 105159), the bacterial load was significantly reduced compared with the corresponding infection groups. The bacterial loads at 24-hour, 48-hour, and 72-hour were significantly reduced to 5.15 Ig, 5.39 Ig, and 4.22 Ig respectively (P<0.001).

The effect of compound 20-1 (batch 105159) seems to be more stable with the increased treatment duration. See Table 12.

TABLE 12

Design and results of Study III: the antibacterial effect of compound 20-1 in mouse wound infection model with a series of different doses

| Groups | #Animals | Inoculum size | Dosage regimen Starting at 5 min p.i. | Terminal | Ig (CFU/wound site) | ΔIg(CFU/wound site) vs infection control |
|--------|----------|---------------|---------------------------------------|----------|---------------------|-------------------------------------------|
| Infection control | 5 | *S. aureus* NRS 384 | — | 24 h p.i. | 8.77 ± 0.25 | — |
| Vancomycin | 5 | 2.50E+06 CFU/wound site | 1 mg/ml; 10 μL/wound site; 10 μg/wound site, twice a day | | 7.67 ± 0.24 | −1.11 ± 0.24** |
| Vancomycin | 5 | | 1 mg/ml; 50 μL/wound site; 50 μg/wound site, twice a day | | 4.37 ± 0.26 | −4.40 ± 0.26** |
| 20-1 | 5 | | 100 μM; 50 μL/wound site; once a day | | 5.15 ± 1.15 | −3.63 ± 1.15** |
| Infection control | 5 | | — | | 8.57 ± 0.19 | — |
| Vancomycin | 5 | | 1 mg/ml; 10 μL/wound site; 10 μg/wound site, twice a day | 48 h p.i. | 5.29 ± 0.77 | −3.28 ± 0.77** |
| 20-1 | 5 | | 100 μM; 50 μL/wound site; once a day | | 5.39 ± 1.54 | −3.17 ± 1.54** |
| Infection control | 5 | | — | 72 h p.i. | 7.96 ± 0.11 | — |
| Vancomycin | 5 | | 1 mg/ml; 10 μL/wound site; 10 μg/wound site, twice a day | | 5.12 ± 0.65 | −2.83 ± 0.65** |
| 20-1 | 5 | | 100 μM; 50 μL/wound site; once a day | | 4.22 ± 0.16 | −3.74 ± 0.16** |

Note:
**P < 0.001 vs infection group by T-test analysis;
*P < 0.05 vs infection group by T-test analysis.

Study IV

At 12 h and 24 h after infection with *Staphylococcus aureus*, the bacterial loads of wound site reached to 8.59 Ig CFU/wound site and 8.72 Ig CFU/wound site, respectively. After the intervention of compound 21-1 at a concentration of 300 µM, the bacterial loads at 24-hour and 48-hour were significantly reduced to 5.21 Ig CFU/wound site and 5.58 Ig CFU/wound site, respectively (P<0.005).

At 12 h and 24 h after infection with *Staphylococcus aureus*, the bacterial loads of wound site reached to 8.59 Ig CFU/wound site and 8.72 Ig CFU/wound site, respectively. After the intervention of compound 21-1 at a concentration of 100 µM, the bacterial loads at 24-hour and 48-hour were significantly reduced to 6.37 Ig CFU/wound site and 6.80 Ig CFU/wound site, respectively (P<0.005).

At 12 h and 24 h after infection with *Staphylococcus aureus*, the bacterial loads of wound site reached to 8.59 Ig CFU/wound site and 8.72 Ig CFU/wound site, respectively. After the intervention of compound 21-1 at a concentration of 25 µM, the bacterial loads at 24-hour and 48-hour were significantly reduced to 7.81 Ig CFU/wound site and 8.01 Ig CFU/wound site, respectively (P<0.05).

Compared with the corresponding infection groups, compound 21-1 showed manifest antibacterial activity under three different test concentrations, and this activity possessed a dose-effect relationship. See Table 13.

Study V

At 12 h, 24 h and 72 h after infection with *Staphylococcus aureus*, the bacterial loads of wound site were 8.46 Ig CFU/wound site, 8.54 Ig CFU/wound site and 8.26 Ig CFU/wound site, respectively. Compound 20-1 (batch 105159) with a single application decreased the bacterial load by 4.54 Ig CFU/wound site, 2.88 Ig CFU/wound site and 0.43 Ig CFU/wound site at 24-hour post infection, 48-hour post infection, and 72-hour post infection, respectively. That is, its effect gradually reduced from 24 h post infection to 72 h post infection. See Table 14.

TABLE 13

Design and results of Study IV: the activity of a compound 21-1 at three different concentrations

| Groups | #Animals | Inoculum size | Dosage regimen Starting at 5 min p.i. | Terminal | Ig(CFU/wound site) 12 h p.i. | ΔIg(CFU/wound site) vs 12 h infection control | Ig(CFU/wound site)24 h p.i. | ΔIg(CFU/wound site) vs 24 h infection control |
|---|---|---|---|---|---|---|---|---|
| | | | | | | Readout | | |
| Infection control | 5 + 5 | *S. aureus* NRS 384 | — | 12 h/24 h p.i. | 8.59 ± 0.13 | — | 8.72 ± 0.31 | — |
| 21-1 | 5 + 5 | 4.10E+06 CFU/wound site | 300 µM; 50 µL/wound site; once a day | | 5.21 ± 0.37 | −3.37 ± 0.37** | 5.58 ± 0.14 | −3.14 ± 0.14** |
| | 5 + 5 | | 100 µM; 50 µL/wound site; once a day | | 6.37 ± 0.54 | −2.21 ± 0.54** | 6.80 ± 0.91 | −1.93 ± 0.91** |
| | 5 + 5 | | 25 µM; 50 µL/wound site; | | 7.81 ± 0.56 | −0.78 ± 0.56* | 8.01 ± 0.47 | −0.71 ± 0.47* |
| Vancomycin | 5 + 5 | | 1 mg/ml; 10 µL/wound site; 10 µg/wound site, twice a day | | 8.02 ± 0.35 | −0.57 ± 0.35 | 7.29 ± 0.32 | −1.44 ± 0.32** |
| Wound control | 5 | | — | 24 h p.i. | — | — | — | — |

Note:
*P < 0.005 vs infection group by T-test analysis;
**vs infection group by T-test analysis.

TABLE 14

Design and results of Study V, the duration of antibacterial action of compound 20-1 by one application

| Groups | #Animals | Inoculum size | Dosage regimen Starting at 5 min p.i. | Terminal | Ig(CFU/wound site) | ΔIg(CFU/wound site) vs infection control |
|---|---|---|---|---|---|---|
| | | | | | Readout | |
| Infection control | 5 | *S. aureus* NRS 384 | — | 24 h p.i. | 8.46 ± 0.36 | — |
| Vancomycin | 5 | 3.80E+06 CFU/wound site | 0.2 mg/ml; 50 µL/wound site; twice a day | | 6.07 ± 0.52 | −2.39 ± 0.52** |
| 20-1 | 5 | | 100 µM; 50 µL/wound site; Single one administration | | 3.92 ± 1.34 | −4.54 ± 1.34** |
| Infection control | 5 | | — | 48 h p.i. | 8.54 ± 0.43 | — |
| Vancomycin | 5 | | 0.2 mg/ml; 50 µL/wound site; twice a day | | 4.91 ± 0.1.71 | −3.63 ± 0.1.71** |
| 20-1 | 5 | | 100 µM; 50 µL/wound site; Single one administration | | 5.66 ± 1.36 | −2.88 ± 1.36** |
| Infection control | 5 | | — | 72 h p.i. | 8.26 ± 0.18 | — |

TABLE 14-continued

Design and results of Study V, the duration of antibacterial action of compound 20-1 by one application

|  |  |  |  |  | Readout | |
|---|---|---|---|---|---|---|
| Groups | #Animals | Inoculum size | Dosage regimen Starting at 5 min p.i. | Terminal | Ig(CFU/wound site) | ΔIg(CFU/wound site) vs infection control |
| Vancomycin | 5 | | 0.2 mg/ml; 50 μL/wound site; twice a day | | 5.05 ± 0.20 | −3.22 ± 0.20** |
| 20-1 | 5 | | 100 μM; 50 μL/wound site; Single one administration | | 7.84 ± 0.35 | −0.43 ± 0.35* |
| Vehicle control | 5 | | Water; 50 μL/wound site; once a day | | 8.52 ± 0.29 | 0.26 ± 0.29 |
| 20-1 | 5 | | 100 μM; 50 μL/wound site; once a day | | 5.70 ± 0.38 | −2.56 ± 0.38** |

Note:
**P < 0.001 vs infection group by T-test analysis,
*P < 0.05 vs infection group by T-test analysis.

At the concentration at 100 μM with once-a-day application, compound 20-1 (batch 105159) showed 2.56 Ig CFU/wound site reduction on bacterial load compared with the 72-hour infection control group (p<0.005).

Example 2. Mammalian Cell Cytotoxicity Studies

Primary Human Dermal Fibroblast (HDFs) and Human Keratinocyte (HaCaT) cells were selected for cytotoxicity and proliferation testing. HDFs were cultured in high glucose, no glutamine, no phenol red, Dulbecco's Modified Eagle Medium (DMEM) (GIBCO™). HDF media was further supplemented with 10% heat-inactivated fetal bovine serum (GIBCO™), 1% L-glutamine (GIBCO™) and 1% Penicillin-streptomycin (GIBCO™). HaCaTs cells were cultured in high glucose, no glutamine, no calcium DMEM (GIBCO™) supplemented with 10% heat inactivated foetal bovine serum, 1% L-glutamine, 1% Penicillin-streptomycin 1 mM calcium chloride (Sigma) throughout.

Mammalian cell populations were maintained in standard culture conditions at 37° C., 5% $CO_2$ and >95% relative humidity. Upon reaching 80% total confluency, cells were removed from the incubator, the culture media aspirated, and the monolayer washed with Dulbecco's modified eagle medium saline (DPBS). After washing, 10 mL of 1% trypsin (GIBCO™) was added to the flask and incubated to facilitate the detachment of cells from the culture vessel. Following dissociation, 10 mL of culture media was then added to each flask to neutralize the trypsin enzyme activity. The total 20-mL flask volume was transferred into a universal tube and centrifuged at 400 rcf for 5 minutes. Once complete, the pellet of cells was re-suspended in 10 mL warmed culture media and the number of cells per mL was determined using a hemocytometer counting chamber. Cell suspensions were then adjusted to 5×104 cells/mL for HDFs and 1×105 cells/mL for HaCaTs. 100 μL of the cell suspension was added to each well of a sterile, cell-culture-treated 96-well microtiter plate. The plates were incubated in standard culture conditions for 16-24 hours to allow cellular adherence to the culture vessel. Following attachment, stock compounds were thawed and serial two-fold dilutions were prepared for each compound in concentrations ranging from 100 μM to 0.8 μM (compounds 20-1 and 25-1: 2.5 μM to 0.02 μM) in warmed culture media in flat 96-well plates. Culture plates were removed from the incubator, the media removed; and monolayers washed with 100 μL of warmed DPBS. The contents of the test item dilution plates were transferred to the culture plates. This was applied to the mean of three biological replicates each with three technical replicates (n=9) for each dilution in each compound. The plates were returned to the incubator for 24 hours in standard culture conditions.

Cytotoxicity Testing

The secretion of lactate dehydrogenase (LDH) enzyme was used for quantitatively measuring cell damage and cytotoxicity. As damage to the cell plasma membrane releases LDH into the cell culture media, the extracellular LDH in the media can be quantified by a coupled enzymatic reaction in which LDH catalyzes the conversion of lactate to pyruvate via NAD+ reduction to NADH. Oxidation of NADH by diaphorase leads to the reduction of resazurin forming the highly fluorescent resorufin. Resorufin levels, which are directly proportional to the amount of LDH released into the medium, is therefore used to measure cytotoxicity.

Following incubation with the selected compounds, 50 μL of media from each well was transferred to the corresponding well of a fresh 96 well culture plate. The presence of Lactate dehydrogenase (LDH) was then quantified using the INVITROGEN™ CyQUANT™ LDH Cytotoxicity Assay, fluorescence kit. Total fluorescence was measured by reading the plates on a plate reader at an excitation of 560 nm and an emission of 590 nm.

Cell Proliferation Testing

After the collection of media for LDH quantification, the remaining cell culture media was aspirated, and the cell monolayers washed with 100 μL of warmed DPBS and fresh culture media added. CELLTITER 96® Aqueous One Solution Cell Proliferation Assay was then used to determine the number of cells present in the remaining culture vessels. The assay utilizes a tetrazolium compound (3-(4,5-dimethylthiazol-2-yl)-5-(3-carboxymethoxyphenyl)-2-(4-sulfophenyl)-2H-tetrazolium, inner salt) that is bio reduced by NADPH or NADH in metabolically active cells into a colored formazan product.

In each well, 20 μL of MTS (CELLTITER 96® Aqueous One Solution Cell Proliferation Assay) solution was added and the plates returned to the incubator for 4 hours. The cell plates were collected and the colorimetric change detected on the plate reader at absorbance 490 nm. The number of viable cells present in each treatment condition was determined using a calibration curve.

Microbiology Methods: Bacterial Strains and Media Culture Conditions

All microbial work was carried out in a class II biosafety hood. Clinically isolated strains of *Klebsiella pneumoniae*

KL1 (isolated from leg wound swab) and *Staphylococcus aureus* MR1 (Methicillin Resistant *Staphylococcus aureus* (MRSA) isolated from leg ulcer) were provided from our bank of nosocomial clinical isolates. All other strains were obtained from the ATCC. Table 15 describes all bacterial strains used in this study. In all subsequent experiments Mueller-Hinton (MH) medium was used as a broth. Overnight cultures (ONC) were prepared by inoculating bacteria from a single colony maintained on MH agar into 5 mL MH broth and incubating overnight at 37° C. for 14-15 h with continuous shaking (200 rpm).

ity were observed at treatment concentrations comparable to those able to inhibit bacterial growth. A majority of compounds caused cell cytotoxicity at the higher treatment concentrations (50 µM, 100 µM). A dose-dependent decrease in cytotoxicity and cell death was observed for almost all compounds.

Compound 20-1 (batches 105159 and 99367) delivered a dose-dependent increase in LDH secretion at 0.31 µM.

For compound 39637 (batches 105543 and 109466), LDH secretion in the HDF and HaCaT populations began to rapidly exceed control levels at 3.12 µM. Batch 105543

TABLE 15

Bacterial strains used in this study

| # | Species | Strain | Gram | Source |
|---|---------|--------|------|--------|
| 1 | *Klebsiella pneumoniae* | KL1 | -VE | Nosocomial isolate |
| 2 | *Pseudomonas aeruginosa* | ATCC 27853 | -VE | ATCC |
| 3 | *Enterococcus faecalis* | ATCC 51299 | +VE | ATCC |
| 4 | *Enterococcus faecalis* | ATCC 19433 | +VE | ATCC |
| 5 | *Staphylococcus aureus* | ATCC 29213 | +VE | ATCC |
| 6 | *Escherichia coli* | ATCC 25922 | -VE | ATCC |
| 7 | *Staphylococcus aureus* | MR1 | +VE | Nosocomial isolate |

Summary of Results

TABLE 16

Summarized cell toxicity values for tested compounds.
Mammalian Cell Cytotoxicity (µM)

| Compound_Batch | HDF | HaCaT |
|----------------|-----|-------|
| 23-1_105402 | 6.25 | 6.25 |
| 23-1_109634 | 25 | 25 |
| 20-1_105159 | 0.63 | 0.63 |
| 20-1_99367 | 0.31 | 0.63 |
| 39637_105543 | 6.3 | 6.3 |
| 39637_109466 | 6.3 | 6.3 |
| 22-—1_109590 | 3.12 | 3.12 |
| 21-1_109770 | 3.12 | 3.12 |
| 24-1_109781 | 6.25 | 6.25 |
| 40840_110435 | >100 | >100 |
| 25-1_110417 | 0.16 | 0.63 |
| 40598_109448* | >100 | >100 |
| 28-1_109666 | 100 | 100 |
| 26-1_109831 | 3.12 | 3.12 |
| 40597_109444** | 100 | 100 |
| 27-1_110420 | 0.78 | 0.78 |

*Compound 40598 corresponds to
    C₆H₁₃

[chemical structure] Br⁻

**Compound 40597 corresponds to
    C₁₂H₂₅

[chemical structure] Br⁻

There was strong agreement between cell viability (MTS) and overall cytotoxicity (LDH). Overall cytotoxicity appeared to be marginally higher in the HDF population. No positive effect on mammalian cell proliferation was observed in response to any of the screened compounds. For a majority of the compounds, negative effects on cell viabilappeared to exhibit a slightly higher cytotoxic influence. However, for both batches, an almost total absence of viable cells was observed in each cell population at 6.3 µM.

The concentrations at which compound 22-1 (batch 109590) and compound 21-1 (batch 109770) demonstrated cytotoxicity were highly similar, with an almost complete absence of HDF and HaCaT viable cells at 3.12 µM.

Compound 24-1 (batch 109781) had a slightly reduced cytotoxic influence on mammalian cells, with a spike in LDH secretion and lack of viable cells observed at 6.25 µM.

Compounds 40840 and 40598 showed minimal cytotoxicity against mammalian cells: 13.8% increase in overall HDF cytotoxicity versus control.

Compounds 40840, 40598, 28-1 (batch 109666) and 40597 (batch 10944) demonstrated minimal cellular cytotoxicity. These compounds also displayed limited antimicrobial activity.

Compound 20-1 (batch 105159) and compound 20-1 (batch 99367) displayed broad range antimicrobial activity at relatively low concentrations. Compound 20-1 (batch 105159) and compound 20-1 (batch 99367) also displayed high mammalian cell cytotoxicity alongside broad range antimicrobial activity at relatively low concentrations.

Compounds 26-1 and 27-1 were cytotoxic to mammalian cells at all tested concentrations. Compound 26-1 had selective antimicrobial activity against both *Staphylococcus aureus* strains ATCC 29213 and clinical isolate MR1.

Compound 25-1 was the most active against all Gram +VE species at relatively low µM concentrations (6.25 µM) and including one Gram -VE species, *Klebsiella pneumoniae* KL1.

Example 3. Antimicrobial Activity Studies

Minimum Inhibitory Concentration (MIC)

The standard broth microdilution method was used to investigate the antimicrobial efficacy of the tested compounds. Serial two-fold dilutions were prepared for each compound in concentrations ranging from 100 μM to 0.8 μM in sterile MH broth in flat 96-well plates. ONC of each bacterial strain was adjusted to give a standard bacterial concentration ($5 \times 10^5$ CFU/mL) and added to each dilution to determine the MIC in a total volume of 100 μL MH broth. All plates were statically incubated at 37° C. for 24 h. Sterile dH$_2$O was used as a vehicle only control, for each bacterial strain positive (bacteria only) and negative (MH media only) controls were included. To determine the MIC breakpoint plates were stained with 10 μL of 0.02% resazurin and incubated at 37° C. for 30 min. Following incubation, all plates were imaged, and absorbance was measured at 570 nm (Plate reader). The MIC is defined as the lowest concentration of compounds that inhibits growth. MH media was used as a negative control and bacteria only was used as a positive control on each plate for all compounds tested. Serial two-fold dilutions were performed by mixing 50 μL of the highest concentration (×2) from row A to H containing 50 μL sterile MH broth.

MIC Data Analysis

The data was exported to Microsoft Excel and background normalized by subtracting OD570 nm values from media only wells (−VE control). MIC values were determined by plotting the OD570 nm values (Y) against the log concentration of each compound (X). A modified Gompertz model was used to fit the data to obtain a more accurate MIC. The average OD570 nm for each test compound concentration was fitted to a sigmoidal curve using the modified Gompertz function (y=A+Ce−e(B(x−M))), and the minimum inhibitory concentration (MIC) was identified from the point of inflexion of the lower asymptote (Graph-Pad Prism 9.0). This was applied to the mean of three biological replicates each with four technical replicates (n=12) for each dilution in each compound.

Minimum Bactericidal Concentration (MBC) Procedure

To determine MBC compound concentrations breakpoints were estimated from MIC curves. Overnight cultures were set up as described above for all bacterial strains. The following day overnight cultures were adjusted to give a cell density of $5 \times 10^5$ cells per mL. Briefly, cultures were adjusted to the McFarland standard (0.08-0.12) and diluted (1:150). Adjusted cultures were inoculated into 96 well plates with 50 μL sterile Muller-Hinton broth (MHB) and 2 concentrations of each compound. MBC plates were statically incubated for 24 hours at 37° C. Sterile dH$_2$O was used as a vehicle control, positive (bacteria only) and negative controls (media only) were also included in the assay. MBC cultures were quantified by serial dilution in a 96 well plate and spot plating onto Muller-Hinton agar (MHA). MHA plates were incubated at 37° C. for 24 h and counted. Results are presented as CFU per mL.

Summary of Results

TABLE 17

Summarized MIC values for compounds tested against listed bacteria. All values are μM.

| | MIC* | | | | | | |
| | Gram −VE | | | Gram +VE | | | |
| Compd_Batch | KL1 | PA27853 | EC25922 | EF51299 | EF19433 | SA29213 | MR1 |
|---|---|---|---|---|---|---|---|
| 23-1_105402 | 0.00 | Unstable | 82.82 | 20.04^ | 22.50^ | 4.55 | 4.21^ |
| 23-1_109634 | 0.00 | 58.40^ | 4.50E+06 | 61.47^ | 91.59^ | 8.39 | 17.35^ |
| 20-1_105159* | 3.36E+08 | 3.93E+25 | 1.26E+04 | 0.00 | 5.48E+09 | 1.12E+15 | 7.25E+11 |
| 20-1_99367* | 2.87E+12 | 18.57^ | 0.00 | 2.93 | 68443.00 | 2.94 | 2.98 |
| 39637_105543 | +infinity | 53.54 | 42.96 | 62.65^ | 3.20^ | 3.16 | 10.58^ |
| 39637_109466 | 2.06 | 62.14^ | 59.94 | 16.81^ | 2.59^ | 3.05 | 10.78^ |
| 22-1_109590 | 2.54E+11 | 119.70^ | 7.55 | 29.17^ | 7.68^ | 3.05 | 4.22^ |
| 21-1_109770 | 0.00 | +infinity | 2.92 | 3.62^ | 2.18^ | 2.08 | 1.43^ |
| 24-1_109781 | 6455.00 | 6.36 | 4.21 | 0.00^ | 20.16^ | 3.33 | 0.00^ |
| 40840_110435 | 1.76 | 0.00 | 0.03 | +infinity | 0.00 | 1.99 | +infinity |
| 25-1_110417 | +infinity | +infinity | 0.00 | 3.26E+13 | 3.99E+04 | 0.00 | 0.00 |
| 40598_109448 | 48.98 | 0.00 | 0.06 | 0.83 | 4.82E+10 | 1.93 | 0.00 |
| 28-1_109666 | 2.16 | 19847.00 | 5.74 | 4.24 | 0.01 | 0.00 | 1.78^ |
| 26-1_109831 | 0.36 | 42.19^ | 4.26E+09 | 0.00 | 74346.00^ | 6.01 | 1.05^ |
| 40597_109444 | 0.01 | 2.84 | 0.00 | 27.19^ | 1.63^ | 0.00 | 0.94 |

*MIC values were estimated by using a modified Gompertz model to fit the data to obtain a more accurate MIC.
Values marked with ^ indicate reliable estimation of MIC, whereas all other values indicate unreliable estimation using the model, interpret with caution.

TABLE 18

Summarized MBC values for compounds tested against listed bacteria. All values are μM.

| | MBC | | | | | | |
| | Gram −VE | | | Gram +VE | | | |
| Compd_Batch | KL1 | PA27853 | EC25922 | EF51299 | EF19433 | SA29213 | MR1 |
|---|---|---|---|---|---|---|---|
| 23-1_105402 | 50 | 75 | 50 | 25 | 6.25 | 3.12 | 6.25 |
| 23-1_109634 | — | — | 50 | 25 | — | — | 12.5 |
| 20-1_105159 | 0.78 | 0.78 | 1.5 | 0.4 | 6.25 | 0.4 | 0.4 |

TABLE 18-continued

Summarized MBC values for compounds tested
against listed bacteria. All values are μM.

| | MBC | | | | | | |
|---|---|---|---|---|---|---|---|
| | Gram −VE | | | Gram +VE | | | |
| Compd_Batch | KL1 | PA27853 | EC25922 | EF51299 | EF19433 | SA29213 | MR1 |
| 20-1_99367 | 50 | 12 | 0.78 | 0.4 | 6.25 | 0.4 | 0.4 |
| 39637_105543 | — | — | 25 | — | 1.57 | 1.57 | 6.25 |
| 39637_109466 | 50 | — | 25 | 1.57 | 1.57 | 1.57 | 6.25 |
| 22-1_109590 | 25 | — | 3.1 | 50 | 6.25 | 3.12 | 3.12 |
| 21-1_109770 | 6.25 | — | 1.57 | 6.25 | 1.57 | 3.25 | — |
| 24-1_109781 | — | — | — | — | — | >6.25 | — |
| 40840_110435 | — | — | — | — | — | — | — |
| 25-1_110417 | 6.25 | — | — | 6.25 | 6.25 | 6.25 | 6.25 |
| 40598_109448 | — | — | — | — | — | — | — |
| 28-1_109666 | — | — | — | — | — | — | >50 |
| 26-1_109831 | 25 | — | — | >50 | — | >6.25 | 6.25 |
| 40597_109444 | — | — | — | — | — | — | — |

—: no activity observed

Compounds 23-1 (batches 105402 and 109634), 39637 (batches 105543 and 109466), 22-1 (batch 109590), 21-1 (batch 109770), and 24-1 (batch 109781) showed strong antimicrobial activity towards the gram +ve species *Enterococcus faecalis* and *Staphylococcus aureus*.

In the Gram-negative species (*Klebsiella pneumonia* and *Pseudomonas aeruginosa*) three compounds were able to display an inhibitory effect within the investigated range of concentrations: compounds 20-1 (batch 105159), 20-1 (batch 99367), and 22-1 (batch 109590).

Compounds 39637 (batches 105543 and 109466), 22-1 (batch 109590), and 21-1 (batch 109770) inhibited *Staphylococcus aureus* at concentrations from 1.57 μM to 6.25 μM.

Of all the compounds tested, the most effective MIC and MBCs were lower in Gram positive bacteria; however, there does appear to be broad spectrum activity with Gram negative bacteria at much higher concentrations.

Compound 20-1 (batches 105159 and 99367) exhibited the most effective MBC inhibition profile across all bacterial strains. MBC values clearly show inhibition of all strains at relatively low concentrations.

Of all compounds tested above, the following exhibited the lowest antimicrobial activity: compounds 40840 (batch 110435), 40598 (batch 109448), 28-1 (batch 109666), 26-1 (batch 109831), and 40597 (batch 109444). Compound 25-1 (batch 110417) showed low antimicrobial efficacy via MIC, but inhibited five out of the seven strains at 6.25 μM in MBC.

Additional compounds were tested to obtain MIC values against the same bacteria shown in Tables 17 and 18 (see Table 19). **: ≤12.5 μM MIC of QPEI for all tested bacteria; *: >12.5 μM MIC of QPEI and ≤50 μM MIC of QPEI against >50% of the tested bacteria; **: >12.5 μM MIC of QPEI and ≤50 μM MIC of QPEI against <50% of the tested bacteria; *: >100 μM MIC of QPEI for all tested bacteria.

TABLE 19

| Compound | Antibacterial Efficiency |
|---|---|
| 29-1 | **** |
| 30-1 | ** |
| 31-1 | **** |
| 32-1 | **** |

TABLE 19-continued

| Compound | Antibacterial Efficiency |
|---|---|
| 32-2 | **** |
| 32-3 | **** |
| 32-4 | **** |
| 32-5 | *** |
| 32-6 | *** |
| 32-7 | *** |
| 32-8 | * |
| 32-9 | ** |

Example 4. Efficacy of Biofilm
Inhibition—Microscopy Results

General Bacterial Cell Culture

All culture techniques were performed utilising aseptic technique and carried out in class II microbiological safety cabinet (Microflow, Bioquell, Hampshire, UK). All surfaces and items within the class II hood were sprayed with 70% ethanol in order to contribute to aseptic working conditions. As and when required, stock plates were created by streaking a single Microbank bead onto Mueller Hinton agar plates (MHA; Oxoid, UK) followed by incubation of the plate for 24 hours at 37° C. Stock plates were then wrapped in parafilm to reduce moisture loss and stored at 4° C. for up to 2 months.

Biofilm Preparation

Bacterial overnight (O/N) cultures of *S. aureus* were created by inoculating 10 mL Mueller Hinton Broth (MHB; Oxoid, UK) with a single colony followed by incubation at 37° C. for 16 hours with 140 rpm shaking (Labnet 211 DS shaking incubator, Labnet International, USA). O/N cultures in the stationary growth phase were diluted to obtain cell densities at 107 CFU/mL, verified by spot plating and colony counts. Biofilms were prepared by inoculating sterile filter membranes (0.22 μm, GE Healthcare, USA) on Mueller Hinton Agar (MHA; Oxoid, UK) with 4 μL of adjusted inoculum. Once dry, plates were then incubated upright at 37° C. for 4 hrs. Following incubation, biofilms were removed from the incubator and treated with 4 μL of various concentrations (100, 50, 25, 12.5, or 6.25 μM) of a select compound from Table 19. Biofilms were again incubated upright at 37° C. for the duration of the specific treatment incubation.

Scanning Electron Microscopy

Following treatment with the select compound, biofilm-containing filter membranes were aseptically removed from the agar surface and transferred into 6-well plates. In each well, 3-4 mL of 1% (v/v) glutaraldehyde (Sigma-Aldrich; Poole, UK) in pure water was to cover the biofilms. The glutaraldehyde solution was then left for at least one hour at RT (room temperature). After one hour, the 1% glutaraldehyde was removed and replaced with pure water. This step was repeated two or three times to ensure the complete removal of the glutaraldehyde solution. In each well, 3-4 mL of 10% (v/v) ethanol in pure water was added to the biofilms and left for 30 mins. This process was then repeated with successive solutions of ethanol in pure water from 30%, 50%, 70% and 90% (v/v). Following incubation with increasing strength ethanol solutions, biofilms were submerged in 100% EtOH for 30 mins. This process was repeated for a second time with fresh 100% EtOH. Following all ethanol washes, biofilms underwent critical point drying using the E3100 Critical Point Dryer (Quorum, Houston, US). This process replaces any remaining ethanol in the sample with liquid carbon dioxide, creating a dry sample. After drying, biofilms were coated with 5 nm of gold using a Polaron T-100 coater/thickness monitor (Ladd, Williston, US). Scanning electron microscopy was then used to image the samples using a zeiss EVO-60 microscope. Imaging was conducted using a LaB6 emitter at an EHT of 20 kilovolts (kV) and a probe current of 100 pA. Biological triplicates were used for all biofilm treatment conditions (n=3).

Figure 1A:
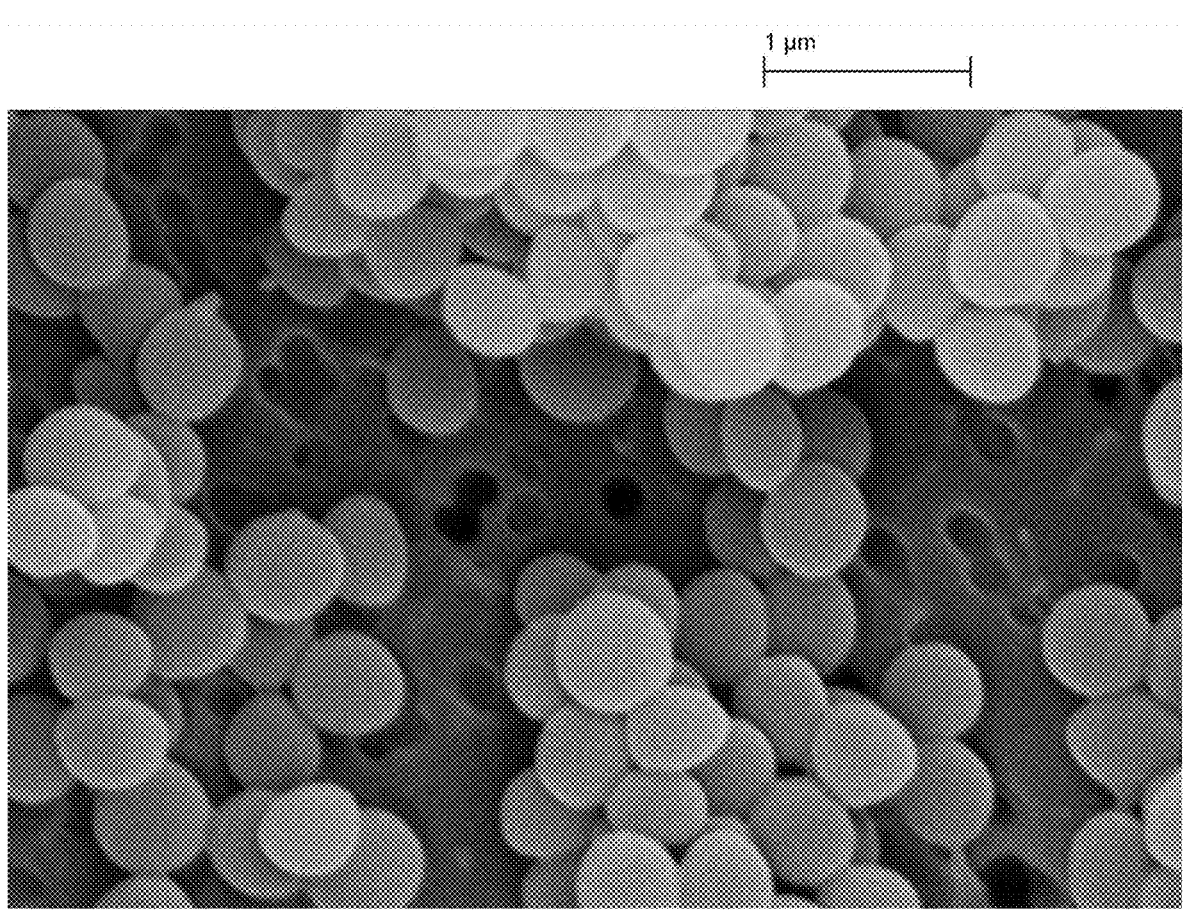
FIG. 1A depicts a SEM image of control *S. aureus* biofilm.
Figure 1B:
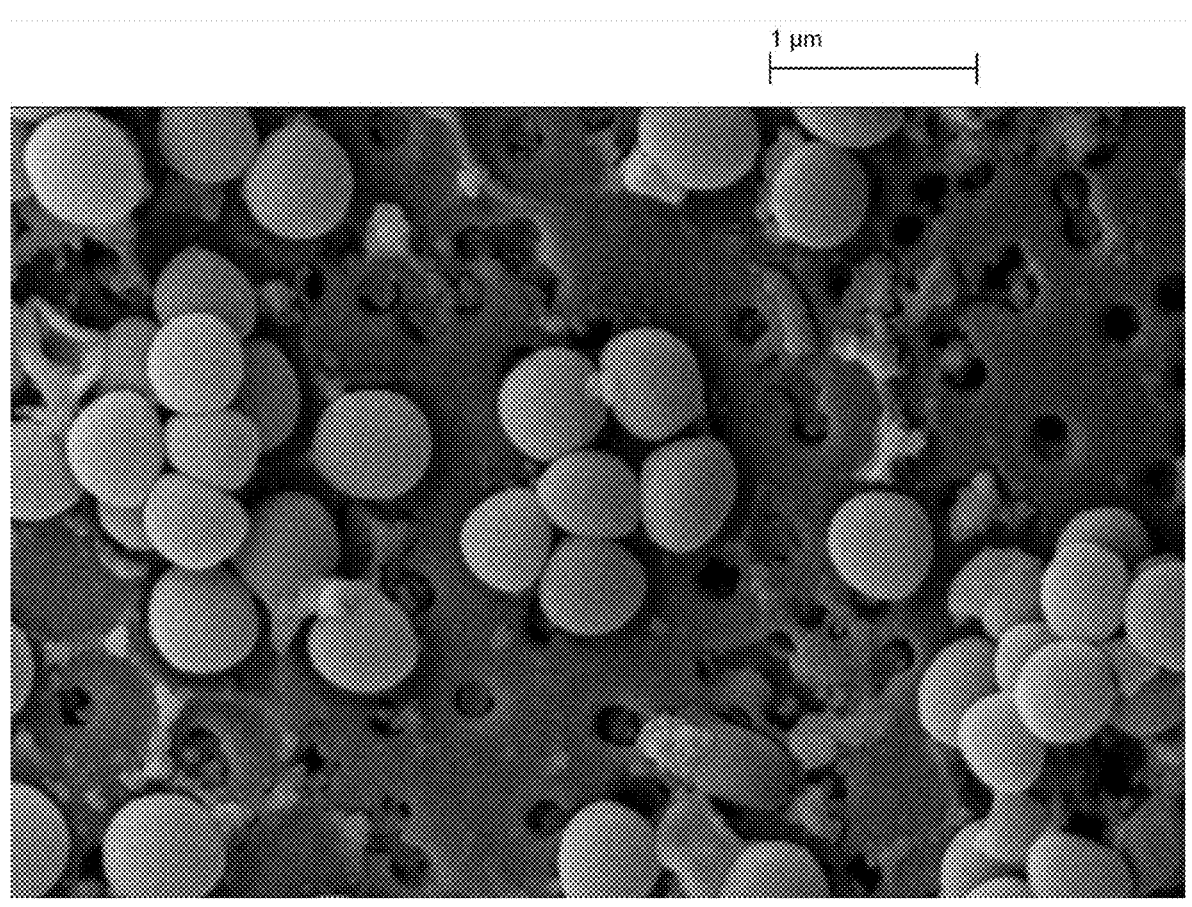
FIG. 1B depicts a SEM image of *S. aureus* biofilm treated with a compound disclosed herein (100 μM), as discussed in Example 4.

SEM images of the control biofilm and biofilm treated with the select compound (100 µM) are shown in FIG. 1A and FIG. 1B, respectively.

Confocal Microscopy

Following treatment with the select compound, biofilm-containing filter membranes were stained with FILMTRACER™ LIVE/DEAD® Biofilm Viability Kit prepared as per manufacturers' instructions. LIVE/DEAD® biofilm viability staining incorporates SYTO 9 (LIVE cell-permeable stain) and Propidium Iodide (PI) (DEAD cell-impermeable stain). Staining solution (4 µL) was applied directly onto the surface of the biofilm and incubated at RT for 20 min in the dark. Biofilm-containing filter membranes were inverted on a clean coverslip.

Confocal laser microscopy imaging was carried out using a Zeiss LSM710 Laser Scanning Confocal Microscope. For acquiring signals, a 488 nm laser was used for SYTO 9 and 561 nm for PI. For 3D images, z-stack series was performed for over 10 slices at 45 µM for all samples. Representative images were taken from the maximum intensity projection for each sample. For quantification of the LIVE/DEAD® signal, the relative intensity for both tracks (SYTO9 & PI)

in each sample was measured over the corresponding area. Biological triplicates were used for all biofilm treatment conditions (n=3).

Figure 2A:
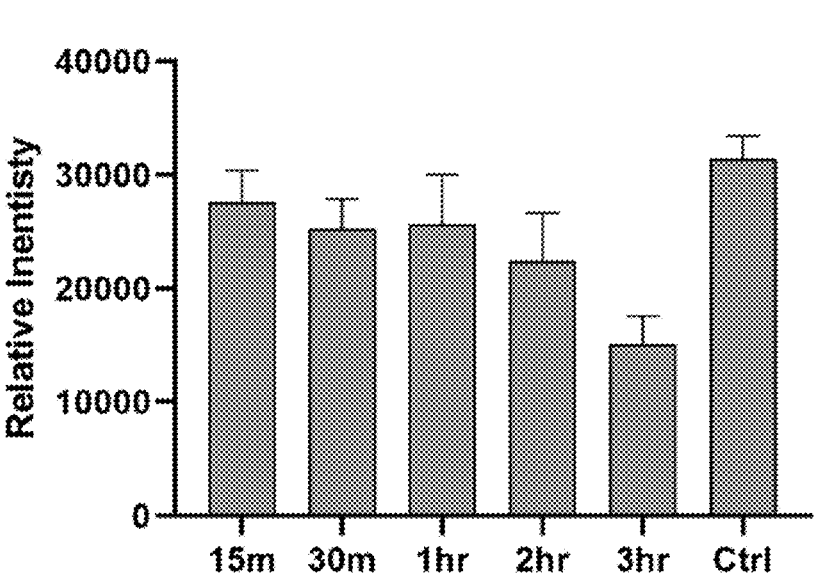
FIG. 2A and FIG. 2B depict quantification using SYTO 9 staining or propidium iodide staining, respectively, of activity of a compound disclosed herein (25 μM) over time on *S.*
Figure 2B:
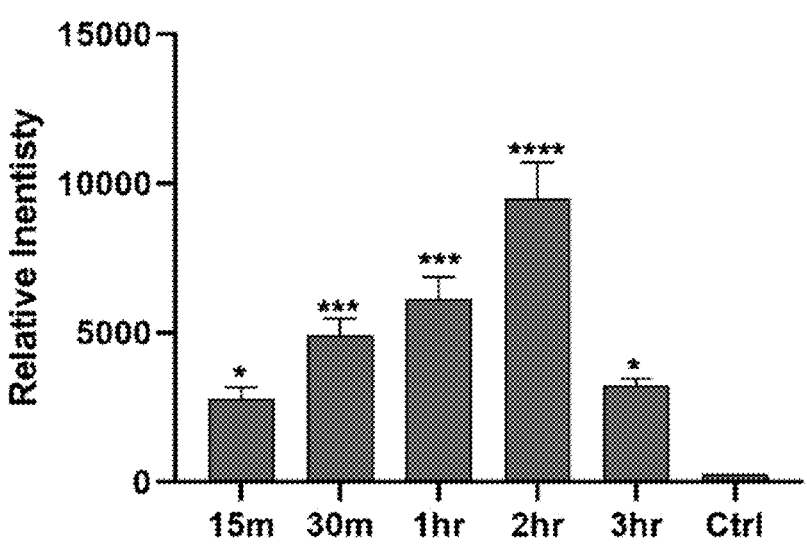

Quantification of activity of the select compound (25 µM) on S. aureus colony biofilms over the course of 3 hours is shown in FIG. 2A (SYTO 9) and FIG. 2B (Propidium Iodide). Quantification of activity of the same compound at different concentrations on S. aureus colony biofilms is shown in FIG. 3A (SYTO 9) and FIG. 3B (Propidium Iodide). The select compound inhibits biofilm viability quickly with measurable levels of dead cells at 15 min compared to untreated control, suggesting that the mode of action is immediate and most likely contact dependent via membrane disruption and/or membrane permeabilization.

Example 5. In Vitro Efficacy of Compounds Against Gram-Positive and Gram-Negative Bacteria The bacterial strains tested included CLSI and NCTC reference and quality control (QC) strains from the following organism groups: Acinetobacter baumannii, Enterococcus faecalis, Escherichia coli, Klebsiella pneumoniae, Pseudomonas aeruginosa, and Staphylococcus aureus. Some strains contained molecularly characterized β-lactamase genes including carbapenemase (KPC-2) and extended-spectrum β-lactamase (SHV-18) genes.

Isolates were tested for antimicrobial susceptibility using broth microdilution methodology according to CLSI M07 (2018) and M100 (2023) guidelines. Frozen-form, 96-well MIC panels were produced. The testing medium was cation-adjusted Mueller-Hinton broth (CAMHB). Single MIC values were measured for 8 test compounds against each of the 9 strains tested. Additional MIC values were generated for levofloxacin (comparator agent) against several of the QC strains.

Compound stock solutions were prepared and allowed to mix overnight as needed. The pH of each stock solution was checked and adjusted as necessary until a minimum pH of 5.0 was achieved (pH range 5.0-7.0). Some compound stock solutions also required the addition of heat to assist in solubilization.

Current CLSI quality assurance practices were followed when performing the broth microdilution susceptibility testing. MIC values were validated by concurrently testing a control agent (levofloxacin) against CLSI-recommended QC strains including S. aureus ATCC 29213 (methicillin susceptible), E. coli ATCC 25922, Enterococcus faecalis ATCC 29212, and P. aeruginosa ATCC 27853. The initial inoculum density (target, $5 \times 10^5$ CFU/mL) during susceptibility testing was monitored by bacterial colony counts.

The MIC values for the 8 test compounds and levofloxacin tested against the 9 QC and reference strains are shown in Table 20.

TABLE 20

| | MIC (µg/mL) | MIC (µM) | | | | | | | |
|---|---|---|---|---|---|---|---|---|---|
| | Levo | A | B | C | D | E | F | G | H |
| (I) | 4 | 12.5 | >0.8* | 6.25 | 6.25 | 0.8 | 6.25 | 0.8 | >0.4* |
| (II) | 1 | 6.25 | 0.2 | 1.6 | 1.6 | 0.2 | 6.25 | 0.8 | >0.4* |
| (III) | 0.5 | 6.25 | 0.2 | 3.125 | 1.6 | 0.2 | 6.25 | 0.4 | 0.4 |
| (IV) | 0.015 | 12.5 | >0.8* | 6.25 | 6.25 | 0.8 | 12.5 | 0.8 | >0.4* |
| (V) | 0.03 | 12.5 | >0.8* | 12.5 | 6.25 | 0.8 | 12.5 | 0.8 | >0.4* |
| (VI) | 0.5 | 25 | >0.8* | 25 | >6.25* | 1.6 | 50 | 0.8 | >0.4* |

TABLE 20-continued

| MIC (μg/mL) | MIC (μM) | | | | | | | |
|---|---|---|---|---|---|---|---|---|
| | Levo | A | B | C | D | E | F | G | H |
| (VII) | >8 | 50 | 0.8 | 25 | >6.25* | 1.6 | >100 | >0.8* | >0.4* |
| (VIII) | 1 | 25 | 0.8 | 25 | >6.25* | >1.6* | 100 | 0.8 | >0.4* |
| (IX) | 0.12 | 3.125 | 0.2 | 0.8 | 0.4 | ≤0.1 | 1.5 | 0.4 | 0.4 |

(I) = A. baumannii (NCTC 13304); (II) = E. faecalis (ATCC 29212); (III) = E. faecalis (ATCC 51299); (IV) = E. coli (ATCC 25922); (V) = E. coli (ATCC BAA-2452); (VI) = K. pneumoniae (ATCC 700603); (VII) = K. pneumoniae (ATCC BAA 1705); (VIII) = P. aeruginosa (ATCC 27853); (IX) = S. aureus (ATCC 29213).
A = compound 32-10; B = compound 21-1; C = compound 29-1; D = compound 32-2B; E = compound 32-1B; F = compound 22-1; G = compound 32-11; H = compound 32-3; Levo = levofloxacin
*indicates the highest compound concentration that could be tested due to compound solubility in CAMHB Compound 32-10 demonstrated broad spectrum antibacterial activity with Gram-positive MIC values ranging from 3.125 μM-6.25 μM against S. aureus and E. faecalis, respectively, and Gram-negative activity ranging from 12.5 μM-50 μM against Enterobacterales and non-fermenters (A. baumannii and P. aeruginosa).

Gram-positive activity was observed for compound 21-1 against S. aureus and E. faecalis isolates with MIC values of 0.2 μM. Due to solubility issues in CAMHB, the highest concentration of compound 21-1 where an MIC value could be determined was 0.8 μM. Against Gram-negative bacteria, compound 21-1 MIC values ranged from 0.8 μM to >8 μM.

Compound 29-1 demonstrated broad spectrum activity with Gram positive MIC values of 0.8 μM against S. aureus and 1.6 μM-3.125 μM against E. faecalis. Gram-negative activity ranged from 6.25 μM-25 μM against the Enterobacterales (E. coli and K. pneumoniae) and non-fermenter (A. baumannii and P. aeruginosa) isolates tested.

Gram-positive activity was observed for compound 32-2 against S. aureus and E. faecalis isolates with MIC values of 0.4 μM and 1.6 μM, respectively. Due to solubility issues in CAMHB, the highest concentration of compound 32-2 where an MIC value could be determined was 6.25 μM. Against Gram-negative bacteria, compound 32-2 MIC values ranged from 6.25 μM to >6.25 μM.

Compound 32-1 demonstrated broad-spectrum activity with Gram-positive MIC values of 50.1 μM against S. aureus and 0.2 μM against E. faecalis. Due to solubility issues in CAMHB, the highest concentration of compound 32-1 where an MIC value could be determined was 1.6 μM. Gram-negative activity ranged from 0.8 μm to 1.5 μM against the Enterobacterales (E. coli and K. pneumoniae) and non-fermenter (A. baumannii and P. aeruginosa) isolates tested.

Compound 22-1 demonstrated broad spectrum activity with Gram-positive MIC values of 1.6 μM against S. aureus and 6.25 μM against E. faecalis. Gram-negative activity ranged from 6.25 μM for A. baumannii, 12.5 μM for E. coli, and 50 μM to 100 μM for K. pneumoniae and P. aeruginosa.

Compound 32-11 demonstrated broad-spectrum activity with Gram-positive MIC values of 0.4 μM against S. aureus and 0.4 μM-0.8 μM against E. faecalis. Due to solubility issues in CAMHB, the highest concentration of compound 32-11 where an MIC value could be determined was 0.8 μM. Gram-negative activity ranged from 0.8 μm to >0.8 μM against the Enterobacterales (E. coli and K. pneumoniae) and non-fermenter (A. baumannii and P. aeruginosa) isolates tested.

Compound 32-3 demonstrated potent Gram-positive activity with MIC values of 0.4 μM against S. aureus and 0.4 μM to >0.4 μM against E. faecalis. Due to solubility issues in CAMHB, the highest concentration of compound 32-3 where an MIC value could be determined was 0.4 μM. Gram-negative activity was >0.4 μM against the Enterobacterales (E. coli and K. pneumoniae) and non-fermenter (A. baumannii and P. aeruginosa) isolates tested.

Example 6. In Vivo Antimicrobial Efficacy of Compounds

A murine wound infection model was used to evaluate the antimicrobial efficacy of test compounds: compound 32-1, compound 32-2, compound 32-1B, and compound 32-2D.

Staphylococcus aureus NRS384 was used in these wound infection studies. S. aureus NRS384 was inoculated in 10 mL Tryptic Soy Broth (TSB) and incubated at 37° C. overnight with shaking. Overnight bacterial cultures were pelleted at 3000 rpm for 10 minutes and washed twice in sterile Dulbecco's Phosphate Buffered Saline (DPBS) to remove residual TSB. Cells were resuspended in sterile DPBS to desired colony forming unit (CFU) concentrations as determined by previous standard curves. Bacteria applied to wounds are reported as CFU/10 μL (where 10 μL bacterial suspension was applied to each wound), while bacterial enumeration data is reported as CFU/mL (where each wound was digested in 1 mL DPBS).

Stocks of compound 32-1, compound 32-1B, and compound 32-2 were prepared in sterile filtered (0.22 μM) distilled water (dH₂O) to 0.57 mM concentration. Both compounds were dissolved in sterile filtered dH₂O overnight at 37° C. with continuous shaking (200 rpm). For pH adjusted compounds, all compounds were dissolved in ~4 mL dH₂O then adjusted with NaOH to pH 7.0 (confirmed using pH test strips). Sterile dH₂O was then added to give a final stock volume of 5 mL and concentration of 0.57 mM for each pH-adjusted compound. All working concentrations were prepared by diluting the 0.57 mM stocks in sterile dH₂O to the desired concentrations.

The stock concentration of compound 32-2D was assumed to be ~7 mM in EtOH based 50% w/w as supplied by the manufacturer. 1 mM working stocks of compound 32-2D and 0.57 mM compound 32-1B stocks were prepared in sterile filtered (0.22 μM) distilled water (dH₂O). All compounds were dissolved in dH₂O overnight at 37° C. with continuous shaking (200 rpm). The pH was confirmed to be 7, using pH test strips. All working concentrations were prepared by diluting working stocks in sterile dH₂O to the desired concentrations. All prepared compounds were kept at 4° C. until use. For all mouse studies, fresh batches of compounds were prepared 2-3 days prior to the study. For preparation of positive controls, stock solutions of Fusidic Acid and Vancomycin were prepared in sterile dH₂O to 2 mg/mL and 1 mg/mL, respectively. Fusidic acid and Vancomycin were topically applied to each wound in a 10 μL volume to give final concentrations of 20 μg and 10 μg per wound, respectively.

Male and female wild-type (balb/c) mice (approx. 8 weeks old) received standard chow and water ad libitum. Mice were maintained at defined temperature and humidity, with a 12-hour light: dark cycle. Animals were anesthetized (oxygen, isoflurane, and nitrous oxide) and 1×6 mm dorsal excisional wound was created on each animal. Animals were split into groups for the studies described below. "Control" wounds were topically treated with 10 μL $dH_2O$ and 10 μL DPBS (vehicles for antimicrobial treatments and bacterial suspensions). Specific treatment regimens are described in more detail below. All treated wounds were dressed in TEGADERM™.

Animals were collected for enumeration of bacterial load post wounding at specific timepoints described in each study. For anaesthesia induction and maintenance, 2 L min-1 oxygen and 2 L min-1 nitrous oxide was used with 2-2.5% isoflurane. Buprenorphine (0.1 mg/Kg) was administered at the time of operation. Animals were recovered in a warming cabinet and returned to fresh cages containing alpha pad, reverse osmosis (RO) water, irradiated diet, mash, and bedding. Mice were singly housed post-wounding. Observations were performed 2 hours and 6 hours post-op ensuring mice recovered well. Further observations were made twice daily during the live phase experiment. All mice were collected via rising $CO_2$ and cervical dislocation. Termination weights were recorded, and wound tissue harvested for bacterial enumeration.

Following culling, TEGADERM™ dressings were removed from the mice, mouse wounds were then imaged and excised, with each wound being placed in a separate universal tube containing 5 mL sterile borosilicate glass beads and 1 mL sterile DPBS. Wound tissue samples were manually dissociated by dicing with a sterile scalpel blade. Wound tissue was then placed back in the universal tube containing borosilicate glass beads in DPBS and vortexed for 1 min. The resulting suspension was serially diluted 6-fold and used to enumerate bacterial CFU/wound. A combination of spread plate and spot plating methods was used. For bacterial enumeration, bacteria were plated on Tryptic Soy Agar (TSA), control bacterial wounds were also plated on *Staphylococcus aureus* selective agar (CHRO-Magar™ Staph *aureus*) for confirmation of *Staphylococcus aureus* colony phenotype. All bacterial counts are reported as Log 10-transformed CFU/wound tissue for each animal.

Data was analysed using GraphPad Prism 9 software. All data are presented as mean±standard error of the mean (SEM). To statistically determine antimicrobial efficacy of tested compounds, an ordinary one-way ANOVA test was used, followed by a Dunnett's multiple comparison test to compare all treatment groups to the bacteria only control. A P-value of less than 0.05 was deemed statistically significant.

Study 1: In Vivo Efficacy of Compound 32-1 and Compound 32-2

The in vivo antimicrobial efficacy up to 72 hours post seeding treatment groups at both medium (28.5 μM) and high (57 μM) concentrations for compound 32-1 and compound 32-2 was investigated. Both compounds maintain potent antimicrobial efficacy up to 72 hrs post inoculation and treatment, causing over 4-log reduction in *S. aureus* load at 28.5 μm and 57 μm (FIG. 6A). Activity up to 96 hrs post seeding was also observed (FIG. 6B). Collectively, these data demonstrate that compound 32-1 and compound 32-2 maintain antimicrobial efficacy against *S. aureus* in the in vivo wound infection model, up to 96 hours post-seeding (at 57 μm).

Study 2: In Vivo Efficacy of Compounds 32-1B and 32-2D

The in vivo efficacy of compounds 32-1B and 32-2D up to 72 hrs post-seeding was investigated. A dose dependent in vivo response over four concentrations compared to both an infection control and a positive antibiotic control was also evaluated. This study was split into two in vivo studies, the first as a pilot study to validate efficacy at the highest concentration (57 μm) before moving on to a full study to assess compounds 32-1B and 32-2D efficacy at four concentrations (2.85 μM, 11.4 μM, 28.5 μM and 57 μM).

The pilot study demonstrated that a single dose of compounds 32-1B and 32-2D was able to maintain potent efficacy, causing a 6-7 log reduction in wound *S. aureus* at 24 and 72 hours post-seeding (FIG. 7A and FIG. 7B). Both compounds 32-1B and 32-2D were significantly potent compared to the positive antibiotic control, where daily application of vancomycin led to only a 1-log reduction in wound *S. aureus* at 24 hrs and 72 hrs post-seeding.

With the full study, the efficacy of compounds 32-1B and 32-2D across four concentrations up to 72 hrs post-seeding and treatment was assessed (FIG. 8A and FIG. 8B). Although a significant reduction in *S. aureus* burden in compounds 32-1B and 32-2D treated wounds was observed, the results were highly variable. This was deemed to be due to the fact that the test compounds came out of solution and the suspensions were not evenly distributed. Nevertheless, the data shows that compounds 32-1B and 32-2D were still more effective than the vancomycin treatment and maintained efficacy down to 2.85 μm.

Study 3: Long-Term In Vivo Efficacy of Compounds 32-1B and 32-2D

Compounds 32-1B and 32-2D were assessed in a 7-day long-term in vivo antimicrobial study to assess their extended efficacy in female BALB/c mice. Compounds 32-1B and 32-2D maintained extended efficacy at both medium (11.4 μM) and high (57 μM) concentrations (FIG. 9). Both test compounds are significantly more effective compared to the positive antibiotic control (Vancomycin, 10 μg/mL), which could only be treated up to 72 hrs due to high bacterial load and severity of infection.

Compounds 32-1B and 32-2D were also assessed in a separate smaller study in male BALB/c mice for direct comparison to previous female BALB/c in vivo studies. Similar to previous female in vivo studies, >6 log fold reduction was observed in *S. aureus* CFU/wound in test compound-treated wounds compared to the control bacteria group (FIG. 10).

Example 7. Antimicrobial Efficacy of Compound 32-2 in HYDROFIBER® Loaded Dressings in a Murine Wound Infection Model

*Staphylococcus aureus* NRS384 was used in this wound infection study. Bacterial culture conditions and treatment were as described in Example 6. Solutions of compound 32-2 and positive controls (Fusidic acid and Vancomycin) were prepared as described in Example 6.

Female wild-type (balb/c) mice (approx. 8 weeks old) received standard chow and water ad libitum. Mice were maintained at defined temperature and humidity, with a 12-hour light: dark cycle. Animals were anaesthetised (oxygen, isoflurane, and nitrous oxide) and 1×6 mm dorsal excisional wound was created on each animal. "Control" wounds were topically treated with 10 µL dH₂O and 10 µL DPBS (vehicles for antimicrobial treatments and bacterial suspensions). Treated wounds were dressed in TEGADERM™ or, for HYDROFIBER® loaded dressing, 20 µL of treatment (compound 32-2, 57 µM) was applied to a 4 mm piece of HYDROFIBER® dressing, and the HYDROFIBER® dressing was applied to the wound seeded topically with bacteria.

At 24 hrs post-wounding, animals were collected for enumeration of bacterial load. For anaesthesia induction and maintenance, 2 L min-1 oxygen and 2 L min-1 nitrous oxide was used with 2-2.5% isoflurane. Buprenorphine (0.1 mg/Kg) was administered at the time of operation. Animals were recovered in a warming cabinet and returned to fresh cages containing alpha pad, reverse osmosis (RO) water, irradiated diet, mash, and bedding. Mice were singly housed post-wounding. Observations were performed 2 hours and 6 hours post-op ensuring mice recovered well. Further observations were made twice daily during the live phase experiment. All mice were collected via rising CO₂ and cervical dislocation. Termination weights were recorded, and wound tissue harvested for bacterial enumeration.

Total bacteria were enumerated from wounds, the 4 mm HYDROFIBER® loaded dressing, and the TEGADERM™ dressing. Following culling, TEGADERM™ or HYDROFIBER® dressings were removed from the mice, mouse wounds were then imaged and excised, with each wound being placed in a separate universal tube containing 5 mL sterile borosilicate glass beads and 1 mL sterile DPBS. Wound tissue samples were manually dissociated by dicing with a sterile scalpel blade. Wound tissue was then placed back in the universal tube containing borosilicate glass beads in DPBS and vortexed for 1 min. The resulting suspension was serially diluted 6-fold and used to enumerate bacterial CFU/wound. A combination of spread plate and spot plating methods was used. For bacterial enumeration, bacteria were plated on both Tryptic Soy Agar (TSA) and Staphylococcus aureus selective agar (CHROMagar™ Staph aureus). All bacterial counts are reported as Log 10-transformed CFU/wound tissue for each animal.

Data was analyzed using GraphPad Prism 9 software. All data are presented as mean±standard error of the mean (SEM). To statistically determine antimicrobial efficacy of tested compounds, an ordinary one-way ANOVA test was used, followed by a Dunnett's multiple comparison test to compare all treatment groups to the bacteria only control. A P-value of less than 0.05 was deemed statistically significant.

HYDROFIBER® dressings loaded with compound 32-2 significantly reduced S. aureus load by 3.6-log at 24 hrs (FIG. 11A and FIG. 11B).

Example 8. Assessment of MIC of Select Compounds

Each test compound (250 µL) was placed in sterile Eppendorf LOBIND® (1.5 mL) vials (pre-weighed). Ethanol was evaporated away using vacuum dryer overnight until solid material remained. The solid material was re-suspended in 500 µL DMSO and diluted to stock concentration of 30 mg/mL in DMSO. Working stocks were pre-pared in sterile H₂O. 32-2E was soluble in H₂O at 1.75 mg/mL. DMSO controls were included and prepared exactly as the compound stocks.

TABLE 21

| | MIC Concentration (µM) | | | | | | | |
| | Gram +VE | | | | | Gram −VE | | |
| Compd | A | B | C | D | E | F | G | H |
| 32-1 | 0.72 | 0.58 | 0.44 | 1.77 | 0.86 | 2.96 | 14.25 | 2.37 |
| 32-2 | 0.72 | 1.46 | 0.72 | 3.56 | 1.77 | 3.56 | 11.88 | 3.56 |
| 32-1A | 0.86 | 0.86 | 0.44 | 3.56 | 1.77 | 1.77 | 3.56 | 3.56 |
| 32-1B | 0.11 | 0.11 | 0.06 | 0.15 | 0.11 | 0.44 | 1.77 | 0.37 |
| 32-2A | 0.72 | 1.33 | 0.72 | 2.96 | 1.77 | 3.56 | 7.13 | 2.96 |
| 32-2B | 0.23 | 0.30 | 0.23 | 0.51 | 0.37 | 0.63 | 4.75 | 1.16 |
| 32-2C | 0.39 | 0.78 | 0.39 | 0.78 | 1.50 | 6.25 | 6.25 | 3.10 |
| 32-2D | 0.32 | 0.39 | 0.26 | 0.52 | 0.65 | 3.10 | 12.50 | 2.03 |
| 32-2E | 0.09 | 0.18 | 0.18 | 0.18 | 0.71 | 1.43 | 1.43 | 0.36 |
| 32-2F | 0.09 | 0.18 | 0.18 | 0.18 | 0.71 | 1.43 | >1.43 | 0.36 |
| 32-2G | 0.18 | 0.18 | 0.18 | 0.18 | 0.71 | 1.43 | >1.43 | 0.36 |
| 32-2H | 0.36 | 0.36 | 0.36 | 0.36 | 0.71 | >1.43 | >1.43 | 0.36 |
| 32-2I | 0.18 | 0.18 | 0.18 | 0.18 | 0.71 | 1.43 | >1.43 | 0.36 |
| FA | 0.04 | 1.25 | 0.04 | 5.00 | 5.00 | 1.25 | 2.50 | 1.25 |
| Van | 0.04 | 0.04 | 0.04 | 0.00 | 5.00 | 0.63 | 5.00 | 0.63 |

A = Staphylococcus aureus 29213; B = Staphylococcus aureus MR1; C = Staphylococcus aureus NRS384; D = Enterococcus faecalis EF51299; E = Enterococcus faecalis EF19433; F = Klebisella oxytoca KL1; G = Pseudomonas aeruginosa 27853; H = Escherichia coli EC25922;
FA = fusidic acid; Van = vancomycin.

Example 9. Evaluation of Test Compounds for Broad Range Antibacterial Activity Against Gram-Positive and Gram-Negative Pathogens Compound Preparation Stock concentrations of all compounds were prepared in sterile filtered (0.22 µM) H₂O. Stocks (1 mM) were prepared for each compound.

All compounds were dissolved in H₂O overnight at 37° C. with continuous shaking. Solutions were resuspended by pipetting as most compounds appeared quite hygroscopic and stuck to the sides of the tube, final stock solutions appeared cloudy after overnight incubation. For pH adjusted compounds, all compounds were dissolved in ~4 mL H₂O then adjusted with NaOH to pH 7.0 (confirmed by pH strips), sterile H₂O was added to give a final volume of 5 mL, 1 mM pH 7.0 stock for each compound. All working stocks were prepared by diluting the 1 mM stocks in sterile H₂O to the desired concentrations. All prepared compounds were kept at 4° C. until further use.

Mammalian Cell Cytotoxicity Testing

Mammalian cell cytotoxicity and proliferation testing were conducted on 11 compounds using primary human fibroblasts and an immortalized human keratinocyte cell line. MTS screening was used to assess cell proliferation and cell viability, alongside LDH testing to determine cellular cytotoxicity.

Primary Human Dermal Fibroblast (HDFs) and Human Keratinocyte (HaCaT) cells were selected for cytotoxicity and proliferation testing. HDFs were cultured in high glucose, no glutamine, no phenol red, Dulbecco's Modified Eagle Medium (DMEM). HDF media was further supplemented with 10% heat-inactivated foetal bovine serum, 1% glutamine and 1% Penicillin-streptomycin. HaCaTs cells were cultured in high glucose, no glutamine, no calcium DMEM supplemented with 10% heatinactivated foetal bovine serum, 1% L-glutamine, 1% Penicillin-streptomycin 1 mM calcium chloride throughout.

Mammalian cell populations were maintained in standard culture conditions at 37° C., 5% $CO_2$ and >95% relative humidity. Upon reaching 80% total confluency, cells were removed from the incubator, the culture media aspirated, and the monolayer washed with Dulbecco's modified eagle medium saline (DPBS). After washing, 10 mL of 1% trypsin was added to the flask and incubated to facilitate the detachment of cells from the culture vessel. Following dissociation, 10 mL of culture media was then added to each flask to neutralize the trypsin enzyme activity. The total 20 mL flask volume was transferred into a universal tube and centrifuged at 400 rcf for 5 minutes. Once complete, the cell pellet was resuspended in 10 mL warmed culture media and the number of cells per mL was determined using a haemo-cytometer counting chamber. Cell suspensions were then adjusted to $5 \times 10^4$ cells/mL for HDFs and $1 \times 105$ cells/mL for HaCaTs. 100 μL of the cell suspension was added to each well of a sterile, cell-culture-treated 96-well microtiter plate. The plates were incubated in standard culture conditions for 16-24 hours to allow cellular adherence to the culture vessel.

Following attachment, stock compounds were thawed, and serial two-fold dilutions were prepared for each compound in concentrations ranging from 100 μM to 0.8 μM in warmed culture media in 96-well plates. Culture plates were removed from the incubator, the media removed; and mono-layers washed with 100 μL of warmed DPBS. The contents of the test item dilution plates were transferred to the culture plates. This was applied to the mean of three biological replicates each with three technical replicates (n=9) for each dilution of each compound. The plates were returned to the incubator for 24 hours in standard culture conditions.

Lactate dehydrogenase (LDH) enzyme assay was used to quantitatively measure cell damage and cytotoxicity. Damage to the cell plasma membrane releases LDH into the cell culture media, the extracellular LDH in the media can be quantified by a coupled enzymatic reaction in which LDH catalyzes the conversion of lactate to pyruvate via NAD+ reduction to NADH. Oxidation of NADH by diaphorase leads to the reduction of resazurin forming the highly fluorescent resorufin. Resorufin levels, which are directly proportional to the amount of LDH released into the medium, is therefore used to measure cytotoxicity.

Following incubation with the selected compounds, 50 μL of media from each well was transferred to the corresponding well of a fresh 96 well culture plate. The presence of Lactate dehydrogenase (LDH) was then quantified using the INVITROGEN™ CYQUANT™ LDH Cytotoxicity Assay, fluorescence kit. Total fluorescence was measured by reading the plates on a plate reader at an excitation of 560 nm and an emission of 590 nm.

Cell Proliferation Testing

After the collection of media for LDH quantification, the remaining cell culture media was aspirated, and the cell monolayers washed with 100 μL of warmed DPBS, and fresh culture media added. CELLTITER 96® Aqueous One Solution Cell Proliferation Assay was then used to determine the number of cells present in the remaining culture vessels. The assay utilizes a tetrazolium compound [3-(4,5-dimeth-ylthiazol-2-yl)-5-(3-carboxymethoxyphenyl)-2-(4-sulfophe-nyl)-2H-tetrazolium, inner salt; that is bio reduced by NADPH or NADH in metabolically active cells into a colored formazan product.

In each well, 20 μL of MTS (CELLTITER 96® Aqueous One Solution Cell Proliferation Assay) solution was added and the plates returned to the incubator for 4 hours. The cell plates were collected, and the colorimetric change detected on the plate reader at absorbance 490 nm. The number of viable cells present in each treatment condition was deter-mined using a calibration curve.

Table 22 summarizes the cytotoxicity values for all com-pounds tested in both cell types (HDF and HaCaT).

TABLE 22

| Cell toxicity values for tested compounds | | |
| --- | --- | --- |
| Compound | HDF (μM) | HaCaT (μM) |
| 32-3 | 0.78 | 3.12 |
| 32-17 | 0.78 | 3.12 |
| 32-18 | 3.12 | 12.5 |
| 29-1 | 3.12 | 3.12 |
| 32-1 | 3.12 | 3.12 |
| 32-2 | 3.12 | 3.12 |
| 32-11 | 0.78 | 0.78 |
| 32-13 | 0.78 | 3.12 |
| 32-15 | 0.78 | 0.78 |
| 32-10 | 1.56 | 3.12 |

Assessment of MIC and MBC

Select compounds were screened for antimicrobial activ-ity against a range of clinically relevant gram-positive and gram-negative pathogens. The lowest effective MIC value was determined, and log reduction in antimicrobial activity was quantified by MBC assay around the lowest MIC value.

Bacterial Strains and Media Culture Conditions

All microbial work was carried out in a class II biosafety hood. Clinically isolated strains of *Klebsiella pneumoniae* KL1 (isolated from leg wound swab) and *Staphylococcus aureus* MR1 (Methicillin Resistant *Staphylococcus aureus* (MRSA) isolated from leg ulcer) were provided from a bank of nosocomial clinical isolates. All other strains were obtained from the ATCC. In all subsequent experiments Mueller-Hinton (MH) medium was used as a broth. Over-night cultures (ONC) were prepared by inoculating bacteria from a single colony maintained on MH agar into 5 mL MH broth and incubating overnight at 37° C. for 14-15 h with continuous shaking (200 rpm).

Minimum Inhibitory Concentration (MIC)

The standard broth microdilution method was used to investigate the antimicrobial efficacy of the tested com-pounds. Serial two-fold dilutions were prepared for each compound in concentrations ranging from 100 μM to 0.8 μM in sterile MH broth in flat 96-well plates. ONC of each bacterial strain was adjusted to give a standard bacterial concentration ($5 \times 10^5$ CFU/mL) and added to each dilution to determine the MIC in a total volume of 100 μL MH broth. All plates were statically incubated at 37° C. for 24 hrs. Sterile $dH_2O$ was used as a vehicle only control, for each bacterial strain positive (bacteria only) and negative (MH media only) controls were included. To determine the MIC breakpoint plates were stained with 10 μL of 0.02% resa-zurin and incubated at 37° C. for 30 mins. Following incubation all plates were imaged and absorbance measured at 570 nm (Plate reader). The MIC is defined as the lowest concentration of compound that inhibits growth.

MIC Data Analysis

The data was exported to Microsoft Excel and back-ground normalized by subtracting OD570 nm values from media only wells (−VE control). MIC values were deter-mined by plotting the OD570 nm values (Y) against the log concentration of each compound (X). A modified Gompertz model was used to fit the data to obtain a more accurate MIC. The average OD570 nm for each tested compound concentration was fitted to a sigmoidal curve using the modified Gompertz function (y=A+Ce−e(B(x−M))), and the minimum inhibitory concentration (MIC) was identified from the point of inflexion of the lower asymptote (Graph-Pad Prism 9.0). This was applied to the mean of three biological replicates each with four technical replicates (n=12) for each dilution in each compound.

Minimum Bactericidal Concentration (MBC) Procedure

To determine MBC compound concentrations, breakpoints were estimated from MIC curves. Overnight cultures were set up as described above for all bacterial strains. The following day overnight cultures were adjusted to give a cell density of $5 \times 10^5$ cells per mL. Briefly, cultures were adjusted to the McFarland standard (0.08-0.12) and diluted (1:150). Adjusted cultures were inoculated into 96 well plates with 50 µL sterile Muller-Hinton broth (MHB) and 2 concentrations of each compound. MBC plates were statically incubated for 24 hours at 37° C. Sterile $dH_2O$ was used as a vehicle control, positive (bacteria only) and negative controls (media only) were also included in the assay. MBC cultures were quantified by serial dilution in a 96 well plate and spot plating onto Muller-Hinton agar (MHA). MHA plates were incubated at 37° C. for 24 hours and counted.

MIC and MBC values are shown in Tables 23 and 24.

TABLE 23

| | MIC Concentration (µM) | | | | | | | |
| | Gram +VE | | | | | Gram −VE | | |
| Compd | A | B | C | D | E | F | G | H |
|---|---|---|---|---|---|---|---|---|
| 32-17 | 0.9 | 1.1 | 1.7 | 253.2 | 0.8 | 2.0 | 1.8 | 1.8 |
| 32-18 | 0.0 | 0.0 | 62.5 | 73.0 | 0.1 | 0.0 | LD | 1.3 |
| 32-5 | 100.0 | 13.9 | 19.7 | 8.6 | 9.5 | 0.8 | 102.8 | 26.1 |
| 32-9 | 55.2 | 25.0 | 688.1 | 51.0 | 0.0 | 86.7 | 1.1 | 12.8 |
| 32-3 | 1.1 | 100.0 | 157.1 | 272.6 | 100.0 | 0.8 | 0.9 | LD |
| 29-1 | LD | 2.0 | LD | LD | LD | 2.2 | 8.9 | 1.4 |
| 32-1 | 0.4 | 0.2 | LD | LD | LD | 1.8 | 4.2 | 0.6 |
| 32-2 | 0.0 | 1.4 | LD | LD | LD | 2.0 | 7.7 | 1.0 |
| 32-2** | 0.7 | 1.4 | LD | LD | LD | 1.8 | 11.6 | 0.6 |
| 32-11 | 71.7 | 1.1 | 0.8 | 0.8 | nd* | 0.9 | 1.3 | 1.6 |
| 32-13 | LD | 37.6 | 2.4 | LD | 4.3 | 12.8 | 100.0 | 34.1 |
| 32-15 | LD | LD | 49.3 | 100.0 | 9.9 | 14.4 | 40.6 | 33.2 |
| 32-14 | LD | 1.0 | 62.9 | 100.0 | 43.1 | 100.0 | 41.1 | 42.7 |
| 32-16 | LD | 104.9 | 40.7 | 43.5 | 40.0 | 100.0 | 50.0 | 100.0 |
| 32-10 | 2.2 | 2.2 | 4.9 | 5.6 | 2.2 | 9.8 | 3.4 | 5.7 |
| Vehicle | — | — | — | — | — | — | — | — |

*compound not tested;

**different batch through same synthetic protocol

LD = This value indicates that the minimum concentration tested still inhibits growth, and concentrations lower than the lowest tested concentration might still inhibit bacterial growth.

A = *Enterococcus faecalis* EF51299; B = *Enterococcus faecalis* EF19433; C = *Staphylococcus aureus* 29213; D = *Staphylococcus aureus* MR1; E = *Staphylococcus aureus* NRS384; F = *Klebisella pneumoniae* KL1; G = *Pseudomonas aeruginosa* 27853; H = *Escherichia coli* EC25922; Vehicle = $H_2O$.

TABLE 24

| | MBC Concentration (µM) | | | | | | | |
| | Gram +VE | | | | | Gram −VE | | |
| Compd | A | B | C | D | E | F | G | H |
|---|---|---|---|---|---|---|---|---|
| 32-17 | 0.78 | 0.78 | 0.78 | 0.39 | 0.78 | 1.56 | 12.50 | 0.78 |
| 32-18 | 0.78 | 0.78 | 0.78 | 0.39 | 0.39 | 0.78 | 12.50 | 0.78 |
| 32-3 | 0.39 | 0.39 | 0.39 | 0.39 | 0.39 | 0.39 | 6.25 | 0.78 |
| 29-1 | 1.77 | 1.77 | 0.22 | 0.22 | 0.22 | 1.77 | 7.13 | 0.89 |
| 32-1 | 0.44 | 0.44 | 0.22 | 0.22 | 0.22 | 0.89 | — | 0.44 |
| 32-2 | 0.89 | 0.89 | 0.22 | 0.22 | 0.22 | 0.89 | 0.89 | 0.44 |
| 32-2* | 0.89 | 0.89 | 0.22 | 0.22 | 0.22 | 0.89 | 0.44 | 0.44 |

TABLE 24-continued

| | MBC Concentration (µM) | | | | | | | |
| | Gram +VE | | | | | Gram −VE | | |
| Compd | A | B | C | D | E | F | G | H |
|---|---|---|---|---|---|---|---|---|
| 32-11 | 0.78 | 0.78 | 0.39 | 0.39 | — | 0.78 | — | 0.78 |
| 32-13 | — | — | 6.25 | — | — | — | — | — |
| 32-10 | 1.56 | 1.56 | 3.10 | 3.10 | 0.78 | 6.25 | | 3.10 |

*different batch through same synthetic protocol

A = *Enterococcus faecalis* EF51299; B = *Enterococcus faecalis* EF19433; C = *Staphylococcus aureus* 29213; D = *Staphylococcus aureus* MR1; E = *Staphylococcus aureus* NRS384; F = *Klebisella pneumoniae* KL1; G = *Pseudomonas aeruginosa* 27853; H = *Escherichia coli* EC25922.

Bacterial Strains and Media Culture Conditions for Colony Biofilms

All colony biofilm optimization was carried on the clinically relevant *Staphylococcus aureus* NRS 384 strain. *S. aureus* NRS 384 was grown in Mueller-Hinton (MH) medium. Overnight cultures (ONC) were prepared by inoculating bacteria from a single colony maintained on MH agar into 10 mL MH broth and incubating overnight at 37° C. for 14-15 h with continuous shaking (200 rpm).

Colony Biofilm Preparation

Colony biofilms were grown on sterile polycarbonate/nitrocellulose membranes resting on MH agar plates. Planktonic cultures of *S. aureus* were grown overnight in MHB and diluted to an optical density of 0.050 at 600 nm (with a 1-cm path length). 4-µL drop of diluted planktonic culture was used to inoculate membranes (25-mm, 0.22-µm pore size) resting on MH agar plates. The plates were inverted and incubated at 37° C. Colony biofilms were treated with various concentrations of compounds by applying 4 µL directly onto the biofilm allowing to dry and placed back in the incubator at 37° C. Colony biofilms were subjected to a range of treatment times and seeding densities. Colony biofilms were visually assessed and quantified after either 16 hr or 24 hr incubation 37° C. by scoring biofilm growth.

Select data shown on Tables 25-29 for antibiofilm efficacy against gram-positive biofilms. Select data shown in Tables 30-35 for antibiofilm efficacy against gram-negative biofilms.

TABLE 25

| Effect of high and low concentrations of test compound on *S. aureus* NRS384 colony biofilm formation ** | | | | | | |
| | Conc. | Effect at time point** | | | | |
| Compound | (µM) | 2 hr | 4 hr | 6 hr | 8 hr | 10 hr |
|---|---|---|---|---|---|---|
| 32-17 | 1000 | 0 | 0 | 0 | 0 | 0 |
| 32-17 | 100 | 0 | 0 | 0 | 0 | 0 |
| 32-17 | 1.5 | 2 | 3 | 3 | 3 | 3 |
| 32-18 | 1000 | 0 | 0 | 0 | 0 | 0 |
| 32-18 | 100 | 0 | 0 | 0 | 1 | 1 |
| 32-18 | 1.5 | 2 | 3 | 3 | 3 | 3 |

TABLE 25-continued

Effect of high and low concentrations of test compound on *S. aureus* NRS384 colony biofilm formation **

| Compound | Conc. (μM) | 2 hr | 4 hr | 6 hr | 8 hr | 10 hr |
|---|---|---|---|---|---|---|
| | | \multicolumn | | Effect at time point** | | |
| 32-3 | 1000 | 0 | 0 | 0 | 0 | 0 |
| 32-3 | 100 | 0 | 0 | 0 | 0 | 0 |
| 32-3 | 1.5 | 2 | 3 | 3 | 3 | 3 |

*Colony biofilms were seeded at $1 \times 10^7$ CFU/mL and treated at time 0 hrs. Biofilms were incubated at 37° C. for 24 hrs, then imaged and scored.
**0 = no biofilm growth; 1 = weak biofilm growth; 2 = moderate biofilm growth; 3 = strong biofilm growth

TABLE 26

Effect of high and low concentrations of test compound on *S. aureus* NRS384 colony biofilm formation*

| Compound | Conc. (μM) | 0 hr | 2 hr | 4 hr | 6 hr | 8 hr | 10 hr |
|---|---|---|---|---|---|---|---|
| 32-18 | 50.0 | 0 | 1 | 3 | 3 | 3 | 3 |
| 32-18 | 25.0 | 1 | 1 | 2 | 3 | 3 | 3 |
| 32-18 | 12.5 | 1 | 2 | 3 | 3 | 3 | 3 |
| 32-18 | 6.3 | 3 | 3 | 3 | 3 | 3 | 3 |
| 32-18 | 3.1 | 3 | 3 | 3 | 3 | 3 | 3 |
| 32-3 | 50.0 | 0 | 0 | 0 | 0 | 0 | 0 |
| 32-3 | 25.0 | 0 | 0 | 0 | 0 | 2 | 3 |
| 32-3 | 12.5 | 0 | 0 | 0 | 2 | 3 | 3 |
| 32-3 | 6.3 | 0 | 0 | 1 | 3 | 3 | 3 |
| 32-3 | 3.1 | 0 | 2 | 3 | 3 | 3 | 3 |
| 29-1 | 28.5 | 0 | 0 | 0 | 0 | 1 | 1 |
| 29-1 | 14.3 | 0 | 0 | 0 | 1 | 2 | 2 |
| 29-1 | 7.1 | 1 | 1 | 1 | 2 | 3 | 3 |
| 29-1 | 3.6 | 3 | 3 | 3 | 3 | 3 | 3 |
| 29-1 | 1.8 | 3 | 3 | 3 | 3 | 3 | 3 |
| 32-1 | 28.5 | 0 | 0 | 0 | 0 | 0 | 0 |
| 32-1 | 14.3 | 0 | 0 | 0 | 0 | 0 | 3 |
| 32-1 | 7.1 | 1 | 1 | 2 | 2 | 3 | 3 |
| 32-1 | 3.6 | 3 | 3 | 3 | 3 | 3 | 3 |
| 32-1 | 1.8 | 3 | 3 | 3 | 3 | 3 | 3 |
| 32-2 | 28.5 | 0 | 0 | 0 | 0 | 0 | 0 |
| 32-2 | 14.3 | 0 | 0 | 0 | 0 | 1 | 1 |
| 32-2 | 7.1 | 1 | 1 | 1 | 2 | 2 | 2 |
| 32-2 | 3.6 | 3 | 3 | 3 | 3 | 3 | 3 |
| 32-2 | 1.8 | 3 | 3 | 3 | 3 | 3 | 3 |
| 32-2*** | 28.5 | 0 | 0 | 0 | 0 | 1 | 2 |
| 32-2*** | 14.3 | 0 | 0 | 0 | 1 | 2 | 2 |
| 32-2*** | 7.1 | 1 | 0 | 1 | 2 | 3 | 3 |
| 32-2*** | 3.6 | 1 | 1 | 2 | 3 | 3 | 3 |
| 32-2*** | 1.8 | 3 | 3 | 3 | 3 | 3 | 3 |

*Colony biofilms were seeded at $6 \times 10^7$ CFU/mL and treated at specified time points. Biofilms were incubated at 37° C. for 24 hrs, then imaged and scored.
**0 = no biofilm growth; 1 = weak biofilm growth; 2 = moderate biofilm growth; 3 = strong biofilm growth
***different batch through same synthetic protocol

TABLE 27

Effect of different seeding densities at high concentrations of test compound against *S. aureus* NRS384 colony biofilm at specific time points*

| Compound | Conc. (μM) | Time (hr) | $3.1 \times 10^6$ | $5.6 \times 10^5$ | $5.9 \times 10^7$ | $9.7 \times 10^4$ |
|---|---|---|---|---|---|---|
| 32-18 | 57 | 2 | 0 | 0 | 0 | 0 |
| 32-18 | 57 | 4 | 0 | 0 | 0 | 0 |
| 32-18 | 57 | 6 | 0 | 0 | 0 | 0 |
| 32-18 | 57 | 8 | 0 | 0 | 0 | 0 |
| 32-18 | 57 | 10 | 0 | 0 | 1 | 0 |
| 32-3 | 57 | 2 | 0 | 0 | * | 0 |
| 32-3 | 57 | 4 | 0 | 0 | * | 0 |

TABLE 27-continued

Effect of different seeding densities at high concentrations of test compound against *S. aureus* NRS384 colony biofilm at specific time points*

| Compound | Conc. (μM) | Time (hr) | $3.1 \times 10^6$ | $5.6 \times 10^5$ | $5.9 \times 10^7$ | $9.7 \times 10^4$ |
|---|---|---|---|---|---|---|
| 32-3 | 57 | 6 | 0 | 0 | 0 | 0 |
| 32-3 | 57 | 8 | 0 | 0 | 2 | 0 |
| 32-3 | 57 | 10 | 0 | 0 | 2 | 1 |
| 32-17 | 57 | 2 | 0 | 0 | 0 | 0 |
| 32-17 | 57 | 4 | 0 | 0 | 0 | 0 |
| 32-17 | 57 | 6 | 0 | 0 | 0 | 0 |
| 32-17 | 57 | 8 | 0 | 0 | 2 | 0 |
| 32-17 | 57 | 10 | 0 | 0 | 2 | 0 |
| control | 0 | 10 | 3 | 3 | 3 | 3 |

*Colony biofilms were seeded at $6 \times 10^7$ CFU/mL and treated at specified time points. Biofilms were incubated at 37° C. for 24 hrs, then imaged and scored.
**0 = no biofilm growth; 1 = weak biofilm growth; 2 = moderate biofilm growth; 3 = strong biofilm growth

TABLE 28

Effect of seeding densities at high concentrations of compound 32-2 against *S. aureus* NRS384 colony biofilm at specific time points*

| Compound | Conc. (μM) | Time (hr) | +1 log | −1 log | N |
|---|---|---|---|---|---|
| 32-2 | 14.3 | 2 | 2.0 | 1.0 | 1.7 |
| 32-2 | 7.1 | 2 | 3.0 | 2.0 | 3.0 |
| 32-2 | 3.6 | 2 | 3.0 | 3.0 | 3.0 |
| 32-2 | 14.3 | 4 | 2.7 | 0.7 | 2.3 |
| 32-2 | 7.1 | 4 | 3.0 | 3.0 | 3.0 |
| 32-2 | 3.6 | 4 | 3.0 | 3.0 | 3.0 |
| 32-2 | 14.3 | 6 | 2.7 | 1.3 | 2.7 |
| 32-2 | 7.1 | 6 | 3.0 | 3.0 | 3.0 |
| 32-2 | 3.6 | 6 | 3.0 | 3.0 | 3.0 |
| 32-2 | 14.3 | 8 | 3.0 | 3.0 | 3.0 |
| 32-2 | 7.1 | 8 | 3.0 | 3.0 | 3.0 |
| 32-2 | 3.6 | 8 | 3.0 | 3.0 | 3.0 |
| 32-2 | 14.3 | 10 | 3.0 | 3.0 | 3.0 |
| 32-2 | 7.1 | 10 | 3.0 | 3.0 | 3.0 |
| 32-2 | 3.6 | 10 | 3.0 | 3.0 | 3.0 |
| Control | 0 | 10 | 3.0 | 3.0 | 3.0 |

*Colony biofilms were seeded at either +1 log or −1 log $6 \times 10^7$ CFU/mL and treated at specified time points. Biofilms were incubated at 37° C. for 24 hrs, then imaged and scored.
**0 = no biofilm growth; 1 = weak biofilm growth; 2 = moderate biofilm growth; 3 = strong biofilm growth

TABLE 29

Extended efficacy of high concentration of test compound against *S. aureus* NRS384 colony biofilm formation*

| Compound | Conc. (μM) | 12 hr | 14 hr | 16 hr | 18 hr |
|---|---|---|---|---|---|
| 29-1 | 570 | 1 | 2 | 3 | 3 |
| 32-1 | 570 | 0 | 1 | 3 | 3 |
| 32-2 | 570 | 0 | 1 | 3 | 3 |
| 32-2*** | 570 | 0 | 1 | 3 | 3 |
| 29-1 | 57 | 1 | 2 | 3 | 3 |
| 32-1 | 57 | 0 | 1 | 3 | 3 |
| 32-2 | 57 | 0 | 1 | 3 | 3 |
| 32-2*** | 57 | 0 | 1 | 3 | 3 |
| Control | — | 3 | 3 | 3 | 3 |

*Colony biofilms were seeded at $6 \times 10^7$ CFU/mL and treated at specified time points. Biofilms were incubated at 37° C. for 24 hrs, then imaged and scored.
**0 = no biofilm growth; 1 = weak biofilm growth; 2 = moderate biofilm growth; 3 = strong biofilm growth
***different batch through same synthetic protocol

TABLE 30

Effect of high concentrations of test compound against
*Pseudomonas aeruginosa* 27853 biofilm formation*

| | | Effect at time point** | | | | |
|---|---|---|---|---|---|---|
| Compound | Conc. (μM) | 2 hr | 4 hr | 6 hr | 8 hr | 10 hr |
| 32-3 | 1000 | 0.0 | 1.0 | 2.0 | 2.0 | 2.0 |
| 29-1 | 570 | 0.3 | 0.0 | 1.7 | 2.0 | 2.0 |
| 32-1 | 570 | 0.0 | 0.0 | 1.7 | 2.0 | 2.0 |
| 32-2 | 570 | 0.0 | 0.0 | 1.3 | 2.0 | 2.0 |
| 32-2*** | 570 | 0.0 | 0.0 | 2.0 | 2.0 | 2.0 |
| 29-1 | 57 | 2.0 | 3.0 | 3.0 | 3.0 | 3.0 |
| 32-1 | 57 | 1.0 | 3.0 | 3.0 | 3.0 | 3.0 |
| 32-2 | 57 | 1.0 | 3.0 | 3.0 | 3.0 | 3.0 |
| 32-2*** | 57 | 2.0 | 3.0 | 3.0 | 3.0 | 3.0 |
| Control | 0 | 1.0 | 2.0 | 3.0 | 3.0 | 3.0 |

*Colony biofilms were seeded at ~6 × $10^7$ CFU/mL and treated at specified time points with various concentrations. Biofilms were incubated at 37° C. for 24 hrs, then imaged and scored.
**0 = no biofilm growth; 1 = weak biofilm growth; 2 = moderate biofilm growth; 3 = strong biofilm growth
***different batch through same synthetic protocol

TABLE 31

Effect of high concentrations of test compound against
*Klebsiella pneumoniae* KL1 biofilm formation*

| | Conc. | Effect at time point** | | | | |
|---|---|---|---|---|---|---|
| Compound | (μM) | 2 hr | 4 hr | 6 hr | 8 hr | 10 hr |
| 32-3 | 1000 | 0.0 | 0.0 | 0.0 | 0.0 | 0.0 |
| 29-1 | 570 | 0.0 | 0.0 | 0.0 | 0.0 | 0.7 |
| 32-1 | 570 | 0.0 | 0.0 | 0.7 | 0.0 | 0.7 |
| 32-2 | 570 | 0.0 | 0.0 | 0.3 | 0.3 | 0.3 |
| 32-2*** | 570 | 0.0 | 0.0 | 1.0 | 1.0 | 1.0 |
| 29-1 | 57 | 0.3 | 3.0 | 3.0 | 3.0 | 3.0 |
| 32-1 | 57 | 1.0 | 2.0 | 3.0 | 3.0 | 3.0 |
| 32-2 | 57 | 0.0 | 2.0 | 3.0 | 3.0 | 3.0 |
| 32-2*** | 57 | 0.3 | 3.0 | 3.0 | 3.0 | 3.0 |
| Control | 0 | 1.0 | 2.0 | 3.0 | 3.0 | 3.0 |

*Colony biofilms were seeded at ~6 × $10^7$ CFU/mL and treated at specified time points with various concentrations. Biofilms were incubated at 37° C. for 24 hrs, then imaged and scored.
**0 = no biofilm growth; 1 = weak biofilm growth; 2 = moderate biofilm growth; 3 = strong biofilm growth
***different batch through same synthetic protocol

TABLE 32

Dosing range of test compounds against *Pseudomonas aeruginosa*
27853 biofilm formation*

| | | Effect at Conc.** | | | |
|---|---|---|---|---|---|
| Compound | Time (hr) | 57 μM | 28.5 μM | 14.3 μM | 7.1 μM |
| 29-1 | 16 | 0 | 2 | 3 | 3 |
| 32-1 | 16 | 0 | 1 | 3 | 3 |
| 32-2 | 16 | 0 | 1 | 2 | 3 |
| 32-2*** | 16 | 0 | 2 | 3 | 3 |
| Control | 16 | 3 | 3 | 3 | 3 |

*Colony biofilms were seeded at ~6 × $10^7$ CFU/mL and treated at specified time point with various concentrations. Biofilms were incubated at 37° C. for 24 hrs, then imaged and scored.
**0 = no biofilm growth; 1 = weak biofilm growth; 2 = moderate biofilm growth; 3 = strong biofilm growth
***different batch through same synthetic protocol

TABLE 33

Dosing range of test compounds against *Klebsiella pneumoniae*
KL1 biofilm formation*

| | | Effect at Conc.** | | | |
|---|---|---|---|---|---|
| Compound | Time (hr) | 14.3 μM | 7.1 μM | 3.6 μM | 1.7 μM |
| 29-1 | 16 | 2.0 | 3.0 | 3.0 | 3.0 |
| 32-1 | 16 | 1.0 | 3.0 | 3.0 | 3.0 |
| 32-2 | 16 | 2.0 | 3.0 | 3.0 | 3.0 |
| 32-2*** | 16 | 1.7 | 3.0 | 3.0 | 3.0 |
| Control | 16 | 3.0 | 3.0 | 3.0 | 3.0 |

*Colony biofilms were seeded at ~6 × $10^7$ CFU/mL and treated at specified time point with various concentrations. Biofilms were incubated at 37° C. for 24 hrs, then imaged and scored.
**0 = no biofilm growth; 1 = weak biofilm growth; 2 = moderate biofilm growth; 3 = strong biofilm growth
***different batch through same synthetic protocol

TABLE 34

Effect of −3 log seeding density with test compounds against
*Pseudomonas aeruginosa* 27853 biofilm at specific time points*

| | Conc. | Effect at time point** | | | | |
|---|---|---|---|---|---|---|
| Compound | (μM) | 2 hr | 4 hr | 6 hr | 8 hr | 10 hr |
| 32-3 | 1000 | 0.0 | 0.0 | 0.0 | 0.0 | 0.0 |
| 32-1 | 570 | 0.0 | 0.0 | 0.0 | 0.0 | 0.0 |
| 32-2 | 570 | 0.0 | 0.0 | 0.0 | 0.0 | 0.0 |
| 32-3 | 57 | 0.0 | 0.0 | 0.0 | 0.7 | 0.3 |
| 32-1 | 57 | 0.0 | 0.0 | 2.0 | 1.0 | 1.0 |
| 32-2 | 57 | 0.0 | 0.7 | 1.0 | 1.0 | 3.0 |
| Control | 0 | 1.0 | 2.0 | 3.0 | 3.0 | 3.0 |

*Colony biofilms were seeded at ~6 × $10^7$ CFU/mL and treated at specified time points with various concentrations. Biofilms were incubated at 37° C. for 24 hrs, then imaged and scored.
**0 = no biofilm growth; 1 = weak biofilm growth; 2 = moderate biofilm growth; 3 = strong biofilm growth

TABLE 35

Effect of −3 log seeding density with test compounds against
*Klebsiella pneumoniae* KL1 biofilm at specific time points*

| | Conc. | Effect at time point** | | | | |
|---|---|---|---|---|---|---|
| Compound | (μM) | 2 hr | 4 hr | 6 hr | 8 hr | 10 hr |
| 32-3 | 570 | 0.0 | 0.0 | 0.0 | 0.0 | 0.0 |
| 32-1 | 570 | 0.0 | 0.0 | 0.0 | 0.0 | 0.0 |
| 32-2 | 570 | 0.0 | 0.0 | 0.0 | 0.0 | 0.0 |
| 32-3 | 57 | 0.33 | 0.00 | 1.00 | 2.00 | 3.00 |
| 32-1 | 57 | 0.33 | 1.33 | 1.67 | 3.00 | 3.00 |
| 32-2 | 57 | 0.00 | 0.00 | 0.67 | 2.00 | 3.00 |
| Control | 0 | 1.0 | 2.0 | 3.0 | 3.0 | 3.0 |

*Colony biofilms were seeded at ~6 × $10^7$ CFU/mL and treated at specified time points with various concentrations. Biofilms were incubated at 37° C. for 24 hrs, then imaged and scored.
**0 = no biofilm growth; 1 = weak biofilm growth; 2 = moderate biofilm growth; 3 = strong biofilm growth Overall, compounds 29-1, 32-1, and 32-2 (both batches) were effective against gram-negative bacteria, but at higher concentrations than needed to kill gram-positive bacteria.

Example 10. Investigation of the Impact of Test Compound on Wound Healing in Mice Solutions (11.4 μM, 28.5 μM, or 57 μM) of 32-1B in sterile filtered distilled water (dH$_2$O) and solutions (11.4 μM, 28.5 μM, or 57 μM) of 32-2E in a mixture of DMSO-dH$_2$O (0.47% DMSO) were prepared for use in this study.

Balb/c mice were handled similarly as in Example 6. A wound was created on each animal and 20 μL of test compound solution or vehicle solution was administered to the wound, once on day 0. All treated wounds were dressed in TEGADERM™. Wounds were assessed at days 3, 6, and 9.

Data for percent of wound area remaining is shown in FIG. 12 and FIG. 13. Treatment with 32-1B at 11.4 µM and 28.5 µM resulted in significantly increased wound closure compared to vehicle-only treatment from day 6 post-wounding (p<0.001). Treatment with 32-1B at 57 µM resulted in increased wound closure compared to vehicle-only treatment from day 6 post-wounding (p=0.01). With regard to the 32-2E solutions, no significant negative impact of DMSO vehicle was observed. Treatment with 32-2E at 11.4 µM resulted in increased wound closure compared to vehicle-only treatment from day 6 post-wounding and significant wound closure on day 9 (p=0.04). Treatment with 32-2E at 28.5 µM resulted in increased wound closure compared to vehicle-only treatment from day 6 post-wounding and near significant wound closure on day 9 (p=0.07). Treatment with 32-2E at 57 µM resulted in significantly increased wound closure compared to vehicle-only treatment on days 6 and 9 post-wounding (p=0.00).

Data for wound contraction and re-epithelialization is shown in FIG. 14 and FIG. 15 for 32-1B and in FIG. 16 and FIG. 17 for 32-2E. Treatment with 32-1B at 11.4 µM and 28.5 µM resulted in increased wound contraction compared to vehicle-only treatment from day 6 post-wounding, significantly for 11.4 µM (p=0.01). Treatment with 32-1B at 57 µM resulted in marginal increase in wound contraction at day 9. All three concentrations of 32-1B resulted in significantly increased re-epithelialization on days 6 and 9 (p≤0.02, Mann-Whitney U-test). Treatment with 32-2E at 57 µM resulted in increased wound contraction compared to DMSO vehicle-only treatment from days 3 and 6 post-wounding (not statistically significant). All three concentrations of 32-2E resulted in increased re-epithelialization on days 6 and 9, significantly at 11.4 µM and 57 µM (p≤0.03, Mann-Whitney U-test) and near significant at 28.5 µM on day 6 (p=0.07).

Example 11. Additional Experimental Data

Additional experimental data for compounds 32-1, 32-1A, 32-1B, 32-2, 32-2A, 32-2B3, 32-2C, 32-2D, and 32-2E are described below. This data was obtained using protocols analogous those described above.

These compounds were tested for their MBC against a panel of ATCC and nosocomial bacteria. Results are shown in Table 36.

TABLE 36

| | MBC Concentration (µM) | | | | | | | |
|---|---|---|---|---|---|---|---|---|
| | Gram +VE | | | | | Gram −VE | | |
| Compd | A | B | C | D | E | F | G | H |
| 32-1 | 1.56 | 0.78 | 0.78 | 3.10 | 1.56 | 6.25 | 12.50 | 3.10 |
| 32-2 | 6.25 | 0.78 | 1.56 | 1.56 | 3.10 | 6.25 | 12.50 | 6.25 |
| 32-1A | 1.56 | 1.56 | 1.56 | 6.25 | 3.10 | 3.10 | 6.25 | 3.10 |
| 32-1B | 0.19 | 0.19 | 0.19 | 0.19 | 0.19 | 0.78 | 3.10 | 6.25 |
| 32-2A | 0.78 | 0.78 | 0.78 | 3.10 | 3.10 | 6.25 | 12.50 | 3.10 |
| 32-2B | 0.78 | 0.78 | 0.78 | 1.56 | 0.78 | 6.25 | 25.00 | 3.10 |
| 32-2C | 0.19 | 0.19 | 0.19 | 0.19 | 0.19 | 0.39 | 1.56 | 0.19 |
| 32-2D | 0.09 | 0.09 | 0.09 | 0.09 | 0.09 | 0.19 | 0.39 | 0.09 |
| 32-2E | 0.09 | 0.18 | 0.18 | 0.71 | 0.18 | 0.36 | 1.43 | 0.71 |

154

TABLE 36-continued

| | MBC Concentration (µM) | | | | | | | |
|---|---|---|---|---|---|---|---|---|
| | Gram +VE | | | | | Gram −VE | | |
| Compd | A | B | C | D | E | F | G | H |
| FA | 0.02 | 0.02 | 0.31 | 0.02 | 0.08 | 1.25 | 2.50 | 0.62 |
| Van | 0.02 | 0.02 | 0.02 | 0.04 | 0.08 | 1.25 | 2.50 | 0.31 |

A = *Staphylococcus aureus* 29213; B = *Staphylococcus aureus* MR1; C = *Staphylococcus aureus* NRS384; D = *Enterococcus faecalis* EF51299; E = *Enterococcus faecalis* EF19433; F = *Klebisella pneumoniae* KL1; G = *Pseudomonas aeruginosa* 27853; H = *Escherichia coli* EC25922; FA = fusidic acid; Van = vancomycin.

Three compounds (32-1, 32-1A, and 32-1B) were assessed for MIC against Gram-positive or Gram-negative bacteria (*Staphylococcus aureus* MR1, *Staphylococcus aureus* NRS384, *Staphylococcus aureus* 29213, *Enterococcus faecalis* EF19433, *Enterococcus faecalis* EF51299, *Klebisella pneumoniae* KL1, *Pseudomonas aeruginosa* 27853, *Escherichia coli* EC25922). Results are shown in FIG. 18.

Six compounds (32-2, 32-2A, 32-2B3, 32-2C, 32-2D, 32-2E) were assessed for MIC against Gram-positive or Gram-negative bacteria (*Staphylococcus aureus* MR1, *Staphylococcus aureus* NRS384, *Staphylococcus aureus* 29213, *Enterococcus faecalis* EF19433, *Enterococcus faecalis* EF51299, *Klebisella pneumoniae* KL1, *Pseudomonas aeruginosa* 27853, *Escherichia coli* EC25922). Results are shown in FIG. 19A and FIG. 19B.

Data is shown in Tables 37-39 for select compounds for their antibiofilm efficacy against *Staphylococcus aureus*, *Pseudomonas aeruginosa*, or *Klebsiella oxytoca*.

TABLE 37

| | | Antibiofilm efficacy against *Staphylococcus aureus* | | | | | | |
|---|---|---|---|---|---|---|---|---|
| | Conc. | Effect at time point* | | | | | | |
| Compound | (µM) | 0 hr | 2 hr | 4 hr | 6 hr | 8 hr | 10 hr | 12 hr |
| 32-1 | 142.5 | 0 | 0 | 0 | 0 | 0 | 0 | 1 |
| 32-1 | 57 | 0 | 0 | 0 | 0 | 0 | 0 | 2 |
| 32-1 | 28.5 | 0 | 0 | 0 | 1 | 1 | 3 | 3 |
| 32-1 | 14.25 | 0 | 0 | 1 | 3 | 3 | 3 | 3 |
| 32-1A | 142.5 | 0 | 0 | 0 | 0 | 0 | 0 | 0 |
| 32-1A | 57 | 0 | 0 | 0 | 0 | 0 | 0 | 0 |
| 32-1A | 28.5 | 0 | 0 | 0 | 2 | 2 | 3 | 3 |
| 32-1A | 14.25 | 0 | 0 | 0 | 3 | 3 | 3 | 3 |
| 32-1B | 142.5 | 0 | 0 | 0 | 0 | 0 | 0 | 0 |
| 32-1B | 57 | 0 | 0 | 0 | 0 | 0 | 0 | 0 |
| 32-1B | 28.5 | 0 | 0 | 0 | 0 | 0 | 0 | 0 |
| 32-1B | 14.25 | 0 | 0 | 0 | 0 | 0 | 0 | 0 |
| 32-2 | 142.5 | 0 | 0 | 0 | 0 | 0 | 0 | 0 |
| 32-2 | 57 | 0 | 0 | 0 | 0 | 0 | 0 | 0 |
| 32-2 | 28.5 | 0 | 0 | 0 | 0 | 0 | 1 | 3 |
| 32-2 | 14.25 | 0 | 0 | 0 | 3 | 3 | 3 | 3 |
| 32-2A | 142.5 | 0 | 0 | 0 | 0 | 0 | 0 | 0 |
| 32-2A | 57 | 0 | 0 | 0 | 0 | 0 | 0 | 0 |
| 32-2A | 28.5 | 0 | 0 | 0 | 1 | 3 | 3 | 3 |
| 32-2A | 14.25 | 0 | 0 | 2 | 3 | 3 | 3 | 3 |
| 32-2B | 142.5 | 0 | 0 | 0 | 0 | 0 | 0 | 0 |
| 32-2B | 57 | 0 | 0 | 0 | 0 | 0 | 0 | 1 |
| 32-2B | 28.5 | 0 | 0 | 0 | 1 | 0 | 2 | 3 |
| 32-2B | 14.25 | 0 | 0 | 1 | 3 | 0 | 3 | 3 |
| 32-2C | 142.5 | 0 | 0 | 0 | 0 | 0 | 0 | 0 |
| 32-2C | 57 | 0 | 0 | 0 | 0 | 0 | 0 | 1 |
| 32-2C | 28.5 | 0 | 0 | 1 | 3 | 3 | 3 | 3 |
| 32-2C | 14.25 | 1 | 1 | 3 | 3 | 3 | 3 | 3 |
| 32-2D | 250 | 0 | 0 | 0 | 0 | 0 | 0 | 0 |
| 32-2D | 100 | 0 | 0 | 0 | 0 | 0 | 0 | 3 |
| 32-2D | 50 | 0 | 0 | 0 | 3 | 0 | 0 | 3 |
| 32-2D | 25 | 0 | 0 | 2 | 3 | 0 | 0 | 3 |

*0 = no biofilm growth; 1 = weak biofilm growth; 2 = moderate biofilm growth; 3 = strong biofilm growth

TABLE 38

| Antibiofilm efficacy against *Pseudomonas aeruginosa* | | | | | | | | |
|---|---|---|---|---|---|---|---|---|
| | Conc. | Effect at time point* | | | | | | |
| Compound | (µM) | 0 hr | 2 hr | 4 hr | 6 hr | 8 hr | 10 hr | 12 hr |
| 32-1 | 1000.0 | 0 | 0 | 0 | 1 | 1 | 2 | 3 |
| 32-1 | 500.0 | 0 | 0 | 0 | 2 | 2 | 3 | 3 |
| 32-1 | 100.0 | 3 | 3 | 3 | 3 | 3 | 3 | 3 |
| 32-1 | 50.0 | 3 | 3 | 3 | 3 | 3 | 3 | 3 |
| 32-1A | 1000.0 | 0 | 0 | 1 | 2 | 2 | 3 | 3 |
| 32-1A | 500.0 | 0 | 0 | 2 | 2 | 2 | 3 | 3 |
| 32-1A | 100.0 | 0 | 3 | 3 | 3 | 3 | 3 | 3 |
| 32-1A | 50.0 | 3 | 3 | 3 | 3 | 3 | 3 | 3 |
| 32-1B | 1000.0 | 0 | 0 | 0 | 1 | 1 | 3 | 3 |
| 32-1B | 500.0 | 0 | 0 | 0 | 1 | 2 | 3 | 3 |
| 32-1B | 100.0 | 0 | 2 | 3 | 3 | 3 | 3 | 3 |
| 32-1B | 50.0 | 2 | 3 | 3 | 3 | 3 | 3 | 3 |
| 32-2 | 1000.0 | 0 | 0 | 1 | 2 | 2 | 3 | 3 |
| 32-2 | 500.0 | 0 | 0 | 1 | 2 | 2 | 3 | 3 |
| 32-2 | 100.0 | 3 | 3 | 3 | 3 | 3 | 3 | 3 |
| 32-2 | 50.0 | 3 | 3 | 3 | 3 | 3 | 3 | 3 |
| 32-2A | 1000.0 | 0 | 1 | 1 | 1 | 1 | 3 | 3 |
| 32-2A | 500.0 | 0 | 2 | 1 | 1 | 1 | 3 | 3 |
| 32-2A | 100.0 | 3 | 3 | 3 | 3 | 3 | 3 | 3 |
| 32-2A | 50.0 | 3 | 3 | 3 | 3 | 3 | 3 | 3 |
| 32-2B | 1000.0 | 0 | 0 | 1 | 1 | 2 | 3 | 3 |
| 32-2B | 500.0 | 0 | 0 | 1 | 1 | 2 | 3 | 3 |
| 32-2B | 100.0 | 3 | 3 | 3 | 3 | 3 | 3 | 3 |
| 32-2B | 50.0 | 3 | 3 | 3 | 3 | 3 | 3 | 3 |
| 32-2C | 570 | 0 | 2 | 2 | 2 | 2 | 3 | 3 |
| 32-2C | 285 | 0 | 3 | 3 | 3 | 3 | 3 | 3 |
| 32-2C | 57 | 3 | 3 | 3 | 3 | 3 | 3 | 3 |
| 32-2C | 28.5 | 3 | 3 | 3 | 3 | 3 | 3 | 3 |
| 32-2D | 570 | 0 | 3 | 3 | 3 | 3 | 3 | 3 |
| 32-2D | 285 | 0 | 3 | 3 | 3 | 3 | 3 | 3 |
| 32-2D | 57 | 0 | 3 | 3 | 3 | 3 | 3 | 3 |
| 32-2D | 28.5 | 3 | 3 | 3 | 3 | 3 | 3 | 3 |

*0 = no biofilm growth; 1 = weak biofilm growth; 2 = moderate biofilm growth; 3 = strong biofilm growth

TABLE 39

| Antibiofilm efficacy against *Klebsiella oxytoca* | | | | | | | | |
|---|---|---|---|---|---|---|---|---|
| | Conc. | Effect at time point* | | | | | | |
| Compound | (µM) | 0 hr | 2 hr | 4 hr | 6 hr | 8 hr | 10 hr | 12 hr |
| 32-1 | 570 | 0 | 1 | 0 | 1 | 1 | 2 | 0 |
| 32-1 | 285 | 0 | 1 | 0 | 3 | 2 | 3 | 0 |
| 32-1 | 57 | 0 | 3 | 3 | 3 | 3 | 3 | 0 |
| 32-1 | 28.5 | 0 | 3 | 3 | 3 | 3 | 3 | 0 |
| 32-1A | 570 | 0 | 2 | 0 | 2 | 2 | 2 | 2 |
| 32-1A | 285 | 0 | 2 | 0 | 2 | 3 | 3 | 2 |
| 32-1A | 57 | 0 | 2 | 2 | 3 | 3 | 3 | 2 |
| 32-1A | 28.5 | 3 | 3 | 3 | 3 | 3 | 3 | 2 |
| 32-1B | 570 | 0 | 0 | 0 | 1 | 1 | 1 | 2 |
| 32-1B | 285 | 0 | 0 | 1 | 3 | 1 | 2 | 3 |
| 32-1B | 57 | 0 | 2 | 2 | 3 | 3 | 3 | 3 |
| 32-1B | 28.5 | 0 | 2 | 3 | 3 | 3 | 3 | 3 |
| 32-2 | 570 | 0 | 0 | 1 | 2 | 1 | 2 | 2 |
| 32-2 | 285 | 0 | 0 | 1 | 3 | 2 | 2 | 2 |
| 32-2 | 57 | 2 | 3 | 3 | 3 | 3 | 3 | 3 |
| 32-2 | 28.5 | 3 | 3 | 3 | 3 | 3 | 3 | 3 |
| 32-2A | 570 | 0 | 0 | 0 | 2 | 2 | 1 | 1 |
| 32-2A | 285 | 0 | 1 | 1 | 3 | 3 | 2 | 2 |
| 32-2A | 57 | 0 | 2 | 3 | 3 | 3 | 3 | 3 |
| 32-2A | 28.5 | 3 | 3 | 3 | 3 | 3 | 3 | 3 |
| 32-2B | 570 | 0 | 0 | 0 | 2 | 2 | 0 | 0 |
| 32-2B | 285 | 0 | 0 | 1 | 3 | 2 | 0 | 2 |
| 32-2B | 57 | 1 | 3 | 3 | 3 | 3 | 3 | 3 |
| 32-2B | 28.5 | 3 | 3 | 3 | 3 | 3 | 3 | 3 |
| 32-2C | 570 | 0 | 2 | 2 | 2 | 2 | 2 | 2 |
| 32-2C | 285 | 0 | 2 | 2 | 3 | 3 | 3 | 2 |
| 32-2C | 57 | 3 | 3 | 3 | 3 | 3 | 3 | 3 |
| 32-2C | 28.5 | 3 | 3 | 3 | 3 | 3 | 3 | 3 |
| 32-2D | 570 | 0 | 1 | 1 | 2 | 2 | 1 | 0 |

TABLE 39-continued

| Antibiofilm efficacy against *Klebsiella oxytoca* | | | | | | | | |
|---|---|---|---|---|---|---|---|---|
| | Conc. | Effect at time point* | | | | | | |
| Compound | (µM) | 0 hr | 2 hr | 4 hr | 6 hr | 8 hr | 10 hr | 12 hr |
| 32-2D | 285 | 0 | 1 | 1 | 3 | 2 | 2 | 2 |
| 32-2D | 57 | 3 | 2 | 3 | 3 | 3 | 3 | 3 |
| 32-2D | 28.5 | 3 | 3 | 3 | 3 | 3 | 3 | 3 |

*0 = no biofilm growth; 1 = weak biofilm growth; 2 = moderate biofilm growth; 3 = strong biofilm growth Scanning electron microscopy revealed that select compounds interact directly and disrupt the cell wall of *S. aureus* and *P. aeruginosa*.

Wound dressings impregnated with compounds 32-1 or 32-2 showed dose-dependent zone of inhibition against methicillin resistant Gram +VE (NRS 384/MRSA) bacteria. Results are shown in FIG. 20 for compound 32-1 and FIG. 21 for compound 32-2.

WOUND DRESSING AND WOUND HEALING FORMULATION EXAMPLES

Example 1. Wound Dressing

Wound dressings can absorb large amounts of fluid while simultaneously releasing antibacterial compounds to prevent infections. These dressings can be made of highly absorbent materials such as hydrogels or superabsorbent polymers, which can be infused with the compounds. Non-limiting examples of dressings infused with the compounds include an over-the-skin bandage (FIG. 4A) in which the compound is impregnated in the dressing, an over-the-skin bandage in which any one or more layers can be provided with the compound (FIG. 4B), or foam pad (FIG. 4C). As shown in FIG. 4C, one or more layers containing the compound (depicted with dashes) may be provided, e.g., in one or more of a top surface of the pad, a bottom surface, or an intermediate location. In some embodiments an over-the-skin dressing, pad, or any other dressing disclosed herein may be partially or completely made of electrospun fibers containing the compound.

These dressings can be easy to apply and remove, providing superior protection against infection and contamination. They can also be able to promote wound healing by maintaining a moist environment and reducing the risk of scarring. Moreover, these superabsorbent dressings can be designed to be versatile and adaptable to different types of wounds, from minor cuts and abrasions to more serious burns and surgical incisions.

Certain Embodiments

Embodiment 1. A wound dressing comprising a polymeric component selected from a group consisting of:
(1) a polyethyleneimine intermediate;
(2) a polymer, copolymer, interpenetrating polymer network, polyelectrolyte complex, blend or composite comprising:
(i) a first adduct of a first multifunctional crosslinker and a first quaternary ammonium salt, wherein the first quaternary ammonium salt has a reactive linking group to react with the first multifunctional crosslinker;
(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker;

(3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof.

Embodiment 2. The wound dressing of Embodiment 1, wherein (i) the first adduct and (ii) the polyethyleneimine intermediate or the second adduct are prepared separately and mixed thereafter to form the polymer, the copolymer, the interpenetrating polymer network, the polyelectrolyte complex, the blend, or the composite.

Embodiment 3. The wound dressing of Embodiment 1 or Embodiment 2, wherein the polymeric component is antibacterial against one of or both gram negative strain bacteria and gram positive strain bacteria.

Embodiment 4. The wound dressing of any one of Embodiments 1-3, wherein the polyethyleneimine intermediate has a ratio of total quaternary amines to total hydroxyl groups of at least 1:1.

Embodiment 5. The wound dressing of any one of Embodiments 1-4, wherein an outer layer of the wound dressing contains the polymeric component.

Embodiment 6. The wound dressing of any one of Embodiments 1-4, wherein the polymeric component is impregnated into the wound dressing.

Embodiment 7. The wound dressing of any one of Embodiments 1-6, wherein the wound dressing is selected from the group consisting of a wrap, a covering, a barrier, a layer, a packing, a gauze, a plaster, a bandage, a lint, a suture, a film, a foamed product, a hydrogel, a hydrocolloid, an alginate product, a bioactive product, a tissue-engineered skin substitute, a medicated product, a liquid bandage, a smart dressing, and a composite, or any combination of the foregoing.

Embodiment 8. The wound dressing of any of Embodiments 1-6, wherein the wound dressing is configured to provide an indication of one or more parameters relating to a status of the wound site.

Embodiment 9. A topical formulation comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient;

wherein the polyethyleneimine intermediate has a ratio of total quaternary amines to total hydroxyl groups of at least 1:1.

Embodiment 10. The topical formulation of Embodiment 9 in the form of a cream, a gel, a paste, a foam, a spray, a powder, an emulsion, a liquid, or an ointment.

Embodiment 11. The topical formulation of Embodiment 9 or Embodiment 10, wherein the polymeric component is antibacterial against one of or both gram negative strain bacteria and gram positive strain bacteria.

Embodiment 12. A method of preventing or reducing bacterial growth or reducing infection in a wound, a surgical site, or an implant of a subject, the method comprising applying or coating the wound, the surgical site, or the implant with a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof; and at least one pharmaceutically acceptable excipient.

Embodiment 13. A method of treating a wound or a surgical site in a subject in need thereof, the method comprising applying, to the wound or the surgical site, a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 14. A method of promoting healing of a wound or a surgical site in a subject in need thereof, the method comprising applying, to the wound or the surgical site, a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 15. The method of any one of Embodiments 12-14, wherein the wound is an external wound.

Embodiment 16. The method of any one of Embodiments 12-14, wherein the wound is an internal wound.

Embodiment 17. The method of any one of Embodiments 12-16, wherein the method is part of a regimen for acute wound care.

Embodiment 18. The method of any one of Embodiments 12-16, wherein the method is part of a regimen for chronic wound care.

Embodiment 19. The method of any one of Embodiments 12-18, wherein the wound is infected.

Embodiment 20. The method of any one of Embodiments 12-18, wherein the wound is not infected.

Embodiment 21. A method of protecting a wound site in a subject in need thereof, the method comprising surrounding at least a portion of the wound site with a dressing, and contacting the wound site with a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 22. A method of preventing or reducing infection in a subject in need thereof, the method comprising administering to the subject a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 23. A method to treat infection in a subject in need thereof, the method comprising administering to the subject a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 24. The method of Embodiment 22 or Embodiment 23, wherein the infection is a local infection.

Embodiment 25. The method of Embodiment 22 or Embodiment 23, wherein the infection is a systemic infection.

Embodiment 26. A method to treat sepsis in a subject in need thereof, the method comprising administering to the subject a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 27. A method of preventing or reducing necrosis in a subject in need thereof, the method comprising administering to the subject a composition comprising a polymeric component selected from a group consisting of:

(1) a polyethyleneimine intermediate;

(2) a polymer, copolymer, interpenetrating polymer network, polyelectrolyte complex, blend or composite comprising:

(i) a first adduct of a first multifunctional crosslinker and a first quaternary ammonium salt, wherein the first quaternary ammonium salt has a reactive linking group to react with the first multifunctional crosslinker;

(ii) the polyethyleneimine intermediate, or a second adduct of the polyethyleneimine intermediate and a second multifunctional crosslinker; wherein the polyethyleneimine intermediate comprises optionally substituted hydroxyalkylene functionality that reacts with the first adduct, and nitrogen atoms present in the polyethyleneimine intermediate are at least partially quaternized;

(iii) optionally a polyol;

(iv) optionally a water-soluble polymer; and (v) optionally a third multifunctional crosslinker; or (3) a polymer, copolymer, interpenetrating polymer network, polyelectrolyte complex, blend or composite comprising the first adduct, the polyol, the water-soluble polymer, and optionally the third multifunctional crosslinker;

(4) the second adduct; and (5) a combination of two or more thereof;

and at least one pharmaceutically acceptable excipient.

Embodiment 28. The method of any one of Embodiments 12-27, wherein the subject is a human or animal subject.

Embodiment 29. The method of any one of Embodiments 12-28, wherein the composition is antibacterial against one of or both gram negative strain bacteria and gram positive strain bacteria.

Embodiment 30. The method of any one of Embodiments 12-29, wherein the polyethyleneimine intermediate has a ratio of total quaternary amines to total hydroxyl groups of at least 1:1.

Embodiment 31. The wound dressing, topical formulation, or method of any one of Embodiments 1-30, wherein the polyethyleneimine intermediate comprises a reaction product of reagents comprising a polyethyleneimine and an alkylating agent.

Embodiment 32. The wound dressing, topical formulation, or method of Embodiment 31, wherein the reagents further comprise a mono-epoxide or a lactone.

Embodiment 33. The wound dressing, topical formulation, or method of Embodiment 32, wherein the mono-epoxide or the lactone is optionally substituted with $C_1$-$C_6$ alkyl optionally substituted with a substituent selected from —($C_6$-$C_{10}$ aryl), and —($C_1$-$C_6$ alkoxy) optionally substituted with hydroxy, $C_1$-$C_6$ alkoxy, $C_6$-$C_{10}$ aryl optionally substituted with $C_1$-$C_6$ alkyl, and carboxy.

Embodiment 34. The wound dressing, topical formulation, or method of Embodiment 32, wherein the mono-epoxide is a $C_1$-$C_6$ alkyl oxirane.

Embodiment 35. The wound dressing, topical formulation, or method of Embodiment 34, wherein the $C_1$—C alkyl epoxide is selected from the group consisting of methyl oxirane, ethyl oxirane, propyl oxirane, and butyl oxirane.

Embodiment 36. The wound dressing, topical formulation, or method any one of Embodiments 1-30, wherein the polyethyleneimine intermediate comprises a reaction product of reagents comprising a polyethyleneimine, a mono-epoxide, and optionally an alkylating agent; the mono-epoxide is substituted with —($C_1$-$C_6$ alkylene)-$N^+(R^{20})_3X^-$; each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl); and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

Embodiment 37. The wound dressing, topical formulation, or method of any one of Embodiments 31-36, wherein the alkylating agent comprises one or more $R^{21}$-LG, wherein each $R^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH; and each LG is a leaving group.

Embodiment 38. The wound dressing, topical formulation, or method of Embodiment 37, wherein the alkylating agent is phenacyl halide, benzyl halide, or hexyl halide.

Embodiment 39. The wound dressing, topical formulation, or method of any one of Embodiments 31-38, wherein the reagents for the reaction product comprised in the polyethyleneimine intermediate further comprise a monoisocyanate.

Embodiment 40. The wound dressing, topical formulation, or method of Embodiment 39, wherein the monoisocyanate comprises one or more $R^{30}$—NCO, wherein each $R^{30}$ is independently selected from (1) $C_6$-$C_{20}$ alkyl optionally substituted with 1-3 substituents independently selected from halogen, —$SiR^a(OR^b)(OR^c)$, and —($C_6$-$C_{10}$ aryl); and (2) $C_6$-$C_{10}$ aryl optionally substituted with 1-3 substituents independently selected from halogen, —($C_1$-$C_6$ alkyl), and —$SiR^a(OR^b)(OR^c)$; wherein each $R^a$ is independently $C_1$-$C_6$ alkyl; and each $R^b$ and each $R^c$ are independently selected from —($C_1$-$C_6$ alkyl) and —$Si(C_1$-$C_6$ alkyl)$_3$.

Embodiment 41. The wound dressing, topical formulation, or method of Embodiment 39 or Embodiment 40, wherein the monoisocyanate comprises octylisocyanate, octadecylisocyanate, or a combination thereof.

Embodiment 42. The wound dressing, topical formulation, or method of any one of Embodiments 31-41, wherein the polyethyleneimine has a molecular weight of about 300 to about 270,000 daltons.

Embodiment 43. The wound dressing, topical formulation, or method of any one of Embodiments 31-42, wherein the polyethyleneimine has a molecular weight of about 10,000 to about 200,000 daltons.

Embodiment 44. The wound dressing, topical formulation, or method of any one of Embodiments 31-43, wherein the polyethyleneimine has a molecular weight of about 25,000 to about 120,000 daltons.

Embodiment 45. The wound dressing, topical formulation, or method of any one of Embodiments 31-44, wherein the polyethyleneimine is branched.

Embodiment 46. The wound dressing, topical formulation, or method of any one of Embodiments 31-44, wherein the polyethyleneimine is hyperbranched.

Embodiment 47. The wound dressing, topical formulation, or method of any one of Embodiments 31-46, wherein the polyethyleneimine has a ratio of primary to secondary to tertiary amines of about 1:2:1 to about 1:1:1.

Embodiment 48. The wound dressing, topical formulation, or method of any one of Embodiments 31-46, wherein the polyethyleneimine has a ratio of primary to secondary to tertiary amines of about 1:1:0.7.

Embodiment 49. The wound dressing, topical formulation, or method of any one of Embodiments 1-30, wherein the polyethyleneimine intermediate is one or more selected from -continued and a copolymer or blend of any two or more thereof, wherein:

each $Y^3$ is independently H or —O—$Y^2$;

each $Y^2$ is independently H or —C(O)—$NHR^{30}$;

each n is an integer independently selected from 1 to 3000, preferably an integer independently selected from 10 to 1000;

Z is —($C_2$-$C_6$ alkylene)-;

each $R^{10}$ is independently selected from hydrogen; $C_1$-$C_6$ alkyl optionally substituted with a substituent selected from —$N^+(R^{20})_3X^-$, —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy; and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl);

each $R^{21}$ is independently selected from $C_1$-$C_6$ alkyl optionally substituted with a substituent selected from —OH, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH;

each $R^{30}$ is independently selected from (1) $C_6$-$C_{20}$ alkyl optionally substituted with 1-3 substituents independently selected from halogen, —$SiR^a(OR^b)(OR^c)$, and —($C_6$-$C_{10}$ aryl); and (2) $C_6$-$C_{10}$ aryl optionally substituted with 1-3 substituents independently selected from halogen, —($C_1$-$C_6$ alkyl), and —$SiR^a(OR^b)(OR^c)$; wherein each $R^a$ is independently —($C_1$-$C_6$ alkyl); and each $R^b$ and each $R^c$ are independently selected from —($C_1$-$C_6$ alkyl) and —$Si(C_1$-$C_6$ alkyl)$_3$; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives;

provided:

when $R^{10}$ is $C_1$-$C_6$ alkyl optionally substituted with a substituent selected from —($C_6$-$C_{10}$ aryl), and —($C_1$-$C_6$ alkoxy) optionally substituted with —OH, —($C_1$-$C_6$ alkoxy), —($C_6$-$C_{10}$ aryl) optionally substituted with —($C_1$-$C_6$ alkyl), and carboxy, then the polyethylene-imine intermediate is independently selected from Embodiment 50. The wound dressing, topical formulation, or method of any one of Embodiments 1-30, wherein the polyethyleneimine intermediate is

167

-continued

4 X⁻ wherein each $R^{60}$ is independently selected from —$Y^4$—($C_1$-$C_{18}$ alkyl) optionally substituted with 1-3 substituents selected from —OH, —$N^+(R^{20})_3X^-$, —($C_1$-$C_6$ alkoxy), carboxy, —($C_6$-$C_{10}$ aryl), —C(O)O($C_1$-$C_6$ alkyl), —C(O)—($C_6$-$C_{10}$ aryl), and —($C_1$-$C_6$ alkoxy) optionally substituted with —OH; and at least one $R^{60}$ is substituted with —OH but less than 50% of all $R^{60}$ are substituted with —OH;

$Y^4$ is absent or —C(O)—;

and each $R^{20}$ is independently selected from a group consisting of $C_1$-$C_{18}$ alkyl; $C_1$-$C_{18}$ heteroalkyl having 1 to 4 heteroatoms independently selected from O, S, Si and tertiary-substituted N; and $C_6$-$C_{10}$ aryl optionally substituted with —($C_1$-$C_6$ alkyl), —($C_1$-$C_6$ alkoxy), —C(O)O—($C_1$-$C_6$ alkyl), —C(O)NH($C_1$-$C_6$ alkyl), —C(O)N($C_1$-$C_6$ alkyl)$_2$, or —OC(O)—($C_1$-$C_6$ alkyl);

each n is an integer independently selected from 1 to 3000, preferably an integer independently selected from 10 to 1000; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

Embodiment 51. The wound dressing, topical formulation, or method of any one of Embodiments 1-30, wherein the polyethyleneimine intermediate is

3 X⁻ or

168

-continued

4 X⁻ wherein each $R^{60}$ is independently selected from —$Y^4$—($C_1$-$C_{18}$ alkyl) optionally substituted with 1-3 substituents selected from —OH, —$N^+(R^{20})_3X^-$, —($C_6$-$C_{10}$ aryl), —C(O)O($C_1$-$C_6$ alkyl), and —C(O)—($C_6$-$C_{10}$ aryl); and at least one $R^{60}$ is substituted with —OH but less than 50% of all $R^{60}$ are substituted with —OH;

$Y^4$ is absent or —C(O)—;

and each $R^{20}$ is independently selected from a group consisting of $C_1$-$C_6$ alkyl;

each n is an integer independently selected from 1 to 3000, preferably an integer independently selected from 10 to 1000; and each $X^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

Embodiment 52. The wound dressing, topical formulation, or method of Embodiment 51, wherein each $R^{60}$ is independently selected from —($C_1$-$C_{18}$ alkyl) optionally substituted with —OH; and at least one $R^{60}$ is substituted with —OH but less than 50% of all $R^{60}$ are substituted with —OH.

Embodiment 53. The wound dressing, topical formulation, or method of Embodiment 51, wherein each $R^{60}$ is independently selected from the group consisting of —$CH_3$, —$C_4H_9$, —$C_6H_{13}$, —$C_8H_{17}$, —$C_{18}H_{37}$, —$CH_2Ph$, —$H_2C$(O)$OCH_2CH_3$, —$CH_2C(O)Ph$, —$(CH_2)_3OH$, —$CH_2CH$($CH_3$)OH, —$CH_2CH(OH)CH_2N^+(CH_3)_3$, and —C(O)$(CH_2)_5$ OH.

Embodiment 54. The wound dressing, topical formulation, or method of any one of Embodiments 1-30, wherein the polyethyleneimine intermediate is selected from a group consisting of:

| Compound | General Structure | PEI MW* | $R^{60}$ (mole %)** |
|---|---|---|---|
| 20-1 (batch 105159) | B | 270 kDa (branched) | —$CH_2CH(CH_3)OH$ (<50%) —$C_6H_{13}$ (>50%) |
| 20-1 (batch 99367) | B | 270 kDa (branched) | —$CH_2CH(CH_3)OH$ (50%) —$C_6H_{13}$ (50%) |
| 21-1 | A | 25 kDa (hyperbranched) | —$CH_2CH(CH_3)OH$ (50%) —$C_6H_{13}$ (50%) |
| 22-1 | B | 70 kDa (branched) | —$CH_2CH(CH_3)OH$ (50%) —$C_6H_{13}$ (50%) |
| 23-1 | B | 70 kDa (branched) | —$CH_2CH(CH_3)OH$ (50%) —$CH_2C(O)Ph$ (50%) |
| 24-1 | B | 70 kDa (branched) | —$CH_2CH(CH_3)OH$ (50%) —$CH_2Ph$ (50%) |

-continued

| Compound | General Structure | PEI MW* | $R^{60}$ (mole %)** |
|---|---|---|---|
| 26-1 | B | 70 kDa (branched) | —$CH_2CH(OH)CH_2N^+(CH_3)_3$ $Cl^-$ (100%) |
| 29-1 | B | 70 kDa (branched) | —$(CH_2)_3OH$ (1%) —$C_6H_{13}$ (99%) |
| 30-1 | A | 25 kDa (hyperbranched) | —$(CH_2)_3OH$ (10%) 75:25 —$C_{18}H_{37}$:—$C_8H_{17}$ (90%) |
| 31-1 | B | 70 kDa (branched) | —$C(O)(CH_2)_5OH$ (7%) —$C_6H_{13}$ (93%) |
| 32-1 | B | 70 kDa (branched) | —$(CH_2)_3OH$ (10%) —$C_6H_{13}$ (90%) |
| 32-2 | B | 70 kDa (branched) | —$(CH_2)_3OH$ (5%) —$C_6H_{13}$ (95%) |
| 32-3 | B | 70 kDa (branched) | —$CH_2CH(CH_3)OH$ (5%) —$C_6H_{13}$ (95%) |
| 32-4 | B | 70 kDa (branched) | —$C(O)(CH_2)_5OH$ (7.5%) —$C_6H_{13}$ (92.5%) |
| 32-5 | A | 25 kDa (hyperbranched) | —$CH_2CH(CH_3)OH$ (50%) 50:50 —$C_{18}H_{37}$:—$C_8H_{17}$ (50%) |
| 32-6 | B | 72 kDa (branched) | —$(CH_2)_3OH$ (13%) 75:25 —$C_{18}H_{37}$:—$C_8H_{17}$ (87%) |
| 32-7 | B | 72 kDa (branched) | —$C(O)(CH_2)_5OH$ (6.5%) 75:25 —$C_{18}H_{37}$:—$C_8H_{17}$ (93.5%) |
| 32-8 | A | 25 kDa (hyperbranched) | —$C(O)(CH_2)_5OH$ (7%) 75:25 —$C_{18}H_{37}$:—$C_8H_{17}$ (93%) |
| 32-9 | A | 25 kDa (hyperbranched) | —$CH_2CH(CH_3)OH$ (50%) 25:75 —$C_{18}H_{37}$:—$C_8H_{17}$ (50%) |

*indicates molecular weight of polyethyleneimine precursor

**theoretical stoichiometric ratio (based on amount of reactants used in the synthetic protocol) wherein A is B is and each n is an integer independently selected from 1 to 3000, preferably an integer independently selected from 10 to 100.

Embodiment 55. The wound dressing, topical formulation, or method of Embodiment 54, wherein one or more bromide anions is replaced with $X^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

Embodiment 56. The wound dressing, topical formulation, or method of any one of Embodiments 1-30, wherein the polyethyleneimine intermediate is selected from a group consisting of:

| Compound | General Structure | PEI MW* | $R^{60}$ (mole %)** |
|---|---|---|---|
| 32-10 | A | 25 kDa (hyper-branched) | —$C(O)(CH_2)_5OH$ (11%) —$C_6H_{13}$ (89%) |
| 32-11 | B | 70 kDa (branched) | —$C(O)(CH_2)_5OH$ (9%) —$C_6H_{13}$ (91%) |
| 32-13 | B | 70 kDa (branched) | —$(CH_2)_3OH$ (7%) 75:25 —$C_{18}H_{37}$:—$C_8H_{17}$ (93%) |
| 32-14 | A | 25 kDa (hyperbranched) | —$(CH_2)_3OH$ (7%) 75:25 —$C_{18}H_{37}$:—$C_8H_{17}$ (93%) |
| 32-15 | B | 70 kDa (branched) | —$C(O)(CH_2)_5OH$ (9%) 75:25 —$C_{18}H_{37}$:—$C_8H_{17}$ (91%) |

-continued

| Compound | General Structure | PEI MW* | R$^{60}$ (mole %)** |
|---|---|---|---|
| 32-16 | A | 25 kDa (hyperbranched) | —C(O)(CH$_2$)$_5$OH (11%) 75:25 —C$_{18}$H$_{37}$:—C$_8$H$_{17}$ (89%) |
| 32-17 | B | 70 kDa (branched) | —C$_6$H$_{13}$ (100%) |
| 32-18 | A | 25 kDa (hyperbranched) | —C$_6$H$_{13}$ (100%) |
| 32-1A | B | 70 kDa (branched) | —(CH$_2$)$_3$OH (10%) —C$_6$H$_{13}$ (90%) |
| 32-1B | B | 70 kDa (branched) | —(CH$_2$)$_3$OH (10%) —C$_6$H$_{13}$ (90%) |
| 32-2A | B | 70 kDa (branched) | —(CH$_2$)$_3$OH (5%) —C$_6$H$_{13}$ (95%) |
| 32-2B | B | 70 kDa (branched) | —(CH$_2$)$_3$OH (5%) —C$_6$H$_{13}$ (95%) |
| 32-2C | B | 70 kDa (branched) | —(CH$_2$)$_3$OH (15%)*** —C$_6$H$_{13}$ (85%) |
| 32-2D | B | 70 kDa (branched) | —(CH$_2$)$_3$OH (5%) —C$_6$H$_{13}$ (95%) |
| 32-2E | B | 70 kDa (branched) | —(CH$_2$)$_3$OH (12%)*** —C$_6$H$_{13}$ (88%) |
| 32-2F | B | 70 kDa (branched) | —(CH$_2$)$_3$OH (5%) —C$_6$H$_{13}$ (95%) |
| 32-2G | B | 70 kDa (branched) | —(CH$_2$)$_3$OH (5%) —C$_6$H$_{13}$ (95%) |
| 32-2H | B | 70 kDa (branched) | —(CH$_2$)$_3$OH (5%) —C$_6$H$_{13}$ (95%) |
| 32-2I | B | 70 kDa (branched) | —(CH$_2$)$_3$OH (5%) —C$_6$H$_{13}$ (95%) |

*indicates molecular weight of polyethyleneimine precursor
**theoretical stoichiometric ratio (based on amount of reactants used in the synthetic protocol) unless otherwise indicated
***actual stoichiometric ratio as determined by NMR analysis wherein A is 3 Br$^-$ B is 4 Br$^-$ and each n is an integer independently selected from 1 to 3000, preferably an integer independently selected from 10 to 100.

Embodiment 57. The wound dressing, topical formulation, or method of any one of Embodiments 1-56, wherein at least 20% of the nitrogen atoms of the polyethyleneimine intermediate are quaternized.

Embodiment 58. The wound dressing, topical formulation, or method of any one of Embodiments 1-57, wherein the first quaternary ammonium salt has a chemical structure of wherein R$^1$ is selected from a group consisting of —(C$_8$-C$_{30}$ alkyl), —(C$_8$-C$_{30}$ heteroalkyl), —(C$_8$-C$_{30}$ heteroalkyl)-

(C$_6$-C$_{10}$ aryl), —(C$_6$-C$_{10}$ aryl), —(C$_6$-C$_{10}$ aryl)-(C$_1$-C$_{30}$ alkyl), —(C$_6$-C$_{10}$ aryl)-(C$_1$-C$_{30}$ heteroalkyl), —(CR$^m$R$^n$)$_{x10}$—W$^{10}$—(CR$^p$R$^q$)$_{y10}$—H, and —(CR$^m$R$^n$)$_{x11}$—W$^{11}$—(CR$^p$R$^q$)$_{y11}$H—; wherein —(C$_8$-C$_{30}$ heteroalkyl), —(C$_8$-C$_{30}$ heteroalkyl)-(C$_6$-C$_{10}$ aryl), and —(C$_6$-C$_{10}$ aryl)-(C$_8$-C$_{30}$ heteroalkyl) have 1 to 4 heteroatoms independently selected from O, S, and Si;

R$^2$ is selected from a group consisting of —(C$_1$-C$_4$ alkyl), —(C$_1$-C$_4$ heteroalkyl), —(C$_1$-C$_4$ heteroalkyl)-(C$_6$-C$_{10}$ aryl), —(C$_6$-C$_{10}$ aryl), —(C$_6$-C$_{10}$ aryl)-(C$_1$-C$_4$alkyl), —(C$_6$-C$_{10}$ aryl)-(C$_1$-C$_4$ heteroalkyl); —(CR$^m$R$^n$)$_{x20}$—W$^{20}$—(CR$^p$R$^q$)$_{y20}$—H, and —(CR$^m$R$^n$)$_{x21}$—W$^{21}$—(CR$^p$R$^q$)$_{y21}$—H; wherein —(C$_1$-C$_4$ heteroalkyl), —(C$_1$-C$_4$ heteroalkyl)-(C$_6$-C$_{10}$ aryl), and —(C$_6$-C$_{10}$ aryl)-(C$_1$-C$_4$ heteroalkyl) have 1 to 4 heteroatoms independently selected from O, S, and Si;

$R^3$ is selected from a group consisting of —($C_1$-$C_{30}$ alkyl), —($C_1$-$C_{30}$ heteroalkyl), —($C_1$-$C_{30}$ heteroalkyl)-($C_6$-$C_{10}$ aryl), —($C_6$-$C_{10}$ aryl), —($C_6$-$C_{10}$ aryl)-($C_1$-$C_{30}$ alkyl), —($C_6$-$C_{10}$ aryl)-($C_1$-$C_{30}$ heteroalkyl), —($CR'''R''$)$_{x30}$—$W^{30}$—($CR^pR^q$)$_{y30}$—H, and —($CR'''R''$)$_{x31}$—$W^{31}$—($CR^pR^q$)$_{y31}$—H; wherein —($C_1$-$C_{30}$ heteroalkyl), —($C_1$-$C_{30}$ heteroalkyl)-($C_6$-$C_{10}$ aryl), and —($C_6$-$C_{10}$ aryl)-($C_1$-$C_{30}$ heteroalkyl) have 1 to 4 heteroatoms independently selected from O, S, and Si;

A is a linking group selected from a group consisting of —($C_3$-$C_{20}$ alkylene)-, —($C_3$-$C_{20}$ heteroalkylene)-, —($C_6$-$C_{10}$ arylene)-($C_3$-$C_{20}$ alkylene)-, —($CR'''R''$)$_{x40}$—$W^{40}$—($CR^pR^q$)$_{y40}$—, and —($CR'''R''$)$_{x41}$—$W^{41}$—($CR^pR^q$)$_{y41}$—, wherein —($C_3$-$C_{20}$ heteroalkylene)- has 1 to 4 heteroatoms independently selected from O, S, and Si; and —($C_3$-$C_{20}$ alkylene)- and —($C_3$-$C_{20}$ heteroalkylene)- are optionally substituted with 1 to 6 substituents independently selected from —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl);

each $R'''$, $R''$, $R^p$, and $R^q$ is independently selected from H and $C_1$-$C_4$ alkyl;

$W^{10}$, $W^{20}$, $W^{30}$, and $W^{40}$ are independently selected from —C(O)—; —C(O)O—; —OC(O)—; —C(O)NH—; and —NHC(O)—;

$W^{11}$, $W^{21}$, $W^{31}$, and $W^{41}$ are independently selected from 5- to 6-membered cycloalkyl, $C_6$-$C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x10 is an integer from 1 to 30 and y10 is an integer from 0 to 29, wherein 8≤(×10+y10)≤30;

x11 is an integer from 1 to 30 and y11 is an integer from 0 to 29, wherein 8≤(×11+y11)≤30;

x20 is an integer from 1 to 4 and y20 is an integer from 0 to 3, wherein x20+y20≤4;

x21 is an integer from 1 to 4 and y21 is an integer from 0 to 3, wherein x21+y21≤4;

x30 is an integer from 1 to 30 and y30 is an integer from 0 to 29, wherein x30+y30≤30;

x31 is an integer from 1 to 30 and y31 is an integer from 0 to 29, wherein x31+y31≤30;

x40 is an integer from 1 to 19 and y40 is an integer from 1 to 19, wherein 3≤(×40+y40)≤20;

x41 is an integer from 1 to 20, and y41 is an integer from 0 to 19, wherein 3≤(×41+y41)≤20;

Y is selected from a group consisting of —OH, —NHR$^4$, —SH, —CO$_2$H, —C(O)NHR$^4$, —C(S)NHR$^4$, each $R^4$ is independently selected from a group consisting of H, —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si; and $X^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

Embodiment 59. The wound dressing, topical formulation, or method of Embodiment 58, wherein $R^1$ is selected from a group consisting of —($C_{12}$-$C_{30}$ alkyl), —($C_{12}$-$C_{30}$ heteroalkyl), —($C_{12}$-$C_{30}$ alkyl)-($C_6$-$C_{10}$ aryl), —($C_{12}$-$C_{30}$ heteroalkyl)-($C_6$-$C_{10}$ aryl), —($C_6$-$C_{10}$ aryl)-($C_{12}$-$C_{30}$ alkyl), and —($C_6$-$C_{10}$ aryl)-($C_{12}$-$C_{30}$ heteroalkyl); wherein —($C_{12}$-$C_{30}$ heteroalkyl), —($C_{12}$-$C_{30}$ heteroalkyl)-($C_6$-$C_{10}$ aryl), and —($C_6$-$C_{10}$ aryl)-($C_{12}$-$C_{30}$ heteroalkyl) have 1 to 4 heteroatoms independently selected from O, S, and Si.

Embodiment 60. The wound dressing, topical formulation, or method of Embodiment 58 or Embodiment 59, wherein $R^3$ is selected from a group consisting of —($C_1$-$C_4$ alkyl), —($C_1$-$C_4$ heteroalkyl), —($C_1$-$C_4$ alkyl)-($C_6$-$C_{10}$ aryl), —($C_1$-$C_4$ heteroalkyl)-($C_6$-$C_{10}$ aryl), —($C_6$-$C_{10}$ aryl)-($C_1$-$C_4$ alkyl), and —($C_6$-$C_{10}$ aryl)-($C_1$-$C_4$ heteroalkyl); wherein —($C_1$-$C_4$ heteroalkyl), —($C_1$-$C_4$ heteroalkyl)-($C_6$-$C_{10}$ aryl), and —($C_6$-$C_{10}$ aryl)-($C_1$-$C_4$ heteroalkyl) have 1 to 4 heteroatoms independently selected from O, S, and Si.

Embodiment 61. The wound dressing, topical formulation, or method of any one of Embodiments 58-60, wherein at least one of $R^2$ and $R^3$ is —($C_1$-$C_4$ alkyl).

Embodiment 62. The wound dressing, topical formulation, or method of any one of Embodiments 58-60, wherein $R^2$ and $R^3$ are methyl.

Embodiment 63. The wound dressing, topical formulation, or method of any one of Embodiments 58-62, wherein A is —(CH$_2$)$_m$— or —(CH$_2$CHR$^5$—O—)$_n$—CH$_2$CHR$^5$—, wherein m is an integer from 2 to 20; n is 0, 1, 2, 3, 4, or 5; and each $R^5$ is independently selected from a group consisting of H, —($C_6$-$C_{10}$ aryl)-($C_1$-$C_3$ alkyl), —($C_6$-$C_{10}$ aryl)-($C_1$-$C_3$ heteroalkyl), —($C_1$-$C_3$ alkyl)-($C_6$-$C_{10}$ aryl), —($C_1$-$C_3$ heteroalkyl)-($C_6$-$C_{10}$ aryl), and —($C_6$-$C_{10}$ aryl), wherein —($C_6$-$C_{10}$ aryl)-($C_1$-$C_3$ heteroalkyl) and —($C_1$-$C_3$ heteroalkyl)-($C_6$-$C_{10}$ aryl) have 1 to 4 heteroatoms independently selected from O, S, and Si.

Embodiment 64. The wound dressing, topical formulation, or method of Embodiment 63, wherein $R^5$ is H or methyl.

Embodiment 65. The wound dressing, topical formulation, or method of any one of Embodiments 1-58, wherein the first quaternary ammonium salt is -continued or a combination of two or more thereof.

Embodiment 66. The wound dressing, topical formulation, or method of any one of Embodiments 1-65, wherein the first quaternary ammonium salt is present in the polymer, the copolymer, or the interpenetrating polymer network of polymeric component (1) or (2) in an amount of about 1 wt. % to about 50 wt. %.

Embodiment 67. The wound dressing, topical formulation, or method of any one of Embodiments 1-66, wherein the first multifunctional crosslinker is a bisfunctional crosslinker.

Embodiment 68. The wound dressing, topical formulation, or method of Embodiment 67, wherein the bisfunctional crosslinker is a diisocyanate.

Embodiment 69. The wound dressing, topical formulation, or method of Embodiment 68, wherein the a diisocyanate is selected from a group consisting of hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI).

Embodiment 70. The wound dressing, topical formulation, or method of Embodiment 68 or Embodiment 69, wherein the second multifunctional crosslinker, when present, is a second polyisocyanate; the third multifunctional crosslinker, when present, is a third polyisocyanate; and the second polyisocyanate and the third polyisocyanate are different.

Embodiment 71. The wound dressing, topical formulation, or method of Embodiment 68 or Embodiment 69, wherein the second multifunctional crosslinker, when present, is a second polyisocyanate; the third multifunctional crosslinker, when present, is a third polyisocyanate; and the second polyisocyanate and the third polyisocyanate are the same.

Embodiment 72. The wound dressing, topical formulation, or method of any one of Embodiments 1-66, wherein the first multifunctional crosslinker is a first polyisocyanate; the second multifunctional crosslinker, when present, is a second polyisocyanate; the third multifunctional crosslinker, when present, is a third polyisocyanate; and the first polyisocyanate, the second polyisocyanate, and the third polyisocyanate are different.

Embodiment 73. The wound dressing, topical formulation, or method of any one of Embodiments 1-66, wherein the first multifunctional crosslinker is a first polyisocyanate; the second multifunctional crosslinker, when present, is a second polyisocyanate; the third multifunctional crosslinker, when present, is a third polyisocyanate; and the first polyisocyanate, the second polyisocyanate, and the third polyisocyanate are the same.

Embodiment 74. The wound dressing, topical formulation, or method of Embodiment 72 or Embodiment 73, wherein each of the first, second, and third polyisocyanates has an average isocyanate functionality of 2 to 5.

Embodiment 75. The wound dressing, topical formulation, or method of Embodiment 74, wherein each of the first, second, and third polyisocyanates has an average isocyanate functionality of 3 to 4.

Embodiment 76. The wound dressing, topical formulation, or method of any one of Embodiments 72-75, wherein each of the first, second, and third polyisocyanates is prepared from a diisocyanate independently selected from a group consisting of hexamethylene diisocyanate (HDI), isophorone diisocyanate (IPDI), toluene diisocyanate (TDI), methylene diphenyl diisocyanate (MDI), xylenediisocyanate (XDI), methylene-bis-(4-cyclohexylisocyanate) (H12MDI), meta-tetramethylxylene diisocyanate (TMXDI), and trimethylhexamethylene diisocyanate (TMDI).

Embodiment 77. The wound dressing, topical formulation, or method of any one of Embodiments 72-75, wherein each of the first, second, and third polyisocyanates is independently selected from a group consisting of DESMODUR® N-3300, DESMODUR® N-100, DESMODUR® Z4470SN, WANNATE® T series polyisocyanates, and LUPRANATE® M series polyisocyanates.

Embodiment 78. The wound dressing, topical formulation, or method of any one of Embodiments 72-77, wherein the first adduct has an average isocyanate functionality of 2 to 3.

Embodiment 79. The wound dressing, topical formulation, or method of Embodiment 78, wherein the first adduct has an average isocyanate functionality of about 2.05 to about 2.3.

Embodiment 80. The wound dressing, topical formulation, or method of any one of Embodiments 1-79, wherein the first multifunctional crosslinker is present in the polymer, the copolymer, or the interpenetrating polymer network of polymeric component (1) or (2) in an amount of about 2 wt. % to about 25 wt. %.

Embodiment 81. The wound dressing, topical formulation, or method of any one of Embodiments 1-80, wherein the second multifunctional crosslinker is present in the polymer, the copolymer, or the interpenetrating polymer network of polymeric component (1) or in polymeric component (4) in an amount of about 0.1 wt. % to about 10 wt. %.

Embodiment 82. The wound dressing, topical formulation, or method of any one of Embodiments 1-81, wherein the third multifunctional crosslinker is present in the polymer, the copolymer, or the interpenetrating polymer network of polymeric component (1) or (2) in an amount of about 0.1 wt. % to about 20 wt. %.

Embodiment 83. The wound dressing, topical formulation, or method of any one of Embodiments 1-82, wherein the polyol is selected from a group consisting of polyether polyols, polyester polyols, polyacrylic polyols, polymethacrylic polyols, polycaprolactone polyols, polybutadiene polyols, poly(acrylonitrile-co-butadiene) polyols, polysiloxane polyols, a copolymer of any two or more thereof, and a combination of any two or more thereof.

Embodiment 84. The wound dressing, topical formulation, or method of Embodiment 83, wherein the polyol is selected from a group consisting of poly(tetramethylene glycol), polyethylene glycol, polypropylene glycol, poly(ethylene glycol-b-propylene glycol-b-ethylene glycol), and poly(propylene glycol-b-polyethylene glycol-b-propylene glycol).

Embodiment 85. The wound dressing, topical formulation, or method of any one of Embodiments 1-84, wherein the polyol has a weight average molecular weight from about 300 to about 3000.

Embodiment 86. The wound dressing, topical formulation, or method of any one of Embodiments 1-85, wherein the polyol has a weight average molecular weight from about 400 to about 2000.

Embodiment 87. The wound dressing, topical formulation, or method of any one of Embodiments 1-86, wherein the polyol has a weight average molecular weight from about 600 to about 1500.

Embodiment 88. The wound dressing, topical formulation, or method of any one of Embodiments 1-87, wherein the polyol is present in the polymer, the copolymer, or the interpenetrating polymer network of polymeric component (1) or (2) in an amount of about 1 wt. % to about 40 wt. %.

Embodiment 89. The wound dressing, topical formulation, or method of any one of Embodiments 1-88, wherein polymeric component (1) further comprises (vi) a third adduct of the first multifunctional crosslinker and a second quaternary ammonium salt $$R^{2a}-\overset{\overset{\displaystyle R^{1a}}{|}}{\underset{\displaystyle R^{3a}}{N^+}}\overset{\displaystyle X^-}{\underset{\displaystyle A^1}{\diagdown}}Y^1,$$

wherein $R^{1a}$, $R^{2a}$, and $R^{3a}$ are each independently —$(C_1\text{-}C_{20}$ alkyl), —$(C_1\text{-}C_{20}$ alkyl)-$(C_6\text{-}C_{10}$ aryl), or —$(C_6\text{-}C_{10}$ aryl)-$(C_1\text{-}C_{20}$ alkyl);

$A^1$ is a linking group selected from a group consisting of —$(C_3\text{-}C_{20}$ alkylene)-, —$(C_3\text{-}C_{20}$ heteroalkylene)-, —$(C_6\text{-}C_{10}$ arylene)-$(C_3\text{-}C_{20}$ alkylene)-, —$(CR^{m1}R^{n1})_{x42}$—$W^{42}$—$(CR^{p1}R^{q1})_{y42}$—, and —$(CR^{m1}R^{n1})_{x43}$—$W^{43}$—$(CR^{p1}R^1)_{y43}$—, wherein —$(C_3\text{-}C_{20}$ heteroalkylene)- has 1 to 4 heteroatoms independently selected from O, S, and Si; and —$(C_3\text{-}C_{20}$ alkylene)- and —$(C_3\text{-}C_{20}$ heteroalkylene)- are optionally substituted with 1 to 6 substituents independently selected from —$(C_6\text{-}C_{10}$ aryl)-$(C_1\text{-}C_3$ alkyl), —$(C_6\text{-}C_{10}$ aryl)-$(C_1\text{-}C_3$ heteroalkyl), —$(C_1\text{-}C_3$ alkyl)-$(C_6\text{-}C_{10}$ aryl), —$(C_1\text{-}C_3$ heteroalkyl)-$(C_6\text{-}C_{10}$ aryl), and —$(C_6\text{-}C_{10}$ aryl);

each $R^{m1}$, $R^{n1}$, $R^{p1}$, and $R^{q1}$ is independently selected from H and $C_1\text{-}C_4$ alkyl;

$W^{42}$ is selected from —C(O)—; —C(O)O—; —OC(O)—; —C(O)NH—; and —NHC(O)—;

$W^{43}$ is selected from 5- to 6-membered cycloalkyl, $C_6\text{-}C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein 3≤(x42+y42)≤20;

x43 is an integer from 1 to 20, and y43 is an integer from 0 to 19, wherein 3≤(x43+y43)≤20;

$Y^1$ is selected from a group consisting of —OH, —$NHR^{4a}$, —SH, —$CO_2H$, —$C(O)NHR^{4a}$, —$C(S)NHR^{4a}$, each $R^{4a}$ is independently selected from a group consisting of H, —$(C_6\text{-}C_{10}$ aryl)-$(C_1\text{-}C_3$ alkyl), —$(C_6\text{-}C_{10}$ aryl)-$(C_1\text{-}C_3$ heteroalkyl), —$(C_1\text{-}C_3$ alkyl)-$(C_6\text{-}C_{10}$ aryl), —$(C_1\text{-}C_3$ heteroalkyl)-$(C_6\text{-}C_{10}$ aryl), and —$(C_6\text{-}C_{10}$ aryl), wherein —$(C_6\text{-}C_{10}$ aryl)-$(C_1\text{-}C_3$ heteroalkyl) and —$(C_1\text{-}C_3$ heteroalkyl)-$(C_6\text{-}C_{10}$ aryl) have 1 to 4 heteroatoms independently selected from O, S, and Si; and $X^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

Embodiment 90. The wound dressing, topical formulation, or method of Embodiment 89, wherein at least one of $R^{1a}$, $R^{2a}$, and $R^{3a}$ is —$(C_1\text{-}C_4$ alkyl).

Embodiment 91. The wound dressing, topical formulation, or method of Embodiment 89, wherein two of $R^{1a}$, $R^{2a}$, and $R^{3a}$ is —$(C_1\text{-}C_4$ alkyl).

Embodiment 92. The wound dressing, topical formulation, or method of any one of Embodiments 1-88, wherein polymeric component (1) further comprises (vi) a third adduct of a fourth multifunctional crosslinker and a second quaternary ammonium salt $$R^{2a}-\overset{\overset{\displaystyle R^{1a}}{|}}{\underset{\displaystyle R^{3a}}{N^+}}\overset{\displaystyle X^-}{\underset{\displaystyle A^1}{\diagdown}}Y^1,$$

wherein $R^{1a}$, $R^{2a}$, and $R^{3a}$ are each independently —$(C_1\text{-}C_{20}$ alkyl), —$(C_1\text{-}C_{20}$ alkyl)-$(C_6\text{-}C_{10}$ aryl), or —$(C_6\text{-}C_{10}$ aryl)-$(C_1\text{-}C_{20}$ alkyl);

$A^1$ is a linking group selected from a group consisting of —$(C_3\text{-}C_{20}$ alkylene)-, —$(C_3\text{-}C_{20}$ heteroalkylene)-, —$(C_6\text{-}C_{10}$ arylene)-$(C_3\text{-}C_{20}$ alkylene)-, —$(CR^{m1}R^{n1})_{x42}$—$W^{42}$—$(CR^{p1}R^{q1})_{y42}$—, and —$(CR^{m1}R^{n1})_{x43}$—$W^{43}$—$(CR^{p1}R^1)_{y43}$—, wherein —$(C_3\text{-}C_{20}$ heteroalkylene)- has 1 to 4 heteroatoms independently selected from O, S, and Si; and —$(C_3\text{-}C_{20}$ alkylene)- and —$(C_3\text{-}C_{20}$ heteroalkylene)- are optionally substituted with 1 to 6 substituents independently selected from —$(C_6\text{-}C_{10}$ aryl)-$(C_1\text{-}C_3$ alkyl), —$(C_6\text{-}C_{10}$ aryl)-$(C_1\text{-}C_3$ heteroalkyl), —$(C_1\text{-}C_3$ alkyl)-$(C_6\text{-}C_{10}$ aryl), —$(C_1\text{-}C_3$ heteroalkyl)-$(C_6\text{-}C_{10}$ aryl), and —$(C_6\text{-}C_{10}$ aryl);

each $R^{m1}$, $R^{n1}$, $R^{p1}$, and $R^{q1}$ is independently selected from H and $C_1\text{-}C_4$ alkyl;

$W^{42}$ is selected from —C(O)—; —C(O)O—; —OC(O)—; —C(O)NH—; and —NHC(O)—;

$W^{43}$ is selected from 5- to 6-membered cycloalkyl, $C_6\text{-}C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;

x42 is an integer from 1 to 19 and y42 is an integer from 1 to 19, wherein 3≤(x42+y42)≤20;

x43 is an integer from 1 to 20, and y43 is an integer from 0 to 19, wherein $3 \leq (x43+y43) \leq 20$;

$Y^1$ is selected from a group consisting of —OH, —NHR$^{4a}$, —SH, —CO$_2$H, —C(O)NHR$^{4a}$, —C(S) NHR$^{4a}$, each $R^{4a}$ is independently selected from a group consist- ing of H, —(C$_6$-C$_{10}$ aryl)-(C$_1$-C$_3$ alkyl), —(C$_6$-C$_{10}$ aryl)-(C$_1$-C$_3$ heteroalkyl), —(C$_1$-C$_3$ alkyl)-(C$_6$-C$_{10}$ aryl), —(C$_1$-C$_3$ heteroalkyl)-(C$_6$-C$_{10}$ aryl), and —(C$_6$-C$_{10}$ aryl), wherein —(C$_6$-C$_{10}$ aryl)-(C$_1$-C$_3$ heteroalkyl) and —(C$_1$-C$_3$ heteroalkyl)-(C$_6$-C$_{10}$ aryl) have 1 to 4 heteroatoms independently selected from O, S, and Si; and X$^-$ is independently acetate, halide, sulfate, sulfonate, phosphate, phosphonate, carbonate, silicate, hexafluo- rophosphate, hexafluoroantimonate, triflate, borate, or an organo-substituted derivative of any of the forego- ing.

Embodiment 93. The wound dressing, topical formula- tion, or method of Embodiment 92, wherein at least one of R$^{1a}$, R$^{2a}$, and R$^{3a}$ is —(C$_1$-C$_4$ alkyl).

Embodiment 94. The wound dressing, topical formula- tion, or method of Embodiment 92, wherein two of R$^{1a}$, R$^{2a}$, and R$^{3a}$ is —(C$_1$-C$_4$ alkyl).

Embodiment 95. The wound dressing, topical formula- tion, or method of any one of Embodiments 92-94, wherein the fourth multifunctional crosslinker is present in the poly- mer, the copolymer, or the interpenetrating polymer network of polymeric component (1) in an amount of about 0.1 wt. % to about 15 wt. %.

Embodiment 96. The wound dressing, topical formula- tion, or method of any one of Embodiments 92-95, wherein the fourth multifunctional crosslinker is different from the first multifunctional crosslinker and, when present, from the second multifunctional crosslinker, and, when present, from the third multifunctional crosslinker.

Embodiment 97. The wound dressing, topical formula- tion, or method of any one of Embodiments 92-96, wherein the fourth multifunctional crosslinker is a fourth polyiso- cyanate.

Embodiment 98. The wound dressing, topical formula- tion, or method of Embodiment 97, wherein the fourth polyisocyanate is prepared from a diisocyanate selected from the group consisting of: hexamethylene diisocyanate (HDI), isophorone diisocyanate (IPDI), toluene diisocyanate (TDI), methylene diphenyl diisocyanate (MDI), xylenedii- socyanate (XDI), methylene-bis-(4-cyclohexylisocyanate) (H12MDI), meta-tetramethylxylene diisocyanate (TMXDI), and trimethylhexamethylene diisocyanate (TMDI).

Embodiment 99. The wound dressing, topical formula- tion, or method of Embodiment 97, wherein the fourth polyisocyanate is selected from the group consisting of DESMODUR® N-3300, DESMODUR® N-100, DESMO- DUR® Z4470SN, WANNATE® T series polyisocyanates, and LUPRANATE® M series polyisocyanates.

Embodiment 100. The wound dressing, topical formula- tion, or method of any one of Embodiments 89-99, wherein the second quaternary ammonium salt is

180

(C18DMDEG-Br)

(C2DMDEG-Br)

Embodiment 101. The wound dressing, topical formula- tion, or method of any one of Embodiments 89-100, wherein the second quaternary ammonium salt is present in the polymer, the copolymer, or the interpenetrating polymer network of polymeric component (1) in an amount of about 1 wt. % to about 15 wt. %.

Embodiment 102. The wound dressing, topical formula- tion, or method of any one of Embodiments 89-101, wherein the third adduct has an average isocyanate functionality of 2 to 3.

Embodiment 103. The wound dressing, topical formula- tion, or method of any one of Embodiments 89-102, wherein the third adduct has an average isocyanate functionality of about 2.05 to about 2.3.

Embodiment 104. The wound dressing, topical formula- tion, or method of any one of Embodiments 89-103, wherein the third adduct is present in the polymer, the copolymer, or the interpenetrating polymer network of polymeric compo- nent (1) in an amount of about 2 wt. % to about 30 wt. %.

Embodiment 105. The wound dressing, topical formula- tion, or method of any one of Embodiments 1-104, wherein the polyethyleneimine intermediate is present in the poly- mer, the copolymer, or the interpenetrating polymer network of polymeric component (1), (3) or (4) in an amount of about 0.1 wt. % to about 50 wt. %.

Embodiment 106. The wound dressing, topical formula- tion, or method of any one of Embodiments 1-105, wherein the second adduct is present in the polymer, the copolymer, or the interpenetrating polymer network of polymeric com- ponent (1) or (4) in an amount of about 1 wt. % to about 30 wt. %.

Embodiment 107. The wound dressing, topical formula- tion, or method of any one of Embodiments 1-106, wherein the water-soluble polymer is crosslinked with (a) the first multifunctional crosslinker as incorporated in the first adduct; (b) when present, the second multifunctional cross- linker as incorporated in the second adduct; (c) when present, the third multifunctional crosslinker; or (d) any combination of two or more thereof.

Embodiment 108. The wound dressing, topical formula- tion, or method of any one of Embodiments 1-107, wherein the water-soluble polymer is selected from a group consist- ing of hydroxyethyl cellulose (HEC), hydroxypropyl cellu- lose, polyvinyl alcohol, poly(hydroxyethyl methacrylate-co- alkyl methacrylate), poly(hydroxyethyl methacrylate-co- alkyl acrylate), poly(hydroxyethyl acrylate-co-alkyl methacrylate), poly(hydroxyethyl acrylate-co-alkyl acry- late), polyacrylamide, polyethyleneimine intermediate, a copolymer of two or more thereof, a copolymer of one or more thereof with polyvinylpyrrolidone poly(glycidyl acry- late) or with poly(glycidyl methacrylate), and a combination or blend of two or more thereof.

Embodiment 109. The wound dressing, topical formulation, or method of any one of Embodiments 1-107, wherein the water-soluble polymer is hydroxyethyl cellulose or a hydrophobically modified derivative thereof.

Embodiment 110. The wound dressing, topical formulation, or method of any one of Embodiments 1-107, wherein the water-soluble polymer is another polyethyleneimine intermediate.

Embodiment 111. The wound dressing, topical formulation, or method of any one of Embodiments 1-110, wherein the water-soluble polymer is present in the polymer, the copolymer, or the interpenetrating polymer network of polymeric component (1) or (2) in an amount of about 0.5 wt. % to about 15 wt. %.

Embodiment 112. The wound dressing, topical formulation, or method of any one of Embodiments 1-111, wherein polymeric components (1) and (2) further comprise a chain extender selected from a group consisting of HO—$(C_nH_{2n})$—OH and HO—$(C_nH_{2n\text{-}2})$—OH, or a combination thereof, wherein n is an integral between 2 and 8.

Embodiment 113. The wound dressing, topical formulation, or method of Embodiment 112, wherein the chain extender is propanediol, 1,4-butanediol, neopentyl glycol, hexanediol, cyclohexane dimethanol, or a combination of two or more thereof.

Embodiment 114. The wound dressing, topical formulation, or method of Embodiment 112 or Embodiment 113, wherein the chain extender is present in the polymeric component in an amount of about 0.5 wt. % to about 10 wt. %.

Embodiment 115. The wound dressing, topical formulation, or method of any one of Embodiments 1-114, wherein the polymeric component further comprises a third quaternary ammonium salt $$R^{2a}\!\!\diagdown\!\!\overset{\displaystyle R^{1a}}{\underset{\displaystyle R^{3a}\diagup}{N^+}}\!\!\diagup\!\!\overset{X^-}{\underset{\displaystyle A^2}{}}\!\!\diagdown Y^{1a},$$

wherein
R$^{1a}$, R$^{2a}$, and R$^{3a}$ are each independently methyl or ethyl;
A$^2$ is selected from a group consisting of —$(C_3\text{-}C_{20}$ alkylene)-, —$(C_3\text{-}C_{20}$ heteroalkylene)-, —$(C_6\text{-}C_{10}$ arylene)-$(C_3\text{-}C_{20}$ alkylene)-, —$(CR^{m1}R^{n1})_{x42}$—W$^{42}$—$(CR^{p1}R^{q1})_{y42}$—, and —$(CR^{m1}R^{n1})_{x43}$—W$^{43}$—$(CR^{p1}R^{q1})_{y43}$—, wherein —$(C_3\text{-}C_{20}$ heteroalkylene)- has 1 to 4 heteroatoms independently selected from O, S, and Si; and —$(C_3\text{-}C_{20}$ alkylene)- and —$(C_3\text{-}C_{20}$ heteroalkylene)- are optionally substituted with 1 to 6 substituents independently selected from —$(C_6\text{-}C_{10}$ aryl)-$(C_1\text{-}C_3$ alkyl), —$(C_6\text{-}C_{10}$ aryl)-$(C_1\text{-}C_3$ heteroalkyl), —$(C_1\text{-}C_3$ alkyl)-$(C_6\text{-}C_{10}$ aryl), —$(C_1\text{-}C_3$ heteroalkyl)-$(C_6\text{-}C_{10}$ aryl), and —$(C_6\text{-}C_{10}$ aryl);
each R$^{m1}$, R$^{n1}$, R$^{p1}$, and R$^{q1}$ is independently selected from H and $C_1\text{-}C_4$ alkyl;
W$^{42}$ is selected from —C(O)—; —C(O)O—; —OC (O)—; —C(O)NH—; and —NHC(O)—;
W$^{43}$ is selected from 5- to 6-membered cycloalkyl, $C_6\text{-}C_{10}$ aryl, 5- to 6-membered heterocycloalkyl, and 5- to 6-membered heteroaryl, wherein the heterocycloalkyl contains 1-2 ring heteroatoms selected from O, N, S, and Si; and the heteroaryl contains 1-3 ring heteroatoms selected from O, N, S, and Si;
x42 is an integer from 1 to 19 and y42 is an integer from 1 to 19, wherein 3≤(×42+y42)≤20;
x43 is an integer from 1 to 20, and y43 is an integer from 0 to 19, wherein 3≤(×43+y43)≤20;
Y$^{1a}$ is H;
each R$^{4a}$ is independently selected from a group consisting of H, —$(C_6\text{-}C_{10}$ aryl)-$(C_1\text{-}C_3$ alkyl), —$(C_6\text{-}C_{10}$ aryl)-$(C_1\text{-}C_3$ heteroalkyl), —$(C_1\text{-}C_3$ alkyl)-$(C_6\text{-}C_{10}$ aryl), —$(C_1\text{-}C_3$ heteroalkyl)-$(C_6\text{-}C_{10}$ aryl), and —$(C_6\text{-}C_{10}$ aryl), wherein —$(C_6\text{-}C_{10}$ aryl)-$(C_1\text{-}C_3$ heteroalkyl) and —$(C_1\text{-}C_3$ heteroalkyl)-$(C_6\text{-}C_{10}$ aryl) have 1 to 4 heteroatoms independently selected from O, S, and Si; and
X$^-$ is independently acetate, halide, sulfate, sulfonate, phosphate, phosphonate, carbonate, silicate, hexafluorophosphate, hexafluoroantimonate, triflate, borate, or an organo-substituted derivative of any of the foregoing.

Embodiment 116. The wound dressing, topical formulation, or method of any one of Embodiments 1-57, wherein the polymeric component is the polyethyleneimine intermediate.

Embodiment 117. A method of making the wound dressing of any one of Embodiments 1-8 and 31-116, comprising integrating a composition including the polymeric component into a fibrous material by one of:
(i) spraying the fibrous material with the composition,
(ii) submerging the fibrous material in a fluid containing the composition,
(iii) impregnating fibers of the fibrous material with a fluid containing the composition,
(iv) applying a coating layer containing the composition to a surface of the fibrous material,
(v) adhering a backing containing the composition to the fibrous material,
(vi) applying microneedles containing the composition to the fibrous material,
(vii) embedding a layer containing the composition within the fibrous material;
(viii) constructing fibers of the fibrous material with the composition by electrospinning; or
(ix) interleaving fibers containing the composition with fibers of the fibrous material.

Embodiment 118. A method of making a polyurethane foam wound dressing described herein, comprising integrating a composition including the polymeric component into the polyurethane foam wound dressing by mixing the composition with polyurethane prior to curing to provide the polyurethane foam wound dressing.

Embodiment 119. A polymer having wound healing properties comprising a polyethyleneimine intermediate, wherein the polyethyleneimine intermediate has a ratio of total quaternary amines to total hydroxyl groups of at least 1:1.

Embodiment 120. The polymer of Embodiment 119 selected from a group consisting of:

| Compound | General Structure | PEI MW* | $R^{60}$ (mole %) ** |
|---|---|---|---|
| 20-1 (batch 105159) | B | 270 kDa (branched) | —$CH_2CH(CH_3)OH$ (<50%) —$C_6H_{13}$ (>50%) |
| 20-1 (batch 99367) | B | 270 kDa (branched) | —$CH_2CH(CH_3)OH$ (50%) —$C_6H_{13}$ (50%) |
| 21-1 | A | 25 kDa (hyperbranched) | —$CH_2CH(CH_3)OH$ (50%) —$C_6H_{13}$ (50%) |
| 22-1 | B | 70 kDa (branched) | —$CH_2CH(CH_3)OH$ (50%) —$C_6H_{13}$ (50%) |
| 23-1 | B | 70 kDa (branched) | —$CH_2CH(CH_3)OH$ (50%) —$CH_2C(O)Ph$ (50%) |
| 24-1 | B | 70 kDa (branched) | —$CH_2CH(CH_3)OH$ (50%) —$CH_2Ph$ (50%) |
| 26-1 | B | 70 kDa (branched) | —$CH_2CH(OH)CH_2N^+(CH_3)_3$ $Cl^-$ (100%) |
| 29-1 | B | 70 kDa (branched) | —$(CH_2)_3OH$ (1%) —$C_6H_{13}$ (99%) |
| 30-1 | A | 25 kDa (hyper-branched) | —$(CH_2)_3OH$ (10%) 75:25 —$C_{18}H_{37}$:—$C_8H_{17}$ (90%) |
| 31-1 | B | 70 kDa (branched) | —$C(O)(CH_2)_5OH$ (7%) —$C_6H_{13}$ (93%) |
| 32-1 | B | 70 kDa (branched) | —$(CH_2)_3OH$ (10%) —$C_6H_{13}$ (90%) |
| 32-2 | B | 70 kDa (branched) | —$(CH_2)_3OH$ (5%) —$C_6H_{13}$ (95%) |
| 32-3 | B | 70 kDa (branched) | —$CH_2CH(CH_3)OH$ (5%) —$C_6H_{13}$ (95%) |
| 32-4 | B | 70 kDa (branched) | —$C(O)(CH_2)_5OH$ (7.5%) —$C_6H_{13}$ (92.5%) |
| 32-5 | A | 25 kDa (hyper-branched) | —$CH_2CH(CH_3)OH$ (50%) 50:50 —$C_{18}H_{37}$:—$C_8H_{17}$ (50%) |
| 32-6 | B | 72 kDa (branched) | —$(CH_2)_3OH$ (13%) 75:25 —$C_{18}H_{37}$:—$C_8H_{17}$ (87%) |
| 32-7 | B | 72 kDa (branched) | —$C(O)(CH_2)_5OH$ (6.5%) 75:25 —$C_{18}H_{37}$:—$C_8H_{17}$ (93.5%) |
| 32-8 | A | 25 kDa (hyper-branched) | —$C(O)(CH_2)_5OH$ (7%) 75:25 —$C_{18}H_{37}$:—$C_8H_{17}$ (93%) |
| 32-9 | A | 25 kDa (hyper-branched) | —$CH_2CH(CH_3)OH$ (50%) 25:75 —$C_{18}H_{37}$:—$C_8H_{17}$ (50%) |

*indicates molecular weight of polyethyleneimine precursor

**theoretical stoichiometric ratio (based on amount of reactants used in the synthetic protocol) wherein A is B is and each n is an integer independently selected from 2 to 3000, preferably an integer independently selected from 10 to 100.

Embodiment 121. The polymer of Embodiment 120, wherein one or more bromide anions is replaced with $X^-$ independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

Embodiment 122. The polymer of Embodiment 119 selected from a group consisting of:

| Compound | General Structure | PEI MW* | $R^{60}$ (mole %)** |
|---|---|---|---|
| 32-10 | A | 25 kDa (hyperbranched) | —C(O)(CH$_2$)$_5$OH (11%) —C$_6$H$_{13}$ (89%) |
| 32-11 | B | 70 kDa (branched) | —C(O)(CH$_2$)$_5$OH (9%) —C$_6$H$_{13}$ (91%) |
| 32-13 | B | 70 kDa (branched) | —(CH$_2$)$_3$OH (7%) 75:25 —C$_{18}$H$_{37}$:—C$_8$H$_{17}$ (93%) |
| 32-14 | A | 25 kDa (hyper-branched) | —(CH$_2$)$_3$OH (7%) 75:25 —C$_{18}$H$_{37}$:—C$_8$H$_{17}$ (93%) |
| 32-15 | B | 70 kDa (branched) | —C(O)(CH$_2$)$_5$OH (9%) 75:25 —C$_{18}$H$_{37}$:—C$_8$H$_{17}$ (91%) |
| 32-16 | A | 25 kDa (hyperbranched) | —C(O)(CH$_2$)$_5$OH (11%) 75:25 —C$_{18}$H$_{37}$:—C$_8$H$_{17}$ (89%) |
| 32-1A | B | 70 kDa (branched) | —(CH$_2$)$_3$OH (10%) —C$_6$H$_{13}$ (90%) |
| 32-1B | B | 70 kDa (branched) | —(CH$_2$)$_3$OH (10%) —C$_6$H$_{13}$ (90%) |
| 32-2A | B | 70 kDa (branched) | —(CH$_2$)$_3$OH (5%) —C$_6$H$_{13}$ (95%) |
| 32-2B | B | 70 kDa (branched) | —(CH$_2$)$_3$OH (5%) —C$_6$H$_{13}$ (95%) |
| 32-2C | B | 70 kDa (branched) | —(CH$_2$)$_3$OH (15%)*** —C$_6$H$_{13}$ (85%) |
| 32-2D | B | 70 kDa (branched) | —(CH$_2$)$_3$OH (5%) —C$_6$H$_{13}$ (95%) |
| 32-2E | B | 70 kDa (branched) | —(CH$_2$)$_3$OH (12%)*** —C$_6$H$_{13}$ (88%) |
| 32-2F | B | 70 kDa (branched) | —(CH$_2$)$_3$OH (5%) —C$_6$H$_{13}$ (95%) |
| 32-2G | B | 70 kDa (branched) | —(CH$_2$)$_3$OH (5%) —C$_6$H$_{13}$ (95%) |
| 32-2H | B | 70 kDa (branched) | —(CH$_2$)$_3$OH (5%) —C$_6$H$_{13}$ (95%) |
| 32-2I | B | 70 kDa (branched) | —(CH$_2$)$_3$OH (5%) —C$_6$H$_{13}$ (95%) |

*indicates molecular weight of polyethyleneimine precursor
**theoretical stoichiometric ratio (based on amount of reactants used in the synthetic protocol) unless otherwise indicated
***actual stoichiometric ratio as determined by NMR analysis wherein A is

3 X$^-$

B is

4 X$^-$ each n is an integer independently selected from 2 to 3000, preferably an integer independently selected from 10 to 100; and each X$^-$ is independently selected from the group consisting of acetate, halide, sulfate, sulfonate, phosphate, phosphonate, carbonate, silicate, hexafluorophosphate, hexafluoroantimonate, triflate, and borate, and their organo-substituted derivatives.

cation are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by All patents and other publications; including literature references, issued patents, published patent applications, and co-pending patent applications; cited throughout this application virtue of prior invention or for any other reason. All statements as to the date or representation as to the contents of these documents is based on the information available to the applicants and does not constitute any admission as to the correctness of the dates or contents of these documents.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

What is claimed is:

1. A wound dressing comprising a polymeric component, wherein the polymeric component is a polyethyleneimine intermediate selected from the group consisting of wherein each $R^{60}$ is independently selected from —$(CH_2)_3$ OH and —$C_6H_{13}$; at least one $R^{60}$ is —$(CH_2)_3$ OH but less than 50% of all $R^{60}$ is —$(CH_2)_3$ OH;

each n is an integer independently selected from 1 to 3000;

each $X^-$ is independently selected from the group consisting of acetate, halide, sulfate, sulfonate, phosphate, phosphonate, carbonate, silicate, hexafluorophosphate, hexafluoroantimonate, triflate, and borate;

and the polyethyleneimine intermediate has a ratio of total quaternary amines to total hydroxyl groups of at least 1:1.

2. The wound dressing of claim 1, wherein —$(CH_2)_3OH$ is present in the polyethyleneimine intermediate in an amount of 5 mol % to 20 mol %; and —$C_6H_{13}$ is present in the polyethyleneimine intermediate in an amount of 80 mol % to 95 mol %.

3. The wound dressing of claim 2, wherein the polyethyleneimine intermediate is and —$(CH_2)_3OH$ is present in the polyethyleneimine intermediate as $R^{60}$ in an amount of 10 mol %, and —$C_6H_{13}$ is present in the polyethyleneimine intermediate as $R^{60}$ in an amount of 90 mol %; or —$(CH_2)_3OH$ is present in the polyethyleneimine intermediate as $R^{60}$ in an amount of 12 mol %, and —$C_6H_{13}$ is present in the polyethyleneimine intermediate as $R^{60}$ in an amount of 88 mol %.

4. The wound dressing of claim 3, wherein at least 20% of the nitrogen atoms of the polyethyleneimine intermediate are quaternized.

5. The wound dressing of claim 4, wherein the polymeric component is antibacterial against one of or both gram negative strain bacteria and gram positive strain bacteria.

6. The wound dressing of claim 5, wherein an outer layer of the wound dressing contains the polymeric component.

7. The wound dressing of claim 5, wherein the polymeric component is impregnated into the wound dressing.

8. The wound dressing of claim 5, wherein the wound dressing is selected from the group consisting of a wrap, a packing, a gauze, a plaster, a bandage, a lint, a film, and any combination of the foregoing.

9. The wound dressing of claim 1, wherein —$(CH_2)_3OH$ is present in the polyethyleneimine intermediate in an amount of 10 mol % to 15 mol %; and —$C_6H_{13}$ is present in the polyethyleneimine intermediate in an amount of 85 mol % to 90 mol %.

10. The wound dressing of claim 8, wherein the wound dressing is a foam, a hydrogel, or a hydrocolloid.

11. The wound dressing of claim 1, wherein each n is an integer independently selected from 10 to 1000.

12. A method of promoting healing of a wound or a surgical site in a subject in need thereof, the method comprising applying, to the wound or the surgical site, the wound dressing of claim 1.

* * * * *